United States Patent
Attfield et al.

(10) Patent No.: US 11,473,109 B2
(45) Date of Patent: Oct. 18, 2022

(54) YEAST FOR ETHANOL PRODUCTION

(71) Applicants: Novozymes A/S, Bagsvaerd (DK);
Microbiogen Pty. Ltd., Sydney (AU)

(72) Inventors: Paul Victor Attfield, Mount Colah (AU); Philip John Livingstone Bell, Turramurra (AU); Hamid Rismani Yazdi, Raleigh, NC (US); Xin Li, Raleigh, NC (US); Robert Lyle Osborne, Raleigh, NC (US); Alan Jay House, Cary, NC (US)

(73) Assignees: Novozymes A/S, Bagsvaerd (DK);
Microbiogen Pty. Ltd., Sydney (AU)

( * ) Notice: Subject to any disclaimer, the term of this patent is extended or adjusted under 35 U.S.C. 154(b) by 0 days.

(21) Appl. No.: 16/970,340

(22) PCT Filed: Feb. 15, 2019

(86) PCT No.: PCT/US2019/018249
§ 371 (c)(1),
(2) Date: Aug. 14, 2020

(87) PCT Pub. No.: WO2019/161227
PCT Pub. Date: Aug. 22, 2019

(65) Prior Publication Data
US 2021/0079430 A1    Mar. 18, 2021

Related U.S. Application Data

(60) Provisional application No. 62/631,173, filed on Feb. 15, 2018.

(51) Int. Cl.
*C12N 15/81* (2006.01)
*C12P 7/06* (2006.01)
*C12N 1/18* (2006.01)
*C12R 1/865* (2006.01)

(52) U.S. Cl.
CPC .................. *C12P 7/06* (2013.01); *C12N 1/18* (2013.01); *C12N 1/185* (2021.05); *C12N 15/81* (2013.01); *C12R 2001/865* (2021.05)

(58) Field of Classification Search
CPC ............ C12N 1/185; C12N 15/81; C12P 7/06
See application file for complete search history.

(56) References Cited

U.S. PATENT DOCUMENTS 11,214,810 B2 *   1/2022   Pronk ............ C12Y 101/01001

OTHER PUBLICATIONS

Anonymous, 2017, Proceedings of the 7th Australasian conference on Yeast—1-58.
Bell, 2017, Industrial biotechnology 13(2), 76-84.
Bell, 2018, Bio World Congress on Industrial Biotechnology Conference, Abstract.
Huang et al, 2017, FEMS Yeast research 17, 1-13.
Kroukamp et al, 2017, Biotechnol J 12,1-10.
Snoek et al, 2015, Biotechnology for biofuels 8(32), 1-19.

* cited by examiner

*Primary Examiner* — Tekchand Saidha
(74) *Attorney, Agent, or Firm* — Eric Fechter

(57) ABSTRACT

Described herein are *Saccharomyces cerevisiae* strains MBG5038 and MBG5012 deposited under the Budapest Treaty and having accession Nos. NRRL Y67549 and NRRL Y67700, respectively, or a derivatives of strains NRRL Y67549 or Y67700 which exhibit one or more properties or defining characteristics of *Saccharomyces cerevisiae* strains MBG5038 or MBG5012. Also described are compositions comprising the *Saccharomyces* yeast and naturally occurring and/or non-naturally occurring components, as well as are processes for producing ethanol from starch-containing material using the strains.

6 Claims, 8 Drawing Sheets
Specification includes a Sequence Listing.

YEAST FOR ETHANOL PRODUCTION

CROSS-REFERENCE TO RELATED APPLICATIONS

This application is a 35 U.S.C. 371 national application of PCT/US2019/018249, filed Feb. 15, 2019, which claims priority or the benefit from U.S. Provisional Application Ser. No. 62/631,173, filed Feb. 15, 2018. The contents of these applications are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which is incorporated herein by reference.

FIELD

Described herein are processes, e.g., including a liquefaction step, for producing ethanol from starch-containing material using yeast for converting fermentable sugars into ethanol. Also described are *Saccharomyces* yeast strains having improved ability to ferment sugars to ethanol, methods for the production of *Saccharomyces* yeast strains having improved ability to ferment sugars to ethanol, and the use of *Saccharomyces* yeast strains having improved ability to ferment sugars to ethanol in the production of ethanol. Finally, also described are compositions comprising the *Saccharomyces* yeast strains and naturally occurring and/or non-naturally occurring components.

BACKGROUND

Production of ethanol from starch-containing material is well-known in the art. The production of ethanol as a bio-fuel has become a major industry, with in excess of 24 billion gallons of ethanol being produced worldwide in 2014.

The most commonly industrially used commercial process, often referred to as a "conventional process", includes liquefying gelatinized starch at high temperature (about 85° C.) using typically a bacterial alpha-amylase, followed by simultaneous saccharification and fermentation (SSF) carried out anaerobically in the presence of typically a glucoamylase and a *Saccharomyces cerevisae* yeast.

Yeasts which are used for production of ethanol for use as fuel, such as in the corn ethanol industry, require several characteristics to ensure cost effective production of the ethanol. These characteristics include ethanol tolerance, low by-product yield, rapid fermentation, and the ability to limit the amount of residual sugars remaining in the ferment. Such characteristics have a marked effect on the viability of the industrial process.

Yeast of the genus *Saccharomyces* exhibits many of the characteristics required for production of ethanol. In particular, strains of *Saccharomyces cerevisiae* are widely used for the production of ethanol in the fuel ethanol industry. Strains of *Saccharomyces cerevisiae* that are widely used in the fuel ethanol industry can produce high yields of ethanol under fermentation conditions found in, for example, the fermentation of corn mash. An example of such a strain is the yeast used in commercially available ethanol yeast product called ETHANOL RED®.

Strains of *Saccharomyces cerevisiae* are used in the fuel ethanol industry to ferment sugars such as glucose, fructose, sucrose and maltose to produce ethanol via the glycolytic pathway. These sugars are obtained from sources such as corn and other grains, sugar juice, molasses, grape juice, fruit juices, and starchy root vegetables and may include the breakdown of cellulosic material into glucose.

Although strains of *Saccharomyces cerevisiae* currently used in the fuel ethanol industry are well suited to ethanol production, there is an increasing need for improvements in the efficiency of ethanol production owing to the increased demand for ethanol as a fuel, and the increased availability of starch in new strains of corn.

There is therefore a need for new robust yeast strains of *Saccharomyces* capable of improving the efficiency of ethanol production in industrial scale fermentation.

Further, despite significant improvement of ethanol production processes over the past decade there is still a desire and need for providing processes of producing ethanol from starch-containing material and yeast that can be used in commercial scale ethanol processes.

SUMMARY

Described herein are, inter alia, processes for producing ethanol from starch-containing material and yeast suitable for use in such processes.

A first aspect relates to processes for producing ethanol from starch-containing material comprising the steps of:
  i) liquefying the starch-containing material at a temperature above the initial gelatinization temperature using an alpha-amylase;
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces cerevisiae* strain MBG5038 having defining characteristics of *Saccharomyces cerevisiae* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces cerevisiae* strain MBG5012 having defining characteristics of *Saccharomyces cerevisiae* strain MBG5012.

In some embodiments, the derivative of *Saccharomyces cerevisiae* strain MBG5038 or *Saccharomyces cerevisiae* strain MBG5012 expresses a glucoamylase and/or an alpha-amylase.

As used herein, the terms "properties" and "defining characteristics" of *Saccharomyces cerevisiae* strain MBG5038 and/or *Saccharomyces cerevisiae* strain MBG5012 include at least increased ethanol boost (i.e., ethanol yield) compared to *Saccharomyces cerevisiae* strain Ethanol Red® (deposited under Accession No. V14/007039 at National Measurement Institute, Victoria, Australia) under the same conditions. Other "properties" and "defining characteristics" include, inter alia, reduced acetaldehyde production, increased temperature tolerance, and decreased glycerol production. A fermenting organism described herein, e.g., used in a process described herein may have one or more the above mentioned "properties" and "defining characteristics".

The fermenting organism organism described herein, especially *Saccharomyces cerevisiae* yeast, having properties that are about the same as that of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a derivative of *Saccharomyces cerevisiae* strain MBG5038, or having properties that are about the same as that of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a derivative of *Saccharomyces cerevisiae* strain MBG5012, having one or more, such as all of the following properties and/or defining characteristics of *Saccharomyces cerevisiae* strain MBG5038 or MBG5012;

increased ethanol boost (i.e., ethanol yield) compared to *Saccharomyces cerevisiae* strain Ethanol Red® (deposited under Accession No. V14/007039 at National Measurement Institute, Victoria, Australia) under the same process conditions;

reduced acetaldehyde production compared to *Saccharomyces cerevisiae* strain Ethanol Red® (deposited under Accession No. V14/007039 at National Measurement Institute, Victoria, Australia) under the same process conditions;

increased temperature tolerance compared to *Saccharomyces cerevisiae* strain Ethanol Red® (deposited under Accession No. V14/007039 at National Measurement Institute, Victoria, Australia) under the same process conditions;

decreased glycerol production compared to *Saccharomyces cerevisiae* strain Ethanol Red® (deposited under Accession No. V14/007039 at National Measurement Institute, Victoria, Australia) under the same process conditions.

A fermenting organism described herein may have one or more, such as all, of the above mentioned "properties" or "defining characteristics".

According to the ethanol production process, liquefaction in step i) is carried out by subjecting starch-containing material at a temperature above the initial gelatinization temperature, typically between 80-90° C., using an alpha-amylase. The pH in liquefaction is preferably between 4.5 and 6.0, such as between 4.8 and 5.8. Examples of alpha-amylase can be found below in the "Alpha-Amylase Present and/or Added During Liquefaction"-section. In one embodiment, the alpha-amylase is a thermostable bacterial alpha-amylase. In one embodiment, the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein. Examples of suitable *Bacillus stearothermophilus* alpha-amylase variants can be found below in the "Thermostable Alpha-Amylase"-section and include one from the following group of *Bacillus stearothermophilus* alpha-amylase variants with the following mutations: I181*+G182*, and optionally N193F, and further one of the following substitutions or combinations of substitutions E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 1 for numbering).

Examples of other suitable *Bacillus stearothermophilus* alpha-amylases having increased thermostability compared to a reference alpha-amylase (*Bacillus stearothermophilus* alpha-amylase with the mutations I181*+G182*, and optionally substitution N193F, truncated at the C-terminal to be 485-495 amino acids long, such as about 491 amino acids long) at pH 4.5 and 5.5, 0.12 mM $CaCl_2$ can be found in WO 2011/082425 hereby incorporated by reference. (See also Example 1 below)

Liquefaction in step i) may be carried out using a combination of alpha-amylase and protease. The protease may be a protease having a thermostability value of more than 20% determined as Relative Activity at 80° C./70° C. Examples of suitable proteases are described below in the section "Protease Present and/or Added During Liquefaction".

The protease may be of fungal origin, such as of filamentous fungus origin. Specific examples of suitable fungal proteases are protease variants of metallo protease derived from a strain of the genus *Thermoascus*, preferably a strain of *Thermoascus aurantiacus*, especially the strain *Thermoascus aurantiacus* CGMCC No. 0670 disclosed as the mature part of SEQ ID NO: 2 disclosed in WO 2003/048353 or the mature part of SEQ ID NO: 1 in WO 2010/008841 or SEQ ID NO: 3 herein with one of the following substitutions or combinations of substitutions:
D79L+S87P+A112P+D142L;
D79L+S87P+D142L; and
A27K+D79L+Y82F+S87G+D104P+A112P+A126V+ D142L.

Examples of other suitable protease variants can be found in WO 2011/072191 hereby incorporated by reference (See also Example 2 below).

Suitable proteases also include bacterial proteases. A suitable bacterial protease may be derived from a strain of *Pyrococcus*, preferably a strain of *Pyrococcus furiosus*. In one embodiment, the protease is the one shown in SEQ ID NO: 1 in U.S. Pat. No. 6,358,726 or SEQ ID NO: 13 herein.

In one embodiment, 0.5-50 micro gram *Pyrococcus furiosus* protease per gram DS, such as 1-5 micro gram *Pyrococcus furiosus* protease per gram DS, such as about 1.5 or 3 micro gram *Pyrococcus furiosus* protease per gram DS is present and/or added in liquefaction step i).

In one embodiment, the alpha-amylase and/or the protease added in the liquefaction step i) is further combined with a glucoamylase. Thus, a glucoamylase may also be present and/or added during liquefaction step i). The glucoamylase may be thermostable. That means that the glucoamylase has a heat stability at 85° C., pH 5.3, of at least 20%, such as at least 30%, preferably at least 35% determined as described in Example 4 (heat stability). In one embodiment, the glucoamylase present and/or added in liquefaction has a relative activity pH optimum at pH 5.0 of at least 90%, preferably at least 95%, preferably at least 97%. In one embodiment, the glucoamylase has a pH stability at pH 5.0 of at least at least 80%, at least 85%, at least 90% determined as described in Example 4 (pH optimum).

A suitable glucoamylase present and/or added in liquefaction step i) may be derived from a strain of the genus

*Penicillium*, such as a strain of *Penicillium oxalicum* disclosed as SEQ ID NO: 2 in WO 2011/127802 or SEQ ID NOs: 9 or 14 herein. In one embodiment, the glucoamylase is a variant of the *Penicillium oxalicum* glucoamylase shown in SEQ ID NO: 2 in WO 2011/127802 having a K79V substitution (using the mature sequence shown in SEQ ID NO: 14 for numbering), such as a variant disclosed in WO 2013/053801. In one embodiment, the *Penicillium oxalicum* glucoamylase has a K79V substitution (using SEQ ID NO: 14 for numbering) and further one of the following substitutions or combinations of substitutions:

P11F+T65A+Q327F; and
P2N+P4S+P11F+T65A+Q327F (using SEQ ID NO: 14 for numbering).

Examples of other suitable *Penicillium oxalicum* glucoamylase variants can be found in WO 2013/053801 incorporated by reference (See also Example 15 below).

In one embodiment, the glucoamylase, such as a *Penicillium oxalicum* glucoamylase variant, used in liquefaction has a thermostability determined as DSC Td at pH 4.0 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In one embodiment, the glucoamylase, such as a *Penicillium oxalicum* glucoamylase variant has a thermostability determined as DSC Td at pH 4.0 as described in Example 15 in the range between 70° C. and 95° C., such as between 80° C. and 90° C.

In one embodiment, the glucoamylase, such as a *Penicillium oxalicum* glucoamylase variant, used in liquefaction has a thermostability determined as DSC Td at pH 4.8 as described in Example 15 of at least 70° C., e.g., at least 75° C., at least 80° C., at least 81° C., at least 82° C., at least 83° C., at least 84° C., at least 85° C., at least 86° C., at least 87%, at least 88° C., at least 89° C., at least 90° C., or at least 91° C. In one embodiment, the glucoamylase, such as a *Penicillium oxalicum* glucoamylase variant has a thermostability determined as DSC Td at pH 4.8 as described in Example 15 in the range between 70° C. and 95° C., such as between 80° C. and 90° C.

In one embodiment, the glucoamylase, such as a *Penicillium oxalicum* glucoamylase variant, used in liquefaction has a residual activity determined as described in Example 16 of at least 100%, such as at least 105%, at least 110%, at least 115%, at least 120%, or at least 125%. In one embodiment, the glucoamylase, such as a *Penicillium oxalicum* glucoamylase variant has a thermostability determined as residual activity as described in Example 16 in the range between 100% and 130%.

Further, in one embodiment, a pullulanase may be present during liquefaction in combination with an alpha-amylase, a protease and/or a glucoamylase.

In one embodiment, a glucoamylase may be present and/or added in saccharification and/or fermentation or simultaneous saccharification and fermentation. The glucoamylase may not be the same as the thermostable glucoamylase used in liquefaction.

In one embodiment, the glucoamylase expressed by the derivative of *Saccharomyces cerevisiae* strain MBG5038 or MBG5012, present and/or added in saccharification and/or fermentation is of fungal origin, such as of filamentous fungus origin. In one embodiment, the glucoamylase is derived from a strain of *Aspergillus*, e.g., *A. niger*, *A. awamori*, or *A. oryzae*; or a strain of *Trichoderma*, e.g., *T. reesei*; or a strain of *Talaromyces*, e.g., *T. emersonii*, or a strain of *Pycnoporus*, or a strain of *Gloeophyllum*, such as *G. serpiarium* or *G. trabeum*, or a strain of *Nigrofomes*.

In one embodiment, the glucoamylase expressed by the derivative of *Saccharomyces cerevisiae* strain MBG5038 or MBG5012, present and/or added in saccharification and/or fermentation is derived from *Talaromyces emersonii*, such as the one shown in SEQ ID NO: 19 herein. In another embodiment, the glucoamylase is derived from *Gloeophyllum serpiarium*, such as the one shown in SEQ ID NO: 15 herein. In another embodiment the glucoamylase is derived from *Gloeophyllum trabeum* such as the one shown in SEQ ID NO: 17 herein.

In one embodiment, the glucoamylase expressed by the derivative of *Saccharomyces cerevisiae* strain MBG5038 or MBG5012, present and/or added in saccharification and/or fermentation is a variant of the *Gloeophyllum trabeum* glucoamylase disclosed in WO 2014/177546 (hereby incorporated by reference), especially a variant having one of the following substitutions or combinations of substitutions: V59A; S95P; A121P; T119W; S95P+A121P; V59A+S95P; S95P+T119W; V59A+S95P+A121P; and S95P+T119W+A121P, especially S95P+A121P (using SEQ ID NO: 17 herein for numbering).

In one embodiment, the glucoamylase is in combination with an alpha-amylase and optionally a protease. The alpha-amylase may be of fungal or bacterial origin.

The alpha-amylase expressed by the derivative of *Saccharomyces cerevisiae* strain MBG5038 or MBG5012, present and/or added in combination with a glucoamylase may be derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 16 herein.

In one embodiment, the alpha-amylase expressed by the derivative of *Saccharomyces cerevisiae* strain MBG5038 or MBG5012, present and/or added is derived from a strain of *Rhizomucor pusillus*, e.g., with an *Aspergillus niger* glucoamylase linker and starch-binding domain (SBD), such as the one disclosed as SEQ ID NO: 16 herein, and may have one or more of the following substitutions: G128D, D143N, such as G128D+D143N (using SEQ ID NO: 16 for numbering).

In one embodiment, a protease is present and/or added in saccharification and/or fermentation, or SSF, which may result in increased ethanol yield. As described, e.g., in U.S. Pat. No. 5,231,017 (hereby incorporated by reference) the protease may, e.g., be an acid fungal protease. A protease may also be present and/or added in saccharification and/or fermentation or SSF to improve the oil yield.

In one embodiment, a cellulolytic enzyme composition is present and/or added in saccharification, fermentation or simultaneous saccharification and fermentation (SSF). Examples of such compositions can be found in the "Cellulolytic Enzyme Composition present and/or added during Saccharification and/or Fermentation"-section below. In one embodiment, the cellulolytic enzyme composition is present and/or added together with a glucoamylase, such as one disclosed in the "Glucoamylase Present And/Or Added in Saccharification and/or Fermentation"-section below.

A second aspect relates to processes of producing ethanol from starch-containing material, such as granular starch, comprising:

(i) saccharifying a starch-containing material at a temperature below the initial gelatinization temperature; and
(ii) fermenting using a fermentation organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815

University Street, Peoria, Ill., USA) or a fermenting organism having properties that are about the same as that of *Saccharomyces cerevisiae* strain MBG5038 or a derivative of *Saccharomyces cerevisiae* strain MBG5038 having defining characteristics of *Saccharomyces cerevisiae* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces cerevisiae* strain MBG5012 having defining characteristics of *Saccharomyces cerevisiae* strain MBG5012.

In some embodiments, the derivative of *Saccharomyces cerevisiae* strain MBG5038 or *Saccharomyces cerevisiae* strain MBG5012 expresses a glucoamylase and/or an alpha-amylase.

In one embodiment, is a process of producing ethanol from starch-containing material, such as granular starch, comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase and alpha-amylase, and optionally protease; and
wherein the fermenting organism is a *Saccharomyces* yeast strain providing:
an ethanol yield boost compared to *Saccharomyces cerevisiae* strain Ethanol Red® (deposited under Accession No. V14/007039 at National Measurement Institute, Victoria, Australia) under the same fermentation conditions;
reduced acetaldehyde production compared to *Saccharomyces cerevisiae* strain Ethanol Red® (deposited under Accession No. V14/007039 at National Measurement Institute, Victoria, Australia) under the same process conditions;
increased temperature tolerance compared to *Saccharomyces cerevisiae* strain Ethanol Red® (deposited under Accession No. V14/007039 at National Measurement Institute, Victoria, Australia) under the same process conditions; and/or
decreased glycerol production compared to *Saccharomyces cerevisiae* strain Ethanol Red® (deposited under Accession No. V14/007039 at National Measurement Institute, Victoria, Australia) under the same process conditions.

In one embodiment, the fermenting organism is a derivative of *Saccharomyces cerevisiae* strain MBG5038 having the defining characteristics (e.g., high ethanol yield boost and/or decreased glycerol production of *Saccharomyces cerevisiae* strain MBG5038). In some embodiments, the derivative of *Saccharomyces cerevisiae* strain MBG5038 expresses a glucoamylase and/or an alpha-amylase.

In one embodiment, the fermenting organism is a derivative of *Saccharomyces cerevisiae* strain MBG5012 having the defining characteristics (e.g., high ethanol yield boost and/or decreased glycerol production of *Saccharomyces cerevisiae* strain MBG5012). In some embodiments, the derivative of *Saccharomyces cerevisiae* strain MBG5012 expresses a glucoamylase and/or an alpha-amylase.

Examples of suitable enzymes used, especially glucoamylases, alpha-amylases, proteases, cellulolytic enzyme compositions etc are described in the "Enzymes And Enzyme Blends Used In A Raw Starch Hydrolysis Process" section below.

A third aspect provides (1) a *Saccharomyces cerevisiae* yeast strain deposited under the Budapest Treaty and having NRRL accession no. NRRL Y67549, or a derivative of *Saccharomyces cerevisiae* strain NRRL Y67549. In some embodiments, the derivative of *Saccharomyces cerevisiae* strain NRRL Y67549 expresses a glucoamylase and/or an alpha-amylase; or (2) a *Saccharomyces cerevisiae* yeast strain deposited under the Budapest Treaty and having NRRL accession no. NRRL Y67700, or a derivative of *Saccharomyces cerevisiae* strain NRRL Y67700. In some embodiments, the derivative of *Saccharomyces cerevisiae* strain NRRL Y67700 expresses a glucoamylase and/or an alpha-amylase.

A fourth aspect provides a method of producing a derivative of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) comprising:
(a) culturing a first yeast strain with a second yeast strain, wherein the second yeast strain is *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012), under conditions which permit combining of DNA between the first yeast strain and the second yeast strain; and
(b) isolating hybrid strains; and
(c) optionally repeating steps (a) and (b) using a hybrid strain isolated in step (b) as the first yeast strain and/or the second yeast strain. In some embodiments, the derivative of *Saccharomyces cerevisiae* strain MBG5038 or MBG5012 expresses a glucoamylase and/or an alpha-amylase.

A fifth aspect provides a method of producing a *Saccharomyces* strain having the defining characteristics of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA), or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) comprising:
(a) providing: (i) a first yeast strain; and (ii) a second yeast strain, wherein the second yeast strain is *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012);
(b) culturing the first yeast strain and the second yeast strain under conditions which permit combining of DNA between the first yeast strain and the second yeast strain;
(c) screening or selecting for a derivative of *Saccharomyces cerevisiae* strain MBG5038;
(d) optionally repeating steps (b) and (c) with the screened or selected strain from step (c) as the first and/or second strain, until a derivative is obtained which exhibits the defining characteristics of *Saccharomyces cerevisiae* strain MBG5038 or MBG5012. In some embodiments, the derivative of *Saccharomyces cerevisiae* strain MBG5038 or MBG5012 expresses a glucoamylase and/or an alpha-amylase.

A sixth aspect provides a method of producing a recombinant derivative of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) comprising:

(a) transforming *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012) with one or more expression vectors encoding a glucoamylase and/or an alpha-amylase; and (b) isolating the transformed strain.

A seventh aspect provides a *Saccharomyces* strain produced by the method of the fourth, fifth, or sixth aspect.

An eighth aspect provides a *Saccharomyces* strain having the defining characteristics of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or the defining characteristics of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA).

A ninth aspect provides a method of producing ethanol, comprising incubating a strain of the first, fourth or fifth aspect with a substrate comprising a fermentable sugar under conditions which promote fermentation of the fermentable sugar to produce ethanol.

A tenth aspect provides use of a strain of the third, sixth or seventh aspect in the production of ethanol.

An eleventh aspect provides a method of producing distiller's grain, comprising:

(a) incubating a *Saccharomyces* strain of the third, seventh or eighth aspect with a substrate comprising fermentable sugar under conditions which allow fermentation of the fermentable sugar to produce ethanol and distiller's grains;

(b) isolating the distiller's grains.

A twelfth aspect provides distiller's grain produced by the method of the tenth aspect.

A thirteenth aspect provides use of a strain of the third, seventh or eighth aspect in the production of distiller's grains.

A fourteenth aspect provides use of a strain of the third, seventh or eighth aspect in the production of a *Saccharomyces* strain which exhibits one or more defining characteristics of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA).

A fifteenth aspect provides a composition comprising a *Saccharomyces* strain of the third, seventh or eighth aspect.

Also described are compositions comprising a *Saccharomyces* yeast strain described herein, e.g., *Saccharomyces cerevisiae* strain MBG5038 or MBG5012, or a derivative thereof, and naturally occurring and/or non-naturally occurring components.

DEFINITIONS

Figure 1:
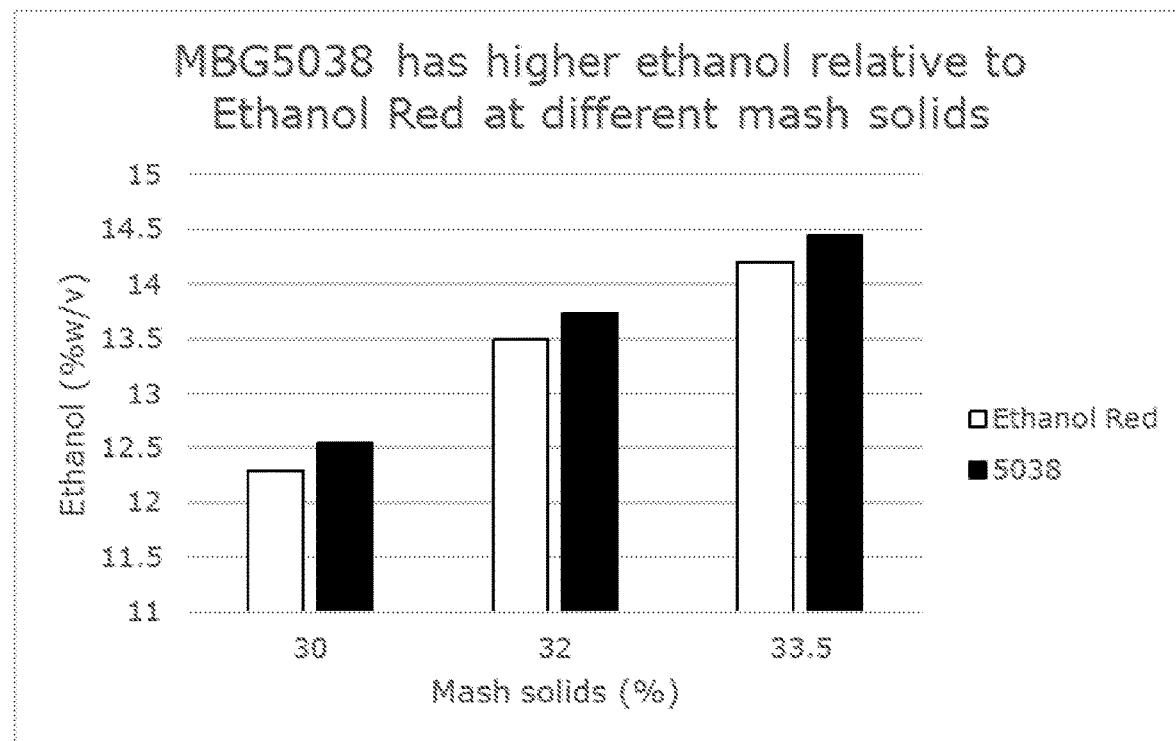
FIG. 1 shows improved ethanol yield from fermentation of *Saccharomyces cerevisiae* strain MBG5038 under non-stress conditions at varying mash solids (%).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has pullulanas activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having protease activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

As used herein, the singular forms "a", "an" and "the" include plural reference unless the context clearly indicates otherwise. Thus, for example, a reference to "a cell" includes a plurality of such cells. Unless defined otherwise, all technical and scientific terms used herein have the same meaning as commonly understood by one of ordinary skill in the art.

Reference to "about" a value or parameter herein includes aspects that are directed to that value or parameter per se. For example, description referring to "about X" includes the aspect "X".

As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

DETAILED DESCRIPTION

Processes

Described herein are processes for producing ethanol from starch-containing material in a process including liquefaction, saccharification and fermentation. Fermentable sugars generated during saccharification are converted to ethanol during fermentation by yeast. In a first aspect is a process for producing ethanol from starch-containing material comprising the steps of:

i) liquefying the starch-containing material at a temperature above the initial gelatinization temperature using an alpha-amylase;

ii) saccharifying using a glucoamylase;

iii) fermenting using a fermenting organism;

wherein the fermenting organism is:

(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces cerevisiae* strain MBG5038 having defining characteristics of *Saccharomyces cerevisiae* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces cerevisiae* strain MBG5012 having defining characteristics of *Saccharomyces cerevisiae* strain MBG5012.

In some embodiments, the derivative of *Saccharomyces cerevisiae* strain MBG5038 or MBG5012 expresses a glucoamylase and/or an alpha-amylase.

Steps ii) and iii) are carried out either sequentially or simultaneously (SSF). In one embodiment, steps ii) and iii) are carried out simultaneously (SSF).

Nitrogens-Source Added During Fermentation

Generally, fermenting organisms such as yeast, including *Saccharomyces cerevisiae* yeast, require an adequate source of nitrogen for propagation and fermentation. Many sources of nitrogen can be used and such sources of nitrogen are well known in the art. The nitrogen source may be organic, such as urea, DDGs, wet cake or corn mash, or inorganic, such as ammonia or ammonium hydroxide. In one embodiment, the nitrogen source is urea.

Liquefaction Step i)

According to processes described herein, liquefaction in step i) may be carried out by subjecting starch-containing material at a temperature above the initial gelatinization temperature to an alpha-amylase and optionally a protease, and/or a glucoamylase. Other enzymes such as a pullulanase and phytase may also be present and/or added in liquefaction.

Liquefaction step i) may be carried out for 0.5-5 hours, such as 1-3 hours, such as typically about 2 hours.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Stärke* 44(12): 461-466.

Liquefaction is typically carried out at a temperature in the range from 70-100° C. In one embodiment, the temperature in liquefaction is between 75-95° C., such as between 75-90° C., between 80-90° C., or between 82-88° C., such as about 85° C.

A jet-cooking step may be carried out prior to liquefaction in step i). The jet-cooking may be carried out at a temperature between 110-145° C., 120-140° C., 125-135° C., or about 130° C. for about 1-15 minutes, for about 3-10 minutes, or about 5 minutes.

The pH during liquefaction may be between 4 and 7, such as pH 4.5-6.5, pH 5.0-6.5, pH 5.0-6.0, pH 5.2-6.2, or about 5.2, about 5.4, about 5.6, or about 5.8.

In one embodiment, the process further comprises, prior to the step i), the steps of:

a) reducing the particle size of the starch-containing material, preferably by dry milling;

b) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein).

Wet milling is often applied at locations where the starch hydrolysate is used in production of, e.g., syrups. Both dry milling and wet milling are well known in the art of starch processing. In one embodiment the starch-containing material is subjected to dry milling. In one embodiment, the particle size is reduced to between 0.05 to 3.0 mm, e.g., 0.1-0.5 mm, or so that at least 30%, at least 50%, at least 70%, or at least 90% of the starch-containing material fit through a sieve with a 0.05 to 3.0 mm screen, e.g., 0.1-0.5 mm screen. In another embodiment, at least 50%, e.g., at least 70%, at least 80%, or at least 90% of the starch-containing material fit through a sieve with #6 screen.

The aqueous slurry may contain from 10-55 w/w-% dry solids (DS), e.g., 25-45 w/w-% dry solids (DS), or 30-40 w/w-% dry solids (DS) of starch-containing material.

The alpha-amylase, optionally a protease, optionally a glucoamylase may initially be added to the aqueous slurry to initiate liquefaction (thinning). In one embodiment, only a portion of the enzymes (e.g., about ⅓) is added to the aqueous slurry, while the rest of the enzymes (e.g., about ⅔) are added during liquefaction step i).

A non-exhaustive list of examples of alpha-amylases can be found below in the "Alpha-Amylase Present and/or Added During Liquefaction"-section. In one embodiment, the alpha-amylase is a bacterial alpha-amylase. Bacterial alpha-amylases are typically thermostable. In one embodiment, the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

In one embodiment, the alpha-amylase has an improved stability compared to a reference alpha-amylase (*Bacillus stearothermophilus* alpha-amylase with the mutations I181*+G182*, optionally with a N193F substitution, truncated to about 491 amino acids, i.e., from 480-495 amino acids, (using SEQ ID NO: 1 herein for numbering) determined by incubating the reference alpha-amylase and variants at pH 4.5 and 5.5 and temperatures of 75° C. and 85° C. with 0.12 mM $CaCl_2$ followed by residual activity determination using the EnzChek® substrate (EnzChek® Ultra Amylase assay kit, E33651, Molecular Probes). This is described in Example 1.

Examples of suitable *Bacillus stearothermophilus* alpha-amylase variants can be found below in the "Thermostable Alpha-Amylase"-section and include one from the following group of *Bacillus stearothermophilus* alpha-amylase variants with the following mutations: I181*+G182*, and optionally substitution N193F, and further one of the following substitutions or combinations of substitutions:

E129V+K177L+R179E;

V59A+Q89R+E129V+K177L+R179E+H208Y+K220P+N224L+Q254S;

V59A+Q89R+E129V+K177L+R179E+Q254S+M284V;

V59A+E129V+K177L+R179E+Q254S+M284V; and

E129V+K177L+R179E+K220P+N224L+S242Q+Q254S (using SEQ ID NO: 1 for numbering).

Examples of other suitable *Bacillus stearothermophilus* alpha-amylases having increased thermostability compared to a reference alpha-amylase (*Bacillus stearothermophilus* alpha-amylase with the mutations I181*+G182*, and optionally a N193F substitution, C-terminally truncated to be 485-495 amino acids long, such as about 491 amino acids long) at pH 4.5 and 5.5, 0.12 mM $CaCl_2$ can be found in WO 2011/082425 hereby incorporated by reference. (See also Example 1 below)

Liquefaction in step i) may be carried out using a combination of alpha-amylase and protease. The protease may be a protease having a thermostability value of more than 20% determined as Relative Activity at 80° C./70° C. determined as described in Example 2 (Relative Activity). Examples of suitable proteases are described below in the section "Protease Present and/or Added During Liquefaction".

The protease may be of fungal origin, such as of filamentous fungus origin. Specific examples of suitable fungal proteases are protease variants of metallo protease derived from a strain of the genus *Thermoascus*, e.g., a strain of *Thermoascus aurantiacus*, such as the strain *Thermoascus aurantiacus* CGMCC No. 0670 disclosed as the mature part of SEQ ID NO. 2 disclosed in WO 2003/048353 or the mature part of SEQ ID NO: 1 in WO 2010/008841 or SEQ ID NO: 3 herein with one of the following substitutions or combinations of substitutions:

D79L+S87P+A112P+D142L;
D79L+S87P+D142L; and
A27K+D79L+Y82F+S87G+D104P+A112P+A126V+D142L.

More examples of suitable variants of the *Thermoascus aurantiacus* protease can be found in WO 2011/072191 hereby incorporated by reference (See also Example 2 below).

Suitable proteases also include bacterial proteases. A suitable bacterial protease may be derived from a strain of *Pyrococcus*, e.g., a strain of *Pyrococcus furiosus*. In one embodiment, the protease is the one shown in SEQ ID NO: 1 in U.S. Pat. No. 6,358,726 or SEQ ID NO: 13 herein.

In one embodiment, the alpha-amylase and/or protease, added in the liquefaction step i), is/are further combined with a glucoamylase. Thus, a glucoamylase may also be present and/or added during liquefaction step i). The glucoamylase may be thermostable. This means that the glucoamylase has a heat stability at 85° C., pH 5.3, of at least 20%, such as at least 30%, preferably at least 35% determined as described in Example 4 (heat stability). In one embodiment, the glucoamylase present and/or added in liquefaction has a relative activity pH optimum at pH 5.0 of at least 90%, e.g., at least 95%, or at least 97%. In one embodiment, the glucoamylase has a pH stability at pH 5.0 of at least at least 80%, e.g., at least 85%, or at least 90% determined as described in Example 4 (pH stability).

A suitable glucoamylase present and/or added in liquefaction step i) may be derived from a strain of the genus *Penicillium*, especially a strain of *Penicillium oxalicum* disclosed as SEQ ID NO: 2 in WO 2011/127802 or SEQ ID NOs: 9 or 14 herein. In one embodiment, the glucoamylase is a variant of the *Penicillium oxalicum* glucoamylase shown in SEQ ID NO: 2 in WO 2011/127802 having a K79V substitution (using the mature sequence shown in SEQ ID NO: 14 herein for numbering), such as a variant disclosed in WO 2013/053801. In one embodiment, the *Penicillium oxalicum* glucoamylase has a K79V substitution (using SEQ ID NO: 14 for numbering) and further one of the following substitutions or combinations of substitutions:

P11F+T65A+Q327F; and
P2N+P4S+P11F+T65A+Q327F (using SEQ ID NO: 14 for numbering).

Examples of other suitable *Penicillium oxalicum* glucoamylase variants can be found in WO 2013/053801 incorporated by reference (see also Examples 10-16 below, such as the *Penicillium oxalicum* glucoamylase variants in Table 15).

Further, according to the processes described herein, a pullulanase may be present during liquefaction in combination with an alpha-amylase, a protease and/or a glucoamylase.

Saccharification and Fermentation

A glucoamylase is expressed by the derivative of *Saccharomyces cerevisiae* strain MBG5038 or MBG5012, present and/or added in saccharification step ii) and/or fermentation step iii) or simultaneous saccharification and fermentation (SSF). The glucoamylase expressed by the derivative of *Saccharomyces cerevisiae* strain MBG5038 or MBG5012, added in saccharification step ii) and/or fermentation step iii) or simultaneous saccharification and fermentation (SSF) is typically different from the glucoamylase, optionally added in liquefaction step i). In one embodiment, the glucoamylase is express or added together with a fungal alpha-amylase. Examples of glucoamylases can be found in the "Glucoamylases Present and/or Added In Saccharification and/or Fermentation"-section below.

When doing sequential saccharification and fermentation, saccharification step ii) may be carried out under conditions well-known in the art. For instance, saccharification step ii) may last up to from about 24 to about 72 hours. In one embodiment, pre-saccharification is done. Pre-saccharification is typically done for 40-90 minutes at a temperature between 30-65° C., typically about 60° C. Pre-saccharification is, in one embodiment, followed by saccharification during fermentation in simultaneous saccharification and fermentation (SSF). Saccharification is typically carried out at temperatures from 20-75° C., preferably from 40-70° C., typically about 60° C., and typically at a pH between 4 and 5, such as about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. However, it is also contemplated to add the fermenting organism and enzyme(s) separately. SSF is typically carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours. In one embodiment, the pH is between 4-5.

In one embodiment, a cellulolytic enzyme composition is present and/or added in saccharification, fermentation or simultaneous saccharification and fermentation (SSF). Examples of such cellulolytic enzyme compositions can be found in the "Cellulolytic Enzyme Composition present and/or added during Saccharification and/or Fermentation"-section below. The cellulolytic enzyme composition is present and/or added together with a glucoamylase, such as one disclosed in the "Glucoamylase Present And/Or Added in Saccharification and/or Fermentation"-section below.

Starch-Containing Materials

Any suitable starch-containing starting material may be used with the processes described herein. The starting material is generally selected based on the desired fermentation product, here ethanol. Examples of starch-containing starting materials include cereal, tubers or grains. Specifically, the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In one embodiment, the starch-containing starting material is corn. In one embodiment, the starch-containing starting material is wheat. In one embodiment, the starch-containing starting material is barley. In one embodiment, the starch-containing starting material is rye.

In one embodiment, the starch-containing starting material is milo. In one embodiment, the starch-containing starting material is sago. In one embodiment, the starch-containing starting material is cassava. In one embodiment, the starch-containing starting material is tapioca. In one embodiment, the starch-containing starting material is sorghum. In one embodiment, the starch-containing starting material is rice. In one embodiment, the starch-containing starting material is peas. In one embodiment, the starch-containing starting material is beans. In one embodiment, the starch-containing starting material is sweet potatoes. In one embodiment, the starch-containing starting material is oats.

Fermentation

Fermentation is carried out in a fermentation medium. The fermentation medium includes the fermentation substrate, that is, the carbohydrate source that is metabolized by the fermenting organism. With the processes described herein, the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

*Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038, or a derivative of *Saccharomyces cerevisiae* strain MBG5038 having defining characteristics of strain MBG5038, or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012, or a derivative of *Saccharomyces cerevisiae* strain MBG5012 having defining characteristics of strain MBG5012 may be used in a process described herein. In one embodiment, the fermenting organism has properties that are about the same as that of *Saccharomyces cerevisiae* strain MBG5038 or MBG5012 as it provides an increase in ethanol yield compared to *Saccharomyces cerevisiae* strain Ethanol Red® (deposited under Accession No. V14/007039 at National Measurement Institute, Victoria, Australia) under the same process conditions.

In one embodiment, the fermenting organism strain having properties that are about the same as that of *Saccharomyces cerevisiae* strain MBG5038 or MBG5012 has at least the one or more, such as all of following properties and defining characteristics:

increases ethanol yield compared to *Saccharomyces cerevisiae* strain Ethanol Red® (deposited under Accession No. V14/007039 at National Measurement Institute, Victoria, Australia) under the same process conditions, e.g., conditions as described herein;

reduces acetaldehyde production compared to *Saccharomyces cerevisiae* strain Ethanol Red® (deposited under Accession No. V14/007039 at National Measurement Institute, Victoria, Australia) under the same process conditions, e.g., conditions as described herein;

increases temperature tolerance compared to *Saccharomyces cerevisiae* strain Ethanol Red® (deposited under Accession No. V14/007039 at National Measurement Institute, Victoria, Australia) under the same process conditions, e.g., conditions as described herein; and decreases glycerol production compared to *Saccharomyces cerevisiae* strain Ethanol Red® (deposited under Accession No. V14/007039 at National Measurement Institute, Victoria, Australia) under the same process conditions, conditions as described herein.

In one embodiment, the fermenting organism having properties that are about the same as that of *Saccharomyces cerevisiae* strain MBG5038 or MBG5012 provides an ethanol yield boost over *Saccharomyces cerevisiae* strain Ethanol Red® (deposited under Accession No. V14/007039 at National Measurement Institute, Victoria, Australia) of more than 1.0%, e.g., more than 2.0%, such as more than 2.5%, such as about 2.9% using the same process set-up and conditions, e.g., conditions described herein.

In one embodiment, the fermenting organism having properties that are about the same as that of *Saccharomyces cerevisiae* strain MBG5038 or MBG5012 reduces acetaldehyde production more than 10%, e.g., more than 20%, more than 30%, more than 40%, more than 45%, such as between 5-60%, such as 30-50%, compared to *Saccharomyces cerevisiae* strain Ethanol Red® (deposited under Accession No. V14/007039 at National Measurement Institute, Victoria, Australia) under the same process conditions, e.g., conditions described herein.

In one embodiment, the fermenting organism having properties that are about the same as that of *Saccharomyces cerevisiae* strain MBG5038 or MBG5012 increases the temperature tolerance compared to *Saccharomyces cerevisiae* strain Ethanol Red® (deposited under Accession No. V14/007039 at National Measurement Institute, Victoria, Australia) under the same process conditions, e.g., conditions described herein.

Increased temperature tolerance is an advantage as the fermentation temperature may fluctuate to some degree. In the early part of fermentation plants often do not actively heat the fermentation. The temperature may therefore increase naturally from the yeast's metabolism. The plant may use heat exchangers to control early fermentation temperatures so it does not go too high. During the majority of the year the plants can easily control the early temperature and the peak temperature is typically about 34° C. However, during the summer months the cooling water used in heat exchangers is not cold enough to control the temperatures. Therefore, in plants that do not have chillers (i.e., a water refrigeration system), the early fermentation temperatures can reach above 36.5° C. which stresses the yeast.

In one embodiment, the fermenting organism having properties that are about the same as that of *Saccharomyces cerevisiae* strain MBG5038 or MBG5012 decreases glycerol production by more than 3%, e.g., more than 4%, more than 5%, more than 6%, more than 7%, such as between 2-15%, such as 5-10%, compared to *Saccharomyces cerevisiae* strain Ethanol Red® (deposited under Accession No. V14/007039 at National Measurement Institute, Victoria, Australia) under the same process conditions, e.g., conditions described herein.

Recovery

Subsequent to fermentation, e.g., SSF, the ethanol may be separated from the fermentation medium. The slurry may be distilled to recover/extract the desired fermentation product (i.e., ethanol). Alternatively, the desired fermentation product (i.e., ethanol) may be extracted from the fermentation medium by micro or membrane filtration techniques. The fermentation product (i.e., ethanol) may also be recovered by stripping or other method well known in the art.

Alpha-Amylase Present and/or Added in Liquefaction

The alpha-amylase used herein may be present and/or added in liquefaction optionally together with a protease and/or glucoamylase, and/or optional pullulanase, e.g., as disclosed in WO 2012/088303 (Novozymes) or WO 2013/082486 (Novozymes) which references are both incorporated by reference.

The alpha-amylase added in liquefaction step i) may be any alpha-amylase. In one embodiment, the alpha-amylase is a bacterial alpha-amylase, which may be stable at temperature.

Any alpha-amylase described herein, including any bacterial, hybrid and/or thermostable alpha-amylase described below, may be expressed by the *Saccharomyces cerevisiae* strain MBG5038 or MBG5012.

Bacterial Alpha-Amylase

The term "bacterial alpha-amylase" means any bacterial alpha-amylase classified under EC 3.2.1.1. A bacterial alpha-amylase used herein may, e.g., be derived from a strain of the genus *Bacillus*, which is sometimes also referred to as the genus *Geobacillus*. In one embodiment, the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp.

Specific examples of bacterial alpha-amylases include the *Bacillus stearothermophilus* alpha-amylase (BSG) of SEQ ID NO: 3 in WO 99/19467 or SEQ ID NO: 1 herein, the *Bacillus amyloliquefaciens* alpha-amylase (BAN) of SEQ ID NO: 5 in WO 99/19467, and the *Bacillus licheniformis* alpha-amylase (BLA) of SEQ ID NO: 4 in WO 99/19467 or SEQ ID NO: 21 herein (all sequences are hereby incorporated by reference). In one embodiment, the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In one embodiment, the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 1 herein.

In one embodiment, the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases may naturally be truncated during recombinant production. For instance, the *Bacillus stearothermophilus* alpha-amylase may be a truncated at the C-terminal, so that it is from 480-495 amino acids long, such as about 491 amino acids long, e.g., so that it lacks a functional starch binding domain (compared to SEQ ID NO: 3 in WO 99/19467) or SEQ ID NO: 1 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (each hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), such as corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering (which reference is hereby incorporated by reference). In some embodiments, the *Bacillus* alpha-amylases, such as *Bacillus stearothermophilus* alpha-amylases, have a double deletion corresponding to a deletion of positions 181 and 182 and further optionally comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 1 herein. The bacterial alpha-amylase may also have a substitution in a position corresponding to S239 in the *Bacillus licheniformis* alpha-amylase shown in SEQ ID NO: 4 in WO 99/19467 or SEQ ID NO: 21 herein, or a S242 and/or E188P variant of the *Bacillus stearothermophilus* alpha-amylase of SEQ ID NO: 3 in WO 99/19467 or SEQ ID NO: 1 herein.

In one embodiment, the variant is a S242A, E or Q variant, e.g., a S242Q variant, of the *Bacillus stearothermophilus* alpha-amylase (using SEQ ID NO: 1 herein for numbering).

In one embodiment, the variant is a position E188 variant, e.g., E188P variant of the *Bacillus stearothermophilus* alpha-amylase (using SEQ ID NO: 1 herein for numbering).

The bacterial alpha-amylase may, in one embodiment, be a truncated *Bacillus* alpha-amylase. In one embodiment, the truncation is so that, e.g., the *Bacillus stearothermophilus* alpha-amylase shown in SEQ ID NO: 3 in WO 99/19467 or SEQ ID NO: 1 herein, is about 491 amino acids long, such as from 480 to 495 amino acids long, or so it lacks a functional starch bind domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In one embodiment, this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467) or SEQ ID NO: 21 herein. In some embodiments, the variants have one or more of the following mutations (or corresponding mutations in other *Bacillus* alpha-amylases): H154Y, A181T, N190F, A209V and Q264S and/or the deletion of two residues between positions 176 and 179, e.g., deletion of E178 and G179 (using SEQ ID NO: 5 of WO 99/19467 for position numbering or SEQ ID NO: 21 herein).

In one embodiment, the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

The alpha-amylase may be a thermostable alpha-amylase, such as a thermostable bacterial alpha-amylase, e.g., from *Bacillus stearothermophilus*. In one embodiment, the alpha-amylase used in a process described herein has a T½ (min) at pH 4.5, 85° C., 0.12 mM CaCl$_2$ of at least 10 determined as described in Example 1.

In one embodiment, the thermostable alpha-amylase has a T½ (min) at pH 4.5, 85° C., 0.12 mM CaCl$_2$, of at least 15.

In one embodiment, the thermostable alpha-amylase has a T½ (min) at pH 4.5, 85° C., 0.12 mM CaCl$_2$, of as at least 20.

In one embodiment, the thermostable alpha-amylase has a T½ (min) at pH 4.5, 85° C., 0.12 mM CaCl$_2$, of as at least 25.

In one embodiment, the thermostable alpha-amylase has a T½ (min) at pH 4.5, 85° C., 0.12 mM CaCl$_2$, of as at least 30.

In one embodiment, the thermostable alpha-amylase has a T½ (min) at pH 4.5, 85° C., 0.12 mM CaCl$_2$, of as at least 40.

In one embodiment, the thermostable alpha-amylase has a T½ (min) at pH 4.5, 85° C., 0.12 mM CaCl$_2$, of at least 50.

In one embodiment, the thermostable alpha-amylase has a T½ (min) at pH 4.5, 85° C., 0.12 mM CaCl$_2$, of at least 60.

In one embodiment, the thermostable alpha-amylase has a T½ (min) at pH 4.5, 85° C., 0.12 mM CaCl$_2$, between 10-70.

In one embodiment, the thermostable alpha-amylase has a T½ (min) at pH 4.5, 85° C., 0.12 mM CaCl$_2$, between 15-70.

In one embodiment, the thermostable alpha-amylase has a T½ (min) at pH 4.5, 85° C., 0.12 mM CaCl$_2$, between 20-70.

In one embodiment, the thermostable alpha-amylase has a T½ (min) at pH 4.5, 85° C., 0.12 mM CaCl$_2$, between 25-70.

In one embodiment, the thermostable alpha-amylase has a T½ (min) at pH 4.5, 85° C., 0.12 mM CaCl$_2$, between 30-70.

In one embodiment, the thermostable alpha-amylase has a T½ (min) at pH 4.5, 85° C., 0.12 mM CaCl$_2$, between 40-70.

In one embodiment, the thermostable alpha-amylase has a T½ (min) at pH 4.5, 85° C., 0.12 mM CaCl$_2$, between 50-70.

In one embodiment, the thermostable alpha-amylase has a T½ (min) at pH 4.5, 85° C., 0.12 mM CaCl$_2$, between 60-70.

In one embodiment, the alpha-amylase is a bacterial alpha-amylase, e.g., derived from the genus *Bacillus*, such as a strain of *Bacillus stearothermophilus*, e.g., the *Bacillus stearothermophilus* as disclosed in WO 99/019467 as SEQ ID NO: 3 (SEQ ID NO: 1 herein) with one or two amino acids deleted at positions R179, G180, I181 and/or G182, in particular with R179 and G180 deleted, or with I181 and G182 deleted, with mutations in below list of mutations.

In some embodiment, the *Bacillus stearothermophilus* alpha-amylases have double deletion I181+G182, and optional substitution N193F, further comprising one of the following substitutions or combinations of substitutions:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
V59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91L+M96I+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V; and
V59A+E129V+K177L+R179E+Q254S+M284V;

In one embodiment, the alpha-amylase is selected from the group of *Bacillus stearothermophilus* alpha-amylase variants with double deletion I181*+G182*, and optionally substitution N193F, and further one of the following substitutions or combinations of substitutions:

E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 1 herein, or variants thereof, are truncated in the C-terminal and are typically from 480-495 amino acids long, such as about 491 amino acids long, e.g., so that it lacks a functional starch binding domain.

In one embodiment, the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 1 herein.

In one embodiment, the bacterial alpha-amylase, e.g., Bacillus alpha-amylase, such as especially Bacillus stearothermophilus alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In one embodiment, the bacterial alpha-amylase, e.g., Bacillus alpha-amylase, such as especially Bacillus stearothermophilus alpha-amylases, or variant thereof, is dosed to liquefaction in a concentration of between 0.0001-1 mg EP (Enzyme Protein)/g DS, e.g., 0.0005-0.5 mg EP/g DS, such as 0.001-0.1 mg EP/g DS.

Protease Present and/or Added in Liquefaction

In the processes described herein, the protease may optionally be present and/or added in liquefaction together with alpha-amylase, and an optional glucoamylase, and/or pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In one embodiment, the thermostable protease used according to a process described herein is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process described herein as long as it fulfills the thermostability properties defined below.

In one embodiment the protease is of fungal origin.

The protease may be a variant of, e.g., a wild-type protease as long as the protease has the thermostability properties defined herein. In one embodiment, the thermostable protease is a variant of a metallo protease as defined above. In one embodiment, the thermostable protease used in a process described herein is of fungal origin, such as a fungal metallo protease, such as a fungal metallo protease derived from a strain of the genus Thermoascus, preferably a strain of Thermoascus aurantiacus, especially Thermoascus aurantiacus CGMCC No. 0670 (classified as EC 3.4.24.39).

In one embodiment, the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein further with one of the following substitutions or combinations of substitutions:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L; and
D79L+S87P+D142L.

In one embodiment, the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 3 herein with one of the following substitutions or combinations of substitutions:

D79L+S87P+A112P+D142L;
D79L+S87P+D142L; and
A27K+D79L+Y82F+S87G+D104P+A112P+A126V+D142L.

In one embodiment, the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

The thermostable protease may also be derived from any bacterium as long as the protease has the thermostability properties.

In one embodiment, the thermostable protease is derived from a strain of the bacterium *Pyrococcus*, such as a strain of *Pyrococcus furiosus* (pfu protease).

In one embodiment, the protease is one shown as SEQ ID NO: 1 in U.S. Pat. No. 6,358,726-B1 (Takara Shuzo Company), or SEQ ID NO: 13 herein.

In one embodiment, the thermostable protease is SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Bio, Japan.

The *Pyrococcus furiosus* protease is a thermostable protease. The commercial product *Pyrococcus furiosus* protease (PfuS) was found to have a thermostability of 110% (80° C./70° C.) and 103% (90° C./70° C.) at pH 4.5 determined as described in Example 2.

In one embodiment, a thermostable protease used in a process described herein has a thermostability value of more than 20% determined as Relative Activity at 80° C./70° C. determined as described in Example 2.

In one embodiment, the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In one embodiment, protease has a thermostability of between 20 and 50%, such as between 20 and 40%, such as 20 and 30% determined as Relative Activity at 80° C./70° C. In one embodiment, the protease has a thermostability between 50 and 115%, such as between 50 and 70%, such as between 50 and 60%, such as between 100 and 120%, such as between 105 and 115% determined as Relative Activity at 80° C./70° C.

In one embodiment, the protease has a thermostability value of more than 10% determined as Relative Activity at 85° C./70° C. determined as described in Example 2.

In one embodiment, the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In one embodiment, the protease has a thermostability of between 10% and 50%, such as between 10% and 30%, such as between 10% and 25% determined as Relative Activity at 85° C./70° C.

In one embodiment, the protease has more than 20%, more than 30%, more than 40%, more than 50%, more than 60%, more than 70%, more than 80%, more than 90% determined as Remaining Activity at 80° C.; and/or the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2.

In one embodiment, the protease may have a themostability for above 90, such as above 100 at 85° C. as determined using the Zein-BCA assay as disclosed in Example 3.

In one embodiment, the protease has a themostability above 60%, such as above 90%, such as above 100%, such as above 110% at 85° C. as determined using the Zein-BCA assay.

In one embodiment, protease has a themostability between 60-120, such as between 70-120%, such as between 80-120%, such as between 90-120%, such as between 100-120%, such as 110-120% at 85° C. as determined using the Zein-BCA assay.

In one embodiment, the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay.

Glucoamylase Expressed, Present and/or Added in Liquefaction Step i)

A glucoamylase may optionally be expressed, present and/or added in liquefaction step i). In one embodiment, the glucoamylase is added together with or separately from the alpha-amylase and/or the optional protease and/or pullulanase.

In one embodiment, the glucoamylase has a Relative Activity heat stability at 85° C. of at least 20%, at least 30%, or at least 35% determined as described in Example 4 (heat stability).

In one embodiment, the glucoamylase has a relative activity pH optimum at pH 5.0 of at least 90%, e.g., at least 95%, at least 97%, or 100% determined as described in Example 4 (pH optimum).

In one embodiment, the glucoamylase has a pH stability at pH 5.0 of at least 80%, at least 85%, at least 90% determined as described in Example 4 (pH stability).

In one embodiment, the glucoamylase, such as a *Penicillium oxalicum* glucoamylase variant, used in liquefaction has a thermostability determined as DSC Td at pH 4.0 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C. In one embodiment, the glucoamylase, such as a *Penicillium oxalicum* glucoamylase variant has a thermostability determined as DSC Td at pH 4.0 as described in Example 15 in the range between 70° C. and 95° C., such as between 80° C. and 90° C.

In one embodiment, the glucoamylase, such as a *Penicillium oxalicum* glucoamylase variant, used in liquefaction has a thermostability determined as DSC Td at pH 4.8 as described in Example 15 of at least 70° C., preferably at least 75° C., such as at least 80° C., such as at least 81° C., such as at least 82° C., such as at least 83° C., such as at least 84° C., such as at least 85° C., such as at least 86° C., such as at least 87%, such as at least 88° C., such as at least 89° C., such as at least 90° C., such as at least 91° C. In one embodiment, the glucoamylase, such as a *Penicillium oxalicum* glucoamylase variant has a thermostability determined as DSC Td at pH 4.8 as described in Example 15 in the range between 70° C. and 95° C., such as between 80° C. and 90° C.

In one embodiment, the glucoamylase, such as a *Penicillium oxalicum* glucoamylase variant, used in liquefaction has a residual activity determined as described in Example 16 of at least 100% such as at least 105%, such as at least 110%, such as at least 115%, such as at least 120%, such as at least 125%. In one embodiment, the glucoamylase, such as a *Penicillium oxalicum* glucoamylase variant has a thermostability determined as residual activity as described in Example 16 in the range between 100% and 130%.

In one embodiment, the glucoamylase, e.g., of fungal origin such as a filamentous fungi, from a strain of the genus *Penicillium*, e.g., a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 9 or 14 herein.

In one embodiment, the glucoamylase has at least 80%, e.g., at least 85%, at least 90%, at least 91%, at least 92%, at least 93%, at least 94%, at least 95%, at least 96%, at least 97%, at least 98%, at least 99% or 100% identity to the mature polypeptide shown in SEQ ID NO: 2 in WO 2011/127802 or SEQ ID NOs: 9 or 14 herein.

In one embodiment, the glucoamylase is a variant of the *Penicillium oxalicum* glucoamylase disclosed as SEQ ID NO: 2 in WO 2011/127802 and shown in SEQ ID NO: 9 and 14 herein, having a K79V substitution (using the mature sequence shown in SEQ ID NO: 14 herein for numbering). The K79V glucoamylase variant has reduced sensitivity to protease degradation relative to the parent as disclosed in WO 2013/036526 (which is hereby incorporated by reference).

In one embodiment, the glucoamylase is derived from *Penicillium oxalicum*. In one embodiment, the glucoamylase is a variant of the *Penicillium oxalicum* glucoamylase disclosed as SEQ ID NO: 2 in WO 2011/127802 and shown in SEQ ID NO: 9 and 14 herein. In one embodiment, the *Penicillium oxalicum* glucoamylase is the one disclosed as SEQ ID NO: 2 in WO 2011/127802 and shown in SEQ ID NO: 9 and 14 herein having Val (V) in position 79 (using SEQ ID NO: 14 herein for numbering).

Contemplated *Penicillium oxalicum* glucoamylase variants are disclosed in WO 2013/053801 which is hereby incorporated by reference.

In one embodiment, these variants have reduced sensitivity to protease degradation.

In one embodiment, these variant have improved thermostability compared to the parent.

In one embodiment, the glucoamylase has a K79V substitution (using SEQ ID NO: 14 herein for numbering), corresponding to the PE001 variant, and further comprises one of the following alterations or combinations of alterations:

T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K330+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+V79A+Q327F+E501V+Y504T; P2N+P4S+P11F+T65A+V79G+Q327F+E501V+Y504T; P2N+P4S+P11F+T65A+V79I+Q327F+E501V+Y504T; P2N+P4S+P11F+T65A+V79L+Q327F+E501V+Y504T; P2N+P4S+P11F+T65A+V79S+Q327F+E501V+Y504T; P2N+P4S+P11F+T65A+L72V+Q327F+E501V+Y504T; S255N+Q327F+E501V+Y504T; P2N+P4S+P11F+T65A+E74N+V79K+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; and P2N+P4S+P11F+T65A+Q327F+T477N+E501V+Y504T.

In one embodiment, the *Penicillium oxalicum* glucoamylase variant has a K79V substitution (using SEQ ID NO: 14 herein for numbering), corresponding to the PE001 variant, and further comprises one of the following substitutions or combinations of substitutions:

P11F+T65A+Q327F;
P2N+P4S+P11F+T65A+Q327F;
P11F+D26C+K330+T65A+Q327F;
P2N+P4S+P11F+T65A+Q327W+E501V+Y504T;
P2N+P4S+P11F+T65A+Q327F+E501V+Y504T; and
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Pullulanase Present and/or Added in Liquefaction Step i)

Optionally a pullulanase may be present and/or added during liquefaction step i) together with an alpha-amylase, and/or optional protease and/or glucoamylase.

The pullulanase may be present and/or added in liquefaction step i) and/or saccharification step ii) or simultaneous saccharification and fermentation (SSF).

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated include the pullulanases from *Pyrococcus woesei*, specifically from *Pyrococcus woesei* DSM No. 3773 disclosed in WO92/02614.

In one embodiment, the pullulanase is a family GH57 pullulanase. In one embodiment, the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12 herein). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference) and disclosed in SEQ ID NO: 12 herein.

In another embodiment the pullulanase is one comprising an X46 domain disclosed in WO 2011/076123 (Novozymes).

The pullulanase may be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (DuPont-Danisco, USA), and AMANO 8 (Amano, Japan).

Glucoamylase Expressed, Present and/or Added in Saccharification and/or Fermentation Glucoamylase may be expressed, present and/or added in saccharification, fermentation or simultaneous saccharification and fermentation (SSF). The glucoamylse may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti*, *Talaromyces thermophilus* (U.S. Pat. No. 4,587,215). In one embodiment, the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulate* (SEQ ID NO: 20), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated. Examples include the hybrid glucoamylases disclosed in WO 2005/045018. Specific examples include the hybrid glucoamylase disclosed in Table 1 and 4 of Example 1 (which hybrids are hereby incorporated by reference).

In one embodiment, the glucoamylase is derived from a strain of the genus *Pycnoporus*, in particular a strain of *Pycnoporus* as described in WO 2011/066576 (SEQ ID NOs 2, 4 or 6), including the *Pycnoporus sanguineus* glucoamylase disclosed as SEQ ID NO: 18 herein, or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In one embodiment, the glucoamylase is SEQ ID NO: 2 in WO 2011/068803 or SEQ ID NO: 15 herein (i.e. *Gloeophyllum sepiarium* glucoamylase).

In one embodiment, the glucoamylase is SEQ ID NO: 17 herein (i.e., *Gloeophyllum trabeum* glucoamylase disclosed as SEQ ID NO: 3 in WO2014/177546). In another embodiment the glucoamylase is derived from a strain of the genus *Nigrofomes*, in particular a strain of *Nigrofomes* sp. disclosed in WO 2012/064351 (SEQ ID NO: 2) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs:

15, 17, 18 or 19 herein, respectively, preferably SEQ ID NO: 15 herein or SEQ ID NO: 17 herein.

Glucoamylases may be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may be added to the saccharification and/or fermentation in an amount of 1-1,000 µg EP/g DS, preferably 10-500 µg/gDS, especially between 25-250 µg/g DS.

In one embodiment, the glucoamylase is added as a blend further comprising an alpha-amylase. In one embodiment, the alpha-amylase is a fungal alpha-amylase, especially an acid fungal alpha-amylase. The alpha-amylase is typically a side activity.

In one embodiment, the glucoamylase is a blend comprising *Talaromyces emersonii* glucoamylase disclosed in WO 99/28448 as SEQ ID NO: 34 and SEQ ID NO: 19 herein and *Trametes cingulata* glucoamylase disclosed as SEQ ID NO: 2 in WO 06/069289 and SEQ ID NO: 20 herein.

In one embodiment, the glucoamylase is a blend comprising *Talaromyces emersonii* glucoamylase disclosed in WO 99/28448 (SEQ ID NO: 19 herein), *Trametes cingulata* glucoamylase disclosed as SEQ ID NO: 2 in WO 06/69289 and SEQ ID NO: 20 herein, and an alpha-amylase.

In one embodiment, the glucoamylase is a blend comprising *Talaromyces emersonii* glucoamylase disclosed in WO99/28448 (SEQ ID NO: 19 herein), *Trametes cingulata* glucoamylase disclosed in WO 06/69289 (SEQ ID NO: 20 herein), and *Rhizomucor pusillus* alpha-amylase with *Aspergillus niger* glucoamylase linker and SBD disclosed as V039 in Table 5 in WO 2006/069290 or SEQ ID NO: 16 herein.

In one embodiment, the glucoamylase is a blend comprising *Gloeophyllum* sepiarium glucoamylase shown as SEQ ID NO: 2 in WO 2011/068803 (SEQ ID NO: 15 herein) and an alpha-amylase, in particular *Rhizomucor pusillus* alpha-amylase with an *Aspergillus niger* glucoamylase linker and starch-binding domain (SBD), disclosed SEQ ID NO: 3 in WO 2013/006756, in particular with the following substitutions: G128D+D143N.

In one embodiment, the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In one embodiment, the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 16 herein.

In one embodiment, the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+ Y141W; A76G+Y141W; G128D+Y141W; G128D+D143N; P219C+Y141W; N142D+D143N; Y141W+K192R; Y141W+D143N; Y141W+N383R; Y141W+P219C+ A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; and G128D+Y141W+ D143N+K192R; or G128D+Y141W+D143N+K192R+ P219C (using SEQ ID NO: 3 in WO 2013/006756 for numbering or SEQ ID NO: 16 herein).

In one embodiment, the glucoamylase blend comprises *Gloeophyllum sepiarium* glucoamylase (e.g., SEQ ID NO: 2 in WO 2011/068803 or SEQ ID NO: 15 herein) and *Rhizomucor pusillus* alpha-amylase.

In one embodiment, the glucoamylase blend comprises *Gloeophyllum sepiarium* glucoamylase shown as SEQ ID NO: 2 in WO 2011/068803 or SEQ ID NO: 15 herein and *Rhizomucor pusillus* with an *Aspergillus niger* glucoamylase linker and starch-binding domain (SBD), disclosed SEQ ID NO: 3 in WO 2013/006756 and SEQ ID NO: 16 herein with the following substitutions: G128D+D143N.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™, and AMG™ E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

Cellulolytic Enzyme Composition Present and/or Added During Saccharification and/or Fermentation A cellulolytic enzyme composition comprising a beta-glucosidase, a cellobiohydrolase and an endoglucanase may be present in saccharification or fermentation or simultaneous saccharification and fermentation (SSF).

Examples of suitable cellulolytic enzyme composition can be found in WO 2008/151079 and WO 2013/028928 which are incorporated by reference.

In preferred embodiments the cellulolytic enzyme composition is derived from a strain of *Trichoderma*, *Humicola*, or *Chrysosporium*.

In one embodiment, the cellulolytic enzyme composition is derived from a strain of *Trichoderma reesei*, *Humicola insolens* and/or *Chrysosporium lucknowense*.

In one embodiment, the cellulolytic enzyme composition comprises a beta-glucosidase, e.g., one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in WO 2005/047499 (SEQ ID NO: 29 herein) or an *Aspergillus fumigatus* beta-glucosidase variant disclosed in WO 2012/044915 (Novozymes), such as one with the following substitutions: F100D, S283G, N456E, F512Y (using SEQ ID NO: 29 herein for numbering); or a strain of the genus a strain *Penicillium*, such as a strain of the *Penicillium brasilianum* disclosed in WO 2007/019442, or a strain of the genus *Trichoderma*, such as a strain of *Trichoderma reesei*.

In one embodiment, the cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 and SEQ ID NO: 30 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 31 herein.

In one embodiment, the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 2 in WO 2013/028928 or SEQ ID NO: 32 herein, or a strain of the genus *Trichoderma*, such as a strain of *Trichoderma reesei*.

In one embodiment, the cellulolytic enzyme composition comprises a cellobiohydrolase II (CBH II, such as one derived from a strain of the genus *Aspergillus*, such as a strain of *Aspergillus fumigatus*, such as the one disclosed as SEQ ID NO: 4 in WO 2013/028928 or SEQ ID NO: 33 herein); or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In one embodiment, the cellulolytic enzyme composition comprises a GH61 polypeptide having cellulolytic enhancing activity and a beta-glucosidase.

In one embodiment, the cellulolytic enzyme composition comprises a GH61 polypeptide having cellulolytic enhancing activity, a beta-glucosidase, and a CBH I.

In one embodiment, the cellulolytic enzyme composition comprises a GH61 polypeptide having cellulolytic enhancing activity, a beta-glucosidase, a CBH I, and a CBH II.

In one embodiment, the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein), and *Aspergillus oryzae* beta-glucosidase fusion protein (WO 2008/057637).

In one embodiment, the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

In one embodiment, the cellulolytic enzyme composition is a *Trichoderma reesei* cellulolytic enzyme composition further comprising *Penicillium emersonii* GH61A polypeptide having cellulolytic enhancing activity disclosed as SEQ ID NO: 2 in WO 2011/041397 or SEQ ID NO: 31 herein and *Aspergillus fumigatus* beta-glucosidase (SEQ ID NO: 2 of WO 2005/047499 or SEQ ID NO: 29 herein) or a variant thereof with the following substitutions F100D, S283G, N456E, F512Y (using SEQ ID NO; 29 for numbering).

In one embodiment, the cellulolytic enzyme composition comprising one or more of the following components:
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof; and
(iv) a *Penicillium* sp. GH61 polypeptide having cellulolytic enhancing activity; or homologs thereof.

In one embodiment, the cellulolytic enzyme composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 31 herein, *Aspergillus fumigatus* beta-glucosidase (SEQ ID NO: 2 in WO 2005/047499 or SEQ ID NO: 29 herein) variant with the following substitutions: F100D, S283G, N456E, F512Y) disclosed in WO 2012/044915; *Aspergillus fumigatus* Cel7A CBH1 disclosed as SEQ ID NO: 6 in WO2011/057140 or SEQ ID NO: 32 herein and *Aspergillus fumigatus* CBH II disclosed as SEQ ID NO: 18 in WO 2011/057140 or SEQ ID NO: 33 herein.

In one embodiment, the cellulolytic enzyme composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Examples of Preferred Processes

In one embodiment, is a process for producing ethanol from starch-containing material comprising the steps of:
i) liquefying the starch-containing material at a temperature above the initial gelatinization temperature using an alpha-amylase derived from *Bacillus stearothermophilus* (e.g., SEQ ID NO: 1 herein);
ii) saccharifying using a glucoamylase;
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038; or
(2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

In one embodiment, the derivative of *Saccharomyces cerevisiae* strain MBG5038 or MBG5012 expresses a glucoamylase and/or an alpha-amylase.

In one embodiment, a protease is added in saccharification and/or fermentation or SSF.

In one embodiment, is processes for producing ethanol from starch-containing material comprising the steps of:
i) liquefying the starch-containing material at a temperature above the initial gelatinization temperature using an alpha-amylase derived from *Bacillus stearothermophilus* comprising a double deletion at positions I181+G182, and optionally a N193F substitution; (using SEQ ID NO: 1 for numbering);
ii) saccharifying using a glucoamylase, e.g., one derived from a strain of *Gloephyllum*, such as *Gloephyllum serpiarium* or *Gloephyllum trabeum*;
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
(1) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5012 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature above the initial gelatinization temperature using:
    an alpha-amylase derived from *Bacillus stearothermophilus* (e.g., SEQ ID NO: 1);
    a protease having a thermostability value of more than 20% determined as Relative Activity at 80° C./70° C., preferably derived from *Pyrococcus furiosus* and/or *Thermoascus aurantiacus*; and
    optionally a *Penicillium oxalicum* glucoamylase;
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature above the initial gelatinization temperature using
    an alpha-amylase, preferably derived from *Bacillus stearothermophilus*, in particular one comprising a double deletion at positions I181+G182, and optionally a N193F substitution (using SEQ ID NO: 1 for numbering) and having a T½ (min) at pH 4.5, 85° C., 0.12 mM CaCl$_2$ of at least 10;
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature between 80-90° C.:
    an alpha-amylase, preferably derived from *Bacillus stearothermophilus*, in particular one having a T½ (min) at pH 4.5, 85° C., 0.12 mM CaCl$_2$ of at least 10;
    a protease, preferably derived from *Pyrococcus furiosus* and/or *Thermoascus aurantiacus*, having a thermostability value of more than 20% determined as Relative Activity at 80° C./70° C.;
    optionally a *Penicillium oxalicum* glucoamylase
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is processes for producing ethanol from starch-containing material comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F; and optionally further one of the following substitutions or combinations of substitutions:
    E129V+K177L+R179E;
    V59A+Q89R+E129V+K177L+R179E+H208Y+K220P+N224L+Q254S:
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S (using SEQ ID NO: 1 herein for numbering);
  ii) saccharifying using a glucoamylase, such as one from a strain of *Gloephyllum*, such as a strain of *Gloeophyllum serpiarium;*
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:

i) liquefying the starch-containing material at a temperature above the initial gelatinization temperature using:
   an alpha-amylase derived from *Bacillus stearothermophilus* having a double deletion at positions I181+G182, and optional substitution N193F, and optionally further one of the following substitutions or combinations of substitutions:
   E129V+K177L+R179E;
   V59A+Q89R+E129V+K177L+R179E+H208Y+K220P+N224L+Q254S:
   V59A+Q89R+E129V+K177L+R179E+Q254S+M284V;
   V59A+E129V+K177L+R179E+Q254S+M284V; and
   E129V+K177L+R179E+K220P+N224L+S242Q+Q254S (using SEQ ID NO: 1 herein for numbering).
   a protease having a thermostability value of more than 20% determined as Relative Activity at 80° C./70° C., preferably derived from *Pyrococcus furiosus* and/or *Thermoascus aurantiacus*; and
   optionally a *Penicillium oxalicum* glucoamylase shown in SEQ ID NO: 14 having one of the following substitutions or combinations of substitutions:
   K79V;
   K79V+P11F+T65A+Q327F;
   K79V+P2N+P4S+P11F+T65A+Q327F;
   K79V+P11F+D26C+K33C+T65A+Q327F;
   K79V+P2N+P4S+P11F+T65A+Q327W+E501V+Y504T;
   K79V+P2N+P4S+P11F+T65A+Q327F+E501V+Y504T; and
   K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is:
   (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
   (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:

i) liquefying the starch-containing material at a temperature between 80-90° C. using:
   an alpha-amylase derived from *Bacillus stearothermophilus* having a double deletion at positions I181+G182, and optional substitution N193F, and further optionally one of the following substitutions or combinations of substitutions:
   E129V+K177L+R179E;
   V59A+Q89R+E129V+K177L+R179E+H208Y+K220P+N224L+Q254S;
   V59A+Q89R+E129V+K177L+R179E+Q254S+M284V;
   V59A+E129V+K177L+R179E+Q254S+M284V; and
   E129V+K177L+R179E+K220P+N224L+S242Q+Q254S (using SEQ ID NO: 1 herein for numbering),
   a protease having a thermostability value of more than 20% determined as Relative Activity at 80° C./70° C., preferably derived from *Pyrococcus furiosus* and/or *Thermoascus aurantiacus;*
   a *Penicillium oxalicum* glucoamylase shown in SEQ ID NO: 14 having one of the following substitutions or combinations of substitutions:
   K79V;
   K79V+P11F+T65A+Q327F;
   K79V+P2N+P4S+P11F+T65A+Q327F;
   K79V+P11F+D26C+K33C+T65A+Q327F;
   K79V+P2N+P4S+P11F+T65A+Q327W+E501V+Y504T;
   K79V+P2N+P4S+P11F+T65A+Q327F+E501V+Y504T; and
   K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is:
   (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
   (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F;
    a protease having a thermostability value of more than 20% determined as Relative Activity at 80° C./70° C., preferably derived from *Pyrococcus furiosus* and/or *Thermoascus aurantiacus*; and
    optionally a pullulanase;
    a *Penicillium oxalicum* glucoamylase having a K79V substitution (using SEQ ID NO: 14 for numbering);
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature above the initial gelatinization temperature using:
    an alpha-amylase, preferably derived from *Bacillus stearothermophilus*, having a T½ (min) at pH 4.5, 85° C., 0.12 mM CaCl$_2$) of at least 10;
    between 0.5 and 10 micro grams *Pyrococcus furiosus* protease per g DS;
  ii) saccharifying using a glucoamylase selected from the group of glucoamylase derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloeophyllum*, such as *G. serpiarium* or *G. trabeum*, or a strain of the *Nigrofomes*;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature between 80-90° C. using;
    an alpha-amylase, preferably derived from *Bacillus stearothermophilus* having a double deletion at positions I181+G182, and optional substitution N193F and having a T½ (min) at pH 4.5, 85° C., 0.12 mM CaCl$_2$ of at least 10;
    between 0.5 and 10 micro grams *Pyrococcus furiosus* protease per g DS;
    optionally a pullulanase;
    a *Penicillium oxalicum* glucoamylase;
  ii) saccharifying using a glucoamylase;
  iii) fermenting using a fermenting organism;
wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
  i) liquefying the starch-containing material at a temperature a temperature between 80-90° C. using;
    an alpha-amylase derived from *Bacillus stearothermophilus* having a double deletion I181+G182 and optional substitution N193F; and optionally further one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S (using SEQ ID NO: 1 herein for numbering);

between 0.5 and 10 micro grams *Pyrococcus furiosus* protease per g DS; and optionally a pullulanase;
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K330+T65A+Q327F;
K79V+P2N+P4S+P11F+T65A+Q327W+E501V+Y504T;
K79V+P2N+P4S+P11F+T65A+Q327F+E501V+Y504T; and
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
(2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, is a processes for producing ethanol from starch-containing material comprising the steps of:
i) liquefying the starch-containing material at a temperature between 80-90° C. using:
an alpha-amylase derived from *Bacillus stearothermophilus* having a double deletion I181+G182 and optional substitution N193F; and further one of the following substitutions or combinations of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 herein for numbering);
a protease having a thermostability value of more than 20% determined as Relative Activity at 80° C./70° C., preferably derived from *Pyrococcus furiosus* and/or *Thermoascus aurantiacus*;
optionally a pullulanase; and
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+Y504T;
K79V+P2N+P4S+P11F+T65A+Q327F+E501V+Y504T; and
K79V+P11F+T65A+Q327W+E501V+Y504T (using SEQ ID NO: 14 for numbering);
ii) saccharifying using a glucoamylase selected from the group of glucoamylase derived from a strain of *Aspergillus*; or a strain of *Trichoderma*; a strain of *Talaromyces*, a strain of *Pycnoporus*; a strain of *Gloeophyllum*; and a strain of the *Nigrofomes;*
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or
(2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
i) liquefying the starch-containing material at a temperature between 80-90° C. at a pH between 5.0 and 6.5 using:
an alpha-amylase derived from *Bacillus stearothermophilus* having a double deletion I181+G182 and optional substitution N193F; and optionally further one of the following substitutions or combinations of substitutions:
E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 herein for numbering).
a protease derived from *Pyrococcus furiosus*, preferably the one shown in SEQ ID NO: 13 herein;
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+Y504T;
K79V+P2N+P4S+P11F+T65A+Q327F+E501V+Y504T; and
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a process comprises the steps of:
i) liquefying the starch-containing material at a temperature between 80-90° C. at a pH between 5.0 and 6.5 using:
an alpha-amylase derived from *Bacillus stearothermophilus* having a double deletion I181+G182, and optional substitution N193F; and optionally further one of the following substitutions or combinations of substitutions:
E129V+K177L+R179E;
V59A+Q89R+E129V+K177L+R179E+H208Y+ K220P+N224L+Q254S;
V59A+Q89R+E129V+K177L+R179E+Q254S+ M284V;
V59A+E129V+K177L+R179E+Q254S+M284V; and
E129V+K177L+R179E+K220P+N224L+S242Q+ Q254S (using SEQ ID NO: 1 herein for numbering);
a protease derived from *Pyrococcus furiosus*, preferably the one shown in SEQ ID NO: 13 herein present and/or added in a dosage of 1-5 micro gram protease per gram DS, such as about 1.5 or 3 micro gram protease per gram DS; and
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+ Y504T;
K79V+P2N+P4S+P11F+T65A+Q327F+E501V+ Y504T; and
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one embodiment, is a processes for producing ethanol from starch-containing material comprising the steps of:
i) liquefying the starch-containing material at a temperature above the initial gelatinization temperature using an alpha-amylase derived from *Bacillus stearothermophilus;*
ii) saccharifying using a glucoamylase;
iii) fermenting using a fermenting organism;
wherein the fermenting organism increases ethanol yield compared to *Saccharomyces cerevisiae* strain Ethanol Red® (deposited under Accession No. V14/007039 at National Measurement Institute, Victoria, Australia) under the same process conditions, e.g., conditions as described herein.

Raw Starch Hydrolysis Process

This aspect concerns improved raw starch hydrolysis processes for producing ethanol using a fermenting organism and yeast strains suitable for use in processes and methods thereof.

More specifically, this aspect relates to processes of producing ethanol from starch-containing material, such as granular starch, comprising:
(i) saccharifying a starch-containing material at a temperature below the initial gelatinization temperature; and
(ii) fermenting using a fermentation organism;
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative of *Saccharomyces* strain MBG5038 having defining characteristics of strain *Saccharomyces* strain MBG5038; or (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative of *Saccharomyces* strain MBG5038 having defining characteristics of strain *Saccharomyces* strain MBG5012.

In one embodiment, the derivative of *Saccharomyces cerevisiae* strain MBG5038 or MBG5012 expresses a glucoamylase and/or an alpha-amylase.

In one aspect is a processes of producing ethanol from starch-containing material, such as granular starch, comprising:
(i) saccharifying a starch-containing material at a temperature below the initial gelatinization temperature; and
(ii) fermenting using a fermentation organism;
wherein
saccharification and/or fermentation is done in the presence of the following enzymes: glucoamylase and alpha-amylase, and optionally protease; and the fermenting organism is a *Saccharomyces* yeast strain providing one or more, such as all, of the following improvements:

an ethanol yield boost compared to *Saccharomyces cerevisiae* strain Ethanol Red® (deposited under Accession No. V14/007039 at National Measurement Institute, Victoria, Australia) under the same fermentation conditions (e.g., conditions as described herein);

reduced acetaldehyde production compared to *Saccharomyces cerevisiae* strain Ethanol Red® (deposited under Accession No. V14/007039 at National Measurement Institute, Victoria, Australia) under the same process conditions (e.g., conditions as described herein);

increased temperature tolerance compared to *Saccharomyces cerevisiae* strain Ethanol Red® (deposited under Accession No. V14/007039 at National Measurement Institute, Victoria, Australia) under the same process conditions (e.g., conditions as described herein);

decreased glycerol production compared to *Saccharomyces cerevisiae* strain Ethanol Red® (deposited under Accession No. V14/007039 at National Measurement Institute, Victoria, Australia) under the same process conditions (e.g., conditions as described herein).

In one embodiment, the fermenting organism used in a process is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA), or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA). In one embodiment, the fermenting organism used in a process is a derivative of *Saccharomyces cerevisiae* strain MBG5038 or MBG5012 that expresses a glucoamylase and/or an alpha-amylase.

A raw starch chydrolysis process using the yeast described herein results in one or more, such as all, of the following improvements compared to a corresponding process carried out under the same conditions using *Saccharomyces cerevisiae* strain Ethanol Red® (deposited under Accession No. V14/007039 at National Measurement Institute, Victoria, Australia) as the fermenting organism:

an ethanol yield boost compared to *Saccharomyces cerevisiae* strain Ethanol Red® (deposited under Accession No. V14/007039 at National Measurement Institute, Victoria, Australia) under the same fermentation conditions (e.g., conditions as described herein);

reduced acetaldehyde production compared to *Saccharomyces cerevisiae* strain Ethanol Red® (deposited under Accession No. V14/007039 at National Measurement Institute, Victoria, Australia) under the same process conditions (e.g., conditions as described herein);

increased temperature tolerance compared to *Saccharomyces cerevisiae* strain Ethanol Red® (deposited under Accession No. V14/007039 at National Measurement Institute, Victoria, Australia) under the same process conditions (e.g., conditions as described herein);

decreased glycerol production compared to *Saccharomyces cerevisiae* strain Ethanol Red® (deposited under Accession No. V14/007039 at National Measurement Institute, Victoria, Australia) under the same process conditions (e.g., conditions as described herein).

Examples of suitable enzymes used, especially glucoamylases, alpha-amylases, proteases, cellulolytic enzyme compositions etc are described in the "Enzymes And Enzyme Blends Used In A Raw Starch Hydrolysis Process" section below.

In one embodiment, the following enzymes are expressed, present and/or added in saccharification and/or fermentation: *Trametes cingulata* glucoamylase, e.g., the one shown in SEQ ID NO: 20 herein and an alpha-amylase. In one embodiment, the alpha-amylase is a *Rhizomucor pusillus* alpha-amylase, preferably the *Rhizomucor pusillus* alpha-amylase with a linker and starch-binding domain (SBD), in particular the *Rhizomucor pusillus* alpha-amylase with *Aspergillus niger* glucoamylase linker and starch-binding domain shown in SEQ ID NO: 16 herein.

In one embodiment, the following enzymes are expressed, present and/or added in saccharification and/or fermentation: *Gloeophyllum trabeum* glucoamylase, e.g., the one shown in SEQ ID NO: 17 herein, especially one further having one or more of the following substitutions: S95P, A121P, especially S95P+A121P and an alpha-amylase. In one embodiment, the alpha-amylase is derived from *Rhizomucor pusillus*, e.g., *Rhizomucor pusillus* alpha-amylase with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 16 herein.

In one embodiment of the process the following enzymes are expressed, present and/or added in saccharification and/or fermentation: *Gloeophyllum trabeum* glucoamylase, preferably the one shown in SEQ ID NO: 17 herein, preferably one further having one or more of the following substitutions: S95P, A121P, especially S95P+A121P and an alpha-amylase. The alpha-amylase may be derived from *Rhizomucor pusillus*, preferably *Rhizomucor pusillus* alpha-amylase with a linker and starch-binding domain (SBD), in particular the *Rhizomucor pusillus* alpha-amylase with *Aspergillus niger* glucoamylase linker and starch-binding domain (SBD) shown in SEQ ID NO: 16 herein, preferably one further having one or more of the following substitutions: G128D, D143N, especially G128D+143N.

In one embodiment, the following enzymes are expressed, present and/or added in saccharification and/or fermentation: *Pycnoporus sanguineus* glucoamylase, preferably the one shown in SEQ ID NO: 18 herein and an alpha-amylase. In one embodiment, the alpha-amylase is derived from *Rhizomucor pusillus*, preferably with a linker and starch-binding domain (SBD), e.g., the *Rhizomucor pusillus* with an *Aspergillus niger* glucoamylase linker and starch-binding domain (SBD) disclosed as V039 in Table 5 in WO 2006/069290 or SEQ ID NO: 16 herein, such as one further having one or more of the following substitutions: G128D, D143N (e.g., G128D+D143N).

In one embodiment, a protease is present and/or added in saccharification and/or fermentation. In one embodiment, the protease is a metallo protease or a serine protease. In one embodiment, the metallo protease is derived from a strain of the genus *Thermoascus*, such as a strain of *Thermoascus aurantiacus*, e.g., *Thermoascus aurantiacus* CGMCC No. 0670 (e.g., the metallo protease disclosed as the mature part of SEQ ID NO: 2 disclosed in WO 2003/048353 or the mature polypeptide of SEQ ID NO: 3 herein).

In one embodiment, a cellulolytic enzyme composition is present and/or added in saccharification and/or fermentation.

In one embodiment, the cellulolytic enzyme composition is derived from *Trichoderma reesei*, preferably further comprising *Thermoascus aurantiacus* GH61A polypeptide having cellulolytic enhancing activity (e.g., SEQ ID NO: 2 in WO 2005/074656 or SEQ ID NO: 30 herein) and *Aspergillus fumigatus* beta-glucosidase (e.g., SEQ ID NO: 2 of WO 2005/047499 or SEQ ID NO: 29 herein), or a cellulolytic enzyme composition derived from *Trichoderma reesei*, preferably further comprising *Penicillium emersonii* GH61A polypeptide, e.g., the one disclosed as SEQ ID NO: 2 in WO 2011/041397 or SEQ ID NO: 31 herein, and *Aspergillus fumigatus* beta-glucosidase, e.g., the one disclosed as SEQ ID NO: 2 in WO 2005/047499 or SEQ ID NO: 29 herein, or a variant thereof, such as a variant having one of, or all of, the following substitutions: F100D, S283G, N456E, F512Y, *Aspergillus fumigatus* CBH1, e.g., the one disclosed as SEQ ID NO: 6 in WO2011/057140 and SEQ ID NO: 32 herein, and *Aspergillus fumigatus* CBH II, e.g., the one disclosed as SEQ ID NO: 18 in WO 2011/057140 and as SEQ ID NO: 33 herein.

In one embodiment, the glucoamylase to alpha-amylase ratio is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In one embodiment, the glucoamylase to alpha-amylase ratio is between 100:1 and 1:2, such as between 90:1 and 1:1, such as between 80:1 and 2:1, such as between 70:1 and 3:1, such as 16:1 (determined as AGU:FAU-F).

In one embodiment, the total dose of glucoamylase and alpha-amylase is from 10-1,000 µg/g DS, such as from 50-500 µg/g DS, such as 75-250 µg/g DS.

In one embodiment, the total dose of cellulolytic enzyme composition added is from 10-500 µg/g DS, such as from 20-400 µg/g DS, such as 20-300 µg/g DS.

In one embodiment, the dose of protease added is from 1-200 µg/g DS, such as from 2-100 µg/g DS, such as 3-50 µg/g DS.

In one embodiment, saccharification step (a) and fermentation step (b) are carried out simultaneously.

In one embodiment, the fermenting organism is a non-recombinant *Saccharomyces* strain, e.g., a non-recombinant *Saccharomyces cerevisiae* strain produced using the method described and concerned in U.S. Pat. No. 8,257,959-BB.

Enzymes and Enzyme Blends Used in a Raw Starch Hydrolysis Process

Glucoamylase and an alpha-amylase may be present and/or added in saccharification step (i) and/or fermentation step (ii) (e.g., simultaneous saccharification and fermentation (SSF)). Optionally a protease and/or a cellulolytic enzyme composition is(are) also present and/or added. Other enzymes such as pullulanases, pectinases, and/or trehalases may also be present and/or added.

A non-exhaustive list of suitable and specifically contemplated enzymes and enzyme combinations (e.g., blends) are described below.

In one embodiment, the following enzymes are present and/or added during saccharification and/or fermentation: *Trametes* glucoamylase, preferably *Trametes cingulata* glucoamylase shown in SEQ ID NO: 20 herein and an alpha-amylase.

In one embodiment, the glucoamylase is derived from *Trametes cingulata*, such as the one shown in SEQ ID NO: 20 herein, or a glucoamylase selected from the group consisting of:

(i) a glucoamylase comprising the mature polypeptide of SEQ ID NO: 20 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

In one embodiment, the following enzymes are present and/or added during saccharification and/or fermentation: *Gloeophyllum* glucoamylase, preferably *Gloeophyllum trabeum* glucoamylase, especially the *Gloeophyllum trabeum* glucoamylase shown in SEQ ID NO: 17 herein and an alpha-amylase.

In one embodiment, the glucoamylase is derived from *Gloeophyllum trabeum*, such as the one shown in SEQ ID NO: 17 herein, or a glucoamylase selected from the group consisting of:

(i) a glucoamylase comprising the mature polypeptide of SEQ ID NO: 17 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

In one embodiment, the *Gloeophyllum* glucoamylase, such as the *Gloeophyllum trabeum* glucoamylase shown in SEQ ID NO: 17, has one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 17 for numbering).

The alpha-amylase used in a process described herein is typically a fungal alpha-amylase, such as an acid fungal alpha-amylase. In one embodiment, the alpha-amylase is derived from *Rhizomucor*, such as a *Rhizomucor pusillus* alpha-amylase with a linker and starch-binding domain (SBD), e.g., the *Rhizomucor pusillus* alpha-amylase with an *Aspergillus niger* glucoamylase linker and starch-binding domain (SBD) disclosed as V039 in Table 5 in WO 2006/069290 or SEQ ID NO: 16 herein.

In one embodiment, the alpha-amylase is a *Rhizomucor* alpha-amylase or the *Rhizomucor pusillus* alpha-amylase with an *Aspergillus niger* glucoamylase linker and starch-binding domain (SBD) shown in SEQ ID NO: 16 herein, e.g., one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 16 for numbering).

In one embodiment, the alpha-amylase is selected from the group consisting of:

(i) an alpha-amylase comprising the mature polypeptide of SEQ ID NO: 16 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

In one embodiment, the following enzymes are present and/or added in saccharification and/or fermentation: the

*Trametes cingulata* glucoamylase shown in SEQ ID NO: 20 herein and an alpha-amylase derived from *Rhizomucor pusillus*, preferably with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 16 herein.

In one embodiment, the following enzymes are present and/or added in saccharification and/or fermentation: *Gloeophyllum* glucoamylase, preferably the *Gloeophyllum trabeum* glucoamylase shown in SEQ ID NO: 17 herein and an alpha-amylase derived from *Rhizomucor pusillus*, preferably with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 16 herein.

In one embodiment, the enzymes present and/or added comprises the *Gloeophyllum trabeum* glucoamylase shown in SEQ ID NO: 17 herein having one or more of the following substitutions: S95P, A121P, especially S95P+A121P (using SEQ ID NO: 17 herein for numbering) and the alpha-amylase derived from *Rhizomucor pusillus* with an *Aspergillus niger* glucoamylase linker and starch-binding domain (SBD), preferably one shown in SEQ ID NO: 16 herein, preferably one having one or more of the following substitutions: G128D, D143N, especially especially G128D+D143N (using SEQ ID NO: 16 for numbering).

In one embodiment, the following enzymes are present and/or added in saccharification and/or fermentation: *Pycnoporus* glucoamylase, in particular the *Pycnoporus sanguineus* glucoamylase shown in SEQ ID NO: 18 and the *Rhizomucor pusillus* alpha-amylase with a linker and starch-binding domain (SBD), in particular the *Rhizomucor pusillus* alpha-amylase with an *Aspergillus niger* glucoamylase linker and starch-binding domain (SBD) shown in SEQ ID NO: 16 herein.

In one embodiment, the enzymes present and/or added in saccharification and/or fermentation comprises a *Pycnoporus* glucoamylase, such as the *Pycnoporus sanguineus* glucoamylase shown in SEQ ID NO: 18 herein and the alpha-amylase, in particular an alpha-amylase derived from *Rhizomucor pusillus* with a linker and starch-binding domain (SBD), preferably the *Rhizomucor pusillus* alpha-amylase with an *Aspergillus niger* glucoamylase linker and starch-binding domain (SBD) shown in SEQ ID NO: 16 herein, preferably having one or more of the following substitutions: G128D, D143N, especially G128D+D143N.

The enzymes present and/or added in saccharification and/or fermentation in a process described herein include i) glucoamylase and ii) alpha-amylase; and may optionally further comprise iii) a cellulolytic enzyme composition and/or iv) a protease.

In one embodiment, the protease is a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In one embodiment, the protease, in particular a protease derived from *Thermoascus aurantiacus*, is selected from the group consisting of:

(i) a protease comprising the mature polypeptide of SEQ ID NO: 3 herein;

(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

In one embodiment, the enzymes present and/or added in saccharification and/or fermentation comprises the *Trametes cingulata* glucoamylase shown in SEQ ID NO: 20 herein and the alpha-amylase derived from *Rhizomucor pusillus* with an *Aspergillus niger* glucoamylase linker and starch-binding domain (SBD), such as the one shown in SEQ ID NO: 16 herein, and may have one or more of the following substitutions: G128D, D143N (e.g., G128D+D143N) and optionally further a cellulolytic enzyme composition derived from *Trichoderma reesei*, e.g., further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein); or a cellulolytic enzyme composition derived from *Trichoderma reesei*, e.g., further comprising *Penicillium emersonii* GH61A polypeptide disclosed as SEQ ID NO: 2 in WO 2011/041397 or SEQ ID NO: 31 herein and *Aspergillus fumigatus* beta-glucosidase disclosed as SEQ ID NO: 2 in WO 2005/047499 or SEQ ID NO: 29 herein, or a variant thereof, e.g., a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 32 herein and *Aspergillus fumigatus* CBH II disclosed as SEQ ID NO: 18 in WO 2011/057140 and as SEQ ID NO: 33 herein.

In one embodiment the enzymes present and/or added in saccharification and/or fermentation comprises the *Gloeophyllum trabeum* glucoamylase shown in SEQ ID NO: 17 herein, preferably having one or more of the following substitutions: S95P, A121P, especially S95P+A121P and the alpha-amylase derived from *Rhizomucor pusillus* with an *Aspergillus niger* glucoamylase linker and starch-binding domain (SBD), preferably the one shown in SEQ ID NO: 16 herein, preferably having one or more of the following substitutions: G128D, D143N, especially G128D+D143N, and optionally further a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein); or a cellulolytic enzyme composition derived from *Trichoderma reesei*, preferably further comprising *Penicillium emersonii* GH61A polypeptide disclosed as SEQ ID NO: 2 in WO 2011/041397 or SEQ ID NO: 31 herein and *Aspergillus fumigatus* beta-glucosidase disclosed as SEQ ID NO: 2 in WO 2005/047499 or SEQ ID NO: 29 herein, or a variant thereof, preferably a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 32 herein and *Aspergillus fumigatus* CBH II disclosed as SEQ ID NO: 18 in WO 2011/057140 and as SEQ ID NO: 33 herein.

In one embodiment the enzymes present and/or added in saccharification and/or fermentation comprises the *Pycnoporus sanguineus* glucoamylase shown in SEQ ID NO: 18 herein and the alpha-amylase derived from *Rhizomucor pusillus* with an *Aspergillus niger* glucoamylase linker and starch-binding domain (SBD), preferably the one shown in SEQ ID NO: 16 herein, preferably having one or more of the following substitutions: G128D, D143N, especially G128D+D143N, and optionally further a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: herein) and *Aspergillus fumigatus* beta-glucosidase (SEQ ID NO: 2 of WO 2005/047499 or SEQ ID NO: 30 herein); or a cellulolytic enzyme composition derived from *Trichoderma reesei*, preferably further comprising *Penicillium emersonii* GH61A polypeptide disclosed as SEQ ID NO: 2 in WO 2011/041397 or SEQ ID NO: 31 herein and *Aspergillus fumigatus* beta-glucosidase disclosed as SEQ ID NO: 2 in WO 2005/047499 or SEQ ID NO: 29 herein, or a variant thereof, preferably a variant having one of, preferably all of, the following substitutions: F100D, S283G, N456E, F512Y, *Aspergillus fumigatus* Cel7A CBH I disclosed as SEQ ID NO: 6 in WO2011/057140 and SEQ ID NO: 29 herein and *Aspergillus fumigatus* CBH II disclosed as SEQ ID NO: 18 in WO 2011/057140 and as SEQ ID NO: 33 herein.

In one embodiment, a cellulolytic enzyme composition is one described below in the "Cellulolytic Enzyme Compositions"-section.

The optional cellulolytic enzyme composition, protease or other enzymes, may be added in the process described herein at the same time as the glucoamylase and the alpha-amylase. The enzymes, e.g., in the form of an enzyme composition, may be added to the saccharification and/or fermentation, preferably simultaneous saccharification and fermentation (i.e., one-step process). It should be understood that the enzymes may also be added individually or as two, three, four or more enzyme components/compositions. In one embodiment, the glucoamylase and the alpha-amylase are added as one blend composition and the optional cellulolytic enzyme composition and/and optional protease are added separately. In another embodiment the glucoamylase, the alpha-amylase, and the cellulolytic enzyme composition are added as one enzyme composition and the optional protease is added separately. All enzymes may also in one embodiment be added as one enzyme composition comprising a glucoamylase, an alpha-amylase, a cellulolytic enzyme composition and/or a protease, and optionally other enzymes including pullulanase, trehalase and/or pectinase, such as pectin lyase or polygalacturonase.

Other enzymes may also be present. Specifically contemplated enzymes are described further below.

Glucoamylase

The glucoamylase used in a process described herein may be of any origin, such as of bacterial or fungal origin. Fungal glucoamylases are preferred.

In one embodiment, the glucoamylase may be one derived from a strain of *Trametes*, such as a strain of *Trametes cingulata* (SEQ ID NO: 20 herein); or a strain of *Pachykytospora*, such as a strain of *Pachykytospora papyracea*; or a strain of *Leucopaxillus*, such as a strain of *Leucopaxillus giganteus* (all disclosed in WO 2006/069289).

In one embodiment, the glucoamylase, in particular derived from a strain of *Trametes cingulata*, is selected from the group consisting of:
(i) a glucoamylase comprising the mature polypeptide of SEQ ID NO: 20 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

In one embodiment, the glucoamylase is from a strain of *Aspergillus*, preferably *Aspergillus niger*, *Aspergillus awamori*, or *Aspergillus oryzae*; or a strain of *Trichoderma*, preferably *Trichoderma reesei*; or a strain of *Talaromyces*, preferably *Talaromyces emersonii* (e.g., SEQ ID NO: 19 herein).

In one embodiment, the glucoamylase, such as one derived from a strain of *Talaromyces emersonii*, is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

In another embodiment the glucoamylase is derived from a strain of *Penicillium*, such as a strain of *Penicillium oxalicum*.

In one embodiment, the glucoamylase, such as one derived from a strain of *Penicillium oxalicum*, is selected from the group consisting of:
(i) a glucoamylase comprising the mature polypeptide of SEQ ID NO: 14 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 14 herein.

In one embodiment, the glucoamylase is derived from a strain of *Gloeophyllum*, such as a strain of *Gloeophyllum sepiarium* or *Gloeophyllum trabeum*, such as one disclosed in WO 2011/068803 as any of SEQ ID NOs: 2, 4, 6, 8, 10, 12, 14 or 16. In one embodiment, the glucoamylase is SEQ ID NO: 2 in WO 2011/068803 or SEQ ID NO: 15 herein. In another embodiment the glucoamylase is SEQ ID NO: 18 in WO 2011/068803 (hereby incorporated by reference).

In one embodiment, the glucoamylase, such as one derived from a strain of *Gloeophyllum sepiarium*, is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

In a further embodiment the glucoamylase is derived from a strain of the genus *Pycnoporus*, in particular a strain of *Pycnoporus sanguineus*, such as a strain described in WO 2011/066576 (SEQ ID NOs 2, 4 or 6). In one embodiment, the glucoamylase is the one shown in SEQ ID NO: 4 in WO 2011/066576 or SEQ ID NO: 18 herein.

In one embodiment, the glucoamylase, such as one derived from a strain of *Pycnoporus sanguineus*, is selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

Contemplated are also glucoamylases which exhibit a high identity to any of the above-mentioned glucoamylases, e.g., at least 60%, at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

In one embodiment, the glucoamylase, such as one derived from a strain of *Gloeophyllum trabeum*, is selected from the group consisting of:

(i) a glucoamylase comprising the mature polypeptide of SEQ ID NO: 17 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

In one embodiment, the glucoamylase, such as the one derived from *Gloeophyllum trabeum*, shown in SEQ ID NO: 17 has one of the following substitutions: V59A; S95P; A121P; T119W; S95P+A121P; V59A+S95P; S95P+T119W; V59A+S95P+A121P; or S95P+T119W+A121P, especially S95P+A121P. In one embodiment, the *Gloeophyllum trabeum* glucoamylase shown in SEQ ID NO: 18 has one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 17 herein for numbering). All *Gloeophyllum trabeum* glucoamylase variants, especially variants in SEQ ID NO: 3, disclosed in WO 2014/177546 is hereby incorporated by reference.

A glucoamylase variant may comprise an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 17.

Alpha-Amylase

The alpha-amylase used in a process described herein may be of any origin, such as of fungal or bacterial origin. In one embodiment, the alpha-amylase is an acid alpha-amylase, such as an acid fungal alpha-amylase, i.e., having a pH optimum below pH 7.

In one embodiment, the alpha-amylase may be derived from a strain of the genus *Rhizomucor*, preferably a strain the *Rhizomucor pusillus*, such as the one shown in SEQ ID NO: 3 in WO 2013/006756 (see e.g., Table 1 in Example 1—hereby incorporated by reference), or the genus *Meripilus*, preferably a strain of *Meripilus giganteus*.

In one embodiment, the alpha-amylase is derived from a *Rhizomucor pusillus*, such as one with a linker and a starch-binding domain (SBD), preferably *Aspergillus niger* glucoamylase linker and starch-binding domain (SBD), disclosed as V039 in Table 5 in WO 2006/069290 (incorporated by reference) or SEQ ID NO: 16 herein.

In one embodiment, the alpha-amylase is derived from a *Rhizomucor pusillus* with an *Aspergillus niger* glucoamylase linker and starch-binding domain (SBD), disclosed in WO 2013/006756 (incorporated by reference) or SEQ ID NO: 16 herein.

In one embodiment, the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 16 herein for numbering).

In one embodiment, the *Rhizomucor pusillus* alpha-amylase with an *Aspergillus niger* glucoamylase linker and starch-binding domain (SBD), is selected from the group consisting of:

(i) an alpha-amylase comprising the mature polypeptide of SEQ ID NO: 16 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

In one embodiment, the alpha-amylase is a variant of the *Rhizomucor pusillus* alpha-amylase with an *Aspergillus niger* glucoamylase linker and starch-binding domain (SBD), wherein the alpha-amylase variant comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity, but less than 100% to the mature polypeptide of SEQ ID NO: 16 herein.

In one embodiment, the alpha-amylase variant has one of the above mentioned substitutions, such as: G128D, Y141W, D143W or K192R (using SEQ ID NO: 16 for numbering).

In one embodiment, the alpha-amylase (using SEQ ID NO: 16 herein for numbering) has the following substitutions: Y141W+D143N.

In one embodiment, the alpha-amylase has the following substitutions: G128D+Y141W+D143N.

In one embodiment, the alpha-amylase has the following substitutions: G128D+Y141W+D143N+K192R;

In one embodiment, the alpha-amylase has the following substitutions: G128D+D143N (using SEQ ID NO: 16 for numbering).

A variant may comprise an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 16.

Protease

The enzymes present and/or added to saccharification and/or fermentation may optionally further include a protease. The protease may be of any origin, such as fungal or bacterial origin.

In one embodiment, the protease is of fungal origin.

In one embodiment, the protease is a metallo protease derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In one embodiment, the protease, such as one derived from a strain of *Thermoascus aurantiacus*, is selected from the group consisting of:

(i) a protease comprising the mature polypeptide of SEQ ID NO: 3 herein;

(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

In one embodiment, the protease is of bacterial origin.

In one embodiment, the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 5 herein.

In one embodiment, the protease, such as one derived from *Pyrococcus furiosus*, is selected from the group consisting of:

(i) a protease comprising the mature polypeptide of SEQ ID NO: 5 herein;

(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 5 herein.

Cellulolytic Enzyme Compositions

The enzymes present and/or added to saccharification and/or fermentation may optionally further include a cellulolytic enzyme composition. The cellulolytic enzyme composition may consist of or comprise one or more cellulolytic enzymes. The cellulolytic enzyme composition may be of any origin. In one embodiment, the cellulolytic enzyme composition comprises cellulolytic enzymes of fungal origin.

In one embodiment, the cellulolytic enzyme composition is derived from a strain of *Trichoderma*, such as *Trichoderma reesei*; or a strain of *Humicola*, such as *Humicola insolens*; or a strain of *Chrysosporium*, such as *Chrysosporium lucknowense*; or a strain of *Penicillium*, such as *Penicillium decumbens*. In one embodiment, the cellulolytic enzyme composition is derived from a strain of *Trichoderma reesei*.

The cellulolytic enzyme composition may comprise a beta-glucosidase, a cellobiohydrolase, and an endoglucanase.

In one embodiment, the cellulolytic enzyme composition comprising one or more polypeptides selected from the group consisting of:
  beta-glucosidase (BG);
  cellobiohydrolase I (CBHI);
  cellobiohydrolase II (CBHII);
  or a mixture thereof.

In one embodiment, the cellulolytic enzyme composition further comprises a GH61 polypeptide having cellulolytic enhancing activity. Cellulolytic enhancing activity is defined and determined as described in WO 2011/041397 (incorporated by reference).

The term "GH61 polypeptide having cellulolytic enhancing activity" means a GH61 polypeptide that enhances the hydrolysis of a cellulosic material by enzymes having cellulolytic activity. For purposes of the processes described herein, cellulolytic enhancing activity is determined by measuring the increase in reducing sugars or the increase of the total of cellobiose and glucose from hydrolysis of a cellulosic material by cellulolytic enzyme under the following conditions: 1-50 mg of total protein/g of cellulose in PCS (Pretreated Corn Stover), wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST™1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (see SEQ ID NOs: 74 or 76), or *Aspergillus fumigatus*, such as one disclosed in SEQ ID NO: 2 in WO 2005/047499 or SEQ ID NO: 8 herein; or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*. In one embodiment, the beta-glucosidase is from a strain of *Aspergillus*, such as a strain of *Aspergillus fumigatus*, such as *Aspergillus fumigatus* beta-glucosidase (SEQ ID NO: 29 herein), or a variant thereof, which variant comprises one or more substitutions selected from the group consisting of L89M, G91L, F100D, I140V, I186V, S283G, N456E, and F512Y; such as a variant thereof with the following substitutions:
  F100D+S283G+N456E+F512Y;
  L89M+G91L+I186V+I140V;
  I186V+L89M+G91L+I140V+F100D+S283G+N456E+F512Y.

In one embodiment, the parent beta-glucosidase has at least 60% identity, such as at least 70%, such as at least 80%, such as at least 90%, such as at least 95%, such as at least 96%, such as at least 97%, such as at least 98%, such as at least 99% identity to the mature polypeptide of SEQ ID NO: 29 herein.

In case the beta-glucosidase is a beta-glucosidase variant it has at least 60% identity, such as at least 70%, such as at least 80%, such as at least 90%, such as at least 95%, such as at least 96%, such as at least 97%, such as at least 98%, such as at least 99%, but less than 100% identity to the mature polypeptide of SEQ ID NO:29 herein.

In case the cellulolytic enzyme composition comprises a GH61 polypeptide, it may be one derived from the genus *Thermoascus*, such as a strain of *Thermoascus aurantiacus*, such as the one described in WO 2005/074656 as SEQ ID NO: 2 or SEQ ID NO: 30 herein; or one derived from the genus *Thielavia*, such as a strain of *Thielavia terrestris*, such as the one described in WO 2005/074647 as SEQ ID NO: 7 and SEQ ID NO: 8 (hereby incorporated by reference); or one derived from a strain of *Aspergillus*, such as a strain of *Aspergillus fumigatus*, such as the one described in WO 2010/138754 as SEQ ID NO: 1 and SEQ ID NO: 2 (hereby incorporated by reference); or one derived from a strain from *Penicillium*, such as a strain of *Penicillium emersonii*, such as the one disclosed in WO 2011/041397 as SEQ ID NO: 2 or SEQ ID NO: 31 herein.

In one embodiment, the GH61 polypeptide, such as one derived from a strain of *Thermoascus*, is selected from the group consisting of:

(i) a GH61 polypeptide comprising the mature polypeptide of SEQ ID NO: 30 herein;

(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 30 herein.

In one embodiment, the GH61 polypeptide, such as one derived from a strain of *Penicillium* sp., is selected from the group consisting of:

(i) a GH61 polypeptide comprising the mature polypeptide of SEQ ID NO: 31 herein;

(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 31 herein.

In one embodiment, the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed as SEQ ID NO: 6 in WO 2011/057140 or SEQ ID NO: 32 herein, or a strain of the genus *Trichoderma*, such as a strain of *Trichoderma reesei*.

In one embodiment, the cellobiohydrolase I, such as one derived from a strain of *Aspergillus fumigatus*, is selected from the group consisting of:

(i) a cellobiohydrolase I comprising the mature polypeptide of SEQ ID NO: 32 herein;

(ii) a cellobiohydrolase I comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 32 herein.

In one embodiment, the cellulolytic enzyme composition, comprised in an enzyme composition described herein, comprises a cellobiohydrolase II (CBH II), such as one derived from a strain of the genus *Aspergillus*, such as a strain of *Aspergillus fumigatus*; such as the one disclosed as SEQ ID NO: 33 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In one embodiment, cellobiohydrolase II, such as one derived from a strain of *Aspergillus fumigatus*, is selected from the group consisting of:

(i) a cellobiohydrolase II comprising the mature polypeptide of SEQ ID NO: 33 herein;

(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 33 herein.

In one embodiment, the cellulolytic enzyme composition comprises a GH61 polypeptide having cellulolytic enhancing activity and a beta-glucosidase.

In one embodiment, the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, and a beta-glucosidase.

In one embodiment, the cellulolytic enzyme composition comprises a GH61 polypeptide having cellulolytic enhancing activity, a beta-glucosidase, and a CBH I.

In one embodiment, the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, and a CBHII.

In one embodiment, the cellulolytic enzyme composition, comprised in an enzyme composition described herein, comprises a GH61 polypeptide having cellulolytic enhancing activity, a beta-glucosidase, a CBHI, and a CBHII.

In one embodiment, the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 31 herein, a beta-glucosidase, a CBH I, and a CBH II.

In one embodiment, the cellulolytic enzyme composition is a *Trichoderma reesei* cellulolytic composition further comprising *Thermoascus aurantiacus* GH61A polypeptide (SEQ ID NO: 2 in WO 2005/074656 or SEQ ID NO: 30 herein), and *Aspergillus oryzae* beta-glucosidase fusion protein (WO 2008/057637).

In one embodiment, the cellulolytic enzyme composition is a *Trichoderma reesei* cellulolytic enzyme composition further comprising *Thermoascus aurantiacus* GH61A polypeptide having cellulolytic enhancing activity (SEQ ID NO: 2 in WO 2005/074656 or SEQ ID NO: 30 herein) and *Aspergillus fumigatus* beta-glucosidase (SEQ ID NO: 2 of WO 2005/047499 or SEQ ID NO: 29 herein).

In one embodiment, the cellulolytic enzyme composition is a *Trichoderma reesei* cellulolytic composition further comprising *Penicillium* emersonfiGH61A polypeptide disclosed as SEQ ID NO: 2 in WO 2011/041397 or SEQ ID NO: 31 herein, and *Aspergillus fumigatus* beta-glucosidase disclosed as SEQ ID NO: 2 in WO 2005/047499 or SEQ ID NO: 29 herein, or a variant thereof, which variant has one of, preferably all of, the following substitutions: F100D, S283G, N456E, F512Y, and optionally *Aspergillus fumigatus* CBH I, e.g., the one disclosed as SEQ ID NO: 6 in WO2011/057140 and SEQ ID NO: 32 herein and *Aspergillus fumigatus* CBH II, e.g., the one disclosed as SEQ ID NO: 18 in WO 2011/057140 and as SEQ ID NO: 33 herein.

In one embodiment, the cellulolytic enzyme composition comprises one or more of the following components (i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof.

In one embodiment, the *Aspergillus fumigatus* beta-glucosidase (SEQ ID NO: 29 herein), comprises one or more substitutions selected from the group consisting of L89M, G91L, F100D, I140V, I186V, S283G, N456E, and F512Y; such as a variant thereof, with one of the following substitutions or combinations of substitutions:

F100D+S283G+N456E+F512Y;

L89M+G91L+I186V+I140V; and

I186V+L89M+G91L+I140V+F100D+S283G+N456E+F512Y (using SEQ ID NO: 29 for numbering).

In one embodiment, the cellulolytic enzyme composition further comprises the *Penicillium* sp. GH61 polypeptide shown in SEQ ID NO: 31 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 31 herein.

Pullulanase

The enzymes present and/or added to saccharification and/or fermentation may optionally further include a pullulanase. The pullulanase may be of any origin, such as fungal or bacterial origin.

In one embodiment, the pullulanase is derived from a strain of *Bacillus* sp. such as a strain of *Bacillus deramificans*.

Trehalase

The enzymes present and/or added to saccharification and/or fermentation may optionally further include a trehalase.

The trehalase may be of any origin, such as fungal or bacterial origin.

In one embodiment, the trehalase is of fungal origin, such as derived from a strain of *Trichoderma*, such as *Trichoderma reesei*.

Pectinase

The enzymes present and/or added to saccharification and/or fermentation may optionally further include a pectinase, such as a pectin lyase (also known as pectolyase) and/or a polygalacturonase, or a combination thereof.

The pectinase may be of any origin, such as fungal or bacterial origin.

In one embodiment, the pectinase is a pectin lyase (EC 4.2.2.10).

In one embodiment, the pectin lyase is derived from a strain of *Aspergillus*, such as *Aspergillus niger*.

In one embodiment, the pectinase is a polygalacturonase (EC. 3.2.1.15).

In one embodiment, the polygalacturonase is derived from a strain of *Aspergillus*, such as *Aspergillus aculeatus*.

In one embodiment, the pectinase is a combination of pectin lyase and polygalacturonase. In one embodiment, the pectinase is a combination of pectin lyase derived from *Aspergillus niger* and polygalacturonase derived from *Aspergillus aculeatus*.

Examples of Enzymes (e.g., Blend) Suitable for Use in a Raw Starch Hydrolysis Process In one embodiment, enzymes (e.g., blend) for use in a process described herein comprise a glucoamylase and an alpha-amylase, and optionally a protease and/or cellulolytic enzyme composition. Other optional enzymes may also be used.

In one embodiment, the enzymes (e.g., blend) used in a process described herein comprises or consists of a glucoamylase from *Trametes cingulata* (e.g., SEQ ID NO: 20) and an alpha-amylase from *Rhizomucor pusillus* with an *Aspergillus nigerglucoamylase* linker and starch-binding domain (SBD), e.g., SEQ ID NO: 16.

In one embodiment, the enzymes (e.g., blend) used in a process described herein comprises the *Gloeophyllum trabeum* glucoamylase (e.g., SEQ ID NO: 17 herein) having one or more of the following substitutions: S95P, A121P, preferably S95P+A121P and an alpha-amylase, preferably an alpha-amylase derived from *Rhizomucor pusillus* with an *Aspergillus niger* glucoamylase linker and starch-binding domain (SBD), shown in SEQ ID NO: 16 herein, preferably having one or more of the following substitutions: G128D, D143N, preferably G128D+D143N.

In another embodiment, the enzymes (e.g., blend) used in a process described herein comprises the *Pycnoporus sanguineus* glucoamylase shown in SEQ ID NO: 18 herein and an alpha-amylase, preferably one derived from *Rhizomucor pusillus* with a linker and starch-binding domain (SBD), preferably *Rhizomucor pusillus* with an *Aspergillus niger-glucoamylase* linker and starch-binding domain (SBD), in particular the one shown in SEQ ID NO: 16 herein, preferably having one or more of the following substitutions: G128D, D143N, especially G128D+D143N.

In one embodiment, the enzymes (e.g., blend) used in a process described herein comprises the *Gloeophyllum sepiarium* glucoamylase shown in SEQ ID NO: 15 herein and an alpha-amylase, preferably an alpha-amylase derived from *Rhizomucor pusillus* with a linker and starch-binding domain (SBD), preferably *Rhizomucor pusillus* alpha-amylase with an *Aspergillus nigerglucoamylase* linker and starch-binding domain (SBD) shown in SEQ ID NO: 16 herein, preferably having one or more of the following substitutions: G128D, D143N, preferably G128D+D143N.

In one embodiment, the enzymes (e.g., blend) used in a process described herein comprises the *Trametes cingulata* glucoamylase shown in SEQ ID NO: 20 herein and an alpha-amylase, preferably an alpha-amylase derived from *Rhizomucor pusillus* with an *Aspergillus nigerglucoamylase* linker and starch-binding domain (SBD), shown in SEQ ID NO: 16 herein, having one or more of the following substitutions: G128D, D143N, preferably G128D+D143N.

In one embodiment, the enzymes (e.g., blend) used in a process described herein comprises
 i) fungal glucoamylase;
 ii) fungal alpha-amylase;
 iii) cellulolytic enzyme composition derived from a strain of *Trichoderma reesei*, further comprising a GH61 polypeptide, beta-glucosidase, CBH I and CBH II;
 iv) optionally a protease.

In one embodiment, the enzymes (blend) used in a process described herein comprises
 i) *Trametes cingulata* glucoamylase;
 ii) *Rhizomucor pusillus* alpha-amylase, or variant thereof;
 iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
 iv) optionally a protease from *Thermoascus aurantiacus*, or variant thereof.

In one embodiment, the enzymes (e.g., blend) used in a process described herein comprises a
 i) *Trametes cingulata* glucoamylase;
 ii) *Rhizomucor pusillus* alpha-amylase, or variant thereof;
 iii) cellulolytic enzyme composition derived from a strain of *Trichoderma reesei*, further comprising *Penicillium emersonfiGH61A* polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
 iv) optionally a protease from *Pyropoccus furiosus*.

In one embodiment, the enzymes (e.g., blend) used in a process described herein comprises
 i) glucoamylase derived from *Trametes cingulata*;
 ii) alpha-amylase derived from *Rhizomucor pusillus* with an *Aspergillus niger* glucoamylase linker and starch-binding domain (SBD), or a variant thereof;
 iii) cellulolytic enzyme composition derived from a strain of *Trichoderma reesei*;
 iv) optionally a protease from *Thermoascus aurantiacus*, or a variant thereof and/or *Pyrococcus furiosus*.

In one embodiment, the enzymes (e.g., blend) used in a process described herein comprises
  i) fungal glucoamylase;
  ii) fungal alpha-amylase;
  iii) cellulolytic enzyme composition derived from a strain of *Trichoderma reesei*, further comprising a GH61 polypeptide, beta-glucosidase CBH I and CBH II;
  iv) pectinase, preferably a pectin lyase or a polygalacturonase, or a combination thereof.

In one embodiment, the pectinase is a combination of pectin lyase derived from *Aspergillus niger* and polygalacturonase derived from *Aspergillus aculeatus*.

In one embodiment, the pectinase is a combination of pectin lyase and polygalacturonase. In one embodiment, the pectinase is a combination of pectin lyase derived from *Aspergillus niger* and polygalacturonase derived from *Aspergillus aculeatus*.

In one embodiment, the enzymes (e.g., blend) used in a process described herein comprises
  i) fungal glucoamylase;
  ii) fungal alpha-amylase;
  iii) pectinase, preferably a pectin lyase or a polygalacturonase, or a combination thereof;
  iv) cellulolytic enzyme composition derived from a strain of *Trichoderma reesei*, further comprising a GH61 polypeptide, beta-glucosidase CBH I and CBH II;
  v) protease.

In one embodiment, the enzymes (e.g., blend) used in a process described herein comprises a
  i) fungal glucoamylase;
  ii) fungal alpha-amylase;
  iii) cellulolytic enzyme composition derived from a strain of *Trichoderma reesei*, further comprising a GH61 polypeptide, beta-glucosidase, CBH I and CBH II;
  iv) optionally a protease.

In one embodiment, the enzymes (e.g., blend) used in a process described herein comprises
  i) *Trametes cingulata* glucoamylase;
  ii) *Rhizomucor pusillus* alpha-amylase, or variant thereof;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
  iv) pectin lyase derived from *Aspergillus niger* or polygalacturonase derived from *Aspergillus aculeatus*, or a combination thereof;
  v) protease from *Thermoascus aurantiacus*, or a variant thereof and/or *Pyrococcus furiosus*.

In one embodiment, the enzymes (blend) used in a process described herein comprises
  i) *Gloeophyllum trabeum* glucoamylase shown in SEQ ID NO: 18 herein having one or more of the following substitutions: S95P, A121P, such as S95P+A121P;
  ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

In one embodiment, the enzymes (e.g., blend) used in a process described herein comprises
  i) *Pycnoporus sanguineus* glucoamylase shown in SEQ ID NO: 18 herein;
  ii) alpha-amylase derived from *Rhizomucor pusillus* with an *Aspergillus niger* glucoamylase linker and starch-binding domain (SBD), shown in SEQ ID NO: 16 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

In one embodiment, the enzymes (e.g., blend) used in a process described herein comprises
  i) *Gloeophyllum sepiarium* glucoamylase shown in SEQ ID NO: 15 herein;
  ii) alpha-amylase derived from *Rhizomucor pusillus* with an *Aspergillus niger* glucoamylase linker and starch-binding domain (SBD), shown in SEQ ID NO: 16 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

In one embodiment, the enzymes (e.g., blend) used in a process described herein comprises
  i) *Trametes cingulata* glucoamylase shown in SEQ ID NO: 20 herein;
  ii) alpha-amylase derived from *Rhizomucor pusillus* with an *Aspergillus niger* glucoamylase linker and starch-binding domain (SBD), shown in SEQ ID NO: 16 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

Examples of Raw Starch Hydrolysis Processes

In one embodiment, a process of producing ethanol from starch-containing material comprises:
  (i) saccharifying starch-containing material at a temperature below the initial gelatinization temperature; and
  (ii) fermenting using a fermentation organism;
  wherein
    saccharification and/or fermentation is done in the presence of the following enzymes: glucoamylase and alpha-amylase, and optionally protease and/or cellulolytic enzyme composition; and
    the fermenting organism is a *Saccharomyces* yeast strain providing an ethanol yield boost compared to ETHANOL RED™ under the same fermentation conditions.

In one embodiment, the process provides one or more, such as all, of the following improvement:

an ethanol yield boost compared to ETHANOL RED™ under the same fermentation conditions (e.g., conditions as described herein);

reduced acetaldehyde production compared to ETHANOL RED™ under the same process conditions (e.g., conditions as described herein);

increased temperature tolerance compared to ETHANOL RED™ under the same process conditions (e.g., conditions as described herein);

decreased glycerol production compared to ETHANOL RED™ under the same process conditions (e.g., conditions as described herein). In one embodiment is a process for producing ethanol from starch-containing material comprising:
(i) saccharifying starch-containing material at a temperature below the initial gelatinization temperature; and
(ii) fermenting using a fermentation organism;
wherein
saccharification and/or fermentation is done in the presence of the following enzymes: glucoamylase and alpha-amylase, and optionally protease and/or cellulolytic enzyme composition; and
the fermenting organism is a *Saccharomyces* yeast which provides one or more, such as all of the following improvements:
boosts ethanol yield;
reduces acetaldehyde production;
increased temperature tolerance; and
decreases glycose production.

In one embodiment, the process provides one or more, such as all, of the following improvement:

boosts the ethanol yield over ETHANOL RED™ (ER) of more than 0.5%, e.g., more than 1.0%, more than 2.0%, more than 2.5%, such as about 2.9%, such as between 0.5 and 5%, such as between 1-3%, under the same process conditions (e.g., conditions as described herein);

reduces acetaldehyde production more than 10%, preferably more than 20%, more preferably more than 30%, even more preferably more than 40%, especially more than 45%, such as between 5-60%, such as 30-50%, compared to ETHANOL RED™ under the same process conditions (e.g., conditions as described herein);

increases temperature tolerance compared to ETHANOL RED™ under the same process conditions (e.g., conditions as described herein); and decreases glycerol production by more than 3%, preferably more than 4%, more preferably more than 5%, even more preferably more than 6%, especially more than 7%, such as between 2-15%, such as 5-10%, compared to ETHANOL RED™ under the same process conditions, (e.g., conditions as described herein).

In one embodiment is a process of producing ethanol from starch-containing material comprises:
(i) saccharifying starch-containing material at a temperature below the initial gelatinization temperature; and
(ii) fermenting using a fermentation organism;
wherein saccharification and/or fermentation is done in the presence of the following enzymes: glucoamylase and alpha-amylase, and optionally protease; and
wherein the fermenting organism is:
(1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces cerevisiae* strain MBG5038 having defining characteristics of *Saccharomyces cerevisiae* strain MBG5038; or
(2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces cerevisiae* strain MBG5012 having defining characteristics of *Saccharomyces cerevisiae* strain MBG5012.

In one embodiment, the derivative of *Saccharomyces cerevisiae* strain MBG5038 or *Saccharomyces cerevisiae* strain MBG5012 expresses a glucoamylase and/or an alpha-amylase.

In one embodiment, the process of producing ethanol from starch-containing material comprises:
(a) saccharifying a starch-containing material at a temperature below the initial gelatinization temperature; and
(b) fermenting using a fermentation organism;
wherein
saccharification and/or fermentation is done in the presence of the following enzymes:
i) glucoamylase derived from *Trametes cingulata, Gloeophyllum trabeum, Gloeophyllum sepiarium*, or *Pycnoporus sanguineus*;
ii) alpha-amylase derived from *Rhizomucor pusillus* with an *Aspergillus niger* glucoamylase linker and starch-binding domain (SBD), or a variant thereof;
iii) cellulolytic enzyme composition derived from *Trichoderma reesei*;
iv) optionally a protease from *Thermoascus aurantiacus*, or a variant thereof and/or *Pyrococcus furiosus*; and
wherein
the fermenting organism is a *Saccharomyces* yeast strain providing one or more, such as all of the following improvements:

an ethanol yield boost compared to *Saccharomyces cerevisiae* strain Ethanol Red® (deposited under Accession No. V14/007039 at National Measurement Institute, Victoria, Australia) under the same fermentation conditions (e.g., conditions as described herein);

reduced acetaldehyde production compared to *Saccharomyces cerevisiae* strain Ethanol Red® (deposited under Accession No. V14/007039 at National Measurement Institute, Victoria, Australia) under the same process conditions (e.g., conditions as described herein);

increased temperature tolerance compared to *Saccharomyces cerevisiae* strain Ethanol Red® (deposited under Accession No. V14/007039 at National Measurement Institute, Victoria, Australia) under the same process conditions (e.g., conditions as described herein);

decreased glycerol production compared to *Saccharomyces cerevisiae* strain Ethanol Red® (deposited under Accession No. V14/007039 at National Measurement Institute, Victoria, Australia) under the same process conditions (e.g., conditions as described herein).

In one embodiment, the process of producing ethanol from starch-containing material comprises:
(a) saccharifying a starch-containing material at a temperature below the initial gelatinization temperature; and
(b) fermenting using a fermentation organism;
wherein
saccharification and/or fermentation is done in the presence of the following enzymes:
i) glucoamylase derived from *Gloeophyllum trabeum* disclosed in SEQ ID NO: 17, with the following substitutions: S95P+A121P;

ii) alpha-amylase derived from *Rhizomucor pusillus* with an *Aspergillus niger* glucoamylase linker and starch-binding domain (SBD), or a variant thereof, shown in SEQ ID NO: 16 herein, with the following substitutions: G128D+D143N;

iii) cellulolytic enzyme composition derived from *Trichoderma reesei;* iv) optionally a protease from *Thermoascus aurantiacus*, or a variant thereof; and wherein the fermenting organism is a *Saccharomyces* yeast strain providing an ethanol yield boost compared to *Saccharomyces cerevisiae* strain Ethanol Red® (deposited under Accession No. V14/007039 at National Measurement Institute, Victoria, Australia) under the same fermentation conditions (e.g., provides an ethanol yield boost of at least 1.0%, at least 2.0%, at least 2.5%, such as between 0.5-5%, e.g., between 1-3% compared to ETHANOL RED® under the conditions described herein).

In one embodiment, the process of producing ethanol from starch containing material of comprises:

(a) saccharifying a starch-containing material at a temperature below the initial gelatinization temperature; and (b) fermenting using a fermentation organism;

wherein saccharification and/or fermentation is done in the presence of the following enzymes:

i) glucoamylase derived from *Pycnoporus sanguineus* shown in SEQ ID NO: 18;

ii) alpha-amylase derived from *Rhizomucor pusillus* with an *Aspergillus niger* glucoamylase linker and starch-binding domain (SBD), or a variant thereof, shown in SEQ ID NO: 16 herein, with the following substitutions: G128D+D143N;

iii) cellulolytic enzyme composition derived from *Trichoderma reesei;* iv) optionally a protease from *Thermoascus aurantiacus*, or a variant thereof; and wherein the fermenting organism is a *Saccharomyces* yeast strain providing an ethanol yield boost compared to *Saccharomyces cerevisiae* strain Ethanol Red® (deposited under Accession No. V14/007039 at National Measurement Institute, Victoria, Australia) under the same fermentation conditions (e.g., provides an ethanol yield boost of at least 0.5%, at least 1.0%, at least 2.0%, at least 2.5%, such as between 0.5-5%, e.g., between 1-3% under the same conditions compared to ETHANOL RED®).

In one embodiment, the process of producing ethanol from starch-containing material of comprises:

(a) saccharifying a starch-containing material at a temperature below the initial gelatinization temperature; and (b) fermenting using a fermentation organism;

wherein saccharification and/or fermentation is done in the presence of the following enzymes:

i) glucoamylase derived from *Gloeophyllum sepiarium* shown in SEQ ID NO: 15;

ii) alpha-amylase derived from *Rhizomucor pusillus* with an *Aspergillus niger* glucoamylase linker and starch-binding domain (SBD), or a variant thereof, shown in SEQ ID NO: 16 herein, with the following substitutions: G128D+D143N;

iii) cellulolytic enzyme composition derived from *Trichoderma reesei;* iv) optionally a protease from *Thermoascus aurantiacus*, or a variant thereof;

wherein the fermenting organism is a *Saccharomyces* yeast strain providing an ethanol yield boost compared to *Saccharomyces cerevisiae* strain Ethanol Red® (deposited under Accession No. V14/007039 at National Measurement Institute, Victoria, Australia) under the same fermentation conditions (e.g., provides an ethanol yield boost of at least 0.5%, at least 1.0%, at least 2.0%, at least 2.5%, such as between 0.5-5%, e.g., between 1-3% under the conditions defined in Example 18 compared to ETHANOL RED®).

In one embodiment, the process of producing ethanol from starch-containing material of comprises:

(a) saccharifying a starch-containing material at a temperature below the initial gelatinization temperature; and (b) fermenting using a fermentation organism;

wherein saccharification and/or fermentation is done in the presence of the following enzymes:

i) glucoamylase derived from *Trametes cingulata* shown in SEQ ID NO: 20;

ii) alpha-amylase derived from *Rhizomucor pusillus* with an *Aspergillus niger* glucoamylase linker and starch-binding domain (SBD), or a variant thereof, shown in SEQ ID NO: 16 herein, with the following substitutions: G128D+D143N;

iii) cellulolytic enzyme composition derived from *Trichoderma reesei;* iv) optionally a protease from *Thermoascus aurantiacus*, or a variant thereof; and wherein the fermenting organism is a *Saccharomyces* yeast strain providing an ethanol yield boost compared to ETHANOL RED™ under the same fermentation conditions (e.g., provides an ethanol yield boost of at least 0.5%, at least 1.0%, at least 2.0%, at least 2.5%, such as between 0.5-5%, e.g., between 1-3% under the conditions defined in Example 18, compared to ETHANOL RED™).

Use of *Saccharomyces cerevisiae* strain MBG5038, or derivative of *Saccharomyces cerevisiae* strain MBG5038 expressing a glucoamylase and/or an alpha-amylase.

Use of *Saccharomyces cerevisiae* strain MBG5012, or derivative of *Saccharomyces cerevisiae* strain MBG5012 expressing a glucoamylase and/or an alpha-amylase.

*Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038, or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5038 having defining characteristics of strain MBG5012 may be used for increasing the ethanol yield in fermentation.

In one embodiment, the liquefied mash, to be fermented, has been subjected to alpha-amylase and from 0.5-50 micro gram protease per gram DS, such as 1-5 micro gram protease per gram DS, such as about 1.5 or 3 micro gram protease per gram DS.

The protease may be a bacterial protease. The protease may be derived from a strain of the bacterium *Pyrococcus*, such as a strain of *Pyrococcus furiosus* (pfu protease), such as or SEQ ID NO: 13 herein. The protease may be the one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 13 herein.

The alpha-amylase used for liquefying may be of bacterial origin, such as from the genus *Bacillus*, such as a strain of

*Bacillus stearothermophilus*, in particular a variant of a *Bacillus stearothermophilus* alpha-amylase, such as the one shown in SEQ ID NO: 1 herein. In one embodiment, the *Bacillus stearothermophilus* alpha-amylase variant is selected from the group with the following mutations: I181*+G182* and optionally substitution N193F, and further one of the following substitutions or combinations of substitutions:

E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 for numbering).

In one embodiment, the liquefied mash to be fermented, has been subjected to alpha-amylase, glucoamylase and from 0.5-50 micro gram protease per gram DS, such as 1-5 micro gram protease per gram DS such as about 1.5 or 3 micro gram protease per gram DS. The glucoamylase may be derived from a strain of the genus *Penicillium*, especially a strain of *Penicillium oxalicum* disclosed in SEQ ID NOs: 9 or 14 herein.

The glucoamylase may be a variant of the *Penicillium oxalicum* glucoamylase having a K79V substitution (using the mature sequence shown in SEQ ID NO: 14 for numbering).

In one embodiment, the *Penicillium oxalicum* glucoamylase has a K79V substitution (using SEQ ID NO: 14 for numbering) and further one of the following substitutions or combinations of substitutions:

P11F+T65A+Q327F; and
P2N+P4S+P11F+T65A+Q327F (using SEQ ID NO: 14 for numbering).

Yeast

In one embodiment is a strain of *Saccharomyces cerevisiae* deposited under the Budapest Treaty at the Agricultural Research Service Patent Culture Collection (NRRL) having deposit accession no. NRRL Y67549 (*Saccharomyces cerevisiae* strain MBG5038), or a derivative thereof expressing a glucoamylase and/or an alpha-amylase.

In one embodiment is a strain of *Saccharomyces cerevisiae* deposited under the Budapest Treaty at the Agricultural Research Service Patent Culture Collection (NRRL) having deposit accession no. NRRL Y67700 (*Saccharomyces cerevisiae* strain MBG5012), or a derivative thereof expressing a glucoamylase and/or an alpha-amylase.

The majority of the world's fuel ethanol is produced by industrial scale fermentation of starch-based sugars, in substrates such as corn mash. During industrial scale fermentation, the yeast encounter various physiological challenges including variable concentrations of sugars, high concentrations of yeast metabolites such as ethanol, glycerol, organic acids, osmotic stress, as well as potential competition from contaminating microbes such as wild yeasts and bacteria. As a consequence, many *Saccharomyces* strains, particularly those that are naturally occurring, are not suitable for use in industrial fermentation. A widely used commercially available industrial strain of *Saccharomyces* (i.e. for industrial scale fermentation) is the *Saccharomyces cerevisiae* strain used, for example, in the product ETHANOL RED™. This strain is well suited to industrial ethanol production, however improved strains of *Saccharomyces cerevisiae* are needed.

The Applicants have produced strain NMI V14/004037 (See, WO2015/143324 and WO2015/143317), which is a strain of *Saccharomyces cerevisiae* which produces higher levels of ethanol from corn mash than naturally occurring strains of *Saccharomyces cerevisiae*, and strains of *Saccharomyces cerevisiae* used in the fuel ethanol industry such as ETHANOL RED™. In particular, strain NMI V14/004037 has an ethanol yield from glucose that is higher than other industrial strains such as ETHANOL RED™ during fermentation of corn mash. This means that strain NMI V14/004037 can produce more ethanol per gram of glucose than ETHANOL RED™ during fermentation of corn mash.

The Applicants have further produced strain no. V15/004035, V15/004036, and V15/004037 (See, WO 2016/153924) which are capable of ethanol yields from glucose that are the same or similar to strain V14/004037 under the conditions encountered in industrial scale fermentation, such as those encountered during fermentation of corn mash, and which are higher than commercially available industrial *Saccharomyces cerevisiae* strains used in the ethanol industry and naturally occurring strains of *Saccharomyces cerevisiae*.

The Applicants have further produced stain no. NRRL Y67549 and NRRL Y67700 as described herein which demonstate improved properties as described in the Examples.

The Applicants have further produced derivatives of strain nos. NRRL Y67549 and NRRL Y67700 as described herein which express a glucoamylase and demonstate improved properties as described in the Examples.

Typically, the ethanol produced from fermentation of corn mash is produced from fermentation of sugars that are endogenous to the corn mash. Sugars that are endogenous to the corn mash are sugars that are derived from the corn rather than sugars that are added from an exogenous source.

The ability to produce ethanol rapidly in the first 20 hours of fermentation, the ethanol yield after 50 hours of fermentation, and the ability to utilize much of the glucose present in corn mash substrate within 50 hours of fermentation, are all features which can distinguish the strains herein from naturally occurring strains, and commercially available industrial strains of *Saccharomyces cerevisiae*.

Additionally, *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) and *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) are capable of growth in media in which cysteine is the sole nitrogen source. As a consequence, the ability of strains *Saccharomyces cerevisiae* strain MBG5038 and MBG 5012 to utilize cysteine as the sole nitrogen source is a further characteristic which distinguishes this strain from:

(a) contaminating strains of *Saccharomyces* that do not utilize cysteine as a sole nitrogen source; and (b) other strains used in the ethanol industry that do not have the ethanol producing capabilities of *Saccharomyces cerevisiae* strain MBG5038 or MBG5012; and/or do not utilize cysteine as the sole nitrogen source.

As a result of its ability to utilize cysteine as a sole nitrogen source, *Saccharomyces cerevisiae* strains MBG5038 and MBG5012 are readily differentiated from current strains of *Saccharomyces* that are used in the ethanol industry such as Ethanol Red®. The strain may also be a derivative of *Saccharomyces cerevisiae* strain MBG5038 or MBG5012. As used herein, a "derivative" of *Saccharomyces cerevisiae* strain MBG5038 or MBG5012 is a strain derived from said strain, such as through mutagenesis, recombinant DNA technology, mating, cell fusion, or cytoduction between yeast strains. The strain derived from *Saccharomyces cerevisiae* strain MBG5038 or MBG5012 may be a direct progeny (i.e. the product of a mating between *Saccharomyces cerevisiae* strain MBG5038 or MBG5012, and another strain or itself), or a distant progeny resulting from an initial mating between *Saccharomyces cerevisiae* strain MBG5038 or MBG5012 and another strain or itself, followed by a large number of subsequent matings.

In one embodiment, a derivative of *Saccharomyces cerevisiae* strain MBG5038 or MBG5012 is a hybrid strain produced by culturing a first yeast strain with *Saccharomyces cerevisiae* strain MBG5038 or MBG5012 under conditions which permit combining of DNA between the first yeast strain and *Saccharomyces cerevisiae* strain MBG5038 or MBG5012.

In one embodiment, a recombinant derivative of *Saccharomyces cerevisiae* strain MBG5038 or MBG5012 has been prepared by genetically modifying *Saccharomyces cerevisiae* strain MBG5038 or MBG5012 (or another derivative thereof) to express an alpha-amylase and/or glucoamylase described herein.

In one embodiment is a method of producing a recombinant derivative of

*Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) comprising:

(a) transforming *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012) with one or more expression vectors encoding a glucoamylase and/or an alpha-amylase; and (b) isolating the transformed strain.

In one embodiment, a derivative of *Saccharomyces cerevisiae* strain MBG5038 or MBG5012 may be prepared by:

(a) culturing a first yeast strain with a second yeast strain, wherein the second yeast strain is *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012), under conditions which permit combining of DNA between the first yeast strain and the second yeast strain; and (b) isolating hybrid strains; and (c) optionally repeating steps (a) and (b) using a hybrid strain isolated in step (b) as the first yeast strain and/or the derivative of *Saccharomyces cerevisiae* strain MBG5038 or MBG5012.

In one embodiment, the derivative of *Saccharomyces cerevisiae* strain MBG5038 or MBG5012 exhibits one or more defining characteristics of *Saccharomyces cerevisiae* strain MBG5038 or MBG5012. Derivatives of *Saccharomyces* which exhibit one or more defining characteristics of *Saccharomyces cerevisiae* strain MBG5038 or MBG5012 are produced using *Saccharomyces cerevisiae* strain MBG5038 or MBG5012, respectively. In this regard, *Saccharomyces cerevisiae* strain MBG5038 or MBG5012 forms the basis for preparing other strains having the defining characteristics of *Saccharomyces cerevisiae* strain MBG5038 or MBG5012, respectively. For example, strains of *Saccharomyces* which exhibit one or more defining characteristics of *Saccharomyces cerevisiae* strain MBG5038 or MBG5012 can be derived from *Saccharomyces cerevisiae* strain MBG5038 of MBG5012, respectively using methods such as classical mating, cell fusion, or cytoduction between yeast strains, mutagenesis or recombinant DNA technology.

In one embodiment, a derivative of *Saccharomyces cerevisiae* strain MBG5038 which exhibits one or more defining characteristics of *Saccharomyces cerevisiae* strain MBG5038 or MBG5012 may be produced by:

(a) culturing a first yeast strain with a second yeast strain, wherein the second yeast strain is *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012), under conditions which permit combining of DNA between the first yeast strain and the second yeast strain;

(b) screening or selecting for a derivative of *Saccharomyces cerevisiae* strain MBG5038 or MBG5012, such as screening or selecting for a derivative with increased ethanol production in corn mash compared to the first strain;

(c) optionally repeating steps (a) and (b) with the screened or selected strain as the first yeast strain and/or the second yeast strain, until a derivative of *Saccharomyces cerevisiae* strain MBG5038 or MBG5012 is obtained which exhibits one or more defining characteristics of *Saccharomyces cerevisiae* strain MBG5038 or MBG5012.

The first yeast strain may be any strain of yeast if the DNA of the strain can be combined with the second yeast strain using methods such as classical mating, cell fusion or cytoduction. Typically, the first yeast strain is a *Saccharomyces* strain. More typically, the first yeast strain is a *Saccharomyces cerevisiae* strain. *Saccharomyces cerevisiae* is as defined by Kurtzman (2003) FEMS Yeast Research vol 4 pp. 233-245. The first yeast strain may have desired properties which are sought to be combined with the defining characteristics of *Saccharomyces cerevisiae* strain MBG5038 or MBG5012. The first yeast strain may be, for example, any *Saccharomyces cerevisiae* strain, such as for example ETHANOL RED®. It will also be appreciated that the first yeast strain may be *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012).

The first and second yeast strains are cultured under conditions which permit combining of DNA between the yeast strains. As used herein, "combining of DNA" between yeast strains refers to combining of all or a part of the genome of the yeast strains. Combining of DNA between yeast strains may be by any method suitable for combining DNA of at least two yeast cells, and may include, for example, mating methods which comprise sporulation of the yeast strains to produce haploid cells and subsequent hybridising of compatible haploid cells; cytoduction; or cell fusion such as protoplast fusion.

In one embodiment, culturing the first yeast strain with the second yeast, under conditions which permit combining of DNA between the first yeast strain and the second yeast strain, comprises:

(i) sporulating the first yeast strain and the second yeast strain;

(ii) germinating and hybridizing spores produced by the first yeast strain with spores produced by the second yeast strain.

In one embodiment, the method of producing a derivative of *Saccharomyces cerevisiae* strain MBG5038 or MBG5012 which exhibits one or more defining characteristics of *Saccharomyces cerevisiae* strain MBG5038 or MBG5012, comprises:

(a) providing: (i) a first yeast strain; and (ii) a second yeast strain, wherein the second yeast strain is *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012);

(b) sporulating the first yeast strain and the second yeast strain;

(c) germinating and hybridising the spores of the first yeast strain with germinated spores of the second yeast strain;

(d) screening or selecting for a derivative of *Saccharomyces cerevisiae* strain MBG5038 or MBG5012, such as screening or selecting for a derivative with increased ethanol production in 20 hrs of fermentation in corn mash compared to the first strain, and/or higher ethanol yield from glucose during fermentation of corn mash than the first strain;

(e) optionally repeating steps (b) to (d) with the screened or selected strain as the first and/or second yeast strain.

Methods for sporulating, germinating and hybridising yeast strains, and in particular, *Saccharomyces* strains, are known in the art and are described in, for example, Ausubel, F. M. et al., (1997) Current Protocols in Molecular Biology, Volume 2, pages 13.2.1 to 13.2.5 (John Willey & Sons Inc); Chapter 7, "Sporulation and Hybridisation of yeast" by R. R. Fowell, in "The Yeasts" vol 1, A. H. Rose and J. S. Harrison (Eds), 1969, Academic Press.

In one embodiment, the yeast strains may be cultured under conditions which permit cell fusion. Methods for the generation of intraspecific or interspecific hybrids using cell fusion techniques are described in, for example, Spencer et al. (1990) in, Yeast Technology, Spencer J F T and Spencer D M (Eds), Springer Verlag, New York.

In another embodiment, the yeast strains may be cultured under conditions which permit cytoduction. Methods for cytoduction are described in, for example, Inge-Vechymov et al. (1986) Genetika 22: 2625-2636; Johnston (1990) in, Yeast technology, Spencer J F T and Spencer D M (Eds), Springer Verlag, New York.

In one embodiment, screening or selecting for derivatives of *Saccharomyces cerevisiae* strain MBG5038 or MBG5012 comprises screening or selecting for a derivative with increased ethanol production in the first 20 hours of fermentation of corn mash compared to the first strain, and/or screening or selecting for a hybrid which has a higher ethanol yield from glucose in corn mash compared to the first strain.

As used herein, "ethanol yield from glucose" is the yield of ethanol that would be achieved from glucose if all of the glucose in a substrate were used in the fermentation. In one embodiment, ethanol yield from glucose is calculated as follows:

$$(G \times 0.51) + E$$

wherein

G=% weight/volume glucose remaining following fermentation of the glucose-containing substrate; and E=% weight/volume of ethanol present following fermentation of the glucose-containing substrate.

The derivatives may be screened or selected for ethanol yields by screening for one or more of the following characteristics:

(a) produces a % w/v of acetate that is in the range from an amount higher than that produced by strain Ethanol Red® to the amount produced by *Saccharomyces cerevisiae* strain MBG5038 or MBG5012, under the same conditions in a corn mash fermentation;

(b) produces a ratio of % w/v glycerol to % w/v acetate that is in the range from less than the ratio of % w/v glycerol to % w/v acetate produced by Ethanol Red® to the ratio of % w/v glycerol to % w/v acetate produced by *Saccharomyces cerevisiae* strain MBG5038 or MBG5012, under the same conditions in a corn mash fermentation;

(c) produces a ratio of % w/v ethanol to % w/v acetate that is in the range from less than the ratio of % w/v ethanol to % w/v acetate produced by Ethanol Red® to the ratio of % w/v ethanol to % w/v acetate produced by *Saccharomyces cerevisiae* strain MBG5038 or MBG5012, under the same conditions in a corn mash fermentation.

Methods for determining the amount of ethanol, glycerol and acetate produced by a strain are known in the art. For example, methods for testing for determining the amount of ethanol, glycerol and acetate produced by a strain during fermentation of corn mash are described in, for example, WO 2011/035392. Once the amount of ethanol, glycerol and acetate produced are known, the ratio of ethanol/acetate and glycerol/acetate can be readily determined. Accordingly, strains can be readily screened for production levels of ethanol, acetate and/or glycerol using known methods.

In one embodiment, a derivative of *Saccharomyces cerevisiae* strain MBG5038 or MBG5012 which exhibits one or more defining characteristics of *Saccharomyces cerevisiae* strain MBG5038 or MBG5012 may be a mutant of *Saccharomyces cerevisiae* strain MBG5038 or MBG5012. Methods for producing mutants of *Saccharomyces* yeast, and specifically mutants of *Saccharomyces cerevisiae*, are known in the art and described in, for example, Lawrence C. W. (1991) Methods in Enzymology, 194: 273-281.

In another embodiment, a derivative of *Saccharomyces cerevisiae* strain MBG5038 or MBG5012 which exhibits one or more defining characteristics of *Saccharomyces cerevisiae* strain MBG5038 or MBG5012 may be a recombinant derivative of *Saccharomyces cerevisiae* strain MBG5038 or MBG5012. A recombinant derivative of *Saccharomyces cerevisiae* strain MBG5038 or MBG5012 is a strain produced by introducing into *Saccharomyces cerevisiae* strain MBG5038 or MBG5012, respectively, a nucleic acid using recombinant DNA technology. Methods for the introduction of nucleic acid into *Saccharomyces* yeast cells, and in particular strains of *Saccharomyces*, are known in the art and are described in, for example, Ausubel, F. M. et al. (1997), Current Protocols in Molecular Biology, Volume 2, pages 13.7.1 to 13.7.7, published by John Wiley & Sons Inc.

Also described are methods for the production of ethanol using the strain described herein. In one form, *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012) is incubated with a substrate comprising fermentable sugars under conditions that allow fermentation of the fermentable sugars. The fermentable sugars may be one or more of glucose, galactose, maltose, fructose and sucrose. Typically, the fermentable sugar is glucose. While strains *Saccharomyces cerevisiae* strain MBG5038 and MBG5012 are well suited to fermentation in corn mash, it is envisaged the strain may also be suitable for other fermentation processes. Accordingly, the source of the fermentable sugar in the substrate may be, for example, hydrolysed starch, hydrolysed cellulose, molasses, cane juice, grape juice, fruit juice, glucose, maltodextrins, raw sugar juice, galactose, sucrose, or any other forms of fermentable sugars. In one form, the source of fermentable sugar in the substrate is hydrolysed starch. Typically, the starch is obtained from a substrate such as corn mash. In preparing the substrate, the grain is typically ground and mixed with water and hydrolytic enzyme(s) under conditions which result in hydrolysis of the starch and release of fermentable sugars such as glucose. Typical enzymes for hydrolysis of the starch include α-amylase, amyloglucosidase, pullulanase, alpha-amylase, glucoamylase, or mixtures thereof. Enzymes suitable for hydrolysis are available from, for example, Novozymes or Genencor Inc. In one form, substrate is provided in the form of corn mash. Corn mash is typically produced by: (a) grinding corn to form a meal; (b) mixing the meal with water; and (c) hydrolyzing the starch in the corn meal. Methods for preparation of corn mash are known in the art and described in, for example, Thomas, K. C. et al., (2001) Journal of Applied Microbiology, volume 90, pages 819-828. Methods for the preparation of other starch-based substrates including sorghum, starch streams and combinations thereof are also known in the art and described in, for example, Kwiatkowski J. R. et al. (2003) Industrial Crops and Products 23: 288-296 and Bothast R. J. and Schlicher M. A. (2005) Applied Microbial Biotechnology 67: 19-25

The fermentation is carried out at a temperature which permits fermentation of the fermentable sugars. Typically, the temperature at which the fermentation is carried out is from 25-34° C.

The fermentation results in an alcoholic mash comprising ethanol and residual sugars in solution, and a particulate portion comprising residual solids including yeast. Ethanol is isolated from the mash using methods know in the art such as distillation or filtration.

Methods for fermentation and distillation are known in the art and are described in, for example, Kwiatkowski J. R. et al. (2003) Industrial Crops and Products 23: 288-296 and Bothast R. J. and Schlicher M. A. (2005) Applied Microbial Biotechnology 67: 19-25

Also contemplated are methods of producing distiller's grain. Distiller's grains may be produced from the residual solids produced in the fermentation using methods known in the art and described in, for example, U.S. Pat. No. 7,572,353. Because *Saccharomyces cerevisiae* strains MBG5038 and MBG5012 reduce the level of residual sugars remaining following fermentation, the distiller's grain which results from fermentation using *Saccharomyces cerevisiae* strain MBG5038 or MBG5012 has a lowered glucose content and is therefore more stable and less prone to charring, caramelisation or contamination with unwanted microorganisms.

Furthermore, lower glycerol content in distiller's grains is a process advantage because less time is required for drying the distiller's grains. In addition, less glycerol in the distiller's grains results in improved flowability, and further results in distiller's grains which has a higher nutrient content (e.g. higher protein).

A further aspect provides dried or compressed yeast comprising *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012), typically having the defining characteristics of *Saccharomyces cerevisiae* strain MBG5038 or MBG5012.

A further aspect provides a composition comprising *Saccharomyces cerevisiae* strain MBG5038 (or a derivative of *Saccharomyces cerevisiae* strain MBG5038) or *Saccharomyces cerevisiae* strain MBG5012 (or a derivative of *Saccharomyces cerevisiae* strain MBG5012). The composition may be, for example, cream yeast, compressed yeast, wet yeast, dry yeast, semi-dried yeast, crumble yeast, stabilized liquid yeast or frozen yeast. Methods for preparing such yeast compositions are known in the art.

In some embodiments, the derivative of *Saccharomyces cerevisiae* strain MBG5038 or MBG5012 expresses a glucoamylase and/or an alpha-amylase. The derivatives expressing glucoamylase and/or alpha-amylase have been generated in order to improve ethanol yield and to improve process economy by cutting enzyme costs since part or all of the necessary enzymes needed to hydrolyse starch will be produced by the yeast organism.

One aspect of the present invention therefore relates to yeast strains comprising one or more expression vectors encoding a glucoamylase and/or an alpha-amylase, wherein the yeast is derived from a parent *Saccharomyces cerevisiae* strain MBG5038 or MBG5012; and wherein the glucoamylase is selected from glucoamylases obtainable from *Gloeophyllum, Pycnoporous, Trametes*.

Another aspect of the present invention therefore relates to yeast strain comprising one or more expression vectors encoding a glucoamylase and/or an alpha-amylase, wherein the yeast is derived from a parent *Saccharomyces cerevisiae* strain MBG5038 or MBG5012; and wherein the alpha-amylase is selected from a *Rhizomucor pusillus* or *Aspergillus terreus* alpha-amylase.

In one embodiment the the glucoamylase is selected from a *Gloeophyllum trabeum, Gloeophyllum sepiarium*, or *Gloeophyllum* abietinum glucoamylase.

In another embodiment the glucoamylase is selected from the group consisting of:

(i) a glucoamylase comprising the polypeptide of SEQ ID NO: 15 or SEQ ID NO: 17;

(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 or SEQ ID NO: 17.

In one embodiment the the glucoamylase is the *Gloeophyllum trabeum* glucoamylase shown in SEQ ID NO: 17 having one of the following substitutions: V59A; S95P; A121P; T119W; S95P+A121P; V59A+S95P; S95P+T119W; V59A+S95P+A121P; or S95P+T119W+A121P, especially S95P+A121P; and wherein the glucoamylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 17.

In one particular embodiment the glucoamylase is selected from a *Trametes cingulata* glucoamylase. More particularly the glucoamylase is selected from the group consisting of:

(i) a glucoamylase comprising the polypeptide of SEQ ID NO: 20;

(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20.

In one particular embodiment the glucoamylase is selected from a *Pycnoporus sanguineus* glucoamylase. More particularly the glucoamylase is selected from the group consisting of:

(i) a glucoamylase comprising the polypeptide of SEQ ID NO: 18;

(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.

In another particular embodiment the alpha-amylase is *Rhizomucor pusillus* alpha-amylase with an *Aspergillus niger* glucoamylase linker and starch-binding domain (SBD) as shown in SEQ ID NO: 16, preferably one having at least one of the following substitutions or combinations of substitutions: D165M; Y141W; Y141R; K136F; K192R; P224A; P224R; S123H+Y141W; G205+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 16 for numbering), and wherein the alpha-amylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.

In another embodiment, the alpha-amylase is an *Aspergillus terreus* alpha-amylase. More particularly the alpha-amylase is selected from the group consisting of:

(i) an alpha-amylase comprising the polypeptide of SEQ ID NO: 6 of WO2017/087330 (the content of which is incorporated by reference);

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 of WO2017/087330.

Compositions

This aspect relates to a formulated *Saccharomyces* yeast composition comprising a yeast strain described herein and a naturally occurring and/or a nonenaturally occurring component.

As mentioned above a *Saccharomyces* yeast strain described herein may be in any viable form, including crumbled, dry, including active dry and instant, compressed, cream (liquid) form etc. In one embodiment, the *Saccharomyces cerevisiae* yeast strain is dry yeast, such as active dry yeast or instant yeast. In one embodiment, the *Saccharomyces cerevisiae* yeast strain is crumbled yeast. In one embodiment, the *Saccharomyces cerevisiae* yeast strain is compressed yeast. In one embodiment, the *Saccharomyces cerevisiae* yeast strain is cream yeast.

In one embodiment is a composition comprising a *Saccharomyces* yeast described herein, in particular *Saccharomyces cerevisiae* strain MBG5038 or MBG5012 and one or more of the component selected from the group consisting of: surfactants, emulsifiers, gums, swelling agent, and anti-oxidants and other processing aids.

Surfactant

The compositions described herein may comprise a *Saccharomyces* yeast described herein, in particular *Saccharomyces cerevisiae* strain MBG5038 or MBG5012 and any suitable surfactants. In one embodiment, the surfactant(s) is/are an anionic surfactant, cationic surfactant, and/or non-ionic surfactant.

Emulsifier

The compositions described herein may comprise a *Saccharomyces* yeast described herein, in particular *Saccharomyces cerevisiae* strain MBG5038 or MBG5012 and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a *Saccharomyces* yeast described herein, in particular *Saccharomyces cerevisiae* strain MBG5038 or MBG5012, and Olindronal SMS, Olindronal SK, or Olindronal SPL including composition concerned in European Patent No. 1,724,336 (hereby incorporated by reference). These products are commercially available from Bussetti, Austria, for active dry yeast.

Gum

The compositions described herein may comprise a *Saccharomyces* yeast described herein, in particular *Saccharomyces cerevisiae* strain MBG5038 or MBG5012 and any suitable gum. In one embodiment, the gum is selected from the group of carob, guar, tragacanth, arabic, xanthan and acacia gum, in particular for cream, compressed and dry yeast.

Swelling Agents

The compositions described herein may comprise a *Saccharomyces* yeast described herein, in particular *Saccharomyces cerevisiae* strain MBG5038 or MBG5012 and any suitable swelling agent. In one embodiment, the swelling agent is methyl cellulose or carboxymethyl cellulose.

Antioxidant

The compositions described herein may comprise a *Saccharomyces* yeast described herein, in particular *Saccharomyces cerevisiae* strain MBG5038 or MBG5012, and any suitable anti-oxidant. In one embodiment, the antioxidant is butylated hydroxyanisol (BHA) and/or butylated hydroxytoluene (BHT), or ascorbic acid (vitamin C), particular for active dry yeast.

The invention may further be described in the following numbered paragraphs:

Paragraph 1. A process for producing ethanol from starch-containing material comprising the steps of:

i) liquefying the starch-containing material at a temperature above the initial gelatinization temperature using an alpha-amylase;

ii) saccharifying using a glucoamylase;

iii) fermenting using a fermenting organism;

wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 2. The process of paragraph 1, wherein the fermenting organism has at least one or more, such as all, of the following properties and defining characteristics:

increases ethanol yield compared to *Saccharomyces cerevisiae* strain Ethanol Red® (deposited under Accession No. V14/007039 at National Measurement Institute, Victoria, Australia) under the same process conditions, e.g., process conditions described herein; and/or decreased glycerol production compared to *Saccharomyces cerevisiae* strain Ethanol Red® (deposited under Accession No. V14/007039 at National Measurement Institute, Victoria, Australia) under the same process conditions, e.g., process conditions described herein.

Paragraph 3. The process of paragraph 1 or 2, wherein the fermenting organism provides an ethanol yield boost over *Saccharomyces cerevisiae* strain Ethanol Red® (deposited under Accession No. V14/007039 at National Measurement Institute, Victoria, Australia) of more than 0.5%, e.g., more than 1.0%, more than 2.0%, more than 2.5%, such as about 2.9%, such as between 0.5 and 5%, such as between 1-3%, under the same process conditions, e.g., conditions as described herein.

Paragraph 4. The process of any of paragraphs 1-3, wherein the fermenting organism reduces acetaldehyde production more than 10%, e.g., more than 20%, more than 30%, more than 40%, more than 45%, such as 5-60%, such as 30-50%, compared to *Saccharomyces cerevisiae* strain Ethanol Red® (deposited under Accession No. V14/007039 at National Measurement Institute, Victoria, Australia) under the same process conditions, e.g., process conditions described herein.

Paragraph 5. The process of any of paragraphs 1-4, wherein the fermenting organism increases temperature tolerance compared to *Saccharomyces cerevisiae* strain Ethanol Red® (deposited under Accession No. V14/007039 at National Measurement Institute, Victoria, Australia) under the same process conditions, e.g., process conditions described herein.

Paragraph 6. The process of any of paragraphs 1-5, wherein the fermenting organism decreases glycerol production by more than 3%, e.g., more than 4%, more than 5%, more than 6%, more than 7%, such as 2-15%, such as 5-10%, compared to *Saccharomyces cerevisiae* strain Ethanol Red® (deposited under Accession No. V14/007039 at National Measurement Institute, Victoria, Australia) under the same process conditions, e.g., conditions described herein.

Paragraph 7. The process of any of paragraphs 1-6, wherein the fermenting organism:

(a) produces a higher titre of ethanol in the first 20 hours of fermentation than *Saccharomyces cerevisiae* strain Ethanol Red® (deposited under Accession No. V14/007039 at National Measurement Institute, Victoria, Australia), under the same conditions in a corn mash fermentation, e.g., conditions described herein;

(b) leaves less glucose remaining following 50 hours of fermentation than *Saccharomyces cerevisiae* strain Ethanol Red® (deposited under Accession No. V14/007039 at National Measurement Institute, Victoria, Australia), under the same conditions in a corn mash fermentation, e.g., conditions described herein;

(c) has a higher ethanol yield than *Saccharomyces cerevisiae* strain Ethanol Red® (deposited under Accession No. V14/007039 at National Measurement Institute, Victoria, Australia) following 50 hours of fermentation under the same conditions in a corn mash fermentation, e.g., conditions described herein.

Paragraph 8. The process of any of paragraphs 1-7, wherein a protease is added in saccharification or fermentation or SSF.

Paragraph 9. The process of any of paragraphs 1-8, further comprises, prior to the liquefaction step i), the steps of:

x) reducing the particle size of the starch-containing material, preferably by dry milling;

y) forming a slurry comprising the starch-containing material and water.

Paragraph 10. The process of any of paragraphs 1-9, wherein at least 50%, e.g., at least 70%, at least 80%, at least 90% of the starch-containing material fits through a sieve with #6 screen.

Paragraph 11. The process of any of paragraphs 1-10, wherein the pH in liquefaction is between 4-7, such as pH 4.5-6.5, such as pH 5.0-6.5, such as pH 5.0-6.0, such as pH 5.2-6.2, such as about 5.2, such as about 5.4, such as about 5.6, such as about 5.8.

Paragraph 12. The process of any of paragraphs 1-11, wherein the temperature in liquefaction is in the range of 70-100° C., such as 75-95° C., 75-90° C., 80-90° C., or 82-88° C., such as about 85° C.

Paragraph 13. The process of any of paragraphs 1-12, wherein a jet-cooking step is carried out prior to liquefaction in step i).

Paragraph 14. The process of paragraph 13, wherein the jet-cooking is carried out at a temperature of 110-145° C., e.g, 120-140° C., such as 125-135° C., or about 130° C. for about 1-15 minutes, e.g., for about 3-10 minutes, or about 5 minutes.

Paragraph 15. The process of any of paragraphs 1-14, wherein saccharification and fermentation is carried out sequentially or simultaneously (SSF).

Paragraph 16. The process of any of paragraphs 1-15, wherein saccharification is carried out at a temperature from 20-75° C., e.g., from 40-70° C., such as about 60° C., and at a pH between 4 and 5.

Paragraph 17. The process of any of paragraphs 1-16, wherein fermentation or simultaneous saccharification and fermentation (SSF) is carried out carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours.

Paragraph 18. The process of any of paragraphs 1-17, wherein the fermentation product is recovered after fermentation, such as by distillation.

Paragraph 19. The process of any of paragraphs 1-18, wherein the fermentation product is an alcohol, preferably ethanol, especially fuel ethanol, potable ethanol and/or industrial ethanol.

Paragraph 20. The process of any of paragraphs 1-19, wherein the starch-containing starting material is whole grains.

Paragraph 21. The process of any of paragraphs 1-20, wherein the starch-containing material is derived from corn, wheat, barley, rye, milo, sago, cassava, manioc, tapioca, sorghum, oats, rice or potatoes.

Paragraph 22. The process of any of paragraphs 1-21, wherein the alpha-amylase used or added in liquefaction step i) is of bacterial origin.

Paragraph 23. The process of any of paragraphs 1-22, wherein the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein.

Paragraph 24. The process of paragraph 23, wherein the *Bacillus stearothermophilus* alpha-amylase or variant thereof is truncated at the C-terminal, preferably to be from 485-495 amino acids long, such as about 491 amino acids long.

Paragraph 25. The process of any of paragraphs 23 or 24, wherein the *Bacillus stearothermophilus* alpha-amylase has a double deletion at positions I181+G182, and optionally substitution N193F, or deletion of R179+G180 (using SEQ ID NO: 1 for numbering).

Paragraph 26. The process of any of paragraphs 23-25, wherein the *Bacillus stearothermophilus* alpha-amylase has a substitution in position S242, e.g., S242Q substitution (using SEQ ID NO: 1 for numbering).

Paragraph 27. The process of any of paragraphs 23-26, wherein the *Bacillus stearothermophilus* alpha-amylase has a substitution in position E188, e.g., E188P substitution (using SEQ ID NO: 1 for numbering).

Paragraph 28. The process of any of paragraphs 1-27, wherein the alpha-amylase has a T½ (min) at pH 4.5, 85° C., 0.12 mM CaCl$_2$) of at least 10, such as at least 15, such as at least 20, such as at least 25, such as at least 30, such as at least 40, such as at least 50, such as at least 60, such as 10-70, such as 15-70, such as 20-70, such as 25-70, such as 30-70, such as 40-70, such as 50-70, such as 60-70.

Paragraph 29. The process of any of paragraphs 1-28, wherein the alpha-amylase present and/or added in liquefaction step i) is selected from the group of *Bacillus stearothermophilus* alpha-amylase variants with one of the following substitutions or combinations of substitutions in addition to I181*+G182*, and optionally substitution N193F:
V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
V59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91L+M96I+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V;
and
V59A+E129V+K177L+R179E+Q254S+M284V;

Paragraph 30. The process of any of paragraphs 1-29, wherein the alpha-amylase present and/or added in liquefaction step i) is selected from the following group of *Bacillus stearothermophilus* alpha-amylase variants comprising the following mutations: I181*+G182*, and optionally substitution N193F, and further one of the following substitutions or combinations of substitutions:
E129V+K177L+R179E;
V59A+Q89R+E129V+K177L+R179E+H208Y+K220P+N224L+Q254S
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 1 herein for numbering).

Paragraph 31. The process of any of paragraphs 1-30, wherein a glucoamylase is present and/or added in saccharification and/or fermentation.

Paragraph 32. The process of paragraph 31, wherein the glucoamylase present and/or added in saccharification, fermentation or simultaneous saccharification and fermentation (SSF) is of fungal origin, preferably from a strain of *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*, or a strain of *Pycnoporus*, or a strain of *Gloeophyllum*, such as *Gloeophyllum serpiarium* or *Gloeophyllum trabeum*, or a strain of the *Nigrofomes*.

Paragraph 33. The process of any of paragraphs 1-32, wherein the glucoamylase is derived from *Talaromyces emersonii*, such as the one shown in SEQ ID NO: 19 herein.

Paragraph 34. The process of any of paragraphs 1-33, wherein the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

Paragraph 35. The process of any of paragraphs 1-34, wherein the glucoamylase present and/or added in saccharification is derived from *Gloeophyllum serpiarium*, such as the one shown in SEQ ID NO: 15 herein.

Paragraph 36. The process of any of paragraphs 1-35, wherein the glucoamylase present and/or added in saccharification is selected from the group consisting of:
(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

Paragraph 37. The process of any of paragraphs 1-36, wherein the glucoamylase present and/or added in saccharification is derived from *Gloeophyllum trabeum* such as the one shown in SEQ ID NO: 17 herein.

Paragraph 38. The process of any of paragraphs 1-37, wherein the glucoamylase present and/or added in saccharification is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

Paragraph 39. The process of any of paragraphs 1-38, wherein the glucoamylase is present and/or added in saccharification and/or fermentation in combination with an alpha-amylase.

Paragraph 40. The process of paragraph 39, wherein the alpha-amylase is present and/or added in saccharification and/or fermentation is of fungal or bacterial origin.

Paragraph 41. The process of paragraph 40 or 41, wherein the alpha-amylase present and/or added in saccharification and/or fermentation is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having a linker and a starch-binding domain, in particular having an *Aspergillus niger* linker and starch-bonding domain, such as the one shown in SEQ ID NO: 16 herein.

Paragraph 42. The process of any of paragraphs 39-41, wherein the alpha-amylase present and/or added in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

Paragraph 43. The process of any of paragraphs 39-42, wherein the alpha-amylase is a variant of the alpha-amylase shown in SEQ ID NO: 16 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; and G128D+Y141W+D143N+K192R; or G128D+Y141W+D143N+K192R+P219C (using SEQ ID NO: 16 for numbering).

Paragraph 44. The process of any of paragraphs 39-43, wherein the alpha-amylase is derived from a *Rhizomucor pusillus* with an *Aspergillus niger* glucoamylase linker and starch-binding domain (SBD), preferably disclosed as SEQ ID NO: 16 herein, e.g., having one or more of the following substitutions: G128D, D143N, such as G128D+D143N (using SEQ ID NO: 16 for numbering).

Paragraph 45. The process of any of paragraphs 39-44, wherein the alpha-amylase variant has at least 75% identity preferably at least 80%, e.g., at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 16 herein.

Paragraph 46. The process of any of paragraphs 1-42, wherein liquefaction step i) is carried out using:
an alpha-amylase;
a protease having a thermostability value of more than 20% determined as Relative Activity at 80° C./70° C.; and
optionally a glucoamylase.

Paragraph 47. The process of 46, wherein the protease with a thermostability value of more than 25% determined as Relative Activity at 80° C./70° C.

Paragraph 48. The process of paragraphs 46-47, wherein the protease has a thermostability of more than 30%, e.g., more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

Paragraph 49. The process of any of paragraphs 46-48, wherein the protease has a thermostability of between 20 and 50%, such as between 20 and 40%, such as 20 and 30% determined as Relative Activity at 80° C./70° C.

Paragraph 50. The process of any of paragraphs 46-49, wherein the protease has a thermostability of between 50 and 115%, such as between 50 and 70%, such as between 50 and 60%, such as between 100 and 120%, such as between 105 and 115% determined as Relative Activity at 80° C./70° C.

Paragraph 51. The process of any of paragraphs 46-50, wherein the protease has a thermostability of more than 10%, e.g., more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

Paragraph 52. The process of any of paragraphs 46-51, wherein the protease has a thermostability of between 10 and 50%, such as between 10 and 30%, such as between 10 and 25% determined as Relative Activity at 85° C./70° C.

Paragraph 53. The process of any of paragraphs 46-52, wherein the protease has a thermostability above 60%, such as above 90%, such as above 100%, such as above 110% at 85° C. as determined using the Zein-BCA assay.

Paragraph 54. The process of any of paragraphs 46-53, wherein the protease has a themostability between 60-120, such as between 70-120%, such as between 80-120%, such as between 90-120%, such as between 100-120%, such as 110-120% at 85° C. as determined using the Zein-BCA assay.

Paragraph 55. The process of any of paragraphs 46-54, wherein the protease is of fungal origin.

Paragraph 56. The process of any of paragraphs 46-55, wherein the protease is a variant of the metallo protease derived from a strain of the genus *Thermoascus*, preferably a strain of *Thermoascus aurantiacus*, especially *Thermoascus aurantiacus* CGMCC No. 0670.

Paragraph 57. The process of any of paragraphs 46-56, wherein the protease is a variant of the metallo protease disclosed as the mature part of SEQ ID NO: 2 disclosed in WO2003/048353 or the mature part of SEQ ID NO: 1 in WO2010/008841 or SEQ ID NO: 3 herein, with one of the following substitutions or combinations of substitutions:
S5*+D79L+S87P+A112P+D142L;
D79L+S87P+A112P+T124V+D142L;

S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M1610;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L; and
D79L+S87P+D142L.

Paragraph 58. The process of any of paragraphs 46-57, wherein the protease is a variant of the metallo protease disclosed as the mature part of SEQ ID NO: 2 disclosed in WO2003/048353 or the mature part of SEQ ID NO: 1 in WO 2010/008841 or SEQ ID NO: 3 herein with one of the following substitutions or combinations of substitutions:
D79L+S87P+A112P+D142L:
D79L+S87P+D142L; and
A27K+D79L+Y82F+S87G+D104P+A112P+A126V+D142L.

Paragraph 59. The process of any of paragraphs 46-58, wherein the protease variant has at least 75% identity, e.g., at least 80%, at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

Paragraph 60. The process of any of paragraphs 46-59, wherein the protease variant of the *Thermoascus aurantiacus* protease shown in SEQ ID NO: 3 herein comprises one of the following substitutions or combinations of substitutions:
D79L S87P D142L; D79L S87P A112P D142L; D79L Y82F S87P A112P D142L; S38T D79L S87P A112P A126V D142L; D79L Y82F S87P A112P A126V D142L; A27K D79L S87P A112P A126V D142L; S49P D79L S87P A112P D142L; S50P D79L S87P A112P D142L; D79L S87P D104P A112P D142L; D79L Y82F S87G A112P D142L; 570V D79L Y82F S87G Y97WA112P D142L; D79L Y82F S87G Y97W D104P A112P D142L; S70V D79L Y82F S87G A112P D142L; D79L Y82F S87G D104P A112P D142L; D79L Y82F S87G A112P A126V D142L; Y82F S87G S70V D79L D104P A112P D142L; Y82F S87G D79L D104P A112P A126V D142L; and A27K D79L Y82F S87G D104P A112P A126V D142L.

Paragraph 61. The process of any of paragraphs 46-60, wherein the protease is of bacterial origin.

Paragraph 62. The process of any of paragraphs 46-61, wherein the protease is derived from a strain of *Pyrococcus*, preferably a strain of *Pyrococcus furiosus*.

Paragraph 63. The process of any of paragraphs 46-62, wherein the protease is the one shown in SEQ ID NO: 1 in U.S. Pat. No. 6,358,726, or SEQ ID NO: 13 herein.

Paragraph 64. The process of any of paragraphs 46-63, wherein the protease is one having at least 80%, e.g., at least 85%, at least 90%, at least 95%, at least 96%, at least 97%, at least 98%, at least 99% identity to in SEQ ID NO: 1 in U.S. Pat. No. 6,358,726 or SEQ ID NO: 13 herein.

Paragraph 65. The process of any of paragraph 46-64, wherein 0.5-100 micro gram *Pyrococcus furiosus* protease per gram DS, such as 1-50 micro gram *Pyrococcus furiosus* protease per gram DS, such as 1-10 micro gram *Pyrococcus furiosus* protease per gram DS, such as 1.5-5 micro gram *Pyrococcus furiosus* protease per gram DS, such as about or more than 1.5 micro gram *Pyrococcus furiosus* protease per gram DS are present and/or added in liquefaction step i).

Paragraph 66. The process of any of paragraphs 46-65, wherein 2-100 micro gram *Pyrococcus furiosus* protease per gram DS, such as 2.5-50 micro gram *Pyrococcus furiosus* protease per gram DS, such as 2.5-10 micro gram *Pyrococcus furiosus* protease per gram DS, such as 2.5-5 micro gram *Pyrococcus furiosus* protease gram DS, especially about 3 micro gram *Pyrococcus furiosus* protease per gram DS are present and/or added in liquefaction step i).

Paragraph 67. The process of any of paragraphs 1-66, wherein a glucoamylase is present and/or added during liquefaction step i).

Paragraph 68. The process of paragraph 67, wherein the glucoamylase present and/or added in liquefaction has a heat stability at 85° C., pH 5.3, of at least 20%, such as at least 30%, or at least 35%.

Paragraph 69. The process of paragraph 67 or 68, wherein the glucoamylase present and/or added in liquefaction has a relative activity pH optimum at pH 5.0 of at least 90%, preferably at least 95%, preferably at least 97%.

Paragraph 70. The process of any of paragraphs 67-68, wherein the glucoamylase present and/or added in liquefaction has pH stability at pH 5.0 of at least at least 80%, at least 85%, at least 90%.

Paragraph 71. The process of any of paragraphs 67-70, wherein the glucoamylase present and/or added in liquefaction step i) is derived from a strain of the genus *Penicillium*, especially a strain of *Penicillium oxalicum* disclosed as SEQ ID NO: 2 in WO 2011/127802 or SEQ ID NOs: 9 or 14 herein.

Paragraph 72. The process of any of paragraphs 67-71, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

Paragraph 73. The process of any of paragraphs 67-72, wherein the glucoamylase is a variant of the *Penicillium oxalicum* glucoamylase shown in SEQ ID NO: 2 in WO 2011/127802 having a K79V substitution (using the mature sequence shown in SEQ ID NO: 14 herein for numbering), such as a variant disclosed in WO 2013/053801.

Paragraph 74. The process of any of paragraph 67-73, wherein the *Penicillium oxalicum* glucoamylase has a K79V substitution (using SEQ ID NO: 14 for numbering) and further one of the following substitutions or combinations of substitutions:
T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+K79A+Q327F+E501V+Y504T; P2N+P4S+P11F+T65A+K79G+Q327F+E501V+Y504T; P2N+P4S+P11F+T65A+K79I+Q327F+E501V+Y504T; P2N+P4S+P11F+T65A+K79L+Q327F+E501V+Y504T; P2N+P4S+P11F+T65A+K79S+Q327F+E501V+Y504T; P2N+P4S+P11F+T65A+L72V+Q327F+E501V+Y504T; S255N+Q327F+E501V+Y504T; P2N+P4S+P11F+T65A+E74N+V79K+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; and P2N+P4S+P11F+T65A+Q327F+T477N+E501V+Y504T.

Paragraph 75. The process of any of paragraphs 67-74, wherein the glucoamylase present and/or added in liquefaction is the *Penicillium oxalicum* glucoamylase has a K79V substitution (using SEQ ID NO: 14 herein for numbering) and further one of the following substitutions or combinations of substitutions: P11F+T65A+Q327F; and P2N+P4S+P11F+T65A+Q327F (using SEQ ID NO: 14 herein for numbering).

Paragraph 76. The process of any of paragraphs 67-75, wherein the glucoamylase variant has at least 75% identity, e.g., at least 80%, at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 14 herein.

Paragraph 77. The process of any of paragraphs 1-76, further wherein a pullulanase is present during liquefaction and/or saccharification.

Paragraph 78. The process of any of paragraphs 1-77, comprising the steps of:
  i) liquefying the starch-containing material at a temperature above the initial gelatinization temperature using an alpha-amylase derived from *Bacillus stearothermophilus;*
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 79. The process of any of paragraphs 1-78, comprising the steps of:
  i) liquefying the starch-containing material at a temperature above the initial gelatinization temperature using an alpha-amylase derived from *Bacillus stearothermophilus* comprising a double deletion at positions I181+G182, and optionally a N193F substitution (using SEQ ID NO: 1 herein for numbering);
  ii) saccharifying using a glucoamylase derived from a strain of *Gloephyllum*, such as *Gloephyllum serpiarium* or *Gloephyllum trabeum.*
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 80. The process of any of paragraphs 1-79, comprising the steps of:
  i) liquefying the starch-containing material at a temperature above the initial gelatinization temperature using:
    an alpha-amylase derived from *Bacillus stearothermophilus*;
    a protease having a thermostability value of more than 20% determined as Relative Activity at 80° C./70° C., preferably derived from *Pyrococcus furiosus* and/or *Thermoascus aurantiacus*; and optionally a *Penicillium oxalicum* glucoamylase;
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 81. A process of paragraphs 1-80, comprising the steps of:
  i) liquefying the starch-containing material at a temperature above the initial gelatinization temperature using an alpha-amylase, preferably derived from *Bacillus stearothermophilus*, comprising a double deletion at positions I181+G182, and optionally a N193F substitution (using SEQ ID NO: 1 for numbering) and having a T½ (min) at pH 4.5, 85° C., 0.12 mM CaCl$_2$ of at least 10;
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 82. A process of paragraphs 1-81, comprising the steps of:
  i) liquefying the starch-containing material at a temperature between 80-90° C. using:
    an alpha-amylase, preferably derived from *Bacillus stearothermophilus*, having a T½ (min) at pH 4.5, 85° C., 0.12 mM CaCl$_2$ of at least 10;
    a protease, preferably derived from *Pyrococcus furiosus* and/or *Thermoascus aurantiacus*, having a thermostability value of more than 20% determined as Relative Activity at 80° C./70° C.; and optionally a *Penicillium oxalicum* glucoamylase;
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 83. A process of paragraphs 1-82, comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F; and optionally further one of the following substitutions or combinations of substitutions: E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V;
    and E129V+K177L+R179E+K220P+N224L+S242Q+Q254S (using SEQ ID NO: 1 herein for numbering);
  ii) saccharifying using a glucoamylase, such as one from a strain of *Gloephyllum*, such as a strain of *Gloephyllum serpiarium*;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 84. A process of paragraphs 1-83, comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F, and optionally further one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S (using SEQ ID NO: 1 herein for numbering);
    a protease having a thermostability value of more than 20% determined as Relative Activity at 80° C./70° C., preferably derived from *Pyrococcus furiosus* and/or *Thermoascus aurantiacus*; and
    optionally a *Penicillium oxalicum* glucoamylase shown in SEQ ID NO: 14 having one of the following substitutions or combinations of substitutions:
    K79V;
    K79V+P11F+T65A+Q327F;
    K79V+P2N+P4S+P11F+T65A+Q327F;
    K79V+P11F+D26C+K33C+T65A+Q327F;
    K79V+P2N+P4S+P11F+T65A+Q327W+E501V+Y504T;
    K79V+P2N+P4S+P11F+T65A+Q327F+E501V+Y504T; and
    K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 85. A process of paragraphs 1-84, comprising the steps of:
  i) liquefying the starch-containing material at a temperature between 80-90° C. using:
    an alpha-amylase derived from *Bacillus stearothermophilus* having a double deletion at positions I181+G182, and optionally substitution N193F, and further optionally one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S
    (using SEQ ID NO: 1 herein for numbering),
    a protease having a thermostability value of more than 20% determined as Relative Activity at 80° C./70° C., preferably derived from *Pyrococcus furiosus* and/or *Thermoascus aurantiacus*;
    a *Penicillium oxalicum* glucoamylase shown in SEQ ID NO: 14 having one of the following substitutions or combinations of substitutions:
    K79V;
    K79V+P11F+T65A+Q327F;
    K79V+P2N+P4S+P11F+T65A+Q327F;
    K79V+P11F+D26C+K33C+T65A+Q327F;
    K79V+P2N+P4S+P11F+T65A+Q327W+E501V+Y504T;
    K79V+P2N+P4S+P11F+T65A+Q327F+E501V+Y504T; and
    K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 86. The process of any of paragraphs 1-85, comprising the steps of:
  i) liquefying the starch-containing material at a temperature above the initial gelatinization temperature using:
    an alpha-amylase derived from *Bacillus stearothermophilus* having a double deletion at positions I181+G182, and optionally substitution N193F (using SEQ ID NO: 1 herein for numbering);
    a protease having a thermostability value of more than 20% determined as Relative Activity at 80° C./70° C., preferably derived from *Pyrococcus furiosus* and/or *Thermoascus aurantiacus*;
    a *Penicillium oxalicum* glucoamylase having a K79V substitution (using SEQ ID NO: 14 herein for numbering); and optionally a pullulanase;
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 87. A process of paragraphs 1-86, comprising the steps of:
  i) liquefying the starch-containing material at a temperature above the initial gelatinization temperature using:
    an alpha-amylase, preferably derived from *Bacillus stearothermophilus*, having a T½ (min) at pH 4.5, 85° C., 0.12 mM CaCl$_2$ of at least 10; between 0.5 and 10 micro grams *Pyrococcus furiosus* protease per g DS;
    ii) saccharifying using a glucoamylase selected from the group of glucoamylase derived from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloephyllum*, such as *G. serpiarium* or *G. trabeum*, or a strain of the *Nigrofomes*;
    iii) fermenting using a fermenting organism;
    wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 88. A process of paragraphs 1-87, comprising the steps of:
  i) liquefying the starch-containing material at a temperature between 80-90° C. using;
    an alpha-amylase, preferably derived from *Bacillus stearothermophilus* having a double deletion at positions I181+G182, and optional substitution N193F and having a T½ (min) at pH 4.5, 85° C., 0.12 mM CaCl$_2$ of at least 10;
    between 0.5 and 10 micro grams *Pyrococcus furiosus* protease per g DS;
    a *Penicillium oxalicum* glucoamylase; and optionally a pullulanase;
  ii) saccharifying using a glucoamylase;
  iii) fermenting using a fermenting organism;
  wherein the fermenting organism *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 89. A process of paragraphs 1-88, comprising the steps of:
  i) liquefying the starch-containing material at a temperature a temperature between 80-90° C. using;
    an alpha-amylase derived from *Bacillus stearothermophilus* having a double deletion I181+G182 and optional substitution N193F; and optionally further one of the following substitutions or combinations of substitutions:
    E129V+K177L+R179E;
    V59A+Q89R+E129V+K177L+R179E+H208Y+K220P+N224L+Q254S;

V59A+Q89R+E129V+K177L+R179E+Q254S+ M284V;
V59A+E129V+K177L+R179E+Q254S+M284V; and
E129V+K177L+R179E+K220P+N224L+S242Q+ Q254S (using SEQ ID NO: 1 herein for numbering);
between 0.5 and 10 micro grams *Pyrococcus furiosus* protease per g DS;
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K330+T65A+Q327F;
K79V+P2N+P4S+P11F+T65A+Q327W+E501V+ Y504T;
K79V+P2N+P4S+P11F+T65A+Q327F+E501V+ Y504T; and
K79V+P11F+T65A+Q327W+E501V+Y504T (using SEQ ID NO: 14 for numbering); and
optionally a pullulanase;
ii) saccharifying using a glucoamylase;
iii) fermenting using a fermenting organism;
wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 90. A process of paragraphs 1-89, comprising the steps of:
i) liquefying the starch-containing material at a temperature between 80-90° C. using:
an alpha-amylase derived from *Bacillus stearothermophilus* having a double deletion I181+G182, and optional substitution N193F; and further one of the following substitutions or combinations of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 herein for numbering);
a protease having a thermostability value of more than 20% determined as Relative Activity at 80° C./70° C., preferably derived from *Pyrococcus furiosus* and/or *Thermoascus aurantiacus;*
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+ Y504T;
K79V+P2N+P4S+P11F+T65A+Q327F+E501V+Y504T; and
K79V+P11F+T65A+Q327W+E501V+Y504T (using SEQ ID NO: 14 for numbering); and optionally a pullulanase;
ii) saccharifying using a glucoamylase selected from the group of glucoamylase derived from a strain of *Aspergillus;*
or a strain of *Trichoderma;* a strain of *Talaromyces,* a strain of *Pycnoporus;* a strain of *Gloephyllum;* and a strain of the *Nigrofomes;*
iii) fermenting using a fermenting organism;
wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 91. A process of any of paragraphs 1-90, comprising the steps of:
i) liquefying the starch-containing material at a temperature between 80-90° C. at a pH between 5.0 and 6.5 using:
an alpha-amylase derived from *Bacillus stearothermophilus* having a double deletion I181+G182 and optionally substitution N193F; and optionally further one of the following substitutions or combinations of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V;
E129V+K177L+R179E+K220P+N224L+S242Q+Q254S (using SEQ ID NO: 1 herein for numbering);
a protease derived from *Pyrococcus furiosus,* preferably the one shown in SEQ ID NO: 13 herein;
a *Penicillium oxalicum* glucoamylase shown in SEQ ID NO: 14 having one of the following substitutions or combinations of substitutions:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 92. The process of any of paragraphs 1-91, wherein a cellulolytic enzyme composition is present in saccharification, fermentation or simultaneous saccharification and fermentation (SSF).

Paragraph 93. The process of any of paragraphs 1-92, wherein the fermenting organism has properties that are about the same as that of *Saccharomyces cerevisiae* strain MBG5038, or a derivative of *Saccharomyces cerevisiae* strain MBG5038 having the defining characteristics of *Saccharomyces cerevisiae* strain MBG5038, as it provides one or more, such as all of, the following properties or defining characteristics an increase in ethanol yield compared to *Saccharomyces cerevisiae* strain Ethanol Red® (deposited under Accession No. V14/007039 at National Measurement Institute, Victoria, Australia) under the same process conditions e.g., as described herein; and/or decreased glycerol production compared to *Saccharomyces cerevisiae* strain Ethanol Red® (deposited under Accession No. V14/007039 at National Measurement Institute, Victoria, Australia) under the same process conditions, e.g., as described herein.

Paragraph 94. The process of any of paragraphs 1-93, wherein the fermenting organism, provides an ethanol yield boost over *Saccharomyces cerevisiae* strain Ethanol Red® (deposited under Accession No. V14/007039 at National Measurement Institute, Victoria, Australia) of more than 0.5%, e.g., more than 1.0%, more than 2.0%, more than 2.5%, about 2.9%, such as between 0.5 and 5%, such as 1-3%, under the same process conditions, e.g., conditions described herein.

Paragraph 95. The process of any of paragraphs 1-94, wherein the fermenting organism reduces acetaldehyde production more than 10%, e.g., more than 20%, more than 30%, more than 40%, more than 45%, such as 5-60%, such as 30-50%, compared to *Saccharomyces cerevisiae* strain Ethanol Red® (deposited under Accession No. V14/007039 at National Measurement Institute, Victoria, Australia) under the same process conditions, e.g., conditions described herein.

Paragraph 96. The process of any of paragraphs 1-95, wherein the fermenting organism increases temperature tolerance compared to *Saccharomyces cerevisiae* strain Ethanol Red® (deposited under Accession No. V14/007039 at National Measurement Institute, Victoria, Australia) under the same process conditions, e.g., conditions described herein.

Paragraph 97. The process of any of paragraphs 1-96, wherein the fermenting organism decreases glycerol production by more than 3%, e.g., more than 4%, more than 5%, more than 6%, more than 7%, such as 2-15%, such as 5-10%, compared to *Saccharomyces cerevisiae* strain Ethanol Red® (deposited under Accession No. V14/007039 at National Measurement Institute, Victoria, Australia) under the same process conditions, e.g., conditions described herein.

Paragraph 98. The process of any of paragraphs 1-97, wherein the fermenting organism is a non-recombinant *Saccharomyces* strain, e.g., a non-recombinant *Saccharomyces cerevisiae* strain.

Paragraph 99. The process of any of paragraphs 1-98, wherein the fermenting organism is capable of utilizing cysteine as the sole nitrogen source.

Paragraph 100. A process for producing ethanol from starch-containing material comprising the steps of:
  i) liquefying the starch-containing material at a temperature above the initial gelatinization temperature using an alpha-amylase derived from *Bacillus stearothermophilus;*
  ii) saccharifying using a glucoamylase;
  iii) fermenting using a fermenting organism;
  wherein the fermenting organism has one or more, such as all, of the following properties and defining characteristics:
    increases ethanol yield compared to *Saccharomyces cerevisiae* strain Ethanol Red® (deposited under Accession No. V14/007039 at National Measurement Institute, Victoria, Australia) under the same process conditions, e.g., conditions as described herein;
    reduced acetaldehyde production compared to *Saccharomyces cerevisiae* strain Ethanol Red® (deposited under Accession No. V14/007039 at National Measurement Institute, Victoria, Australia) under the same process conditions, e.g., conditions as described herein;
    increased temperature tolerance compared to *Saccharomyces cerevisiae* strain Ethanol Red® (deposited under Accession No. V14/007039 at National Measurement Institute, Victoria, Australia) under the same process conditions, e.g., conditions as described herein;
    decreased glycerol production compared to *Saccharomyces cerevisiae* strain Ethanol Red® (deposited under Accession No. V14/007039 at National Measurement Institute, Victoria, Australia) under the same process conditions, e.g., conditions as described herein.

Paragraph 101. The process of paragraph 100, wherein the fermenting organism is a *Saccharomyces cerevisiae* yeast Paragraph 102. The process of paragraphs 100 or 101, wherein the fermenting organism is a non-recombinant *Saccharomyces cerevisiae* yeast.

Paragraph 103. A process of any of paragraphs 1-102, comprising the steps of:
  i) liquefying the starch-containing material at a temperature between 80-90° C. at a pH between 5.0 and 6.5 using:
    an alpha-amylase derived from *Bacillus stearothermophilus* having a double deletion I181+G182, and optional substitution N193F; and optionally further one of the following substitutions or combinations of substitutions:
      E129V+K177L+R179E;
      V59A+Q89R+E129V+K177L+R179E+H208Y+K220P+N224L+Q254S;
      V59A+Q89R+E129V+K177L+R179E+Q254S+M284V;
      V59A+E129V+K177L+R179E+Q254S+M284V;
      E129V+K177L+R179E+K220P+N224L+S242Q+Q254S
        (using SEQ ID NO: 1 herein for numbering).
    a protease derived from *Pyrococcus furiosus*, preferably the one shown in SEQ ID NO: 13 herein present and/or added in a dosage of 1-5 micro gram protease per gram DS, such as about 1.5 or 3 micro gram protease per gram DS;
    optionally a *Penicillium oxalicum* glucoamylase shown in SEQ ID NO: 14 having one of the following substitutions or combinations of substitutions:
      K79V;
      K79V+P11F+T65A+Q327F; or
      K79V+P2N+P4S+P11F+T65A+Q327F; or
      K79V+P11F+D26C+K33C+T65A+Q327F; or
      K79V+P2N+P4S+P11F+T65A+Q327W+E501V+Y504T; or
      K79V+P2N+P4S+P11F+T65A+Q327F+E501V+Y504T; or
      K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 104. The process of any of paragraphs 100-103, wherein the fermenting organism is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5038 or a derivative of *Saccharomyces* strain MBG5038 having defining characteristics of strain MBG5038.

Paragraph 105. The process of paragraphs 104, wherein a protease is present or added in saccharification and/or fermentation or simultaneous saccharification and fermentation (SSF).

Paragraph 106. A *Saccharomyces* yeast strain deposited under the Budapest Treaty and having NRRL accession no. NRRL Y67549, or a derivative of strain NRRL Y67549.

Paragraph 107. A method of producing a derivative of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA), comprising:
  a. culturing a first yeast strain with a second yeast strain, wherein the second yeast strain is *Saccharomyces cerevisiae* strain MBG5038 or a derivative thereof, under conditions which permit combining of DNA between the first yeast strain and the second yeast strain; and
  b. isolating hybrid strains; and
  c. optionally repeating steps (a) and (b) using a hybrid strain isolated in step (b) as the first yeast strain and/or the second yeast strain.

Paragraph 108. A method of producing a derivative of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) which exhibits the defining characteristics of *Saccharomyces cerevisiae* strain MBG5038, comprising:
  (a) providing:
    (i) a first yeast strain; and
    (ii) a second yeast strain, wherein the second yeast strain is *Saccharomyces cerevisiae* strain MBG5038 or a derivative thereof;
  (b) culturing the first yeast strain and the second yeast strain under conditions which permit combining of DNA between the first and second yeast strains;
  (c) screening or selecting for a derivative of *Saccharomyces cerevisiae* strain MBG5038.

Paragraph 109. The method of paragraph 108, wherein step (c) comprises screening or selecting for a hybrid strain which exhibits one or more defining characteristic of *Saccharomyces cerevisiae* strain MBG5038.

Paragraph 110. The method of paragraph 108, comprising the further step of:
  (d) repeating steps (b) and (c) with the screened or selected strain from step (c) as the first and/or second strain, until a derivative is obtained which exhibits the defining characteristics of *Saccharomyces cerevisiae* strain MBG5038.

Paragraph 111. The method of paragraph 109 or 110, wherein the culturing step (b) comprises:
  (i) sporulating the first yeast strain and the second yeast strain;
  (ii) hybridizing germinated spores produced by the first yeast strain with germinated spores produced by the second yeast strain.

Paragraph 112. A *Saccharomyces* strain produced by the method of any one of paragraphs 107 to 111.

Paragraph 113. A *Saccharomyces* strain having the defining characteristics of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA).

Paragraph 114. A method of producing ethanol, comprising incubating a strain of any of paragraphs 106, 112 or 113 with a substrate comprising a fermentable sugar under conditions which permit fermentation of the fermentable sugar to produce ethanol.

Paragraph 115. Use of a strain of any of paragraphs 106, 112 or 113 in the production of ethanol.

Paragraph 116. A method of producing distiller's grain, comprising:
  (a) incubating a *Saccharomyces* strain of any of paragraphs 106, 112 or 113 with a substrate comprising fermentable sugar under conditions which allow fermentation of the fermentable sugar to produce ethanol and distiller's grains;
  (b) isolating the distiller's grains.

Paragraph 117. Distiller's grain produced by the method of paragraph 116.

Paragraph 118. Use of a strain of paragraph 106, 112 or 113 in the production of distiller's grains.

Paragraph 119. Use of a strain of paragraphs 106, 112 or 113 in the production of a *Saccharomyces* strain having the defining characteristics of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA).

Paragraph 120. Use of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) in the production of a *Saccharomyces* strain having properties that are about the same as that of *Saccharomyces cerevisiae* strain MBG5038 or which exhibits one or more defining characteristics of *Saccharomyces cerevisiae* strain MBG5038.

Paragraph 121. Use of *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5038 or a derivative thereof in a process according to any of paragraphs 1-120.

Paragraph 122. A composition comprising a *Saccharomyces* yeast of any of claim 106, 112 or 113 and one or more naturally occurring and/or non-naturally occurring components.

Paragraph 123. The composition of claim 122, wherein the components are selected from the group consisting of: surfactants, emulsifiers, gums, swelling agents, and antioxidants.

Paragraph 124. The composition of paragraph 122 or 123, wherein the *Saccharomyces* yeast is *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, Ill., USA).

Paragraph 125. The composition of any of paragraphs 122-124, wherein the *Saccharomyces* yeast is in a viable form, in particular in dry, cream or compressed form.

Paragraph 126. A process of producing ethanol from starch-containing material comprising:
  (a) saccharifying the starch-containing material; and
  (b) fermenting using a fermentation organism;
  wherein
    saccharification and/or fermentation is done in the presence of at least a glucoamylase and optionally an alpha-amylase;
    the fermenting organism is *Saccharomyces cerevisiae;*
    and wherein a glucoamylase and/or an alpha-amylase is expressed from the fermenting organism.

Paragraph 127. The process according to paragraph 126, wherein the starch containing material is either gelatinized or ungelatinized starch.

Paragraph 128. The process according to paragraph 127, wherein a liquefaction step precedes the saccharification step, and wherein the liquefaction step is performed in the presence of at least a bacterial alpha-amylase, such as an alpha-amylase from *Bacillus* sp., particularly *Bacillus stearothermophilus*.

Paragraph 129. The process according to any of paragraphs 126-128, wherein the *Saccharomyces cerevisiae* is MBG5038 (deposited under Accession No. NRRL Y67549 at the Agricultural Research Service Patent Culture Collection (NRRL), Northern Regional Research Center, 1815 University Street, Peoria, Ill., USA) or a fermenting organism having properties that are about the same as that of MBG5038 or a derivative of MBG5038 having defining characteristics of strain MBG5038.

Paragraph 130. The process of paragraphs 126-129, wherein the fermenting organism is a recombinant derivative of MBG5038 that expresses the glucoamylase.

Paragraph 131. The process of paragraphs 126-130, wherein the glucocamylase is a *Gloeophyllum* glucoamylase, preferably *Gloeophyllum trabeum, Gloeophyllum sepiarium*, or *Gloeophyllum abietinum* glucoamylase.

Paragraph 132. The process of paragraphs 126-131, wherein the glucoamylase is selected from the group consisting of:
(i) a glucoamylase comprising the polypeptide of SEQ ID NO: 15 or SEQ ID NO: 17;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 or SEQ ID NO: 17.

Paragraph 133. The process of paragraph 131 or 132, wherein the glucoamylase is the *Gloeophyllum trabeum* glucoamylase shown in SEQ ID NO: 17 having one of the following substitutions: V59A; S95P; A121P; T119W; S95P+A121P; V59A+S95P; S95P+T119W; V59A+S95P+A121P; or S95P+T119W+A121P, especially S95P+A121P.

Paragraph 134. The process of any of paragraphs 126-130, wherein the glucoamylase is expressed from the fermenting organism and is a *Trametes* glucoamylase, preferably a *Trametes cingulata* glucoamylase.

Paragraph 135. The process of paragraph 134, wherein the glucoamylase is selected from the group consisting of:
(i) a glucoamylase comprising the polypeptide of SEQ ID NO: 20;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20.

Paragraph 136. The process of any of paragraphs 126-130, wherein the glucoamylase is expressed from the fermenting organism and is a *Pycnoporus* glucoamylase, particularly *Pycnoporus sanguineus* glucoamylase.

Paragraph 137. The process of paragraph 136, wherein the glucoamylase is selected from the group consisting of:
(i) a glucoamylase comprising the polypeptide of SEQ ID NO: 18;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.

Paragraph 138. The process of any of paragraphs 126-137, wherein the fermenting organism is a recombinant derivative of MBG5038 that expresses the alpha-amylase.

Paragraph 139. The process of paragraphs 126-138, wherein the alpha-amylase expressed from the fermenting organism and is derived from *Rhizomucor pusillus* or *Aspergillus terreus*.

Paragraph 140. The process of paragraph 139, wherein the alpha-amylase is *Rhizomucor pusillus* alpha-amylase with an *Aspergillus niger* glucoamylase linker and starch-binding domain (SBD) as shown in SEQ ID NO: 16, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N, and wherein the alpha-amylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.

Paragraph 141. The process of paragraph 139, wherein the alpha-amylase is an *Aspergillus terreus* alpha-amylase selected from the group consisting of:
(i) an alpha-amylase comprising the polypeptide of SEQ ID NO: 6 of WO2017/087330;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 of WO2017/087330.

Paragraph 142. A *Saccharomyces cerevisiae* yeast strain, wherein the strain is a derivative of MBG5038 comprising one or more expression vectors encoding a glucoamylase and/or an alpha-amylase.

Paragraph 143. The yeast strain according to paragraph 142, wherein the glucoamylase is selected from glucoamylases obtainable from *Gloeophyllum*, Pycnoporous, or *Trametes*.

Paragraph 144. The yeast strain according to paragraph 143, wherein the glucoamylase is selected from a *Gloeophyllum trabeum, Gloeophyllum sepiarium*, or *Gloeophyllum abietinum* glucoamylase.

Paragraph 145. The yeast strain of paragraph 144, wherein the glucoamylase is selected from the group consisting of:
(i) a glucoamylase comprising the polypeptide of SEQ ID NO: 15 or SEQ ID NO: 17;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 or SEQ ID NO: 17.

Paragraph 146. The yeast strain of any of paragraphs 143-145, wherein the glucoamylase is the *Gloeophyllum trabeum* glucoamylase shown in SEQ ID NO: 17 having one of the following substitutions: V59A; S95P; A121P; T119W; S95P+A121P; V59A+S95P; S95P+T119W; V59A+S95P+A121P; or S95P+T119W+A121P, especially S95P+A121P.

Paragraph 147. The yeast strain of paragraph 143, wherein the glucoamylase is a *Trametes cingulata* glucoamylase.

Paragraph 148. The yeast strain of paragraph 147, wherein the glucoamylase is selected from the group consisting of:
(i) a glucoamylase comprising the polypeptide of SEQ ID NO: 20;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20. 149: The yeast strain of paragraph 143, wherein the glucoamylase is s a *Pycnoporus sanguineus* glucoamylase.
Paragraph 150. The yeast strain of paragraph 149, wherein the glucoamylase is selected from the group consisting of:
(i) a glucoamylase comprising the polypeptide of SEQ ID NO: 18;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.
Paragraph 151. The yeast strain of paragraph 142 expression vector wherein the alpha-amylase is selected from a *Rhizomucor pusillus* or *Aspergillus terreus* alpha-amylase.
Paragraph 152. The yeast strain of paragraph 151, wherein the alpha-amylase is *Rhizomucor pusillus* alpha-amylase with an *Aspergillus niger* glucoamylase linker and starch-binding domain (SBD) as shown in SEQ ID NO: 16, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N, and wherein the alpha-amylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.
Paragraph 153. The yeast strain of paragraph 151, wherein the alpha-amylase is *Aspergillus terreus* alpha-amylase selected from the group consisting of:
(i) an alpha-amylase comprising the polypeptide of SEQ ID NO: 6 of WO2017/087330;
(ii) an alpha-amylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 of WO2017/087330.
Paragraph 154. A process for producing ethanol from starch-containing material comprising the steps of:
i) liquefying the starch-containing material at a temperature above the initial gelatinization temperature using an alpha-amylase;
ii) saccharifying using a glucoamylase;
iii) fermenting using a fermenting organism;
wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.
Paragraph 155. The process of paragraph 155, wherein the fermenting organism has at least one or more, such as all, of the following properties and defining characteristics:
increases ethanol yield compared to *Saccharomyces cerevisiae* strain Ethanol Red® (deposited under Accession No. V14/007039 at National Measurement Institute, Victoria, Australia) under the same process conditions, e.g., process conditions described herein; and/or
decreased glycerol production compared to *Saccharomyces cerevisiae* strain Ethanol Red® (deposited under Accession No. V14/007039 at National Measurement Institute, Victoria, Australia) under the same process conditions, e.g., process conditions described herein.
Paragraph 156. The process of paragraph 154 or 155, wherein the fermenting organism provides an ethanol yield boost over *Saccharomyces cerevisiae* strain Ethanol Red® (deposited under Accession No. V14/007039 at National Measurement Institute, Victoria, Australia) of more than 0.5%, e.g., more than 1.0%, more than 2.0%, more than 2.5%, such as about 2.9%, such as between 0.5 and 5%, such as between 1-3%, under the same process conditions, e.g., conditions as described herein.
Paragraph 157. The process of any of paragraphs 154-156, wherein the fermenting organism reduces acetaldehyde production more than 10%, e.g., more than 20%, more than 30%, more than 40%, more than 45%, such as 5-60%, such as 30-50%, compared to *Saccharomyces cerevisiae* strain Ethanol Red® (deposited under Accession No. V14/007039 at National Measurement Institute, Victoria, Australia) under the same process conditions, e.g., process conditions described herein.
Paragraph 158. The process of any of paragraphs 154-157, wherein the fermenting organism increases temperature tolerance compared to *Saccharomyces cerevisiae* strain Ethanol Red® (deposited under Accession No. V14/007039 at National Measurement Institute, Victoria, Australia) under the same process conditions, e.g., process conditions described herein.
Paragraph 159. The process of any of paragraphs 154-158, wherein the fermenting organism decreases glycerol production by more than 3%, e.g., more than 4%, more than 5%, more than 6%, more than 7%, such as 2-15%, such as 5-10%, compared to *Saccharomyces cerevisiae* strain Ethanol Red® (deposited under Accession No. V14/007039 at National Measurement Institute, Victoria, Australia) under the same process conditions, e.g., conditions described herein.
Paragraph 160. The process of any of paragraphs 154-159, wherein the fermenting organism:
(a) produces a higher titre of ethanol in the first 20 hours of fermentation than *Saccharomyces cerevisiae* strain Ethanol Red® (deposited under Accession No. V14/007039 at National Measurement Institute, Victoria, Australia), under the same conditions in a corn mash fermentation, e.g., conditions described herein;
(b) leaves less glucose remaining following 50 hours of fermentation than *Saccharomyces cerevisiae* strain Ethanol Red® (deposited under Accession No. V14/007039 at National Measurement Institute, Victoria, Australia), under the same conditions in a corn mash fermentation, e.g., conditions described herein;
(c) has a higher ethanol yield than *Saccharomyces cerevisiae* strain Ethanol Red® (deposited under Accession No. V14/007039 at National Measurement Institute, Victoria, Australia) following 50 hours of fermentation under the same conditions in a corn mash fermentation, e.g., conditions described herein.

Paragraph 161. The process of any of paragraphs 154-160, wherein a protease is added in saccharification or fermentation or SSF.

Paragraph 162. The process of any of paragraphs 154-161, further comprises, prior to the liquefaction step i), the steps of:

x) reducing the particle size of the starch-containing material, preferably by dry milling;

y) forming a slurry comprising the starch-containing material and water.

Paragraph 163. The process of any of paragraphs 154-162, wherein at least 50%, e.g., at least 70%, at least 80%, at least 90% of the starch-containing material fits through a sieve with #6 screen.

Paragraph 164. The process of any of paragraphs 154-163, wherein the pH in liquefaction is between 4-7, such as pH 4.5-6.5, such as pH 5.0-6.5, such as pH 5.0-6.0, such as pH 5.2-6.2, such as about 5.2, such as about 5.4, such as about 5.6, such as about 5.8.

Paragraph 165. The process of any of paragraphs 154-164, wherein the temperature in liquefaction is in the range of 70-100° C., such as 75-95° C., 75-90° C., 80-90° C., or 82-88° C., such as about 85° C.

Paragraph 166. The process of any of paragraphs 154-165, wherein a jet-cooking step is carried out prior to liquefaction in step i).

Paragraph 167. The process of paragraph 166, wherein the jet-cooking is carried out at a temperature of 110-145° C., e.g, 120-140° C., such as 125-135° C., or about 130° C. for about 1-15 minutes, e.g., for about 3-10 minutes, or about 5 minutes.

Paragraph 168. The process of any of paragraphs 154-167, wherein saccharification and fermentation is carried out sequentially or simultaneously (SSF).

Paragraph 169. The process of any of paragraphs 154-168, wherein saccharification is carried out at a temperature from 20-75° C., e.g., from 40-70° C., such as about 60° C., and at a pH between 4 and 5.

Paragraph 170. The process of any of paragraphs 154-169, wherein fermentation or simultaneous saccharification and fermentation (SSF) is carried out carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours.

Paragraph 171. The process of any of paragraphs 154-170, wherein the fermentation product is recovered after fermentation, such as by distillation.

Paragraph 172. The process of any of paragraphs 154-171, wherein the fermentation product is an alcohol, preferably ethanol, especially fuel ethanol, potable ethanol and/or industrial ethanol.

Paragraph 173. The process of any of paragraphs 154-172, wherein the starch-containing starting material is whole grains.

Paragraph 174. The process of any of paragraphs 154-173, wherein the starch-containing material is derived from corn, wheat, barley, rye, milo, sago, cassava, manioc, tapioca, sorghum, oats, rice or potatoes.

Paragraph 175. The process of any of paragraphs 154-174, wherein the alpha-amylase used or added in liquefaction step i) is of bacterial origin.

Paragraph 176. The process of any of paragraphs 154-175, wherein the alpha-amylase is from the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 1 herein.

Paragraph 177. The process of paragraph 176, wherein the Bacillus stearothermophilus alpha-amylase or variant thereof is truncated at the C-terminal, preferably to be from 485-495 amino acids long, such as about 491 amino acids long.

Paragraph 178. The process of any of paragraphs 176 or 177, wherein the Bacillus stearothermophilus alpha-amylase has a double deletion at positions I181+G182, and optionally substitution N193F, or deletion of R179+G180 (using SEQ ID NO: 1 for numbering).

Paragraph 179. The process of any of paragraphs 176-178, wherein the Bacillus stearothermophilus alpha-amylase has a substitution in position S242, e.g., S242Q substitution (using SEQ ID NO: 1 for numbering).

Paragraph 180. The process of any of paragraphs 176-179, wherein the Bacillus stearothermophilus alpha-amylase has a substitution in position E188, e.g., E188P substitution (using SEQ ID NO: 1 for numbering).

Paragraph 181. The process of any of paragraphs 154-180, wherein the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as 10-70, such as 15-70, such as 20-70, such as 25-70, such as 30-70, such as 40-70, such as 50-70, such as 60-70.

Paragraph 182. The process of any of paragraphs 154-181, wherein the alpha-amylase present and/or added in liquefaction step i) is selected from the group of Bacillus stearothermophilus alpha-amylase variants with one of the following substitutions or combinations of substitutions in addition to I181*+G182*, and optionally substitution N193F:

V59A+Q89R+G112D+E129V+K177L+R179E+K220P+ N224L+Q254S;
V59A+Q89R+E129V+K177L+R179E+H208Y+K220P+ N224L+Q254S;
V59A+Q89R+E129V+K177L+R179E+K220P+N224L+ Q254S+D269E+D281N;
V59A+Q89R+E129V+K177L+R179E+K220P+N224L+ Q254S+I270L;
V59A+Q89R+E129V+K177L+R179E+K220P+N224L+ Q254S+H274K;
V59A+Q89R+E129V+K177L+R179E+K220P+N224L+ Q254S+Y276F;
V59A+E129V+R157Y+K177L+R179E+K220P+N224L+ S242Q+Q254S;
V59A+E129V+K177L+R179E+H208Y+K220P+N224L+ S242Q+Q254S;
V59A+E129V+K177L+R179E+K220P+N224L+S242Q+ Q254S;
V59A+E129V+K177L+R179E+K220P+N224L+S242Q+ Q254S+H274K;
V59A+E129V+K177L+R179E+K220P+N224L+S242Q+ Q254S+Y276F;
V59A+E129V+K177L+R179E+K220P+N224L+S242Q+ Q254S+D281N;
V59A+E129V+K177L+R179E+K220P+N224L+S242Q+ Q254S+M284T;
V59A+E129V+K177L+R179E+K220P+N224L+S242Q+ Q254S+G416V;
V59A+E129V+K177L+R179E+K220P+N224L+Q254S;
V59A+E129V+K177L+R179E+K220P+N224L+Q254S+ M284T;

A91L+M961+E129V+K177L+R179E+K220P+N224L+
S242Q+Q254S;
E129V+K177L+R179E;
E129V+K177L+R179E+K220P+N224L+S242Q+Q254S;
E129V+K177L+R179E+K220P+N224L+S242Q+Q254S+
Y276F+L427M;
E129V+K177L+R179E+K220P+N224L+S242Q+Q254S+
M284T;
E129V+K177L+R179E+K220P+N224L+S242Q+Q254S+
N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A+Q89R+E129V+K177L+R179E+Q254S+M284V;
and
V59A+E129V+K177L+R179E+Q254S+M284V;

Paragraph 183. The process of any of paragraphs 154-182, wherein the alpha-amylase present and/or added in liquefaction step i) is selected from the following group of Bacillus stearothermophilus alpha-amylase variants comprising the following mutations: I181*+G182*, and optionally substitution N193F, and further one of the following substitutions or combinations of substitutions:
E129V+K177L+R179E;
V59A+Q89R+E129V+K177L+R179E+H208Y+K220P+
N224L+Q254S
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 1 herein for numbering).

Paragraph 184. The process of any of paragraphs 154-183, wherein a glucoamylase is present and/or added in saccharification and/or fermentation.

Paragraph 185. The process of paragraph 184, wherein the glucoamylase present and/or added in saccharification, fermentation or simultaneous saccharification and fermentation (SSF) is of fungal origin, preferably from a strain of Aspergillus, preferably A. niger, A. awamori, or A. oryzae; or a strain of Trichoderma, preferably Trichoderma reesei; or a strain of Talaromyces, preferably Talaroomyces emersonii, or a strain of Pycnoporus, or a strain of Gloeophyllum, such as Gloeophyllum serpiarium or Gloeophyllum trabeum, or a strain of the Nigrofomes.

Paragraph 186. The process of any of paragraphs 154-185, wherein the glucoamylase is derived from Talaromyces emersonii, such as the one shown in SEQ ID NO: 19 herein.

Paragraph 187. The process of any of paragraphs 154-186, wherein the glucoamylase is selected from the group consisting of:
(i) a glucoamylase comprising the mature polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

Paragraph 188. The process of any of paragraphs 154-187, wherein the glucoamylase present and/or added in saccharification is derived from Gloeophyllum serpiarium, such as the one shown in SEQ ID NO: 15 herein.

Paragraph 189. The process of any of paragraphs 154-188, wherein the glucoamylase present and/or added in saccharification is selected from the group consisting of:

(i) a glucoamylase comprising the mature polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

Paragraph 190. The process of any of paragraphs 154-189, wherein the glucoamylase present and/or added in saccharification is derived from Gloeophyllum trabeum such as the one shown in SEQ ID NO: 17 herein.

Paragraph 191. The process of any of paragraphs 154-190, wherein the glucoamylase present and/or added in saccharification is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

Paragraph 192. The process of any of paragraphs 154-191, wherein the glucoamylase is present and/or added in saccharification and/or fermentation in combination with an alpha-amylase.

Paragraph 193. The process of paragraph 192, wherein the alpha-amylase is present and/or added in saccharification and/or fermentation is of fungal or bacterial origin.

Paragraph 194. The process of paragraph 192 or 193, wherein the alpha-amylase present and/or added in saccharification and/or fermentation is derived from a strain of the genus Rhizomucor, preferably a strain the Rhizomucor pusillus, such as the one shown in SEQ ID NO: 3 in WO 2013/006756, such as a Rhizomucor pusillus alpha-amylase hybrid having a linker and a starch-binding domain, in particular having an Aspergillus niger linker and starch-bonding domain, such as the one shown in SEQ ID NO: 16 herein.

Paragraph 195. The process of any of paragraphs 192-194, wherein the alpha-amylase present and/or added in saccharification and/or fermentation is selected from the group consisting of:
(i) an alpha-amylase comprising the mature polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

Paragraph 196. The process of any of paragraphs 192-195, wherein the alpha-amylase is a variant of the alpha-amylase shown in SEQ ID NO: 16 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; and G128D+Y141W+D143N+K192R; or G128D+Y141W+D143N+K192R+P219C (using SEQ ID NO: 16 for numbering).

Paragraph 197. The process of any of paragraphs 192-196, wherein the alpha-amylase is derived from a *Rhizomucor pusillus* with an *Aspergillus niger* glucoamylase linker and starch-binding domain (SBD), preferably disclosed as SEQ ID NO: 16 herein, e.g., having one or more of the following substitutions: G128D, D143N, such as G128D+D143N (using SEQ ID NO: 16 for numbering).

Paragraph 198. The process of any of paragraphs 192-197, wherein the alpha-amylase variant has at least 75% identity preferably at least 80%, e.g., at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 16 herein.

Paragraph 199. The process of any of paragraphs 154-198, wherein liquefaction step i) is carried out using:
   an alpha-amylase;
   a protease having a thermostability value of more than 20% determined as Relative Activity at 80° C./70° C.; and
   optionally a glucoamylase.

Paragraph 200. The process of 199, wherein the protease with a thermostability value of more than 25% determined as Relative Activity at 80° C./70° C.

Paragraph 201. The process of paragraph 199 or 200, wherein the protease has a thermostability of more than 30%, e.g., more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

Paragraph 202. The process of any of paragraphs 199-201, wherein the protease has a thermostability of between 20 and 50%, such as between 20 and 40%, such as 20 and 30% determined as Relative Activity at 80° C./70° C.

Paragraph 203. The process of any of paragraphs 199-202, wherein the protease has a thermostability of between 50 and 115%, such as between 50 and 70%, such as between 50 and 60%, such as between 100 and 120%, such as between 105 and 115% determined as Relative Activity at 80° C./70° C.

Paragraph 204. The process of any of paragraphs 199-203, wherein the protease has a thermostability of more than 10%, e.g., more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

Paragraph 205. The process of any of paragraphs 199-204, wherein the protease has a thermostability of between 10 and 50%, such as between 10 and 30%, such as between 10 and 25% determined as Relative Activity at 85° C./70° C.

Paragraph 206. The process of any of paragraphs 199-205, wherein the protease has a themostability above 60%, such as above 90%, such as above 100%, such as above 110% at 85° C. as determined using the Zein-BCA assay.

Paragraph 207. The process of any of paragraphs 199-206, wherein the protease has a themostability between 60-120, such as between 70-120%, such as between 80-120%, such as between 90-120%, such as between 100-120%, such as 110-120% at 85° C. as determined using the Zein-BCA assay.

Paragraph 208. The process of any of paragraphs 199-207, wherein the protease is of fungal origin.

Paragraph 209. The process of any of paragraphs 199-208, wherein the protease is a variant of the metallo protease derived from a strain of the genus *Thermoascus*, preferably a strain of *Thermoascus aurantiacus*, especially *Thermoascus aurantiacus* CGMCC No. 0670.

Paragraph 210. The process of any of paragraphs 199-209, wherein the protease is a variant of the metallo protease disclosed as the mature part of SEQ ID NO: 2 disclosed in WO2003/048353 or the mature part of SEQ ID NO: 1 in WO2010/008841 or SEQ ID NO: 3 herein, with one of the following substitutions or combinations of substitutions:
   S5*+D79L+S87P+A112P+D142L;
   D79L+S87P+A112P+T124V+D142L;
   S5*+N26R+D79L+S87P+A112P+D142L;
   N26R+T46R+D79L+S87P+A112P+D142L;
   T46R+D79L+S87P+T116V+D142L;
   D79L+P81R+S87P+A112P+D142L;
   A27K+D79L+S87P+A112P+T124V+D142L;
   D79L+Y82F+S87P+A112P+T124V+D142L;
   D79L+Y82F+S87P+A112P+T124V+D142L;
   D79L+S87P+A112P+T124V+A126V+D142L;
   D79L+S87P+A112P+D142L;
   D79L+Y82F+S87P+A112P+D142L;
   S38T+D79L+S87P+A112P+A126V+D142L;
   D79L+Y82F+S87P+A112P+A126V+D142L;
   A27K+D79L+S87P+A112P+A126V+D142L;
   D79L+S87P+N98C+A112P+G135C+D142L;
   D79L+S87P+A112P+D142L+T141C+M161C;
   S36P+D79L+S87P+A112P+D142L;
   A37P+D79L+S87P+A112P+D142L;
   S49P+D79L+S87P+A112P+D142L;
   S50P+D79L+S87P+A112P+D142L;
   D79L+S87P+D104P+A112P+D142L;
   D79L+Y82F+S87G+A112P+D142L;
   S70V+D79L+Y82F+S87G+Y97W+A112P+D142L;
   D79L+Y82F+S87G+Y97W+D104P+A112P+D142L;
   S70V+D79L+Y82F+S87G+A112P+D142L;
   D79L+Y82F+S87G+D104P+A112P+D142L;
   D79L+Y82F+S87G+A112P+A126V+D142L;
   Y82F+S87G+S70V+D79L+D104P+A112P+D142L;
   Y82F+S87G+D79L+D104P+A112P+A126V+D142L;
   A27K+D79L+Y82F+S87G+D104P+A112P+A126V+D142L;
   A27K+Y82F+S87G+D104P+A112P+A126V+D142L;
   A27K+D79L+Y82F+D104P+A112P+A126V+D142L;
   A27K+Y82F+D104P+A112P+A126V+D142L;
   A27K+D79L+S87P+A112P+D142L; and
   D79L+S87P+D142L.

Paragraph 211. The process of any of paragraphs 199-210, wherein the protease is a variant of the metallo protease disclosed as the mature part of SEQ ID NO: 2 disclosed in WO2003/048353 or the mature part of SEQ ID NO: 1 in WO 2010/008841 or SEQ ID NO: 3 herein with one of the following substitutions or combinations of substitutions:
   D79L+S87P+A112P+D142L:
   D79L+S87P+D142L; and
   A27K+D79L+Y82F+S87G+D104P+A112P+A126V+D142L.

Paragraph 212. The process of any of paragraphs 199-211, wherein the protease variant has at least 75% identity, e.g., at least 80%, at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

Paragraph 213. The process of any of paragraphs 199-212, wherein the protease variant of the *Thermoascus auranti-*

*acus* protease shown in SEQ ID NO: 3 herein comprises one of the following substitutions or combinations of substitutions:

D79L S87P D142L; D79L S87P A112P D142L; D79L Y82F S87P A112P D142L; S38T D79L S87P A112P A126V D142L; D79L Y82F S87P A112P A126V D142L; A27K D79L S87P A112P A126V D142L; S49P D79L S87P A112P D142L; S50P D79L S87P A112P D142L; D79L S87P D104P A112P D142L; D79L Y82F S87G A112P D142L; 570V D79L Y82F S87G Y97W A112P D142L; D79L Y82F S87G Y97W D104P A112P D142L; 570V D79L Y82F S87G A112P D142L; D79L Y82F S87G D104P A112P D142L; D79L Y82F S87G A112P A126V D142L; Y82F S87G S70V D79L D104P A112P D142L; Y82F S87G D79L D104P A112P A126V D142L; and A27K D79L Y82F S87G D104P A112P A126V D142L.

Paragraph 214. The process of any of paragraphs 199-213, wherein the protease is of bacterial origin.

Paragraph 215. The process of any of paragraphs 199-214, wherein the protease is derived from a strain of *Pyrococcus*, preferably a strain of *Pyrococcus furiosus*.

Paragraph 216. The process of any of paragraphs 199-215, wherein the protease is the one shown in SEQ ID NO: 1 in U.S. Pat. No. 6,358,726, or SEQ ID NO: 13 herein.

Paragraph 217. The process of any of paragraphs 199-216, wherein the protease is one having at least 80%, e.g., at least 85%, at least 90%, at least 95%, at least 96%, at least 97%, at least 98%, at least 99% identity to in SEQ ID NO: 1 in U.S. Pat. No. 6,358,726 or SEQ ID NO: 13 herein.

Paragraph 218. The process of any of paragraph 199-217, wherein 0.5-100 micro gram *Pyrococcus furiosus* protease per gram DS, such as 1-50 micro gram *Pyrococcus furiosus* protease per gram DS, such as 1-10 micro gram *Pyrococcus furiosus* protease per gram DS, such as 1.5-5 micro gram *Pyrococcus furiosus* protease per gram DS, such as about or more than 1.5 micro gram *Pyrococcus furiosus* protease per gram DS are present and/or added in liquefaction step i).

Paragraph 219. The process of any of paragraphs 199-218, wherein 2-100 micro gram *Pyrococcus furiosus* protease per gram DS, such as 2.5-50 micro gram *Pyrococcus furiosus* protease per gram DS, such as 2.5-10 micro gram *Pyrococcus furiosus* protease per gram DS, such as 2.5-5 micro gram *Pyrococcus furiosus* protease gram DS, especially about 3 micro gram *Pyrococcus furiosus* protease per gram DS are present and/or added in liquefaction step i).

Paragraph 220. The process of any of paragraphs 154-219, wherein a glucoamylase is present and/or added during liquefaction step i).

Paragraph 221. The process of paragraph 220, wherein the glucoamylase present and/or added in liquefaction has a heat stability at 85° C., pH 5.3, of at least 20%, such as at least 30%, or at least 35%.

Paragraph 222. The process of paragraph 220 or 221, wherein the glucoamylase present and/or added in liquefaction has a relative activity pH optimum at pH 5.0 of at least 90%, preferably at least 95%, preferably at least 97%.

Paragraph 223. The process of any of paragraphs 220-222, wherein the glucoamylase present and/or added in liquefaction has pH stability at pH 5.0 of at least at least 80%, at least 85%, at least 90%.

Paragraph 224. The process of any of paragraphs 220-223, wherein the glucoamylase present and/or added in liquefaction step i) is derived from a strain of the genus *Penicillium*, especially a strain of *Penicillium oxalicum* disclosed as SEQ ID NO: 2 in WO 2011/127802 or SEQ ID NOs: 9 or 14 herein.

Paragraph 225. The process of any of paragraphs 220-224, wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 9 or 14 herein.

Paragraph 226. The process of any of paragraphs 220-225, wherein the glucoamylase is a variant of the *Penicillium oxalicum* glucoamylase shown in SEQ ID NO: 2 in WO 2011/127802 having a K79V substitution (using the mature sequence shown in SEQ ID NO: 14 herein for numbering), such as a variant disclosed in WO 2013/053801.

Paragraph 227. The process of any of paragraph 220-226, wherein the *Penicillium oxalicum* glucoamylase has a K79V substitution (using SEQ ID NO: 14 for numbering) and further one of the following substitutions or combinations of substitutions:

T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K330+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+K79A+Q327F+E501V+

Y504T; P2N+P4S+P11F+T65A+K79G+Q327F+E501V+Y504T; P2N+P4S+P11F+T65A+K79I+Q327F+E501V+Y504T; P2N+P4S+P11F+T65A+K79L+Q327F+E501V+Y504T; P2N+P4S+P11F+T65A+K79S+Q327F+E501V+Y504T; P2N+P4S+P11F+T65A+L72V+Q327F+E501V+Y504T; S255N+Q327F+E501V+Y504T; P2N+P4S+P11F+T65A+E74N+V79K+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; and P2N+P4S+P11F+T65A+Q327F+T477N+E501V+Y504T.

Paragraph 228. The process of any of paragraphs 220-227, wherein the glucoamylase present and/or added in liquefaction is the *Penicillium oxalicum* glucoamylase has a K79V substitution (using SEQ ID NO: 14 herein for numbering) and further one of the following substitutions or combinations of substitutions: P11F+T65A+Q327F; and P2N+P4S+P11F+T65A+Q327F (using SEQ ID NO: 14 herein for numbering).

Paragraph 229. The process of any of paragraphs 220-228, wherein the glucoamylase variant has at least 75% identity, e.g., at least 80%, at least 85%, at least 90%, at least 91%, at least 92%, at least 93%, at least 94%, at least 95%, at least 96%, at least 97%, at least 98%, at least 99%, but less than 100% identity to the mature part of the polypeptide of SEQ ID NO: 14 herein.

Paragraph 230. The process of any of paragraphs 154-229, further wherein a pullulanase is present during liquefaction and/or saccharification.

Paragraph 231. The process of any of paragraphs 154-230, comprising the steps of:
  i) liquefying the starch-containing material at a temperature above the initial gelatinization temperature using an alpha-amylase derived from *Bacillus stearothermophilus;*
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 232. The process of any of paragraphs 154-231, comprising the steps of:
  i) liquefying the starch-containing material at a temperature above the initial gelatinization temperature using an alpha-amylase derived from *Bacillus stearothermophilus* comprising a double deletion at positions I181+G182, and optionally a N193F substitution (using SEQ ID NO: 1 herein for numbering);
  ii) saccharifying using a glucoamylase derived from a strain of *Gloephyllum*, such as *Gloephyllum serpiarium* or *Gloephyllum trabeum.*
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 233. The process of any of paragraphs 154-232, comprising the steps of:
  i) liquefying the starch-containing material at a temperature above the initial gelatinization temperature using:
    an alpha-amylase derived from *Bacillus stearothermophilus;*
    a protease having a thermostability value of more than 20% determined as Relative Activity at 80° C./70° C., preferably derived from *Pyrococcus furiosus* and/or *Thermoascus aurantiacus*; and
    optionally a *Penicillium oxalicum* glucoamylase;
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 234. A process of paragraphs 154-233, comprising the steps of:
  i) liquefying the starch-containing material at a temperature above the initial gelatinization temperature using an alpha-amylase, preferably derived from *Bacillus stearothermophilus*, comprising a double deletion at positions I181+G182, and optionally a N193F substitution (using SEQ ID NO: 1 for numbering) and having a T½ (min) at pH 4.5, 85° C., 0.12 mM CaCl$_2$ of at least 10;
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 235. A process of paragraphs 154-234, comprising the steps of:
  i) liquefying the starch-containing material at a temperature between 80-90° C. using:
    an alpha-amylase, preferably derived from *Bacillus stearothermophilus*, having a T½ (min) at pH 4.5, 85° C., 0.12 mM CaCl$_2$ of at least 10;
    a protease, preferably derived from *Pyrococcus furiosus* and/or *Thermoascus aurantiacus*, having a thermostability value of more than 20% determined as Relative Activity at 80° C./70° C.; and
    optionally a *Penicillium oxalicum* glucoamylase;
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 236. A process of paragraphs 154-235, comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F; and optionally further one of the following substitutions or combinations of substitutions: E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V;
    and E129V+K177L+R179E+K220P+N224L+S242Q+Q254S (using SEQ ID NO: 1 herein for numbering);
  ii) saccharifying using a glucoamylase, such as one from a strain of *Gloephyllum*, such as a strain of *Gloephyllum serpiarium*;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 237. A process of paragraphs 154-236, comprising the steps of:
  i) liquefying the starch-containing material at a temperature above the initial gelatinization temperature using:
    an alpha-amylase derived from *Bacillus stearothermophilus* having a double deletion at positions I181+G182, and optional substitution N193F, and optionally further one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S (using SEQ ID NO: 1 herein for numbering);
    a protease having a thermostability value of more than 20% determined as Relative Activity at 80° C./70° C., preferably derived from *Pyrococcus furiosus* and/or *Thermoascus aurantiacus*; and
    optionally a *Penicillium oxalicum* glucoamylase shown in SEQ ID NO: 14 having one of the following substitutions or combinations of substitutions:
    K79V;
    K79V+P11F+T65A+Q327F;
    K79V+P2N+P4S+P11F+T65A+Q327F;
    K79V+P11F+D26C+K330+T65A+Q327F;
    K79V+P2N+P4S+P11F+T65A+Q327W+E501V+Y504T;
    K79V+P2N+P4S+P11F+T65A+Q327F+E501V+Y504T; and
    K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 238. A process of paragraphs 154-237, comprising the steps of:
  i) liquefying the starch-containing material at a temperature between 80-90° C. using:
    an alpha-amylase derived from *Bacillus stearothermophilus* having a double deletion at positions I181+G182, and optionally substitution N193F, and further optionally one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V; and
    E129V+K177L+R179E+K220P+N224L+S242Q+Q254S (using SEQ ID NO: 1 herein for numbering),
    a protease having a thermostability value of more than 20% determined as Relative Activity at 80° C./70° C., preferably derived from *Pyrococcus furiosus* and/or *Thermoascus aurantiacus*;
    a *Penicillium oxalicum* glucoamylase shown in SEQ ID NO: 14 having one of the following substitutions or combinations of substitutions:
    K79V;
    K79V+P11F+T65A+Q327F;
    K79V+P2N+P4S+P11F+T65A+Q327F;
    K79V+P11F+D26C+K330+T65A+Q327F;
    K79V+P2N+P4S+P11F+T65A+Q327W+E501V+Y504T;
    K79V+P2N+P4S+P11F+T65A+Q327F+E501V+Y504T; and
    K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 239. The process of any of paragraphs 154-238, comprising the steps of:
  i) liquefying the starch-containing material at a temperature above the initial gelatinization temperature using:
    an alpha-amylase derived from *Bacillus stearothermophilus* having a double deletion at positions I181+G182, and optionally substitution N193F (using SEQ ID NO: 1 herein for numbering);
    a protease having a thermostability value of more than 20% determined as Relative Activity at 80° C./70° C., preferably derived from *Pyrococcus furiosus* and/or *Thermoascus aurantiacus*;
    a *Penicillium oxalicum* glucoamylase having a K79V substitution (using SEQ ID NO: 14 herein for numbering); and
    optionally a pullulanase;
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 240. A process of paragraphs 154-239, comprising the steps of:
i) liquefying the starch-containing material at a temperature above the initial gelatinization temperature using:
an alpha-amylase, preferably derived from *Bacillus stearothermophilus*, having a T½ (min) at pH 4.5, 85° C., 0.12 mM $CaCl_2$) of at least 10;
between 0.5 and 10 micro grams *Pyrococcus furiosus* protease per g DS;
ii) saccharifying using a glucoamylase selected from the group of glucoamylase derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloephyllum*, such as *G. serpiarium* or *G. trabeum*, or a strain of the *Nigrofomes*;
iii) fermenting using a fermenting organism;
wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 241. A process of paragraphs 154-240, comprising the steps of:
i) liquefying the starch-containing material at a temperature between 80-90° C. using;
an alpha-amylase, preferably derived from *Bacillus stearothermophilus* having a double deletion at positions I181+G182, and optional substitution N193F and having a T½ (min) at pH 4.5, 85° C., 0.12 mM $CaCl_2$ of at least 10;
between 0.5 and 10 micro grams *Pyrococcus furiosus* protease per g DS;
a *Penicillium oxalicum* glucoamylase; and
optionally a pullulanase;
ii) saccharifying using a glucoamylase;
iii) fermenting using a fermenting organism;
wherein the fermenting organism *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 242. A process of paragraphs 154-241, comprising the steps of:
i) liquefying the starch-containing material at a temperature a temperature between 80-90° C. using;
an alpha-amylase derived from *Bacillus stearothermophilus* having a double deletion I181+G182 and optional substitution N193F; and optionally further one of the following substitutions or combinations of substitutions:
E129V+K177L+R179E;
V59A+Q89R+E129V+K177L+R179E+H208Y+ K220P+N224L+Q254S;
V59A+Q89R+E129V+K177L+R179E+Q254S+ M284V;
V59A+E129V+K177L+R179E+Q254S+M284V; and
E129V+K177L+R179E+K220P+N224L+S242Q+ Q254S (using SEQ ID NO: 1 herein for numbering);
between 0.5 and 10 micro grams *Pyrococcus furiosus* protease per g DS;
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+ Y504T;
K79V+P2N+P4S+P11F+T65A+Q327F+E501V+ Y504T; and
K79V+P11F+T65A+Q327W+E501V+Y504T (using SEQ ID NO: 14 for numbering); and
optionally a pullulanase;
ii) saccharifying using a glucoamylase;
iii) fermenting using a fermenting organism;
wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 243. A process of paragraphs 154-242, comprising the steps of:
i) liquefying the starch-containing material at a temperature between 80-90° C. using:
an alpha-amylase derived from *Bacillus stearothermophilus* having a double deletion I181+G182, and optional substitution N193F; and further one of the following substitutions or combinations of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 1 herein for numbering);
a protease having a thermostability value of more than 20% determined as Relative Activity at 80° C./70° C., preferably derived from *Pyrococcus furiosus* and/or *Thermoascus aurantiacus;*
a *Penicillium oxalicum* glucoamylase shown in SEQ ID NO: 14 having one of the following substitutions or combinations of substitutions:
K79V;
K79V+P11F+T65A+Q327F;
K79V+P2N+P4S+P11F+T65A+Q327F;
K79V+P11F+D26C+K33C+T65A+Q327F;
K79V+P2N+P4S+P11F+T65A+Q327W+E501V+ Y504T;
K79V+P2N+P4S+P11F+T65A+Q327F+E501V+Y504T; and
K79V+P11F+T65A+Q327W+E501V+Y504T (using SEQ ID NO: 14 for numbering); and
optionally a pullulanase;
ii) saccharifying using a glucoamylase selected from the group of glucoamylase derived from a strain of *Aspergillus*; or a strain of *Trichoderma*; a strain of *Talaromyces*, a strain of *Pycnoporus*; a strain of *Gloephyllum*; and a strain of the *Nigrofomes;*
iii) fermenting using a fermenting organism;
wherein the fermenting organism is *Saccharomyces cerevisiae* strain MBG5012 (deposited under Accession No.

NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 244. A process of any of paragraphs 154-243, comprising the steps of:
  i) liquefying the starch-containing material at a temperature between 80-90° C. at a pH between 5.0 and 6.5 using:
    an alpha-amylase derived from *Bacillus stearothermophilus* having a double deletion I181+G182 and optionally substitution N193F; and optionally further one of the following substitutions or combinations of substitutions:
    E129V+K177L+R179E;
    V59A+Q89R+E129V+K177L+R179E+H208Y+K220P+N224L+Q254S;
    V59A+Q89R+E129V+K177L+R179E+Q254S+M284V;
    V59A+E129V+K177L+R179E+Q254S+M284V;
    E129V+K177L+R179E+K220P+N224L+S242Q+Q254S
    (using SEQ ID NO: 1 herein for numbering);
    a protease derived from *Pyrococcus furiosus*, preferably the one shown in SEQ ID NO: 13 herein;
    a *Penicillium oxalicum* glucoamylase shown in SEQ ID NO: 14 having one of the following substitutions or combinations of substitutions:
    K79V;
    K79V+P11F+T65A+Q327F; or
    K79V+P2N+P4S+P11F+T65A+Q327F; or
    K79V+P11F+D26C+K33C+T65A+Q327F; or
    K79V+P2N+P4S+P11F+T65A+Q327W+E501V+Y504T; or
    K79V+P2N+P4S+P11F+T65A+Q327F+E501V+Y504T; or
    K79V+P11F+T65A+Q327W+E501V+Y504T (using SEQ ID NO: 14 for numbering);
  ii) saccharifying using a glucoamylase;
  iii) fermenting using a fermenting organism;
  wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 245. The process of any of paragraphs 154-244, wherein a cellulolytic enzyme composition is present in saccharification, fermentation or simultaneous saccharification and fermentation (SSF).

Paragraph 246. The process of any of paragraphs 154-245, wherein the fermenting organism has properties that are about the same as that of *Saccharomyces cerevisiae* strain MBG5012, or a derivative of *Saccharomyces cerevisiae* strain MBG5012 having the defining characteristics of *Saccharomyces cerevisiae* strain MBG5012, as it provides one or more, such as all of, the following properties or defining characteristics
  an increase in ethanol yield compared to *Saccharomyces cerevisiae* strain Ethanol Red® (deposited under Accession No. V14/007039 at National Measurement Institute, Victoria, Australia) under the same process conditions e.g., as described herein; and/or
  decreased glycerol production compared to *Saccharomyces cerevisiae* strain Ethanol Red® (deposited under Accession No. V14/007039 at National Measurement Institute, Victoria, Australia) under the same process conditions, e.g., as described herein.

Paragraph 247. The process of any of paragraphs paragraph 154-246, wherein the fermenting organism, provides an ethanol yield boost over *Saccharomyces cerevisiae* strain Ethanol Red® (deposited under Accession No. V14/007039 at National Measurement Institute, Victoria, Australia) of more than 0.5%, e.g., more than 1.0%, more than 2.0%, more than 2.5%, about 2.9%, such as between 0.5 and 5%, such as 1-3%, under the same process conditions, e.g., conditions described herein.

Paragraph 248. The process of any of paragraphs 154-247, wherein the fermenting organism reduces acetaldehyde production more than 10%, e.g., more than 20%, more than 30%, more than 40%, more than 45%, such as 5-60%, such as 30-50%, compared to *Saccharomyces cerevisiae* strain Ethanol Red® (deposited under Accession No. V14/007039 at National Measurement Institute, Victoria, Australia) under the same process conditions, e.g., conditions described herein.

Paragraph 249. The process of any of paragraphs 154-248, wherein the fermenting organism increases temperature tolerance compared to *Saccharomyces cerevisiae* strain Ethanol Red® (deposited under Accession No. V14/007039 at National Measurement Institute, Victoria, Australia) under the same process conditions, e.g., conditions described herein.

Paragraph 250. The process of any of paragraphs 154-249, wherein the fermenting organism decreases glycerol production by more than 3%, e.g., more than 4%, more than 5%, more than 6%, more than 7%, such as 2-15%, such as 5-10%, compared to *Saccharomyces cerevisiae* strain Ethanol Red® (deposited under Accession No. V14/007039 at National Measurement Institute, Victoria, Australia) under the same process conditions, e.g., conditions described herein.

Paragraph 251. The process of any of paragraphs 154-250, wherein the fermenting organism is a non-recombinant *Saccharomyces* strain, e.g., a non-recombinant *Saccharomyces cerevisiae* strain.

Paragraph 252. The process of any of paragraphs 154-251, wherein the fermenting organism is capable of utilizing cysteine as the sole nitrogen source.

Paragraph 253. A process for producing ethanol from starch-containing material comprising the steps of:
  i) liquefying the starch-containing material at a temperature above the initial gelatinization temperature using an alpha-amylase derived from *Bacillus stearothermophilus;*
  ii) saccharifying using a glucoamylase;
  iii) fermenting using a fermenting organism;
  wherein the fermenting organism has one or more, such as all, of the following properties and defining characteristics:
    increases ethanol yield compared to *Saccharomyces cerevisiae* strain Ethanol Red® (deposited under Accession No. V14/007039 at National Measurement Institute, Victoria, Australia) under the same process conditions, e.g., conditions as described herein;
    reduced acetaldehyde production compared to *Saccharomyces cerevisiae* strain Ethanol Red® (deposited under Accession No. V14/007039 at National Measurement Institute, Victoria, Australia) under the same process conditions, e.g., conditions as described herein;
    increased temperature tolerance compared to *Saccharomyces cerevisiae* strain Ethanol Red® (deposited under Accession No. V14/007039 at National Measurement Institute, Victoria, Australia) under the same process conditions, e.g., conditions as described herein;

decreased glycerol production compared to *Saccharomyces cerevisiae* strain Ethanol Red® (deposited under Accession No. V14/007039 at National Measurement Institute, Victoria, Australia) under the same process conditions, e.g., conditions as described herein.

Paragraph 254. The process of paragraph 253, wherein the fermenting organism is a *Saccharomyces cerevisiae* yeast Paragraph 255. The process of paragraphs 253 or 254, wherein the fermenting organism is a non-recombinant *Saccharomyces cerevisiae* yeast.

Paragraph 256. A process of any of paragraphs 154-255, comprising the steps of:

i) liquefying the starch-containing material at a temperature between 80-90° C. at a pH between 5.0 and 6.5 using:
an alpha-amylase derived from *Bacillus stearothermophilus* having a double deletion I181+G182, and optional substitution N193F; and optionally further one of the following substitutions or combinations of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V;
E129V+K177L+R179E+K220P+N224L+S242Q+Q254S (using SEQ ID NO: 1 herein for numbering).
a protease derived from *Pyrococcus furiosus*, preferably the one shown in SEQ ID NO: 13 herein present and/or added in a dosage of 1-5 micro gram protease per gram DS, such as about 1.5 or 3 micro gram protease per gram DS;
optionally a *Penicillium oxalicum* glucoamylase shown in SEQ ID NO: 14 having one of the following substitutions or combinations of substitutions:
K79V;
K79V+P11F+T65A+Q327F; or
K79V+P2N+P4S+P11F+T65A+Q327F; or
K79V+P11F+D26C+K33C+T65A+Q327F; or
K79V+P2N+P4S+P11F+T65A+Q327W+E501V+ Y504T; or
K79V+P2N+P4S+P11F+T65A+Q327F+E501V+Y504T; or
K79V+P11F+T65A+Q327W+E501V+Y504T (using SEQ ID NO: 14 for numbering);
ii) saccharifying using a glucoamylase;
iii) fermenting using a fermenting organism;
wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 257. The process of any of paragraphs 153-256, wherein the fermenting organism is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of *Saccharomyces cerevisiae* strain MBG5012 or a derivative of *Saccharomyces* strain MBG5012 having defining characteristics of strain MBG5012.

Paragraph 258. The process of paragraphs 257, wherein a protease is present or added in saccharification and/or fermentation or simultaneous saccharification and fermentation (SSF).

Paragraph 259. A *Saccharomyces* yeast strain deposited under the Budapest Treaty and having NRRL accession no. NRRL Y67700, or a derivative of strain NRRL Y67700.

Paragraph 260. A method of producing a derivative of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA), comprising:

d. culturing a first yeast strain with a second yeast strain, wherein the second yeast strain is *Saccharomyces cerevisiae* strain MBG5012 or a derivative thereof, under conditions which permit combining of DNA between the first yeast strain and the second yeast strain; and
e. isolating hybrid strains; and
f. optionally repeating steps (a) and (b) using a hybrid strain isolated in step (b) as the first yeast strain and/or the second yeast strain.

Paragraph 261. A method of producing a derivative of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) which exhibits the defining characteristics of *Saccharomyces cerevisiae* strain MBG5012, comprising:

(d) providing:
(i) a first yeast strain; and
(iii) a second yeast strain, wherein the second yeast strain is *Saccharomyces cerevisiae* strain MBG5012 or a derivative thereof;
(e) culturing the first yeast strain and the second yeast strain under conditions which permit combining of DNA between the first and second yeast strains;
(f) screening or selecting for a derivative of *Saccharomyces cerevisiae* strain MBG5012.

Paragraph 262. The method of paragraph 261, wherein step (c) comprises screening or selecting for a hybrid strain which exhibits one or more defining characteristic of *Saccharomyces cerevisiae* strain MBG5012.

Paragraph 263. The method of paragraph 261, comprising the further step of:

(d) repeating steps (b) and (c) with the screened or selected strain from step (c) as the first and/or second strain, until a derivative is obtained which exhibits the defining characteristics of *Saccharomyces cerevisiae* strain MBG5012.

Paragraph 264. The method of paragraph 262 or 263, wherein the culturing step (b) comprises:

(i) sporulating the first yeast strain and the second yeast strain;
(ii) hybridizing germinated spores produced by the first yeast strain with germinated spores produced by the second yeast strain.

Paragraph 265. A *Saccharomyces* strain produced by the method of any one of paragraphs 260-264.

Paragraph 266. A *Saccharomyces* strain having the defining characteristics of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA).

Paragraph 267. A method of producing ethanol, comprising incubating a strain of any of paragraphs 259, 265 or 266 with a substrate comprising a fermentable sugar under conditions which permit fermentation of the fermentable sugar to produce ethanol.

Paragraph 268. Use of a strain of any of paragraphs 259, 265 or 266 in the production of ethanol.

Paragraph 269. A method of producing distiller's grain, comprising:
(c) incubating a *Saccharomyces* strain of any of paragraphs 259, 265 or 266 with a substrate comprising fermentable sugar under conditions which allow fermentation of the fermentable sugar to produce ethanol and distiller's grains;
(d) isolating the distiller's grains.

Paragraph 270. Distiller's grain produced by the method of paragraph 269.

Paragraph 271. Use of a strain of paragraph 259, 265 or 266 in the production of distiller's grains.

Paragraph 272. Use of a strain of paragraphs 259, 265 or 266 in the production of a *Saccharomyces* strain having the defining characteristics of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA).

Paragraph 273. Use of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) in the production of a *Saccharomyces* strain having properties that are about the same as that of *Saccharomyces cerevisiae* strain MBG5012 or which exhibits one or more defining characteristics of *Saccharomyces cerevisiae* strain MBG5012.

Paragraph 274. Use of *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA) or a strain having properties that are about the same as that of *Saccharomyces cerevisiae* strain MBG5012 or a derivative thereof in a process according to any of paragraphs 154-273.

Paragraph 275. A composition comprising a *Saccharomyces* yeast of any of paragraphs 259, 265 or 266 and one or more naturally occurring and/or non-naturally occurring components.

Paragraph 276. The composition of paragraph 275, wherein the components are selected from the group consisting of: surfactants, emulsifiers, gums, swelling agents, and antioxidants.

Paragraph 277. The composition of paragraph 275 or 276, wherein the *Saccharomyces* yeast is *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, Ill., USA).

Paragraph 278. The composition of any of paragraphs 275-277, wherein the *Saccharomyces* yeast is in a viable form, in particular in dry, cream or compressed form.

Paragraph 279. A process of producing ethanol from starch-containing material comprising:
(a) saccharifying the starch-containing material; and
(b) fermenting using a fermentation organism;
wherein
saccharification and/or fermentation is done in the presence of at least a glucoamylase and optionally an alpha-amylase;
the fermenting organism is *Saccharomyces cerevisiae*;
and wherein a glucoamylase and/or an alpha-amylase is expressed from the fermenting organism.

Paragraph 280. The process according to paragraph 279, wherein the starch containing material is either gelatinized or ungelatinized starch.

Paragraph 281. The process according to paragraph 280, wherein a liquefaction step precedes the saccharification step, and wherein the liquefaction step is performed in the presence of at least a bacterial alpha-amylase, such as an alpha-amylase from *Bacillus* sp., particularly *Bacillus stearothermophilus*.

Paragraph 282. The process according to any of paragraphs 279-281, wherein the *Saccharomyces cerevisiae* is MBG5012 (deposited under Accession No. NRRL Y67700 at the Agricultural Research Service Patent Culture Collection (NRRL), Northern Regional Research Center, 1815 University Street, Peoria, Ill., USA) or a fermenting organism having properties that are about the same as that of MBG5012 or a derivative of MBG5012 having defining characteristics of strain MBG5012.

Paragraph 283. The process of paragraphs 279-282, wherein the fermenting organism is a recombinant derivative of MBG5012 that expresses the glucoamylase.

Paragraph 284. The process of paragraphs 279-283, wherein the glucocamylase is a *Gloeophyllum* glucoamylase, preferably *Gloeophyllum trabeum, Gloeophyllum sepiarium*, or *Gloeophyllum abietinum* glucoamylase.

Paragraph 285. The process of paragraphs 279-284, wherein the glucoamylase is selected from the group consisting of:
(i) a glucoamylase comprising the polypeptide of SEQ ID NO: 15 or SEQ ID NO: 17;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 or SEQ ID NO: 17.

Paragraph 286. The process of paragraph 284 or 285, wherein the glucoamylase is the *Gloeophyllum trabeum* glucoamylase shown in SEQ ID NO: 17 having one of the following substitutions: V59A; S95P; A121P; T119W; S95P+A121P; V59A+S95P; S95P+T119W; V59A+S95P+A121P; or S95P+T119W+A121P, especially S95P+A121P.

Paragraph 287. The process of any of paragraphs 279-283, wherein the glucoamylase is expressed from the fermenting organism and is a *Trametes* glucoamylase, preferably a *Trametes cingulata* glucoamylase.

Paragraph 288. The process of paragraph 287, wherein the glucoamylase is selected from the group consisting of:
(i) a glucoamylase comprising the polypeptide of SEQ ID NO: 20;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20.

Paragraph 289. The process of any of paragraphs 279-283, wherein the glucoamylase is expressed from the fermenting organism and is a *Pycnoporus* glucoamylase, particularly *Pycnoporus sanguineus* glucoamylase.

Paragraph 290. The process of paragraph 289, wherein the glucoamylase is selected from the group consisting of:
(i) a glucoamylase comprising the polypeptide of SEQ ID NO: 18;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.

Paragraph 291. The process of any of paragraphs 279-290, wherein the fermenting organism is a recombinant derivative of MBG5012 that expresses the alpha-amylase.

Paragraph 292. The process of paragraphs 279-291, wherein the alpha-amylase expressed from the fermenting organism and is derived from *Rhizomucor pusillus* or *Aspergillus terreus*.

Paragraph 293. The process of paragraph 292, wherein the alpha-amylase is *Rhizomucor pusillus* alpha-amylase with an *Aspergillus niger* glucoamylase linker and starch-binding domain (SBD) as shown in SEQ ID NO: 16, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N, and wherein the alpha-amylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.

Paragraph 294. The process of paragraph 292, wherein the alpha-amylase is an *Aspergillus terreus* alpha-amylase selected from the group consisting of:
(i) an alpha-amylase comprising the polypeptide of SEQ ID NO: 6 of WO2017/087330;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 of WO2017/087330.

Paragraph 295. A *Saccharomyces cerevisiae* yeast strain, wherein the strain is a derivative of MBG5012 comprising one or more expression vectors encoding a glucoamylase and/or an alpha-amylase.

Paragraph 296. The yeast strain according to paragraph 295, wherein the glucoamylase is selected from glucoamylases obtainable from *Gloeophyllum, Pycnoporous*, or *Trametes*.

Paragraph 297. The yeast strain according to paragraph 296, wherein the glucoamylase is selected from a *Gloeophyllum trabeum, Gloeophyllum sepiarium*, or *Gloeophyllum abietinum* glucoamylase.

Paragraph 298. The yeast strain of paragraph 297, wherein the glucoamylase is selected from the group consisting of:
(i) a glucoamylase comprising the polypeptide of SEQ ID NO: 15 or SEQ ID NO: 17;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 or SEQ ID NO: 17.

Paragraph 299. The yeast strain of any of paragraphs 296-298, wherein the glucoamylase is the *Gloeophyllum trabeum* glucoamylase shown in SEQ ID NO: 17 having one of the following substitutions: V59A; S95P; A121P; T119W; S95P+A121P; V59A+S95P; S95P+T119W; V59A+S95P+A121P; or S95P+T119W+A121P, especially S95P+A121P.

Paragraph 300. The yeast strain of paragraph 296, wherein the glucoamylase is a *Trametes cingulata* glucoamylase.

Paragraph 301. The yeast strain of paragraph 300, wherein the glucoamylase is selected from the group consisting of:
(i) a glucoamylase comprising the polypeptide of SEQ ID NO: 20;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20.

Paragraph 302: The yeast strain of paragraph 296, wherein the glucoamylase is s a *Pycnoporus sanguineus* glucoamylase.

Paragraph 303. The yeast strain of paragraph 302, wherein the glucoamylase is selected from the group consisting of:
(i) a glucoamylase comprising the polypeptide of SEQ ID NO: 18;
(ii) a glucoamylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.

Paragraph 304. The yeast strain of paragraph 295 expression vector wherein the alpha-amylase is selected from a *Rhizomucor pusillus* or *Aspergillus terreus* alpha-amylase.

Paragraph 305. The yeast strain of paragraph 304, wherein the alpha-amylase is *Rhizomucor pusillus* alpha-amylase with an *Aspergillus niger* glucoamylase linker and starch-binding domain (SBD) as shown in SEQ ID NO: 16, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N, and wherein the alpha-amylase has at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.

Paragraph 306. The yeast strain of paragraph 304, wherein the alpha-amylase is *Aspergillus terreus* alpha-amylase selected from the group consisting of:
(i) an alpha-amylase comprising the polypeptide of SEQ ID NO: 6 of WO2017/087330;
(ii) an alpha-amylase comprising an amino acid sequence having at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 of WO2017/087330.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

DEPOSIT OF BIOLOGICAL MATERIAL

The following biological material has been deposited under the terms of the Budapest Treaty with the Agricultural Research Service Patent Culture Collection (NRRL), Northern Regional Research Center, 1815 University Street, Peoria, Ill., USA, and given the following accession number:

| Deposit | Accession Number | Date of Deposit |
| --- | --- | --- |
| *Saccharomyces cerevisiae* strain MBG5038 | NRRL Y-67549 | Feb. 1, 2018 |
| *Saccharomyces cerevisiae* strain MBG5012 | NRRL Y-67700 | Nov. 16, 2018 |

The following biological material has been deposited under the terms of the Budapest Treaty with the National Measurement Institute, Victoria, Australia and given the following accession number:

| Deposit | Accession Number | Date of Deposit |
| --- | --- | --- |
| Ethanol Red ® | V14/007039 | Mar. 19, 2014 |

The strains were deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Materials & Methods

Materials:

Alpha-Amylase 369 ("AA369"): *Bacillus stearothermophilus* alpha-amylase with the mutations: I181*+G182*+N193F+V59A+Q89R+E129V+K177L+R179E+Q254S+M284V truncated to 491 amino acids (using SEQ ID NO: 1 herein for numbering);

*Penicillium oxalicum* glucoamylase variant PE498 ("PoAMG498"): *Penicillium oxalicum* glucoamylase variant having the following mutations: K79V+P2N+P4S+P11F+T65A+Q327F (using SEQ ID NO: 14 herein for numbering):

Protease Pfu ("PFU"): Protease derived from *Pyrococcus furiosus* shown in SEQ ID NO: 13 herein.

Glucoamylase SA ("GSA") comprises a blend comprising *Talaromyces emersonii* glucoamylase disclosed in WO99/28448 (SEQ ID NO: 19 herein), *Trametes cingulata* glucoamylase disclosed as SEQ ID NO: 2 in WO 06/69289 and SEQ ID NO: 20 herein, and *Rhizomucor pusillus* alpha-amylase with *Aspergillus niger* glucoamylase linker and SBD disclosed as SEQ ID NO: 16 herein with the following substitutions: G128D+D143N (activity ratio AGU:AGU:FAU(F): approx. 30:7:1).

Yeast:

ETHANOL RED™ ("ER"): *Saccharomyces cerevisiae* yeast available from Fermentis/Lesaffre, USA.

Methods

Identity: The relatedness between two amino acid sequences or between two nucleotide sequences is described by the parameter "identity".

For purposes described herein, the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Protease Assays

AZCL-Casein Assay

A solution of 0.2% of the blue substrate AZCL-casein is suspended in Borax/$NaH_2PO_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/$NaH_2PO_4$ buffer pH 9.0). The increase in $OD_{405}$ at room temperature is monitored as a measure of the protease activity.

Glucoamylase activity (AGU) Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation

Substrate: maltose 23.2 mM

Buffer: acetate 0.1 M pH: 4.30±0.05

Incubation temperature: 37° C.±1

Reaction time: 5 minutes

Enzyme working range: 0.5-4.0 AGU/mL

Color Reaction

GlucDH: 430 U/L

Mutarotase: 9 U/L

NAD: 0.21 mM
Buffer: phosphate 0.12 M; 0.15 M NaCl
pH: 7.60±0.05
Incubation temperature: 37° C.±1
Reaction time: 5 minutes
Wavelength: 340 nm A folder (EB-SM-0131.02/01) describing this analytical method in more detail is available on request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

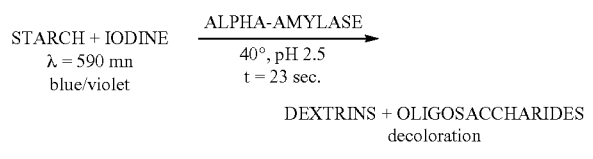

Standard Conditions/Reaction Conditions
Substrate: Soluble starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Alpha-Amylase Activity (KNU-A)

Alpha amylase activity is measured in KNU(A) Kilo Novozymes Units (A), relative to an enzyme standard of a declared strength.

Alpha amylase in samples and α-glucosidase in the reagent kit hydrolyze the substrate (4,6-ethylidene($G_7$)-p-nitrophenyl($G_1$)-α,D-maltoheptaoside (ethylidene-$G_7$PNP) to glucose and the yellow-colored p-nitrophenol.

The rate of formation of p-nitrophenol can be observed by Konelab 30. This is an expression of the reaction rate and thereby the enzyme activity.

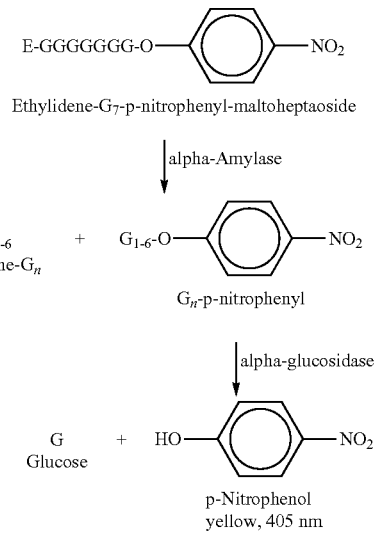

The enzyme is an alpha-amylase with the enzyme classification number EC 3.2.1.1.

| Parameter | Reaction conditions |
|---|---|
| Temperature | 37° C. |
| pH | 7.00 (at 37° C.) |
| Substrate conc. | Ethylidene-$G_7$PNP, R2: 1.86 mM |
| Enzyme conc. (conc. of high/low standard in reaction mixture) | 1.35-4.07 KNU(A)/L |
| Reaction time | 2 min |
| Interval kinetic measuring time | 7/18 sec. |
| Wave length | 405 nm |
| Conc. of reagents/chemicals critical for the analysis | α-glucosidase, R1: ≥3.39 kU/L |

A folder EB-SM-5091.02-D on determining KNU-A activity is available upon request to Novozymes A/S, Denmark, which folder is hereby included by reference.

Alpha-Amylase Activity KNU(S)

BS-amylase in samples and the enzyme alpha-glucosidase in the reagent kit hydrolyze substrate (4,6-ethylidene(G7)-p-nitrophenyl(G1)-alpha-D-maltoheptaoside (ethylidene-G7PNP)) to glucose and the yellow-colored p-nitrophenol.

The rate of formation of p-nitrophenol can be observed by Konelab 30. This is an expression of the reaction rate and thereby the enzyme activity.

Reaction Conditions
Reaction:
pH: 7.15
Temperature: 37° C.
Reaction Time: 180 sec
Detection:
Wavelength: 405 nm
Measuring Time: 120 sec
Unit Definition

*Bacillus stearothermophilus* amylase (BS-amylase) activity is measured in KNU(S), Kilo Novo Units (sterarothermophilus), relative to an enzyme standard of a declared strength.

This analytical method is described in more details in EB-SM-0221.02 (incorporated by reference) available from Novozymes A/S, Denmark, on request.

Determination of FAU(F)

FAU(F) Fungal Alpha-Amylase Units (Fungamyl) is measured relative to an enzyme standard of a declared strength.
Reaction Conditions
Temperature: 37° C.
pH: 7.15
Wavelength: 405 nm
Reaction time: 5 min
Measuring time: 2 min A folder (EB-SM-0216.02) describing this standard method in more detail is available on request from Novozymes A/S, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1: Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1 numbering)) and alpha-amylase variants thereof was determined by incubating the reference alpha-amylase and variants at pH 4.5 and 5.5 and temperatures of 75° C. and 85° C. with 0.12 mM $CaCl_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM $CaCl_2$, pH 5.0). Twenty microliters enzyme sample was transferred to 48-well PCR MTP and 180 microliters stability buffer (150 mM acetate, 150 mM MES, 0.01% Triton X100, 0.12 mM $CaCl_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM $CaCl_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T % (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM $CaCl_2$) | T½ (min) (pH 4.5, 85° C., 0.12 mM $CaCl_2$) | T½ (min) (pH 5.5, 85° C., 0.12 mM $CaCl_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V+ K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |

TABLE 1-continued

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND: not determined

The results demonstrate that the alpha-amylase variants have a significantly greater half-life and stability than the reference alpha-amylase.

Example 2: Preparation of Protease Variants and Test of Thermostability

Strains and Plasmids

*E. coli* DH12S (available from Gibco BRL) was used for yeast plasmid rescue. pJTP000 is a *S. cerevisiae* and *E. coli* shuttle vector under the control of TPI promoter, constructed from pJC039 described in WO 01/92502, in which the *Thermoascus aurantiacus* M35 protease gene (WO 03048353) has been inserted.

*Saccharomyces cerevisiae* YNG318 competent cells: MATa Dpep4[cir+] ura3-52, leu2-D2, his 4-539 was used for protease variants expression. It is described in J. Biol. Chem. 272 (15), pp 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar (2%) and H$_2$O (approx. 761 ml) is autoclaved together, and the separately sterilized SC-glucose solution is added to the agar solution.

YPD: Bacto peptone 20 g/l, yeast extract 10 g/l, 20% glucose 100 ml/l.

YPD+Zn: YPD+0.25 mM ZnSO$_4$.

PEG/LiAc solution: 40% PEG4000 50 ml, 5 M Lithium Acetate 1 ml. 96 well Zein micro titre plate:

Each well contains 200 microL of 0.05-0.1% of zein (Sigma), 0.25 mM ZnSO$_4$ and 1% of agar in 20 mM Sodium Acetate Buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endonucleases) and 1 microL of PCR fragments is mixed.

The DNA mixture, 100 microL of YNG318 competent cells, and 10 microL of YEAST MAKER carrier DNA (Clontech) is added to a 12 ml polypropylene tube (Falcon 2059). Add 0.6 ml PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The *Thermoascus* M35 protease gene was amplified with the primer pair Prot F (SEQ ID NO: 4) and Prot R (SEQ ID NO: 5). The resulting PCR fragments were introduced into *S. cerevisiae* YNG318 together with the pJC039 vector (described in WO 2001/92502) digested with restriction enzymes to remove the *Humicola insolens* cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 6) and AM35 (SEQ ID NO:7) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
| --- | --- | --- |
| 48.5 microL H$_2$O | 1 | 94° C. 2 min |
| 2 beads puRe Taq Ready-To-Go PCR (Amersham Biosciences) | 2 | 94° C. 30 sec |
| 0.5 micro L X 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex. 60° C. and 65° C., 70° C. and 75° C., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml of 12.5% azo-casein in ethanol in 96 ml of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglucosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al. (2001), Appl. Environ. Microbiol. 67, 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH4)2SO4 in small aliquots (corresponding to approx. 2.0-2.2 M (NH4)2SO4 not taking the volume increase into account when adding the compound).
3. After the final addition of (NH4)2SO4, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 ml 50 mM Na-acetate pH 4.0.
6. Filter the sample by vacuum suction using a 0.22 μm PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay
1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 ml Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100× G and 25° C.
7. 200 microL of the supernatant is transferred to a MTP, and the absorbance at 590 nm is recorded.

Results

TABLE 2

Relative activity of protease variants. Numbering of substitution(s) starts from N-terminal of the mature peptide in amino acids 1 to 177 of SEQ ID NO: 3

| Variant | Substitution(s) | Relative activity 65° C./60° C. |
|---|---|---|
| WT | none | 31% |
| JTP004 | S87P | 45% |
| JTP005 | A112P | 43% |
| JTP008 | R2P | 71% |
| JTP009 | D79K | 69% |
| JTP010 | D79L | 75% |
| JTP011 | D79M | 73% |
| JTP012 | D79L/S87P | 86% |
| JTP013 | D79L/S87P/A112P | 90% |
| JTP014 | D79L/S87P/A112P | 88% |
| JTP016 | A73C | 52% |
| JTP019 | A126V | 69% |
| JTP021 | M152R | 59% |

TABLE 3

Relative activity of protease variants. Numbering of substitution(s) starts from N-terminal of the mature peptide in amino acids 1 to 177 of SEQ ID NO: 3

| | | Relative activity | | |
|---|---|---|---|---|
| Variant | Substitution(s) and/or deletion (S) | 70° C./65° C. | 75° C./65° C. | 75° C./70° C. |
| WT | none | 59% | 17% | |
| JTP036 | D79L/S87P/D142L | 73% | 73% | |
| JTP040 | T54R/D79L/S87P | | 71% | |
| JTP042 | Q53K/D79L/S87P/I173V | | 108% | |
| JTP043 | Q53R/D79L/S87P | | 80% | |
| JTP045 | S41R/D79L/S87P | | 82% | |
| JTP046 | D79L/S87P/Q158W | | 96% | |
| JTP047 | D79L/S87P/S157K | | 85% | |
| JTP048 | D79L/S87P/D104R | | 88% | |
| JTP050 | D79L/S87P/A112P/D142L | | 88% | |
| JTP051 | S41R/D79L/S87P/A112P/D142L | | | 102% |
| JTP052 | D79L/S87P/A112P/D142L/S157K | | | 111% |
| JTP053 | S41R/D79L/S87P/A112P/D142L/S157K | | | 113% |
| JTP054 | ΔS5/D79L/S87P | | | 92% |
| JTP055 | ΔG8/D79L/S87P | | | 95% |
| JTP059 | C6R/D79L/S87P | | | 92% |
| JTP061 | T46R/D79L/S87P | | | 111% |
| JTP063 | S49R/D79L/S87P | | | 94% |
| JTP064 | D79L/S87P/N88R | | | 92% |
| JTP068 | D79L/S87P/T114P | | | 99% |
| JTP069 | D79L/S87P/S115R | | | 103% |
| JTP071 | D79L/S87P/T116V | | | 105% |
| JTP072 | N26R/D79L/S87P | | 92% | |
| JTP077 | A27K/D79L/S87P/A112P/D142L | | 106% | |
| JTP078 | A27V/D79L/S87P/A112P/D142L | | 100% | |
| JTP079 | A27G/D79L/S87P/A112P/D142L | | 104% | |

TABLE 4

Relative activity of protease variants. Numbering of substitution(s) starts from N-terminal of the mature peptide in amino acids 1 to 177 of SEQ ID NO: 3

| | | Relative activity | Remaining activity | |
|---|---|---|---|---|
| Variant | Substitution(s) and/or deletion(s) | 75° C./65° C. | 80° C. | 84° C. |
| JTP082 | ΔS5/D79L/S87P/A112P/D142L | 129% | | 53% |
| JTP083 | T46R/D79L/S87P/A112P/D142L | 126% | | |
| JTP088 | Y43F/D79L/S87P/A112P/D142L | 119% | | |
| JTP090 | D79L/S87P/A112P/T124L/D142L | 141% | | |
| JTP091 | D79L/S87P/A112P/T124V/D142L | 154% | 43% | |
| JTP092 | ΔS5/N26R/D79L/S87P/A112P/D142L | | | 60% |

TABLE 4-continued

Relative activity of protease variants. Numbering of substitution(s) starts from N-terminal of the mature peptide in amino acids 1 to 177 of SEQ ID NO: 3

| Variant | Substitution(s) and/or deletion(s) | Relative activity 75° C./65° C. | Remaining activity 80° C. | Remaining activity 84° C. |
|---|---|---|---|---|
| JTP095 | N26R/T46R/D79L/S87P/A112P/D142L | | | 62% |
| JTP096 | T46R/D79L/S87P/T116V/D142L | | | 67% |
| JTP099 | D79L/P81R/S87P/A112P/D142L | | | 80% |
| JTP101 | A27K/D79L/S87P/A112P/T124V/D142L | | 81% | |
| JTP116 | D79L/Y82F/S87P/A112P/T124V/D142L | | 59% | |
| JTP117 | D79L/Y82F/S87P/A112P/T124V/D142L | | 94% | |
| JTP127 | D79L/S87P/A112P/T124V/A126V/D142L | | 53% | |

TABLE 5

Relative activity of protease variants. Numbering of substitution(s) starts from N-terminal of the mature peptide in amino acids 1 to 177 of SEQ ID NO: 3

| Variant | Substitutions | Relative activity 75° C./70° C. | Relative activity 80° C./70° C. | Relative activity 85° C./70° C. |
|---|---|---|---|---|
| JTP050 | D79L S87P A112P D142L | 55% | 23% | 9% |
| JTP134 | D79L Y82F S87P A112P D142L | | 40% | |
| JTP135 | S38T D79L S87P A112P A126V D142L | | 62% | |
| JTP136 | D79L Y82F S87P A112P A126V D142L | | 59% | |
| JTP137 | A27K D79L S87P A112P A126V D142L | | 54% | |
| JTP140 | D79L S87P N98C A112P G135C D142L | 81% | | |
| JTP141 | D79L S87P A112P D142L T141C M161C | 68% | | |
| JTP143 | S36P D79L S87P A112P D142L | 69% | | |
| JTP144 | A37P D79L S87P A112P D142L | 57% | | |
| JTP145 | S49P D79L S87P A112P D142L | 82% | 59% | |
| JTP146 | S50P D79L S87P A112P D142L | 83% | 63% | |
| JTP148 | D79L S87P D104P A112P D142L | 76% | 64% | |
| JTP161 | D79L Y82F S87G A112P D142L | | 30% | 12% |
| JTP180 | S70V D79L Y82F S87G Y97W A112P D142L | | 52% | |
| JTP181 | D79L Y82F S87G Y97W D104P A112P D142L | | 45% | |
| JTP187 | S70V D79L Y82F S87G A112P D142L | | 45% | |
| JTP188 | D79L Y82F S87G D104P A112P D142L | | 43% | |
| JTP189 | D79L Y82F S87G A112P A126V D142L | | 46% | |
| JTP193 | Y82F S87G S70V D79L D104P A112P D142L | | | 15% |
| JTP194 | Y82F S87G D79L D104P A112P A126V D142L | | | 22% |
| JTP196 | A27K D79L Y82F S87G D104P A112P A126V D142L | | | 18% |

TABLE 6

Relative activity of protease variants. Numbering of substitution(s) starts from N-terminal of the mature peptide in amino acids 1 to 177 of SEQ ID NO: 3

| Variant | Substitutions | Relative activity 75° C./70° C. | Relative activity 80° C./70° C. |
|---|---|---|---|
| JTP196 | A27K D79L Y82F S87G D104P A112P A126V D142L | 102% | 55% |
| JTP210 | A27K Y82F S87G D104P A112P A126V D142L | 107% | 36% |
| JTP211 | A27K D79L Y82F D104P A112P A126V D142L | 94% | 44% |
| JTP213 | A27K Y82F D104P A112P A126V D142L | 103% | 37% |

Example 3: Temperature Profile of Selected Variants Using Purified Enzymes

Selected variants showing good thermo-stability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:

1) Mix 10 ul of 10 ug/ml enzyme solutions and 100 ul of 0.025% zein solution in a micro titer plate (MTP).

2) Incubate at various temperatures for 60 min.

3) Add 10 ul of 100% trichloroacetic acid (TCA) solution.

4) Centrifuge MTP at 3500 rpm for 5 min.

5) Take out 15 ul to a new MTP containing 100 ul of BCA assay solution (Pierce Cat #:23225, BCA Protein Assay Kit).

6) Incubate for 30 min. at 60° C.

7) Measure A562.

The results are shown in Table 7. All of the tested variants showed an improved thermo-stability as compared to the wt protease.

TABLE 7

| | Zein-BCA assay | | | | | | |
|---|---|---|---|---|---|---|---|
| WT/ | Sample incubated 60 min at indicated temperatures (° C.) (μg/ml Bovine serum albumin equivalent peptide released) | | | | | | |
| Variant | 60° C. | 70° C. | 75° C. | 80° C. | 85° C. | 90° C. | 95° C. |
| WT | 94 | 103 | 107 | 93 | 58 | 38 | |
| JTP050 | 86 | 101 | 107 | 107 | 104 | 63 | 36 |
| JTP077 | 82 | 94 | 104 | 105 | 99 | 56 | 31 |
| JTP188 | 71 | 83 | 86 | 93 | 100 | 75 | 53 |
| JTP196 | 87 | 99 | 103 | 106 | 117 | 90 | 38 |

Example 4: Characterization of *Penicillium oxalicum* Glucoamylase

The *Penicillium oxalicum* glucoamylase is disclosed in SEQ ID NO: 9 herein.
Substrate. Substrate: 1% soluble starch (Sigma S-9765) in deionized water
Reaction buffer: 0.1 M Acetate buffer at pH 5.3
Glucose concentration determination kit: Wako glucose assay kit (LabAssay glucose, WAKO, Cat #298-65701).
Reaction condition. 20 microL soluble starch and 50 microL acetate buffer at pH 5.3 were mixed. 30 microL enzyme solution (50 micro g enzyme protein/ml) was added to a final volume of 100 microL followed by incubation at 37° C. for 15 min.
The glucose concentration was determined by Wako kits. All the work carried out in parallel.
Temperature optimum. To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 8.

TABLE 8

| Temperature optimum | | | | | |
|---|---|---|---|---|---|
| Temperature (° C.) | 20 | 30 | 40 | 50 | 60 |
| Relative activity (%) | 63.6 | 71.7 | 86.4 | 99.4 | 94.6 |
| Temperature (° C.) | 70 | 80 | 85 | 90 | 95 |
| Relative activity (%) | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.
Heat stability. To assess the heat stability of the *Penicillium oxalicum* glucoamylase the Reaction condition assay was modified in that the the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.
The results are shown in Table 9.

TABLE 9

| Heat stability | | | | | |
|---|---|---|---|---|---|
| Temperature (° C.) | 20 | 30 | 40 | 50 | 60 |
| Relative activity (%) | 91.0 | 92.9 | 88.1 | 100.0 | 96.9 |

TABLE 9-continued

| Heat stability | | | | | |
|---|---|---|---|---|---|
| Temperature (° C.) | 70 | 80 | 85 | 90 | 95 |
| Relative activity (%) | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.
pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.
The results are shown in Table 10.

TABLE 10

| pH optimum | | | | | |
|---|---|---|---|---|---|
| pH | 2.0 | 3.0 | 3.5 | 4.0 | 4.5 | 5.0 |
| Relative activity (%) | 71.4 | 78.6 | 77.0 | 91.2 | 84.2 | 100.0 |
| pH | 6.0 | 7.0 | 8.0 | 9.0 | 10.0 | 11.0 |
| Relative activity (%) | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.
pH stability. To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.
The results are shown in Table 11.

TABLE 11

| pH stability | | | | | |
|---|---|---|---|---|---|
| pH | 2.0 | 3.0 | 3.5 | 4.0 | 4.5 | 5.0 |
| Relative activity (%) | 17.4 | 98.0 | 98.0 | 103.2 | 100.0 | 93.4 |
| pH | 6.0 | 7.0 | 8.0 | 9.0 | 10.0 | 11.0 |
| Relative activity (%) | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5: Thermostability of Protease Pfu

The thermostability of the *Pyrococcus furiosus* protease (Pfu S) purchased from Takara Bio Inc, (Japan) was tested using the same methods as in Example 2. It was found that the thermostability (Relative Activity) was 110% at (80° C./70° C.) and 103% (90° C./70° C.) at pH 4.5.

Example 6: Cloning of *Penicillium oxalicum* Strain Glucoamylase Gene

Preparation of *Penicillium oxalicum* Strain cDNA.

The cDNA was synthesized by following the instruction of 3' Rapid Amplification of cDNA End System (Invitrogen Corp., Carlsbad, Calif., USA).

Cloning of *Penicillium oxalicum* Strain Glucoamylase Gene.

The *Penicillium oxalicum* glucoamylase gene was cloned using the oligonucleotide primer shown below designed to amplify the glucoamylase gene from 5' end.

```
Sense primer:
                                    (SEQ ID NO: 22)
5'-ATGCGTCTCACTCTATTATCAGGTG-3'
```

The full length gene was amplified by PCR with Sense primer and AUAP (supplied by 3' Rapid Amplification of cDNA End System) by using Platinum HIFI Taq DNA polymerase (Invitrogen Corp., Carlsbad, Calif., USA). The amplification reaction was composed of 5 µl of 10×PCR buffer, 2 µl of 25 mM MgCl$_2$, 1 µl of 10 mM dNTP, 1 µl of 10 uM Sense primer, 1 µl of 10 uM AUAP, 2 µl of the first strand cDNA, 0.5 µl of HIFI Taq, and 37.5 µl of deionized water. The PCR program was: 94° C., 3 mins; 10 cycles of 94° C. for 40 secs, 60° C. 40 secs with 1° C. decrease per cycle, 68° C. for 2 min; 25 cycles of 94° C. for 40 secs, 50° C. for 40 secs, 68° C. for 2 min; final extension at 68° C. for 10 mins.

The obtained PCR fragment was cloned into pGEM-T vector (Promega Corporation, Madison, Wis., USA) using a pGEM-T Vector System (Promega Corporation, Madison, Wis., USA) to generate plasmid AMG 1. The glucoamylase gene inserted in the plasmid AMG 1 was sequencing confirmed. *E. coli* strain TOP10 containing plasmid AMG 1 (designated NN059173), was deposited with the Deutsche Sammlung von Mikroorganismen und Zellkulturen GmbH (DSMZ) on Nov. 23, 2009, and assigned accession number as DSM 23123.

Example 7: Expression of Cloned *Penicillium oxalicum* Glucoamylase

The *Penicillium oxalicum* glucoamylase gene was re-cloned from the plasmid AMG 1 into an *Aspergillus* expression vector by PCR using two cloning primer F and primer R shown below, which were designed based on the known sequence and added tags for direct cloning by IN-FUSION™ strategy.

```
Primer F:
                                    (SEQ ID NO: 23)
5' ACACAACTGGGGATCCACCATGCGTCTCACTCTATTATC Primer R:
                                    (SEQ ID NO: 24)
5' AGATCTCGAGAAGCTTAAAACTGCCACACGTCGTTGG
```

A PCR reaction was performed with plasmid AMG 1 in order to amplify the full-length gene. The PCR reaction was composed of 40 µg of the plasmid AMG 1 DNA, 1 µl of each primer (100 µM); 12.5 µl of 2× Extensor Hi-Fidelity master mix (Extensor Hi-Fidelity Master Mix, ABgene, United Kingdom), and 9.5 µl of PCR-grade water. The PCR reaction was performed using a DYAD PCR machine (Bio-Rad Laboratories, Inc., Hercules, Calif., USA) programmed for 2 minutes at 94° C. followed by a 25 cycles of 94° C. for 15 seconds, 50° C. for 30 seconds, and 72° C. for 1 minute; and then 10 minutes at 72° C.

The reaction products were isolated by 1.0% agarose gel electrophoresis using 1×TAE buffer where an approximately 1.9 kb PCR product band was excised from the gel and purified using a GFX® PCR DNA and Gel Band Purification Kit (*GE Healthcare*, United Kingdom) according to manufacturer's instructions. DNA corresponding to the *Penicillium oxalicum* glucoamylase gene was cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

A 2 µl volume of the ligation mixture was used to transform 25 µl of Fusion Blue *E. coli* cells (included in the IN-FUSION™ Dry-Down PCR Cloning Kit). After a heat shock at 42° C. for 45 sec, and chilling on ice, 250 µl of SOC medium was added, and the cells were incubated at 37° C. at 225 rpm for 90 min before being plated out on LB agar plates containing 50 µg of ampicillin per ml, and cultivated overnight at 37° C. Selected colonies were inoculated in 3 ml of LB medium supplemented with 50 µg of ampicillin per ml and incubated at 37° C. at 225 rpm overnight. Plasmid DNA from the selected colonies was purified using Mini JETSTAR (Genomed, Germany) according to the manufacturer's instructions. *Penicillium oxalicum* glucoamylase gene sequence was verified by Sanger sequencing before heterologous expression. One of the plasmids was selected for further expression, and was named XYZ XYZ1471-4.

Protoplasts of *Aspergillus niger* MB in118 were prepared as described in WO 95/02043. One hundred µl of protoplast suspension were mixed with 2.5 µg of the XYZ1471-4 plasmid and 250 microliters of 60% PEG 4000 (Applichem) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were mixed with 6% low melting agarose (Biowhittaker Molecular Applications) in COVE sucrose (Cove, 1996, Biochim. Biophys. Acta 133:51-56) (1M) plates supplemented with 10 mM acetamide and 15 mM CsCl and added as a top layer on COVE sucrose (1M) plates supplemented with 10 mM acetamide and 15 mM CsCl for transformants selection (4 ml topagar per plate). After incubation for 5 days at 37° C. spores of sixteen transformants were picked up and seed on 750 µl YP-2% Maltose medium in 96 deepwell MT plates. After 5 days of stationary cultivation at 30° C., 10 µl of the culture-broth from each well was analyzed on a SDS-PAGE (Sodium dodecyl sulfate-polyacrylamide gel electrophoresis) gel, Griton XT Precast gel (BioRad, CA, USA) in order to identify the best transformants based on the ability to produce large amount of glucoamylase. A selected transformant was identified on the original transformation plate and was preserved as spores in a 20% glycerol stock and stored frozen (−80° C.).

Cultivation. The selected transformant was inoculated in 100 ml of MLC media and cultivated at 30° C. for 2 days in 500 ml shake flasks on a rotary shaker. 3 ml of the culture broth was inoculated to 100 ml of M410 medium and cultivated at 30° C. for 3 days. The culture broth was centrifugated and the supernatant was filtrated using 0.2 μm membrane filters.

Alpha-cyclodextrin affinity gel. Ten grams of Epoxy-activated Sepharose 6B (GE Healthcare, Chalfont St. Giles, U.K) powder was suspended in and washed with distilled water on a sintered glass filter. The gel was suspended in coupling solution (100 ml of 12.5 mg/ml alpha-cyclodextrin, 0.5 M NaOH) and incubated at room temperature for one day with gentle shaking. The gel was washed with distilled water on a sintered glass filter, suspended in 100 ml of 1 M ethanolamine, pH 10, and incubated at 50° C. for 4 hours for blocking. The gel was then washed several times using 50 mM Tris-HCl, pH 8 and 50 mM NaOAc, pH 4.0 alternatively. The gel was finally packed in a 35-40 ml column using equilibration buffer (50 mM NaOAc, 150 mM NaCl, pH 4.5).

Purification of glucoamylase from culture broth. Culture broth from fermentation of *A. niger* MB in 118 harboring the glucoamylase gene was filtrated through a 0.22 μm PES filter, and applied on a alpha-cyclodextrin affinity gel column previously equilibrated in 50 mM NaOAc, 150 mM NaCl, pH 4.5 buffer. Unbound material was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase sample was then dialyzed against 20 mM NaOAc, pH 5.0. The purity was finally checked by SDS-PAGE, and only a single band was found.

Example 8: Construction and Expression of a Site-Directed Variant of *Penicillium oxalicum* Glucoamylase Two PCR reactions were performed with plasmid XYZ1471-4, described in Example 7, using primers K79V F and K79VR shown below, which were designed to substitute lysine K at position 79 from the mature sequence to valine (V) and primers F-NP003940 and R-NP003940 shown below, which were designed based on the known sequence and added tags for direct cloning by IN-FUSION™ strategy.

```
Primer K79V F 18 mer
                                         (SEQ ID NO: 25)
GCAGTCTTTCCAATTGAC Primer K79 VR 18 mer
                                         (SEQ ID NO: 26)
AATTGGAAAGACTGCCCG Primer F-NP003940:
                                         (SEQ ID NO: 27)
5' ACACAACTGGGGATCCACCATGCGTCTCACTCTATTATC Primer R-NP003940:
                                         (SEQ ID NO: 28)
5' AGATCTCGAGAAGCTTAAAACTGCCACACGTCGTTGG
```

The PCR was performed using a PTC-200 DNA Engine under the conditions described below.

| PCR reaction system: | | Conditions: |
|---|---|---|
| 48.5 micro L H2O | 1 | 94° C. 2 min |
| 2 beads puRe Taq Ready-To-Go PCR Beads (Amersham Biosciences) | 2 | 94° C. 30 sec |
| | 3 | 55° C. 30 sec |

-continued

| PCR reaction system: | | Conditions: |
|---|---|---|
| 0.5 micro L X 2 100 pmole/micro L Primers (K79V F + Primer R-NP003940, K79V R + Primer F-NP003940) | 4 | 72° C. 90 sec |
| | 2-4 | 25 cycles |
| | 5 | 72° C. 10 min |
| 0.5 micro L Template DNA | | |

DNA fragments were recovered from agarose gel by the Qiagen gel extraction Kit according to the manufacturer's instruction. The resulting purified two fragments were cloned into an *Aspergillus* expression vector linearized with BamHI and HindIII, using an IN-FUSION™ Dry-Down PCR Cloning Kit (BD Biosciences, Palo Alto, Calif., USA) according to the manufacturer's instructions. The linearized vector construction is as described in WO 2005/042735 A1.

The ligation mixture was used to transform *E. coli* DH5a cells (TOYOBO). Selected colonies were inoculated in 3 ml of LB medium supplemented with 50 μg of ampicillin per ml and incubated at 37° C. at 225 rpm overnight. Plasmid DNA from the selected colonies was purified using Qiagen plasmid mini kit (Qiagen) according to the manufacturer's instructions. The sequence of *Penicillium oxalicum* glucoamylase site-directed variant gene sequence was verified before heterologous expression and one of the plasmids was selected for further expression, and was named pPoPE001.

Protoplasts of *Aspergillus niger* MB in 118 were prepared as described in WO 95/02043. One hundred μl of protoplast suspension were mixed with 2.5 μg of the pPoPE001 plasmid and 250 microliters of 60% PEG 4000 (Applichem) (polyethylene glycol, molecular weight 4,000), 10 mM $CaCl_2$, and 10 mM Tris-HCl pH 7.5 were added and gently mixed. The mixture was incubated at 37° C. for 30 minutes and the protoplasts were mixed with 1% agarose L (Nippon Gene) in COVE sucrose (Cove, 1996, Biochim. Biophys. Acta 133:51-56) supplemented with 10 mM acetamide and 15 mM CsCl and added as a top layer on COVE sucrose plates supplemented with 10 mM acetamide and 15 mM CsCl for transformants selection (4 ml topagar per plate). After incubation for 5 days at 37° C. spores of sixteen transformants were picked up and seed on 750 μl YP-2% Maltose medium in 96 deepwell MT plates. After 5 days of stationary cultivation at 30° C., 10 μl of the culture-broth from each well was analyzed on a SDS-PAGE gel in order to identify the best transformants based on the ability to produce large amount of the glucoamylase.

Example 9: Purification of Site-Directed Po AMG Variant PE001

The selected transformant of the variant and the strain expressing the wild type *Penicillium oxalicum* glucoamylase described in Example 6 was cultivated in 100 ml of YP-2% maltose medium and the culture was filtrated through a 0.22 μm PES filter, and applied on a alpha-cyclodextrin affinity gel column previously equilibrated in 50 mM NaOAc, 150 mM NaCl, pH 4.5 buffer. Unbound materials was washed off the column with equilibration buffer and the glucoamylase was eluted using the same buffer containing 10 mM beta-cyclodextrin over 3 column volumes.

The glucoamylase activity of the eluent was checked to see, if the glucoamylase had bound to the alpha-cyclodextrin affinity gel. The purified glucoamylase samples were then dialyzed against 20 mM NaOAc, pH 5.0.

Example 10: Characterization of PE001 Protease Stability

40 µl enzyme solutions (1 mg/ml) in 50 mM sodium acetate buffer, pH 4.5, were mixed with 1/10 volume of 1 mg/ml protease solutions such as aspergillopepsin I described in Biochem J. 1975 April; 147(1):45-53, or the commercially available product from Sigma and aorsin described in Biochemical journal [0264-6021] Ichishima yr: 2003 vol:371 iss:Pt 2 pg:541 and incubated at 4 or 32° C. overnight. As a control experiment, H$_2$O was added to the sample instead of proteases. The samples were loaded on SDS-PAGE to see if the glucoamylases are cleaved by proteases.

In SDS-PAGE, PE001 only showed one band corresponding to the intact molecule, while the wild type glucoamylase was degraded by proteases and showed a band at lower molecular size at 60 kCa.

TABLE 12

The result of SDS-PAGE after protease treatment

| | Wild type glucoamylase | | | | PE001 | | | | |
|---|---|---|---|---|---|---|---|---|---|
| Protease | aspergill-opepsin I | | aorsin | | aspergill-opepsin I | | aorsin | | control |
| Incubation temperature (° C.) | 4 | 32 | 4 | 32 | 4 | 32 | 4 | 32 | 4 |
| intact glucoamylase (ca. 70 kDa) | 100% | 90% | 40% | 10% | 100% | 100% | 100% | 100% | 100% |
| cleaved glucoamylase (ca. 60 kDa) | N.D. | 10% | 60% | 90% | N.D. | N.D. | N.D. | N.D1 | N.D. |

N.D.: not detected.

Example 11: Less Cleavage During Cultivation

*Aspergillus* transformant of the variant and the wild type *Penicillium oxalicum* glucoamylase were cultivated in 6-well MT plates containing 4x diluted YP-2% maltose medium supplemented with 10 mM sodium acetate buffer, pH4.5, at 32° C. for 1 week.

The culture supernatants were loaded on SDS-PAGE.

TABLE 13

The result of SDS-PAGE of the culture supernatants

| | Wild type glucoamylase | PE001 |
|---|---|---|
| intact glucoamylase (ca. 70 kDa) | 90% | 100% |
| cleaved glucoamylase (ca. 60 kDa) | 10% | N.D. |

N.D.: not detected.

The wild type glucoamylase was cleaved by host proteases during fermentation, while the variant yielded only intact molecule.

Example 12: Glucoamylase Activity of Variant Compared to Parent

The glucoamylase activity measures as AGU as described above was checked for the purified enzymes of the wild type *Penicillium oxalicum* and the variant glucoamylase.

The Glucoamylase Unit (AGU) was defined as the amount of enzyme, which hydrolyzes 1 micromole maltose per minute under the standard conditions (37° C., pH 4.3, substrate: maltose 100 mM, buffer: acetate 0.1 M, reaction time 6 minutes).

TABLE 14

| Relative specific activity | AGU/mg |
|---|---|
| Penicillium oxalicum wt | 100% |
| Penicillium oxalicum PE001 (SEQ ID NO: 14 + K79V substitution) | 102% |

Example 13: Purification of Glucoamylase Variants Having Increased Thermostability The variants showing increased thermostability may be constructed and expressed similar to the procedure described in Example 8. All variants were derived from the PE001. After expression in YPM medium, variants comprising the T65A or Q327F substitution was micro-purified as follows:

Mycelium was removed by filtration through a 0.22 µm filter. 50 µl column material (alpha-cyclodextrin coupled to Mini-Leak divinylsulfone-activated agarose medium according to manufacturer's recommendations) was added to the wells of a filter plate (Whatman, Unifilter 800 µl, 25-30 µm MBPP). The column material was equilibrated with binding buffer (200 mM sodium acetate pH 4.5) by two times addition of 200 µl buffer, vigorous shaking for 10 min (Heidolph, Titramax 101, 1000 rpm) and removal of buffer by vacuum (Whatman, UniVac 3). Subsequently, 400 µl culture supernatant and 100 µl binding buffer was added and the plate incubated 30 min with vigorous shaking. Unbound material was removed by vacuum and the binding step was repeated. Normally 4 wells were used per variant. Three washing steps were then performed with 200 µl buffer of decreasing ionic strength added (50/10/5 mM sodium acetate, pH 4.5), shaking for 15 min and removal of buffer by vacuum. Elution of the bound AMG was achieved by two times addition of 100 µl elution buffer (250 mM sodium acetate, 0.1% alpha-cyclodextrin, pH 6.0), shaking for 15 min and collection of eluted material in a microtiter plate by vacuum. Pooled eluates were concentrated and buffer changed to 50 mM sodium acetate pH 4.5 using centrifugal filter units with 10 kDa cut-off (Millipore Microcon Ultracel YM-10). Micropurified samples were stored at −18° C. until testing of thermostability.

Example 14: Protein Thermal Unfolding Analysis (TSA, Thermal Shift Assay)

Protein thermal unfolding of the T65A and Q327F variants, was monitored using Sypro Orange (In-vitrogen, S-6650) and was performed using a real-time PCR instrument (Applied Biosystems; Step-One-Plus).

In a 96-well plate, 25 microliter micropurified sample in 50 mM Acetate pH4,5 at approx. 100 microgram/ml was mixed (5:1) with Sypro Orange (resulting conc.=5×; stock solution from supplier=5000×). The plate was sealed with an optical PCR seal. The PCR instrument was set at a scan-rate of 76° C. pr. hr, starting at 25° C. and finishing at 96° C.

Protein thermal unfolding of the E501V+Y504T variant, was monitored using Sypro Orange (In-vitrogen, S-6650) and was performed using a real-time PCR instrument (Applied Biosystems; Step-One-Plus).

In a 96-well plate, 15 microliter purified sample in 50 mM Acetate pH4,5 at approx. 50 microgram/ml was mixed (1:1) with Sypro Orange (resulting conc.=5×; stock solution from supplier=5000×) with or without 200 ppm Acarbose (Sigma A8980). The plate was sealed with an optical PCR seal. The PCR instrument was set at a scan-rate of 76 degrees C. pr. hr, starting at 25° C. and finishing at 96° C.

Fluorescence was monitored every 20 seconds using in-built LED blue light for excitation and ROX-filter (610 nm, emission).

Tm-values were calculated as the maximum value of the first derivative (dF/dK) (ref.: Gregory et al; *J Biomol Screen* 2009 14: 700)

TABLE 15a

| Sample | Tm (Deg. Celsius) +/−0.4 |
| --- | --- |
| PO-AMG (PE001) | 80.3 |
| Variant Q327F | 82.3 |
| Variant T65A | 81.9 |

TABLE 15b

| Sample | Tm (Deg. Celsius) +/−0.4 | |
| --- | --- | --- |
| Acarbose: | − | + |
| PO-AMG (PE001) | 79.5 | 86.9 |
| Variant E501V Y504T | 79.5 | 95.2 |

Example 15: Thermostability Analysis by Differential Scanning Calorimetry (DSC)

Additional site specific variants having substitutions and/or deletions at specific positions were constructed basically as described in Example 8 and purified as described in Example 11.

The thermostability of the purified Po-AMG PE001 derived variants were determined at pH 4.0 or 4.8 (50 mM Sodium Acetate) by Differential Scanning calorimetry (DSC) using a VP-Capillary Differential Scanning calorimeter (MicroCal Inc., Piscataway, N.J., USA). The thermal denaturation temperature, Td (° C.), was taken as the top of the denaturation peak (major endothermic peak) in thermograms (Cp vs. T) obtained after heating enzyme solutions in selected buffers (50 mM Sodium Acetate, pH 4.0 or 4.8) at a constant programmed heating rate of 200 K/hr.

Sample- and reference-solutions (approximately 0.3 ml) were loaded into the calorimeter (reference: buffer without enzyme) from storage conditions at 10° C. and thermally pre-equilibrated for 10 minutes at 20° C. prior to DSC scan from 20° C. to 110° C. Denaturation temperatures were determined with an accuracy of approximately +/−1° C.

The isolated variants and the DSC data are disclosed in Table 16 below.

TABLE 16

| Po-AMG name | Mutations | DSC Td (° C.) @ pH 4.0 | DSC Td (° C.) @ pH 4.8 |
| --- | --- | --- | --- |
| PE001 (SEQ ID NO: 14 +K79V) | | 82.1 | 83.4 |
| GA167 | E501V Y504T | 82.1 | |
| GA481 | T65A K161S | 84.1 | 86.0 |
| GA487 | T65A Q405T | 83.2 | |
| GA490 | T65A Q327W | 87.3 | |
| GA491 | T65A Q327F | 87.7 | |
| GA492 | T65A Q327Y | 87.3 | |
| GA493 | P11F T65A Q327F | 87.8 | 88.5 |
| GA497 | R1K D3W K5Q G7V N85 T10K P11S T65A Q327F | 87.8 | 88.0 |
| GA498 | P2N P4S P11F T65A Q327F | 88.3 | 88.4 |
| GA003 | P11F D26C K33C T65A Q327F | 83.3 | 84.0 |
| GA009 | P2N P4S P11F T65A Q327W E501V Y504T | 88.8 | |
| GA002 | R1E D3N P4G G6R G7A N8A T10D P11D T65A Q327F | 87.5 | 88.2 |
| GA005 | P11F T65A Q327W | 87.4 | 88.0 |
| GA008 | P2N P4S P11F T65A Q327F E501V Y504T | 89.4 | 90.2 |
| GA010 | P11F T65A Q327W E501V Y504T | | 89.7 |
| GA507 | T65A Q327F E501V Y504T | | 89.3 |
| GA513 | T65A S105P Q327W | | 87.0 |
| GA514 | T65A S105P Q327F | | 87.4 |
| GA515 | T65A Q327W S364P | | 87.8 |
| GA516 | T65A Q327F S364P | | 88.0 |
| GA517 | T65A S103N Q327F | | 88.9 |
| GA022 | P2N P4S P11F K34Y T65A Q327F | | 89.7 |
| GA023 | P2N P4S P11F T65A Q327F D445N V447S | | 89.9 |
| GA032 | P2N P4S P11F T65A I172V Q327F | | 88.7 |
| GA049 | P2N P4S P11F T65A Q327F N502* | | 88.4 |

TABLE 16-continued

| Po-AMG name | Mutations | DSC Td (° C.) @ pH 4.0 | DSC Td (° C.) @ pH 4.8 |
|---|---|---|---|
| GA055 | P2N P4S P11F T65A Q327F N502T P563S K571E | | 88.0 |
| GA057 | P2N P4S P11F R31S K33V T65A Q327F N564D K571S | | 89.5 |
| GA058 | P2N P4S P11F T65A Q327F S377T | | 88.6 |
| GA064 | P2N P4S P11F T65A V325T Q327W | | 88.0 |
| GA068 | P2N P4S P11F T65A Q327F D445N V447S E501V Y504T | | 90.2 |
| GA069 | P2N P4S P11F T65A I172V Q327F E501V Y504T | | 90.2 |
| GA073 | P2N P4S P11F T65A Q327F S377T E501V Y504T | | 90.1 |
| GA074 | P2N P4S P11F D26N K34Y T65A Q327F | | 89.1 |
| GA076 | P2N P4S P11F T65A Q327F I375A E501V Y504T | | 90.2 |
| GA079 | P2N P4S P11F T65A K218A K221D Q327F E501V Y504T | | 90.9 |
| GA085 | P2N P4S P11F T65A S103N Q327F E501V Y504T | | 91.3 |
| GA086 | P2N P4S T10D T65A Q327F E501V Y504T | | 90.4 |
| GA088 | P2N P4S F12Y T65A Q327F E501V Y504T | | 90.4 |
| GA097 | K5A P11F T65A Q327F E501V Y504T | | 90.0 |
| GA101 | P2N P4S T10E E18N T65A Q327F E501V Y504T | | 89.9 |
| GA102 | P2N T10E E18N T65A Q327F E501V Y504T | | 89.8 |
| GA084 | P2N P4S P11F T65A Q327F E501V Y504T T568N | | 90.5 |
| GA108 | P2N P4S P11F T65A Q327F E501V Y504T K524T G526A | | 88.6 |
| GA126 | P2N P4S P11F K34Y T65A Q327F D445N V447S E501V Y504T | | 91.8 |
| GA129 | P2N P4S P11F R31S K33V T65A Q327F D445N V447S E501V Y504T | | 91.7 |
| GA087 | P2N P4S P11F D26N K34Y T65A Q327F E501V Y504T | | 89.8 |
| GA091 | P2N P4S P11F T65A F80* Q327F E501V Y504T | | 89.9 |
| GA100 | P2N P4S P11F T65A K112S Q327F E501V Y504T | | 89.8 |
| GA107 | P2N P4S P11F T65A Q327F E501V Y504T T516P K524T G526A | | 90.3 |
| GA110 | P2N P4S P11F T65A Q327F E501V N502T Y504* | | 90.6 |

Example 16: Thermostability Analysis by Thermo-Stress Test and pNPG Assay

Starting from one of the identified substitution variants from Example 15, identified as GA008, additional variants were tested by a thermo-stress assay in which the supernatant from growth cultures were assayed for glucoamylase (AMG) activity after a heat shock at 83° C. for 5 min.

After the heat-shock the residual activity of the variant was measured as well as in a non-stressed sample.

Description of Po-AMG pNPG Activity Assay:

The *Penicillium oxalicum* glucoamylase pNPG activity assay is a spectrometric endpoint assay where the samples are split in two and measured thermo-stressed and non-thermo-stressed. The data output is therefore a measurement of residual activity in the stressed samples.

Growth:

A sterile micro titer plate (MTP) was added 200 μL rich growth media (FT X-14 without Dowfax) to each well. The strains of interest were inoculated in triplicates directly from frozen stocks to the MTP. Benchmark was inoculated in 20 wells. Non-inoculated wells with media were used as assay blanks. The MTP was placed in a plastic box containing wet tissue to prevent evaporation from the wells during incubation. The plastic box was placed at 34° C. for 4 days.

Assay:

50 μL supernatant was transferred to 50 μL 0.5 M NaAc pH 4.8 to obtain correct sample pH.

50 μL dilution was transferred to a PCR plate and thermo-stressed at 83° C. for 5 minutes in a PCR machine. The remaining half of the dilution was kept at RT.

20 μL of both stressed and unstressed samples was transferred to a standard MTP. 20 μL pNPG-substrate was added to start the reaction. The plate was incubated at RT for 1 hour.

The reaction was stopped and the colour developed by adding 50 μL 0.5M $Na_2CO_3$. The yellow colour was measured on a plate reader (Molecular Devices) at 405 nm.

Buffers:

0.5 M NaAc pH 4.8

0.25 M NaAc pH 4.8

Substrate, 6 mM pNPG:

15 mg 4-nitrophenyl D-glucopyranoside in 10 mL 0.25 NaAc pH 4.8

Stop/Developing Solution:

0.5 M $Na_2CO_3$

Data Treatment:

In Excel the raw Abs405 data from both stressed and unstressed samples were blank subtracted with their respective blanks. The residual activity (% res. act.=($Abs_{unstressed}$−($Abs_{unstressed}$−$Abs_{stressed}$))/$Abs_{unstressed}$*100%) was calculated and plotted relative to benchmark, Po-amg0008.

TABLE 17

| Po-AMG name | Mutations | % residual activity |
| --- | --- | --- |
| GA008 | P2N P4S P11F T65A Q327F E501V Y504T | 100 |
| GA085 | P2N P4S P11F T65A S103N Q327F E501V Y504T | 127 |
| GA097 | K5A P11F T65A Q327F E501V Y504T | 106 |
| GA107 | P2N P4S P11F T65A Q327F E501V Y504T T516P K524T G526A | 109 |
| GA130 | P2N P4S P11F T65A V79A Q327F E501V Y504T | 111 |
| GA131 | P2N P4S P11F T65A V79G Q327F E501V Y504T | 112 |
| GA132 | P2N P4S P11F T65A V79I Q327F E501V Y504T | 101 |
| GA133 | P2N P4S P11F T65A V79L Q327F E501V Y504T | 102 |
| GA134 | P2N P4S P11F T65A V79S Q327F E501V Y504T | 104 |
| GA150 | P2N P4S P11F T65A L72V Q327F E501V Y504T | 101 |
| GA155 | S255N Q327F E501V Y504T | 105 |

TABLE 18

| Po-AMG name | Mutations | % residual activity |
| --- | --- | --- |
| GA008 | P2N P4S P11F T65A Q327F E501V Y504T | 100 |
| GA179 | P2N P4S P11F T65A E74N V79K Q327F E501V Y504T | 108 |
| GA180 | P2N P4S P11F T65A G220N Q327F E501V Y504T | 108 |
| GA181 | P2N P4S P11F T65A Y245N Q327F E501V Y504T | 102 |
| GA184 | P2N P4S P11F T65A Q253N Q327F E501V Y504T | 110 |
| GA185 | P2N P4S P11F T65A D279N Q327F E501V Y504T | 108 |
| GA186 | P2N P4S P11F T65A Q327F S359N E501V Y504T | 108 |
| GA187 | P2N P4S P11F T65A Q327F D370N E501V Y504T | 102 |
| GA192 | P2N P4S P11F T65A Q327F V460S E501V Y504T | 102 |
| GA193 | P2N P4S P11F T65A Q327F V460T P468T E501V Y504T | 102 |
| GA195 | P2N P4S P11F T65A Q327F T463N E501V Y504T | 103 |
| GA196 | P2N P4S P11F T65A Q327F S465N E501V Y504T | 106 |
| GA198 | P2N P4S P11F T65A Q327F T477N E501V Y504T | 106 |

Example 17: Test for Glucoamylase Activity of Thermo-Stable Variants

All of the above described variants disclosed in tables 15, 16, and 17 have been verified for Glucoamylase activity on culture supernatants using the pNPG assay described in Example 16.

Example 18: Production of *Saccharomyces cerevisiae* Strain MBG5038 and MBG5012

Strains MBG5038 and MBG5012 were derived from breeding and evolutionary programs that targeted improved fermentation performance with regards to features of importance to the industrial production of corn ethanol. Strains from a population with the ability to utilize cysteine as a sole nitrogen source, and demonstrating improved ethanol and temperature tolerance were mated with strains derived from a population which combined xylose utilization with low byproduct yields (e.g., according the breeding procedures described in U.S. Pat. No. 8,257,959). These strains were mated with strains derived from Ethanol Red® and the offspring screened to identify strains with increased temperature tolerance combined with reduced by-products to maximize the yield of ethanol from corn mash fermentations. Haploids derived from this breeding program were screened for their ability to utilize cysteine and used to generate MBG5038 (NRRLY67549) and MBG5038 (NRRLY67700).

Example 19: Fermentation of *Saccharomyces cerevisiae* Strain MBG5038 Under Non-Stress Conditions

Figure 2:
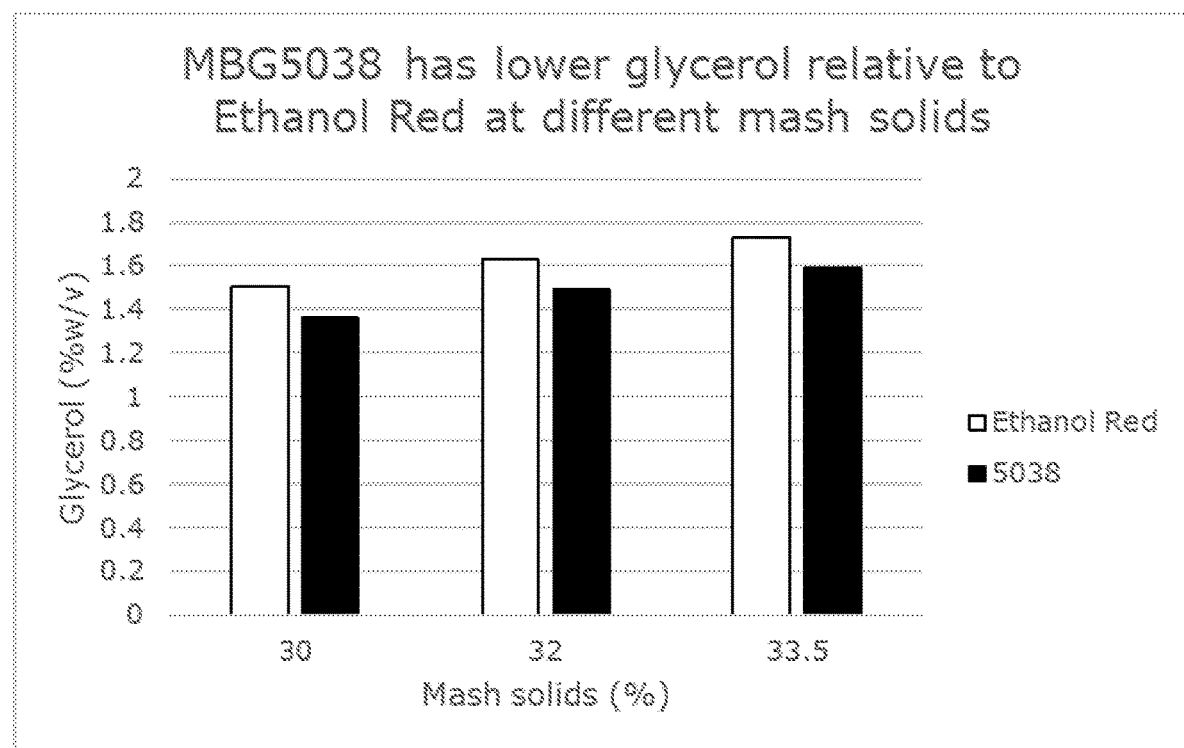
FIG. 2 shows lowered glycerol production from fermentation of *Saccharomyces cerevisiae* strain MBG5038 under non-stress conditions varying mash solids (%).

*Saccharomyces cerevisiae* strains MBG5038 and Ethanol Red® were fermented under the following conditions:
Mash: Liquozyme LpH
Solids: varied
pH: 5.0
Glucoamylose: Spirizyme Achieve (Novozymes A/S)
Glucoamylose dose 0.6 AGU/g DS
Glucoamylose split: 50/50 with remainder added at 8 h
Fermentation time: 55 h
Temp. 32° C.
Scale: 50 g Ankom bottle
As shown in FIGS. 1 and 2, *Saccharomyces cerevisiae* strain MBG5038 demonstrated improved ethanol yields and decreased glycerol levels when compared to Ethanol Red®.

Example 20: Fermentation of *Saccharomyces cerevisiae* Strain MBG5038 Under Stress Conditions

Figure 3:
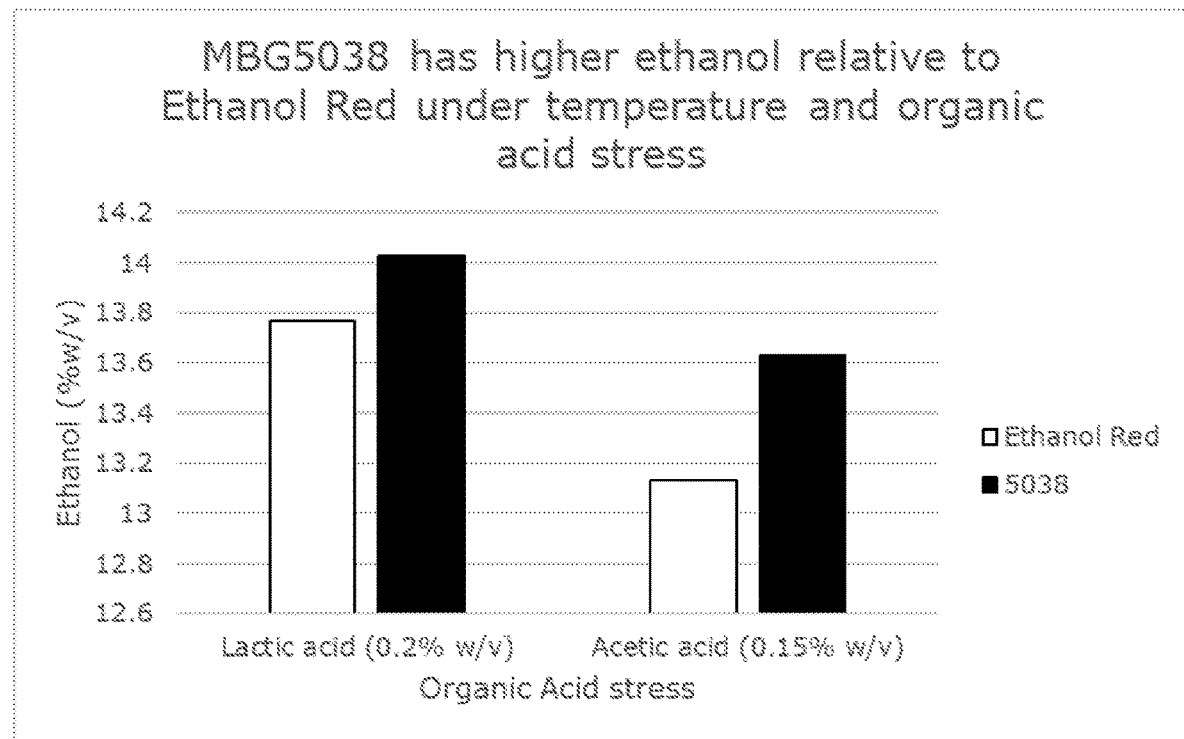
FIG. 3 shows improved ethanol yield from fermentation of *Saccharomyces cerevisiae* strain MBG5038 in the prescence of elevated levels of organic acid.
Figure 4:
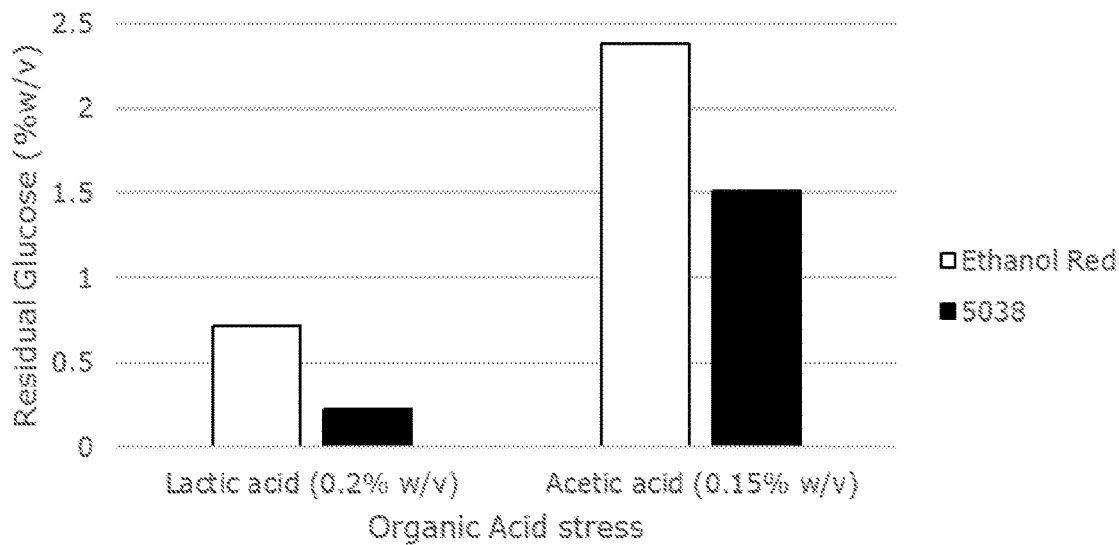
FIG. 4 shows decreased residual glucose from fermentation of *Saccharomyces cerevisiae* strain MBG5038 in the prescence of elevated levels of organic acid.

*Saccharomyces cerevisiae* strains MBG5038 and Ethanol Red® were fermented under the following conditions:
Mash: Avantec Amp
Solids 34.51%
Glucoamylose: Spirizyme Excel (Novozymes A/S)
Glucoamylose dose: 0.6 AGU/g DS
Fermentation time: 54 h
Temp.: 32° C. (7 h)→35° C. (16 h)→32° C. (31 h)
Scale: 5 g tube
As shown in FIGS. 3 and 4, *Saccharomyces cerevisiae* strain MBG5038 demonstrated improved ethanol yield and decreased residual glucose when compared to Ethanol Red® in the prescence of organic acid (lactic acid/acetic acid).

Example 21: Fermentation of *Saccharomyces cerevisiae* Strain MBG5012 Under Non-Stress Conditions

Figure 5:
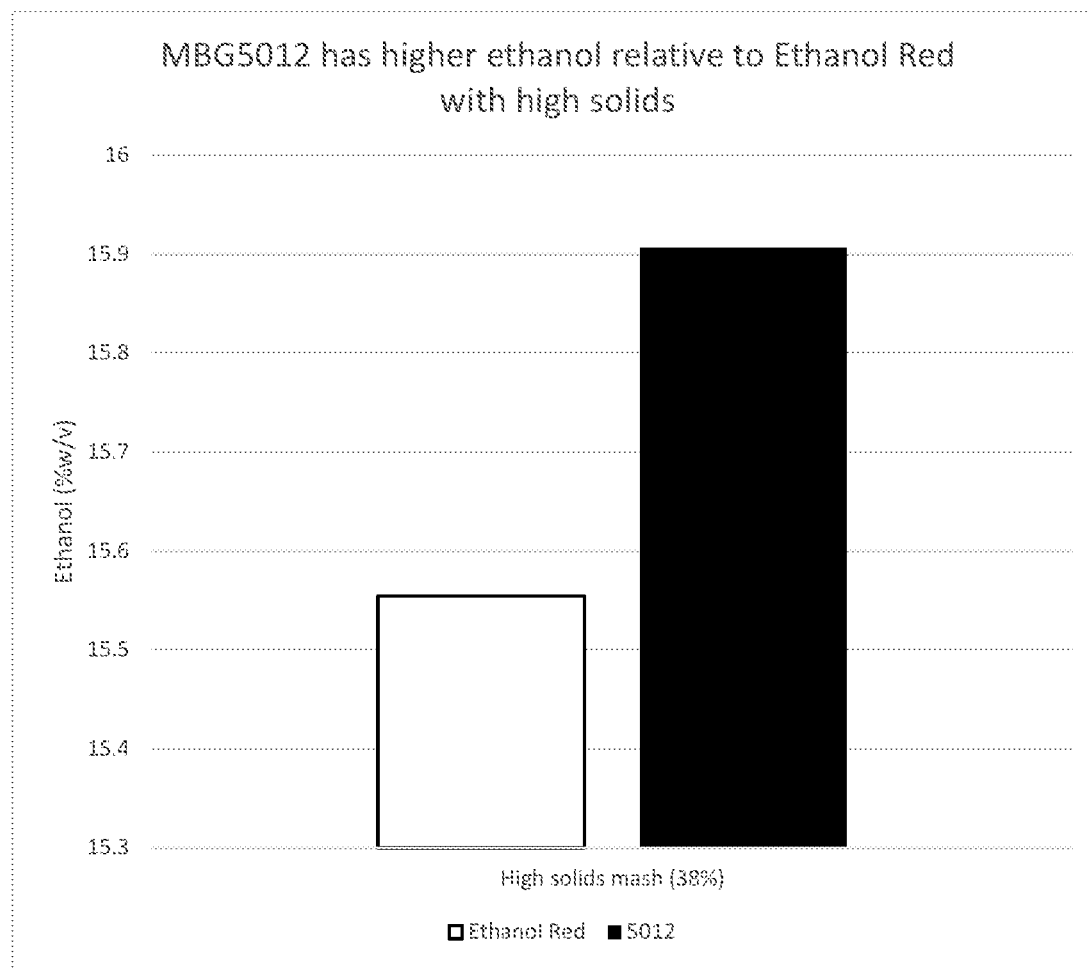
FIG. 5 shows improved ethanol yield from fermentation of *Saccharomyces cerevisiae* strain MBG5012 under non-stress conditions at high mash solids (%).
Figure 6:
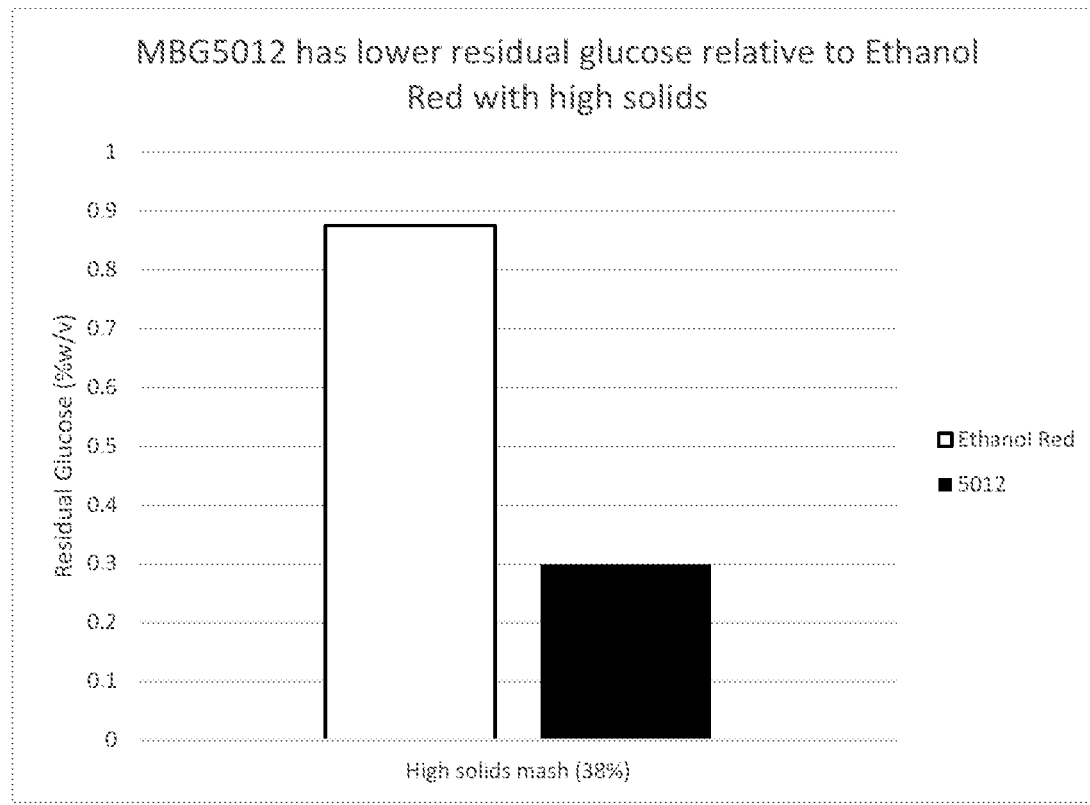
FIG. 6 shows decreased residual glucose from fermentation of *Saccharomyces cerevisiae* strain MBG5012 under non-stress conditions high mash solids (%).

*Saccharomyces cerevisiae* strains MBG5038 and Ethanol Red® were fermented under the following conditions:
Mash: Avantec Amp supplemented with maltodextrin
Solids: 35% final (35% solids liquefact+maltodextrin to achieve 38% total solids)
pH: 5.0
Glucoamylose: Spirizyme Excel (Novozymes A/S)
Glucoamylose dose 0.6 AGU/g DS
Glucoamylose split: 50/50 with remainder added at 8 h
Fermentation time: 54 h
Temp. 32° C.
Scale: 5 g tube As shown in FIGS. 5 and 6, *Saccharomyces cerevisiae* strain MBG5012 demonstrated improved ethanol yields and decreased residual glucose when compared to Ethanol Red®.

Example 22: Fermentation of *Saccharomyces cerevisiae* Strain MBG5012 Under Stress Conditions

Figure 7:
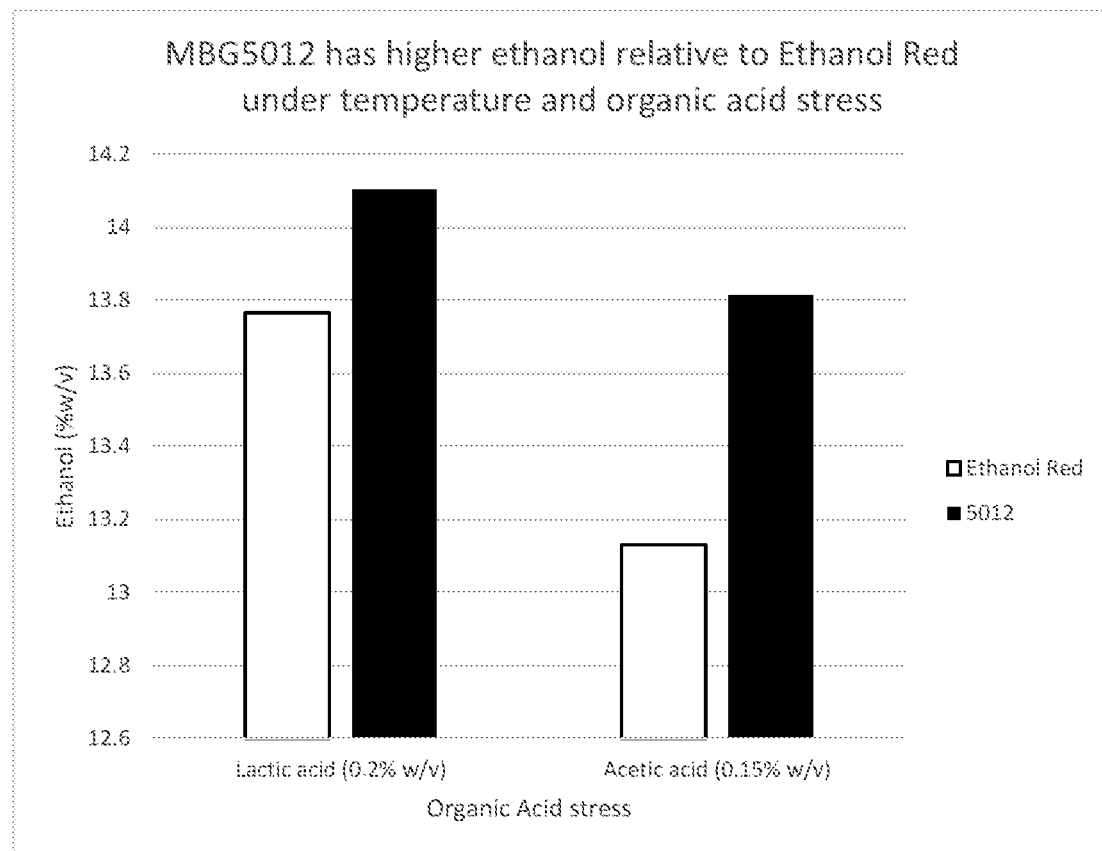
FIG. 7 shows improved ethanol yield from fermentation of *Saccharomyces cerevisiae* strain MBG5012 in the prescence of elevated levels of organic acid.
Figure 8:
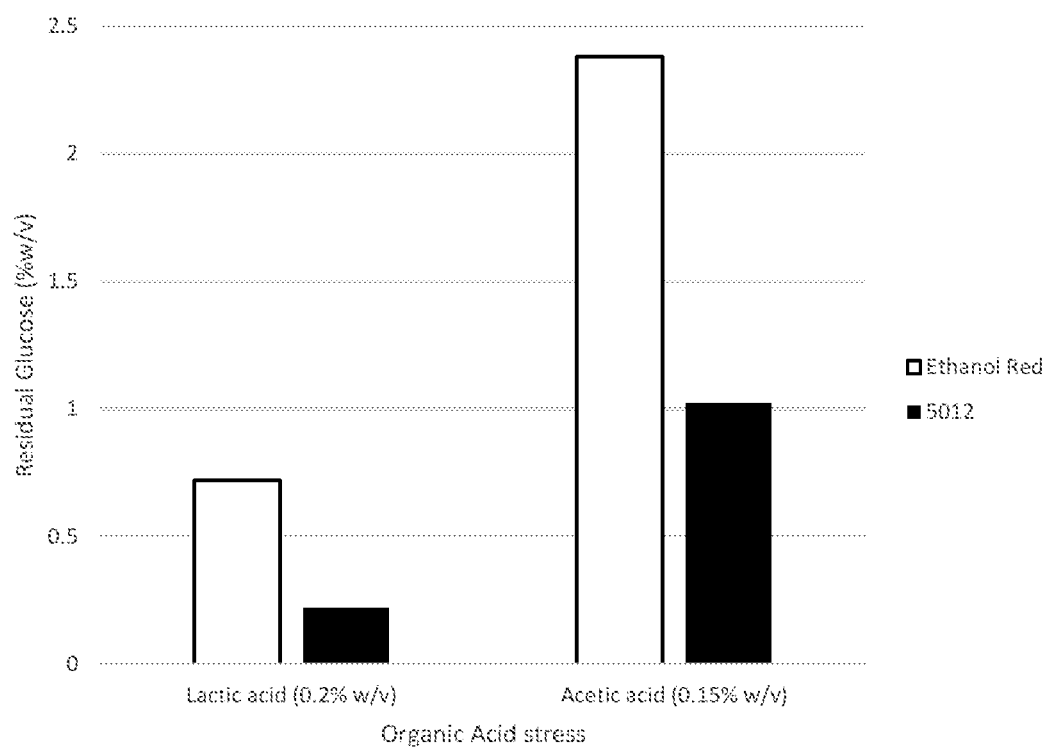
FIG. 8 shows decreased residual glucose from fermentation of *Saccharomyces cerevisiae* strain MBG5012 in the prescence of elevated levels of organic acid.

*Saccharomyces cerevisiae* strains MBG5012 and Ethanol Red® were fermented under the following conditions:
Mash: Avantec Amp
Solids 34.51%
pH: 5.0
Glucoamylose: Spirizyme Excel (Novozymes A/S)
Glucoamylose dose: 0.6 AGU/g DS
Fermentation time: 54 h
Temp.: 32° C. (7 h)→35° C. (16 h)→32° C. (31 h)
Scale: 5 g tube As shown in FIGS. 7 and 8, *Saccharomyces cerevisiae* strain MBG5012 demonstrated improved ethanol yield and decreased residual glucose when compared to Ethanol Red® in the prescence of organic acid (lactic acid/acetic acid).

---

The invention claimed is:

1. A process for producing ethanol from starch-containing material, the process comprising the steps of:
  i) liquefying the starch-containing material at a temperature above the initial gelatinization temperature using an alpha-amylase;
  ii) saccharifying using a glucoamylase;
  iii) fermenting using a fermenting organism;
  wherein the fermenting organism is:
  (1) *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, IL., USA); or
  (2) *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, IL., USA).

2. A *Saccharomyces* yeast strain selected from:
  *Saccharomyces cerevisiae* strain MBG5038 (deposited under Accession No. NRRL Y67549 at the Agricultural Research Service Patent Culture Collection (NRRL), Northern Regional Research Center, 1815 University Street, Peoria, IL., USA); and
  *Saccharomyces cerevisiae* strain MBG5012 (deposited under Accession No. NRRL Y67700 at the Agricultural Research Service Patent Culture Collection (NRRL), Northern Regional Research Center, 1815 University Street, Peoria, IL., USA).

3. The *Saccharomyces* yeast strain of claim 2, wherein the strain is capable of growing on xylose as a sole carbon source.

4. The *Saccharomyces* yeast strain of claim 2, wherein the strain comprises one or more properties and defining characteristics selected from:
   (a) produces a higher titre of ethanol in the first 20 hours of fermentation than *Saccharomyces cerevisiae* strain Ethanol Red® (deposited under Accession No. V14/007039 at National Measurement Institute, Victoria, Australia), under the same conditions in a corn mash fermentation,
   (b) leaves less glucose remaining following 50 hours of fermentation than *Saccharomyces cerevisiae* strain Ethanol Red® (deposited under Accession No. V14/007039 at National Measurement Institute, Victoria, Australia), under the same conditions in a corn mash fermentation,
   (c) has a higher ethanol yield than *Saccharomyces cerevisiae* strain Ethanol Red® (deposited under Accession No. V14/007039 at National Measurement Institute, Victoria, Australia) following 50 hours of fermentation under the same conditions in a corn mash fermentation.

5. The *Saccharomyces* yeast strain of claim 2, wherein the strain is capable of providing an ethanol yield boost over *Saccharomyces cerevisiae* strain Ethanol Red® (deposited under Accession No. V14/007039 at National Measurement Institute, Victoria, Australia) of more than 1.0% under the same process conditions.

6. A composition comprising a *Saccharomyces* yeast strain of claim 2 and one or more naturally occurring and/or non-naturally occurring components selected from surfactants, emulsifiers, gums, swelling agents, and antioxidants.

* * * * *

SEQUENCE LISTING

```
<160> NUMBER OF SEQ ID NOS: 33

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205
```

```
Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2
```

| | | | | | | | | | | | | | | | |
|---|---|---|---|---|---|---|---|---|---|---|---|---|---|---|---|
| atg | cgg | ctc | gtt | gct | tcc | cta | acg | gcc | ttg | gtg | gcc | ttg | tcc | gta | 45 |
| Met | Arg | Leu | Val | Ala | Ser | Leu | Thr | Ala | Leu | Val | Ala | Leu | Ser | Val | |
| | | -175 | | | | -170 | | | | -165 | | | | | |

```
atg cgg ctc gtt gct tcc cta acg gcc ttg gtg gcc ttg tcc gta         45
Met Arg Leu Val Ala Ser Leu Thr Ala Leu Val Ala Leu Ser Val
        -175                -170                -165 cct gtc ttt ccc gct gct gtc aac gtg aag cgt gct tcg tcc tac         90
Pro Val Phe Pro Ala Ala Val Asn Val Lys Arg Ala Ser Ser Tyr
        -160                -155                -150 ctg gag atc act ctg agc cag gtc agc aac act ctg atc aag gcc        135
Leu Glu Ile Thr Leu Ser Gln Val Ser Asn Thr Leu Ile Lys Ala
        -145                -140                -135 gtg gtc cag aac act ggt agc gac gag ttg tcc ttc gtt cac ctg        180
Val Val Gln Asn Thr Gly Ser Asp Glu Leu Ser Phe Val His Leu
        -130                -125                -120 aac ttc ttc aag gac ccc gct cct gtc aaa aag gta tcg gtc tat        225
Asn Phe Phe Lys Asp Pro Ala Pro Val Lys Lys Val Ser Val Tyr
        -115                -110                -105 cgc gat ggg tct gaa gtg cag ttc gag ggc att ttg agc cgc tac aaa    273
Arg Asp Gly Ser Glu Val Gln Phe Glu Gly Ile Leu Ser Arg Tyr Lys
        -100                -95                 -90 tcg act ggc ctc tct cgt gac gcc ttt act tat ctg gct ccc gga gag    321
Ser Thr Gly Leu Ser Arg Asp Ala Phe Thr Tyr Leu Ala Pro Gly Glu
    -85                 -80                 -75 tcc gtc gag gac gtt ttt gat att gct tcg act tac gat ctg acc agc    369
Ser Val Glu Asp Val Phe Asp Ile Ala Ser Thr Tyr Asp Leu Thr Ser
    -70                 -65                 -60 ggc ggc cct gta act atc cgt act gag gga gtt gtt ccc tac gcc acg    417
Gly Gly Pro Val Thr Ile Arg Thr Glu Gly Val Val Pro Tyr Ala Thr
-55             -50                 -45                 -40 gct aac agc act gat att gcc ggc tac atc tca tac tcg tct aat gtg    465
Ala Asn Ser Thr Asp Ile Ala Gly Tyr Ile Ser Tyr Ser Ser Asn Val
            -35                 -30                 -25 ttg acc att gat gtc gat ggc gcc gct gct gcc act gtc tcc aag gca    513
Leu Thr Ile Asp Val Asp Gly Ala Ala Ala Ala Thr Val Ser Lys Ala
        -20                 -15                 -10 atc act cct ttg gac cgc cgc act agg atc agt tcc tgc tcc ggc agc    561
Ile Thr Pro Leu Asp Arg Arg Thr Arg Ile Ser Ser Cys Ser Gly Ser
        -5                  -1  1               5 aga cag agc gct ctt act acg gct ctc aga aac gct gct tct ctt gcc    609
Arg Gln Ser Ala Leu Thr Thr Ala Leu Arg Asn Ala Ala Ser Leu Ala
10                  15                  20                  25 aac gca gct gcc gac gcg gct cag tct gga tca gct tca aag ttc agc    657
Asn Ala Ala Ala Asp Ala Ala Gln Ser Gly Ser Ala Ser Lys Phe Ser
                30                  35                  40 gag tac ttc aag act act tct agc tct acc cgc cag acc gtg gct gcg    705
Glu Tyr Phe Lys Thr Thr Ser Ser Ser Thr Arg Gln Thr Val Ala Ala
            45                  50                  55 cgt ctt cgg gct gtt gcg cgg gag gca tct tcg tct tct tcg gga gcc    753
Arg Leu Arg Ala Val Ala Arg Glu Ala Ser Ser Ser Ser Ser Gly Ala
            60                  65                  70 acc acg tac tac tgc gac gat ccc tac ggc tac tgt tcc tcc aac gtc    801
Thr Thr Tyr Tyr Cys Asp Asp Pro Tyr Gly Tyr Cys Ser Ser Asn Val
    75                  80                  85 ctg gct tac acc ctg cct tca tac aac ata atc gcc aac tgt gac att    849
Leu Ala Tyr Thr Leu Pro Ser Tyr Asn Ile Ile Ala Asn Cys Asp Ile
90                  95                  100                 105 ttc tat act tac ctg ccg gct ctg acc agt acc tgt cac gct cag gat    897
Phe Tyr Thr Tyr Leu Pro Ala Leu Thr Ser Thr Cys His Ala Gln Asp
                110                 115                 120 caa gcg acc act gcc ctt cac gag ttc acc cat gcg cct ggc gtc tac    945
Gln Ala Thr Thr Ala Leu His Glu Phe Thr His Ala Pro Gly Val Tyr
```

```
                 125                 130                     135
agc cct ggc acg gac gac ctg gcg tat ggc tac cag gct gcg atg ggt      993
Ser Pro Gly Thr Asp Asp Leu Ala Tyr Gly Tyr Gln Ala Ala Met Gly
        140                 145                     150 ctc agc agc agc cag gct gtc atg aac gct gac acc tac gct ctc tat    1041
Leu Ser Ser Ser Gln Ala Val Met Asn Ala Asp Thr Tyr Ala Leu Tyr
155                 160                     165 gcg aat gcc ata tac ctt ggt tgc taa                                 1068
Ala Asn Ala Ile Tyr Leu Gly Cys
170                 175

<210> SEQ ID NO 3
<211> LENGTH: 355
<212> TYPE: PRT
<213> ORGANISM: Thermoascus aurantiacus

<400> SEQUENCE: 3

Met Arg Leu Val  Ala Ser Leu Thr  Ala Leu Val Ala  Leu Ser  Val
            -175                -170                -165

Pro Val Phe Pro  Ala Ala Val Asn  Val Lys Arg Ala  Ser Ser  Tyr
            -160                -155                -150

Leu Glu Ile Thr  Leu Ser Gln Val  Ser Asn Thr Leu  Ile Lys  Ala
            -145                -140                -135

Val Val Gln Asn  Thr Gly Ser Asp  Glu Leu Ser Phe  Val His  Leu
            -130                -125                -120

Asn Phe Phe Lys  Asp Pro Ala Pro  Val Lys Lys Val  Ser Val  Tyr
            -115                -110                -105

Arg Asp Gly Ser  Glu Val Gln Phe  Gly Ile Leu Ser  Arg Tyr  Lys
            -100                 -95                 -90

Ser Thr Gly Leu  Ser Arg Asp Ala  Phe Thr Tyr Leu  Ala Pro  Gly  Glu
         -85                 -80                 -75

Ser Val Glu Asp  Val Phe Asp Ile  Ala Ser Thr Tyr  Asp Leu  Thr  Ser
         -70                 -65                 -60

Gly Gly Pro Val  Thr Ile Arg Thr  Glu Gly Val Val  Pro Tyr  Ala  Thr
-55                  -50                 -45                 -40

Ala Asn Ser Thr  Asp Ile Ala Gly  Tyr Ile Ser Tyr  Ser Ser  Asn  Val
                 -35                 -30                 -25

Leu Thr Ile Asp  Val Asp Gly Ala  Ala Ala Thr Val  Ser Lys  Ala
                 -20                 -15                 -10

Ile Thr Pro Leu  Asp Arg Arg Thr  Arg Ile Ser Ser  Cys Ser  Gly  Ser
            -5                 -1  1                  5

Arg Gln Ser Ala  Leu Thr Ala Leu  Arg Asn Ala Ala  Ser Leu  Ala
 10                  15                  20                  25

Asn Ala Ala Ala  Asp Ala Gln Ser  Gly Ser Ala Ser  Lys Phe  Ser
                  30                 35                  40

Glu Tyr Phe Lys  Thr Thr Ser Ser  Thr Arg Gln Thr  Val Ala  Ala
                  45                 50                  55

Arg Leu Arg Ala  Val Ala Arg Glu  Ala Ser Ser Ser  Ser Gly  Ala
             60                 65                  70

Thr Thr Tyr Tyr  Cys Asp Asp Pro  Tyr Gly Tyr Cys  Ser Ser  Asn  Val
 75                  80                 85

Leu Ala Tyr Thr  Leu Pro Ser Tyr  Asn Ile Ile Ala  Asn Cys  Asp  Ile
 90                  95                 100                 105

Phe Tyr Thr Tyr  Leu Pro Ala Leu  Thr Ser Thr Cys  His Ala  Gln  Asp
             110                115                 120
```

```
Gln Ala Thr Thr Ala Leu His Glu Phe Thr His Ala Pro Gly Val Tyr
            125                 130                 135

Ser Pro Gly Thr Asp Asp Leu Ala Tyr Gly Tyr Gln Ala Ala Met Gly
        140                 145                 150

Leu Ser Ser Ser Gln Ala Val Met Asn Ala Asp Thr Tyr Ala Leu Tyr
    155                 160                 165

Ala Asn Ala Ile Tyr Leu Gly Cys
170             175

<210> SEQ ID NO 4
<211> LENGTH: 49
<212> TYPE: DNA
<213> ORGANISM: Artificial Sequence
<220> FEATURE:
<223> OTHER INFORMATION: Synthetic Construct

<400> SEQUENCE: 4
aacgacggta cccggggatc ggatccatgc ggctcgttgc ttccctaac          49

<210> SEQ ID NO 5
<211> LENGTH: 48
<212> TYPE: DNA
<213> ORGANISM: Artificial Sequence
<220> FEATURE:
<223> OTHER INFORMATION: Artificial Construct

<400> SEQUENCE: 5
ctaattacat gatgcggccc ttaattaatt agcaaccaag gtatatgg            48

<210> SEQ ID NO 6
<211> LENGTH: 20
<212> TYPE: DNA
<213> ORGANISM: Artificial Sequence
<220> FEATURE:
<223> OTHER INFORMATION: Artificial Construct

<400> SEQUENCE: 6
taggagttta gtgaacttgc                                          20

<210> SEQ ID NO 7
<211> LENGTH: 18
<212> TYPE: DNA
<213> ORGANISM: Artificial Sequence
<220> FEATURE:
<223> OTHER INFORMATION: Artificial Construct

<400> SEQUENCE: 7
ttcgagcgtc ccaaaacc                                            18

<210> SEQ ID NO 8
<211> LENGTH: 1851
<212> TYPE: DNA
<213> ORGANISM: Penicillium oxalicum
<220> FEATURE:
<221> NAME/KEY: CDS
<222> LOCATION: (1)..(1851)
<220> FEATURE:
<221> NAME/KEY: misc_signal
<222> LOCATION: (1)..(63)

<400> SEQUENCE: 8 atg cgt ctc act cta tta tca ggt gta gcc ggc gtt ctc tgc gca gga    48
Met Arg Leu Thr Leu Leu Ser Gly Val Ala Gly Val Leu Cys Ala Gly
1               5                   10                  15 cag ctg acg gcg gcg cgt cct gat ccc aag ggt ggg aat ctg acg ccg    96
```

```
                Gln Leu Thr Ala Ala Arg Pro Asp Pro Lys Gly Gly Asn Leu Thr Pro
                         20                  25                  30 ttc atc cac aaa gag ggc gag cgg tcg ctc caa ggc atc ttg gac aat      144
Phe Ile His Lys Glu Gly Glu Arg Ser Leu Gln Gly Ile Leu Asp Asn
         35                  40                  45 ctc ggt ggg cga ggt aag aaa aca ccc ggc act gcc gca ggg ttg ttt      192
Leu Gly Gly Arg Gly Lys Lys Thr Pro Gly Thr Ala Ala Gly Leu Phe
 50                  55                  60 att gcc agt cca aac aca gag aat cca aac tat tat tat aca tgg act      240
Ile Ala Ser Pro Asn Thr Glu Asn Pro Asn Tyr Tyr Tyr Thr Trp Thr
 65                  70                  75                  80 cgt gac tca gct ttg act gcc aag tgc ttg atc gac ctg ttc gaa gac      288
Arg Asp Ser Ala Leu Thr Ala Lys Cys Leu Ile Asp Leu Phe Glu Asp
                 85                  90                  95 tct cgg gca aag ttt cca att gac cgc aaa tac ttg gaa aca gga att      336
Ser Arg Ala Lys Phe Pro Ile Asp Arg Lys Tyr Leu Glu Thr Gly Ile
                100                 105                 110 cgg gac tac gtg tcg tcc caa gca atc ctc cag agt gtg tct aat cct      384
Arg Asp Tyr Val Ser Ser Gln Ala Ile Leu Gln Ser Val Ser Asn Pro
            115                 120                 125 tct gga acc ctg aag gat ggc tct ggt ctg ggt gaa ccc aag ttt gag      432
Ser Gly Thr Leu Lys Asp Gly Ser Gly Leu Gly Glu Pro Lys Phe Glu
        130                 135                 140 att gac ctg aat ccc ttt tcg ggt gcc tgg ggt cgg cct cag cgg gat      480
Ile Asp Leu Asn Pro Phe Ser Gly Ala Trp Gly Arg Pro Gln Arg Asp
145                 150                 155                 160 ggc cca gcg ctg cga gcg acc gct atg atc acc tac gcc aac tac ctg      528
Gly Pro Ala Leu Arg Ala Thr Ala Met Ile Thr Tyr Ala Asn Tyr Leu
                165                 170                 175 ata tcc cat ggt cag aaa tcg gat gtg tca cag gtc atg tgg ccg att      576
Ile Ser His Gly Gln Lys Ser Asp Val Ser Gln Val Met Trp Pro Ile
                180                 185                 190 att gcc aat gat cta gca tat gtt ggt caa tac tgg aat aat acc gga      624
Ile Ala Asn Asp Leu Ala Tyr Val Gly Gln Tyr Trp Asn Asn Thr Gly
            195                 200                 205 ttt gac ctg tgg gaa gag gtg gat ggg tca agc ttt ttc acg att gcg      672
Phe Asp Leu Trp Glu Glu Val Asp Gly Ser Ser Phe Phe Thr Ile Ala
        210                 215                 220 gtc cag cac cga gcc ctt gtt gaa ggc tcg caa ctg gcg aaa aag ctc      720
Val Gln His Arg Ala Leu Val Glu Gly Ser Gln Leu Ala Lys Lys Leu
225                 230                 235                 240 ggc aag tcc tgc gat gcc tgt gat tct cag cct ccc cag ata ttg tgt      768
Gly Lys Ser Cys Asp Ala Cys Asp Ser Gln Pro Pro Gln Ile Leu Cys
                245                 250                 255 ttc ctg cag agt ttc tgg aac gga aag tac atc acc tcc aac atc aac      816
Phe Leu Gln Ser Phe Trp Asn Gly Lys Tyr Ile Thr Ser Asn Ile Asn
                260                 265                 270 acg caa gca agc cgc tct ggt atc gac ctg gac tct gtc ctg gga agc      864
Thr Gln Ala Ser Arg Ser Gly Ile Asp Leu Asp Ser Val Leu Gly Ser
            275                 280                 285 att cat acc ttt gat ccc gaa gca gcc tgt gac gat gca act ttc cag      912
Ile His Thr Phe Asp Pro Glu Ala Ala Cys Asp Asp Ala Thr Phe Gln
        290                 295                 300 cct tgt tct gcc cgc gct ctg gcg aac cac aag gtc tat gtg gat tcc      960
Pro Cys Ser Ala Arg Ala Leu Ala Asn His Lys Val Tyr Val Asp Ser
305                 310                 315                 320 ttc cgc tct atc tac aag att aat gcg ggt ctt gca gag gga tcg gct     1008
Phe Arg Ser Ile Tyr Lys Ile Asn Ala Gly Leu Ala Glu Gly Ser Ala
                325                 330                 335
```

| | | | | | | | | | | | | | | | |
|---|---|---|---|---|---|---|---|---|---|---|---|---|---|---|---|
| gcc | aac | gtt | ggc | cgc | tac | ccc | gag | gat | gtt | tac | caa | gga | ggc | aat | cca | 1056
| Ala | Asn | Val | Gly | Arg | Tyr | Pro | Glu | Asp | Val | Tyr | Gln | Gly | Gly | Asn | Pro |
| | | | 340 | | | | 345 | | | | 350 | | | | |

```
gcc aac gtt ggc cgc tac ccc gag gat gtt tac caa gga ggc aat cca      1056
Ala Asn Val Gly Arg Tyr Pro Glu Asp Val Tyr Gln Gly Gly Asn Pro
            340             345             350 tgg tat ctc gcc acc cta ggc gca tct gaa ttg ctt tac gac gcc ttg      1104
Trp Tyr Leu Ala Thr Leu Gly Ala Ser Glu Leu Leu Tyr Asp Ala Leu
        355             360             365 tac cag tgg gac aga ctt ggc aaa ctt gaa gtc tcg gag acc tcg ttg      1152
Tyr Gln Trp Asp Arg Leu Gly Lys Leu Glu Val Ser Glu Thr Ser Leu
370             375             380 tca ttc ttc aaa gac ttt gac gcg acc gtg aaa att ggc tcg tac tcg      1200
Ser Phe Phe Lys Asp Phe Asp Ala Thr Val Lys Ile Gly Ser Tyr Ser
385             390             395             400 agg aac agc aag acc tac aag aaa ttg acc cag tcc atc aag tcg tac      1248
Arg Asn Ser Lys Thr Tyr Lys Lys Leu Thr Gln Ser Ile Lys Ser Tyr
            405             410             415 gcg gac ggg ttc atc cag tta gtg cag cag tac act cct tct aat gga      1296
Ala Asp Gly Phe Ile Gln Leu Val Gln Gln Tyr Thr Pro Ser Asn Gly
        420             425             430 tct ctg gcc gag caa tac gat cgc aat acg gct gct cct ctc tct gca      1344
Ser Leu Ala Glu Gln Tyr Asp Arg Asn Thr Ala Ala Pro Leu Ser Ala
    435             440             445 aac gat ctg act tgg tca ttt gcc tct ttc ttg acg gct acg caa cgc      1392
Asn Asp Leu Thr Trp Ser Phe Ala Ser Phe Leu Thr Ala Thr Gln Arg
450             455             460 cgc gat gcc gtg gtt cct ccc tcc tgg ggc gca aag tcg gca aac aaa      1440
Arg Asp Ala Val Val Pro Pro Ser Trp Gly Ala Lys Ser Ala Asn Lys
465             470             475             480 gtc cca acc act tgt tca gcc tcc cct gtt gtg ggt act tat aag gcg      1488
Val Pro Thr Thr Cys Ser Ala Ser Pro Val Val Gly Thr Tyr Lys Ala
            485             490             495 ccc acg gca act ttc tca tcc aag act aag tgc gtc ccc gct aaa gat      1536
Pro Thr Ala Thr Phe Ser Ser Lys Thr Lys Cys Val Pro Ala Lys Asp
        500             505             510 att gtg cct atc acg ttc tac ctg att gag aac act tac tat gga gag      1584
Ile Val Pro Ile Thr Phe Tyr Leu Ile Glu Asn Thr Tyr Tyr Gly Glu
    515             520             525 aac gtc ttc atg agt ggc aac att act gcg ctg ggt aac tgg gac gcc      1632
Asn Val Phe Met Ser Gly Asn Ile Thr Ala Leu Gly Asn Trp Asp Ala
530             535             540 aag aaa ggc ttc cca ctc acc gca aac ctc tac acg caa gat caa aac      1680
Lys Lys Gly Phe Pro Leu Thr Ala Asn Leu Tyr Thr Gln Asp Gln Asn
545             550             555             560 ttg tgg ttc gcc agt gtc gag ttc atc cca gca ggc aca ccc ttt gag      1728
Leu Trp Phe Ala Ser Val Glu Phe Ile Pro Ala Gly Thr Pro Phe Glu
            565             570             575 tac aag tac tac aag gtc gag ccc aat ggc gat att act tgg gag aag      1776
Tyr Lys Tyr Tyr Lys Val Glu Pro Asn Gly Asp Ile Thr Trp Glu Lys
        580             585             590 ggt ccc aac cgg gtg ttc gtc gct ccc acg gga tgc cca gtt cag cct      1824
Gly Pro Asn Arg Val Phe Val Ala Pro Thr Gly Cys Pro Val Gln Pro
    595             600             605 cac tcc aac gac gtg tgg cag ttt tga                                  1851
His Ser Asn Asp Val Trp Gln Phe
610             615
```

<210> SEQ ID NO 9
<211> LENGTH: 616
<212> TYPE: PRT
<213> ORGANISM: Penicillium oxalicum

<400> SEQUENCE: 9

```
Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Asn Leu Thr Pro
            20                  25                  30

Phe Ile His Lys Glu Gly Glu Arg Ser Leu Gln Gly Ile Leu Asp Asn
            35                  40                  45

Leu Gly Gly Arg Gly Lys Lys Thr Pro Gly Thr Ala Ala Gly Leu Phe
50                      55                  60

Ile Ala Ser Pro Asn Thr Glu Asn Pro Asn Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
            100                 105                 110

Arg Asp Tyr Val Ser Ser Gln Ala Ile Leu Gln Ser Val Ser Asn Pro
            115                 120                 125

Ser Gly Thr Leu Lys Asp Gly Ser Gly Leu Gly Glu Pro Lys Phe Glu
            130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
            165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
            195                 200                 205

Phe Asp Leu Trp Glu Glu Val Asp Gly Ser Ser Phe Phe Thr Ile Ala
            210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
            245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
            275                 280                 285

Ile His Thr Phe Asp Pro Glu Ala Ala Cys Asp Asp Ala Thr Phe Gln
            290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
            325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
            355                 360                 365

Tyr Gln Trp Asp Arg Leu Gly Lys Leu Glu Val Ser Glu Thr Ser Leu
            370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
            405                 410                 415
```

```
Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Tyr Lys Ala
                485                 490                 495

Pro Thr Ala Thr Phe Ser Ser Lys Thr Lys Cys Val Pro Ala Lys Asp
        500                 505                 510

Ile Val Pro Ile Thr Phe Tyr Leu Ile Glu Asn Thr Tyr Tyr Gly Glu
            515                 520                 525

Asn Val Phe Met Ser Gly Asn Ile Thr Ala Leu Gly Asn Trp Asp Ala
        530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
        595                 600                 605

His Ser Asn Asp Val Trp Gln Phe
    610                 615

<210> SEQ ID NO 10
<211> LENGTH: 4014
<212> TYPE: DNA
<213> ORGANISM: Thermococcus hydrothermalis
<220> FEATURE:
<221> NAME/KEY: CDS
<222> LOCATION: (1)..(4011)
<220> FEATURE:
<221> NAME/KEY: misc_signal
<222> LOCATION: (1)..(81)
<220> FEATURE:
<221> NAME/KEY: mat_peptide
<222> LOCATION: (82)..(4014)

<400> SEQUENCE: 10 atg agg cgg gtg gtt gcc ctc ttc att gca att ttg atg ctt gga agc    48
Met Arg Arg Val Val Ala Leu Phe Ile Ala Ile Leu Met Leu Gly Ser
    -25                 -20                 -15 atc gtt gga gcg aac gtt aag agc gtt ggc gcg gcg gag ccg aag ccg    96
Ile Val Gly Ala Asn Val Lys Ser Val Gly Ala Ala Glu Pro Lys Pro
    -10                 -5              -1  1               5 ctc aac gtc ata ata gtc tgg cac cag cac cag ccc tac tac tac gac   144
Leu Asn Val Ile Ile Val Trp His Gln His Gln Pro Tyr Tyr Tyr Asp
                10                  15                  20 cct gtc cag gac gtc tac acc agg ccc tgg gtc agg ctc cac gcg gcg   192
Pro Val Gln Asp Val Tyr Thr Arg Pro Trp Val Arg Leu His Ala Ala
            25                  30                  35 aac aac tac tgg aag atg gcc cac tac ctg agc cag tac ccg gag gtt   240
Asn Asn Tyr Trp Lys Met Ala His Tyr Leu Ser Gln Tyr Pro Glu Val
        40                  45                  50 cac gcc acc att gac ctc tcg ggt tcg ctg ata gcc cag ctt gcc gac   288
His Ala Thr Ile Asp Leu Ser Gly Ser Leu Ile Ala Gln Leu Ala Asp
    55                  60                  65
```

-continued

| | | |
|---|---|---|
| tac atg aac ggc aag aag gac acc tac cag ata atc acc gag aag ata<br>Tyr Met Asn Gly Lys Lys Asp Thr Tyr Gln Ile Ile Thr Glu Lys Ile<br>70                          75                         80                       85 | 336 | |
| gcc aac ggg gaa ccc ctc acc gtc gac gag aag tgg ttc atg ctc cag<br>Ala Asn Gly Glu Pro Leu Thr Val Asp Glu Lys Trp Phe Met Leu Gln<br>                   90                         95                         100 | 384 | |
| gca ccg gga ggg ttc ttc gac aac acc atc ccc tgg aac ggt gaa ccg<br>Ala Pro Gly Gly Phe Phe Asp Asn Thr Ile Pro Trp Asn Gly Glu Pro<br>                 105                       110                       115 | 432 | |
| ata acc gac ccc aac ggc aac ccg ata agg gac ttc tgg gac cgc tac<br>Ile Thr Asp Pro Asn Gly Asn Pro Ile Arg Asp Phe Trp Asp Arg Tyr<br>         120                       125                       130 | 480 | |
| acg gag ctg aag aac aag atg ctc agc gca aag gcc aag tac gca aac<br>Thr Glu Leu Lys Asn Lys Met Leu Ser Ala Lys Ala Lys Tyr Ala Asn<br>135                         140                       145 | 528 | |
| ttc gtg act gag agc cag aag gtc gct gtg acg aac gag ttc aca gag<br>Phe Val Thr Glu Ser Gln Lys Val Ala Val Thr Asn Glu Phe Thr Glu<br>150                         155                       160                       165 | 576 | |
| cag gac tac ata gac cta gcg gtt ctc ttc aat ctc gct tgg att gac<br>Gln Asp Tyr Ile Asp Leu Ala Val Leu Phe Asn Leu Ala Trp Ile Asp<br>                 170                       175                       180 | 624 | |
| tac aat tac atc acg agc acg ccg gag ttc aag gcc ctc tac gac aag<br>Tyr Asn Tyr Ile Thr Ser Thr Pro Glu Phe Lys Ala Leu Tyr Asp Lys<br>         185                       190                       195 | 672 | |
| gtt gac gag ggc ggc tat aca agg gcg gac gtc aaa acc gtt ctc gac<br>Val Asp Glu Gly Gly Tyr Thr Arg Ala Asp Val Lys Thr Val Leu Asp<br>200                         205                       210 | 720 | |
| gcc cag atc tgg ctt ctc aac cac acc ttc gag gag cac gag aag ata<br>Ala Gln Ile Trp Leu Leu Asn His Thr Phe Glu Glu His Glu Lys Ile<br>         215                       220                       225 | 768 | |
| aac ctc ctc ctc gga aac ggc aac gtc gag gtc acg gtc gtt ccc tac<br>Asn Leu Leu Leu Gly Asn Gly Asn Val Glu Val Thr Val Val Pro Tyr<br>230                         235                       240                       245 | 816 | |
| gcc cac ccg ata ggc ccg ata ctc aac gac ttc ggc tgg gac agc gac<br>Ala His Pro Ile Gly Pro Ile Leu Asn Asp Phe Gly Trp Asp Ser Asp<br>                 250                       255                       260 | 864 | |
| ttc aac gac cag gtc aag aag gcc gac gaa ctg tac aag ccg tac ctc<br>Phe Asn Asp Gln Val Lys Lys Ala Asp Glu Leu Tyr Lys Pro Tyr Leu<br>         265                       270                       275 | 912 | |
| ggc ggc ggc acc gcg gtt cca aaa ggc gga tgg gcg gct gag agc gcc<br>Gly Gly Gly Thr Ala Val Pro Lys Gly Gly Trp Ala Ala Glu Ser Ala<br>280                         285                       290 | 960 | |
| ctc aac gac aaa act ctg gag atc ctc gcc gag aac ggc tgg gag tgg<br>Leu Asn Asp Lys Thr Leu Glu Ile Leu Ala Glu Asn Gly Trp Glu Trp<br>         295                       300                       305 | 1008 | |
| gtc atg acc gac cag atg gtt ctc gga aag ctc ggc att gag gga acc<br>Val Met Thr Asp Gln Met Val Leu Gly Lys Leu Gly Ile Glu Gly Thr<br>310                         315                       320                       325 | 1056 | |
| gtc gag aac tac cac aag ccc tgg gtg gcc gag ttc aac gga aag aag<br>Val Glu Asn Tyr His Lys Pro Trp Val Ala Glu Phe Asn Gly Lys Lys<br>                 330                       335                       340 | 1104 | |
| ata tac ctc ttc cca aga aat cac gat cta agt gac aga gtt ggc ttt<br>Ile Tyr Leu Phe Pro Arg Asn His Asp Leu Ser Asp Arg Val Gly Phe<br>         345                       350                       355 | 1152 | |
| acc tac agc gga atg aac cag cag cag gcc gtt gag gac ttc gtc aac<br>Thr Tyr Ser Gly Met Asn Gln Gln Gln Ala Val Glu Asp Phe Val Asn<br>                 360                       365                       370 | 1200 | |
| gag ctc ctc aag ctc cag aag cag aac tac gat ggc tcg ctg gtt tac<br>Glu Leu Leu Lys Leu Gln Lys Gln Asn Tyr Asp Gly Ser Leu Val Tyr | 1248 | |

-continued

|  | 375 |  |  |  | 380 |  |  |  | 385 |  |  |  |
| --- | --- | --- | --- | --- | --- | --- | --- | --- | --- | --- | --- | --- |

```
gtg gtc acg ctc gac ggc gag aac ccc gtg gag aac tac ccc tac gac    1296
Val Val Thr Leu Asp Gly Glu Asn Pro Val Glu Asn Tyr Pro Tyr Asp
390                 395                 400                 405 ggg gag ctc ttc ctc acc gaa ctc tac aag aag ctg acc gaa ctc cag    1344
Gly Glu Leu Phe Leu Thr Glu Leu Tyr Lys Lys Leu Thr Glu Leu Gln
            410                 415                 420 gag cag ggt ctc ata aga acc ctc acc ccg agc gag tac atc cag ctc    1392
Glu Gln Gly Leu Ile Arg Thr Leu Thr Pro Ser Glu Tyr Ile Gln Leu
        425                 430                 435 tac ggc gac aag gcc aac aag ctc aca cct cgg atg atg gag cgc ctt    1440
Tyr Gly Asp Lys Ala Asn Lys Leu Thr Pro Arg Met Met Glu Arg Leu
    440                 445                 450 gac ctc acc gga gac aac gtt aac gcc ctc ctc aag gcc cag agc ctc    1488
Asp Leu Thr Gly Asp Asn Val Asn Ala Leu Leu Lys Ala Gln Ser Leu
455                 460                 465 ggc gaa ctc tac gac atg acc ggc gtt aag gag gag atg cag tgg ccc    1536
Gly Glu Leu Tyr Asp Met Thr Gly Val Lys Glu Glu Met Gln Trp Pro
470                 475                 480                 485 gag agc agc tgg ata gac gga acc ctc tcc acg tgg ata ggc gag ccc    1584
Glu Ser Ser Trp Ile Asp Gly Thr Leu Ser Thr Trp Ile Gly Glu Pro
            490                 495                 500 cag gag aac tac ggc tgg tac tgg ctc tac atg gcc agg aag gcc ctt    1632
Gln Glu Asn Tyr Gly Trp Tyr Trp Leu Tyr Met Ala Arg Lys Ala Leu
        505                 510                 515 atg gag aac aag gat aaa atg agc cag gcg gac tgg gag aag gcc tac    1680
Met Glu Asn Lys Asp Lys Met Ser Gln Ala Asp Trp Glu Lys Ala Tyr
    520                 525                 530 gag tac ctg ctc cgc gcc gag gca agc gac tgg ttc tgg tgg tac gga    1728
Glu Tyr Leu Leu Arg Ala Glu Ala Ser Asp Trp Phe Trp Trp Tyr Gly
535                 540                 545 agc gac cag gac agc ggc cag gac tac acc ttc gac cgc tac ctg aag    1776
Ser Asp Gln Asp Ser Gly Gln Asp Tyr Thr Phe Asp Arg Tyr Leu Lys
550                 555                 560                 565 acc tac ctc tac gag atg tac aag ctg gca gga gtc gag ccg ccg agc    1824
Thr Tyr Leu Tyr Glu Met Tyr Lys Leu Ala Gly Val Glu Pro Pro Ser
            570                 575                 580 tac ctc ttc ggc aac tac ttc ccg gac gga gag ccc tac acc acg agg    1872
Tyr Leu Phe Gly Asn Tyr Phe Pro Asp Gly Glu Pro Tyr Thr Thr Arg
        585                 590                 595 ggc ctg gtc gga ctc aag gac ggc gag atg aag aac ttc tcc agc atg    1920
Gly Leu Val Gly Leu Lys Asp Gly Glu Met Lys Asn Phe Ser Ser Met
    600                 605                 610 tcc ccg ctg gca aag ggc gtg agc gtc tat ttc gac ggc gag ggg ata    1968
Ser Pro Leu Ala Lys Gly Val Ser Val Tyr Phe Asp Gly Glu Gly Ile
615                 620                 625 cac ttc ata gtg aaa ggg aac ctg gac agg ttc gag gtg agc atc tgg    2016
His Phe Ile Val Lys Gly Asn Leu Asp Arg Phe Glu Val Ser Ile Trp
630                 635                 640                 645 gag aag gat gag cgc gtt ggc aac acg ttc acc cgc ctc caa gag aag    2064
Glu Lys Asp Glu Arg Val Gly Asn Thr Phe Thr Arg Leu Gln Glu Lys
            650                 655                 660 ccg gac gag ttg agc tat ttc atg ttc cca ttc tca agg gac agc gtt    2112
Pro Asp Glu Leu Ser Tyr Phe Met Phe Pro Phe Ser Arg Asp Ser Val
        665                 670                 675 ggt ctc ctc ata acc aag cac gtc gtg tac gag aac gga aag gcc gag    2160
Gly Leu Leu Ile Thr Lys His Val Val Tyr Glu Asn Gly Lys Ala Glu
    680                 685                 690 ata tac ggc gcc acc gac tac gag aag agc gag aag ctt ggg gaa gcc    2208
Ile Tyr Gly Ala Thr Asp Tyr Glu Lys Ser Glu Lys Leu Gly Glu Ala
```

```
                                                                                  -continued Ile Tyr Gly Ala Thr Asp Tyr Glu Lys Ser Glu Lys Leu Gly Glu Ala
    695                 700                 705 acc gtc aag aac acg agc gaa gga atc gaa gtc gtc ctt ccc ttt gac        2256
Thr Val Lys Asn Thr Ser Glu Gly Ile Glu Val Val Leu Pro Phe Asp
710                 715                 720                 725 tac ata gaa aac ccc tcc gac ttc tac ttc gct gtc tcg acg gtc aaa        2304
Tyr Ile Glu Asn Pro Ser Asp Phe Tyr Phe Ala Val Ser Thr Val Lys
                730                 735                 740 gat gga gac ctt gag gtg ata agc act cct gtg gag ctc aag ctc ccg        2352
Asp Gly Asp Leu Glu Val Ile Ser Thr Pro Val Glu Leu Lys Leu Pro
            745                 750                 755 acc gag gtc aag gga gtc gtc ata gcc gat ata acc gac cca gaa ggc        2400
Thr Glu Val Lys Gly Val Val Ile Ala Asp Ile Thr Asp Pro Glu Gly
        760                 765                 770 gac gac cat ggg ccc gga aac tac act tat ccc acg gac aag gtc ttc        2448
Asp Asp His Gly Pro Gly Asn Tyr Thr Tyr Pro Thr Asp Lys Val Phe
    775                 780                 785 aag cca ggt gtt ttc gac ctc ctc cgc ttc agg atg ctc gaa cag acg        2496
Lys Pro Gly Val Phe Asp Leu Leu Arg Phe Arg Met Leu Glu Gln Thr
790                 795                 800                 805 gag agc tac gtc atg gag ttc tac ttc aag gac cta ggt ggt aac ccg        2544
Glu Ser Tyr Val Met Glu Phe Tyr Phe Lys Asp Leu Gly Gly Asn Pro
                810                 815                 820 tgg aac gga ccc aac ggc ttc agc ctc cag ata atc gag gtc tac ctc        2592
Trp Asn Gly Pro Asn Gly Phe Ser Leu Gln Ile Ile Glu Val Tyr Leu
            825                 830                 835 gac ttc aag gac ggt gga aac agt tcg gcc att aag atg ttc ccc gac        2640
Asp Phe Lys Asp Gly Gly Asn Ser Ser Ala Ile Lys Met Phe Pro Asp
        840                 845                 850 gga ccg gga gcc aac gtc aac ctc gac ccc gag cat cca tgg gac gtt        2688
Gly Pro Gly Ala Asn Val Asn Leu Asp Pro Glu His Pro Trp Asp Val
    855                 860                 865 gcc ttc agg ata gcg ggc tgg gac tac gga aac ctc atc atc ctg ccg        2736
Ala Phe Arg Ile Ala Gly Trp Asp Tyr Gly Asn Leu Ile Ile Leu Pro
870                 875                 880                 885 aac gga acg gcc atc cag ggc gag atg cag att tcc gca gat ccg gtt        2784
Asn Gly Thr Ala Ile Gln Gly Glu Met Gln Ile Ser Ala Asp Pro Val
                890                 895                 900 aag aac gcc ata ata gtc aag gtt cca aag aag tac atc gcc ata aac        2832
Lys Asn Ala Ile Ile Val Lys Val Pro Lys Lys Tyr Ile Ala Ile Asn
            905                 910                 915 gag gac tac ggc ctc tgg gga gac gtc ctc gtc ggc tcg cag gac ggc        2880
Glu Asp Tyr Gly Leu Trp Gly Asp Val Leu Val Gly Ser Gln Asp Gly
        920                 925                 930 tac ggc ccg gac aag tgg aga acg gcg gca gtg gat gcg gag cag tgg        2928
Tyr Gly Pro Asp Lys Trp Arg Thr Ala Ala Val Asp Ala Glu Gln Trp
    935                 940                 945 aag ctt gga ggt gcg gac ccg cag gca gtc ata aac ggc gtg gcc ccg        2976
Lys Leu Gly Gly Ala Asp Pro Gln Ala Val Ile Asn Gly Val Ala Pro
950                 955                 960                 965 cgc gtc att gat gag ctg gtt ccg cag ggc ttt gaa ccg acc cag gag        3024
Arg Val Ile Asp Glu Leu Val Pro Gln Gly Phe Glu Pro Thr Gln Glu
                970                 975                 980 gag cag ctg agc agc tac gat gca aac gac atg aag ctc gcc act gtc        3072
Glu Gln Leu Ser Ser Tyr Asp Ala Asn Asp Met Lys Leu Ala Thr Val
            985                 990                 995 aag gcg ctg cta ctc ctc aag cag ggc atc gtt gtg acc gac ccg            3117
Lys Ala Leu Leu Leu Leu Lys Gln Gly Ile Val Val Thr Asp Pro
        1000                1005                1010
```

```
gag gga gac gac cac ggg ccg gga acg tac acc tat ccg acg gac    3162
Glu Gly Asp Asp His Gly Pro Gly Thr Tyr Thr Tyr Pro Thr Asp
        1015                1020                1025 aaa gtt ttc aag ccc ggt gtt ttc gac ctc ctc aag ttc aag gtg    3207
Lys Val Phe Lys Pro Gly Val Phe Asp Leu Leu Lys Phe Lys Val
        1030                1035                1040 acc gag gga agc gac gac tgg acg ctg gag ttc cac ttc aaa gac    3252
Thr Glu Gly Ser Asp Asp Trp Thr Leu Glu Phe His Phe Lys Asp
        1045                1050                1055 ctc ggt gga aac ccg tgg aac ggg ccg aac ggc ttc agc ctg cag    3297
Leu Gly Gly Asn Pro Trp Asn Gly Pro Asn Gly Phe Ser Leu Gln
        1060                1065                1070 ata atc gag gta tac ttc gac ttc aag gag ggc ggg aac gtc tcg    3342
Ile Ile Glu Val Tyr Phe Asp Phe Lys Glu Gly Gly Asn Val Ser
        1075                1080                1085 gcc att aag atg ttc ccg gat ggg ccc gga agc aac gtc cgt ctt    3387
Ala Ile Lys Met Phe Pro Asp Gly Pro Gly Ser Asn Val Arg Leu
        1090                1095                1100 gat cca aat cac cca tgg gac ctg gcg ctt agg ata gcc ggc tgg    3432
Asp Pro Asn His Pro Trp Asp Leu Ala Leu Arg Ile Ala Gly Trp
        1105                1110                1115 gac tac gga aac ctg ata att ctg ccc gac gga acc gcc tac caa    3477
Asp Tyr Gly Asn Leu Ile Ile Leu Pro Asp Gly Thr Ala Tyr Gln
        1120                1125                1130 ggc gag atg cag att tcc gca gat ccg gtt aag aac gcc ata ata    3522
Gly Glu Met Gln Ile Ser Ala Asp Pro Val Lys Asn Ala Ile Ile
        1135                1140                1145 gtc aag gtt cca aag aag tac ctg aac ata tcc gac tac gga ctc    3567
Val Lys Val Pro Lys Lys Tyr Leu Asn Ile Ser Asp Tyr Gly Leu
        1150                1155                1160 tac acc gcc gtc atc gtg ggt tcc caa gac ggg tac ggc ccg gac    3612
Tyr Thr Ala Val Ile Val Gly Ser Gln Asp Gly Tyr Gly Pro Asp
        1165                1170                1175 aag tgg agg ccc gtg gcc gct gag gcc gag cag tgg aag ctc gga    3657
Lys Trp Arg Pro Val Ala Ala Glu Ala Glu Gln Trp Lys Leu Gly
        1180                1185                1190 ggc gca gac ccc cag gcg gtc ata gac aac ctc gta cca agg gtc    3702
Gly Ala Asp Pro Gln Ala Val Ile Asp Asn Leu Val Pro Arg Val
        1195                1200                1205 gtt gat gaa ctc gtg ccg gag ggc ttc aag cca acg cag gag gag    3747
Val Asp Glu Leu Val Pro Glu Gly Phe Lys Pro Thr Gln Glu Glu
        1210                1215                1220 cag ctg agc agc tac gac ctt gag aag aag acc ctg gcg acg gtg    3792
Gln Leu Ser Ser Tyr Asp Leu Glu Lys Lys Thr Leu Ala Thr Val
        1225                1230                1235 ctc atg gta ccg ctc gtc aat ggg act ggc ggc gag gaa cca acg    3837
Leu Met Val Pro Leu Val Asn Gly Thr Gly Gly Glu Glu Pro Thr
        1240                1245                1250 ccg acg gag agc cca acg gaa acg acg aca acc aca ccc agc gaa    3882
Pro Thr Glu Ser Pro Thr Glu Thr Thr Thr Thr Pro Ser Glu
        1255                1260                1265 aca acc acc aca act tca acg acc acc ggc cca agc tca acg acc    3927
Thr Thr Thr Thr Thr Ser Thr Thr Thr Gly Pro Ser Ser Thr Thr
        1270                1275                1280 acc agc aca ccc ggc gga gga atc tgc ggc cca ggc att ata gcg    3972
Thr Ser Thr Pro Gly Gly Gly Ile Cys Gly Pro Gly Ile Ile Ala
        1285                1290                1295 ggc ctg gcc ctg ata ccg ctc ctc ctc aag agg agg aac tga        4014
Gly Leu Ala Leu Ile Pro Leu Leu Leu Lys Arg Arg Asn
        1300                1305                1310
```

<210> SEQ ID NO 11
<211> LENGTH: 1337
<212> TYPE: PRT
<213> ORGANISM: Thermococcus hydrothermalis

<400> SEQUENCE: 11

```
Met Arg Arg Val Val Ala Leu Phe Ile Ala Ile Leu Met Leu Gly Ser
    -25                 -20                 -15
Ile Val Gly Ala Asn Val Lys Ser Val Gly Ala Ala Glu Pro Lys Pro
        -10                  -5              -1   1               5
Leu Asn Val Ile Ile Val Trp His Gln His Gln Pro Tyr Tyr Tyr Asp
                     10                  15                  20
Pro Val Gln Asp Val Tyr Thr Arg Pro Trp Val Arg Leu His Ala Ala
                 25                  30                  35
Asn Asn Tyr Trp Lys Met Ala His Tyr Leu Ser Gln Tyr Pro Glu Val
             40                  45                  50
His Ala Thr Ile Asp Leu Ser Gly Ser Leu Ile Ala Gln Leu Ala Asp
         55                  60                  65
Tyr Met Asn Gly Lys Lys Asp Thr Tyr Gln Ile Ile Thr Glu Lys Ile
 70                  75                  80                  85
Ala Asn Gly Glu Pro Leu Thr Val Asp Glu Lys Trp Phe Met Leu Gln
                 90                  95                 100
Ala Pro Gly Gly Phe Phe Asp Asn Thr Ile Pro Trp Asn Gly Glu Pro
             105                 110                 115
Ile Thr Asp Pro Asn Gly Asn Pro Ile Arg Asp Phe Trp Asp Arg Tyr
         120                 125                 130
Thr Glu Leu Lys Asn Lys Met Leu Ser Ala Lys Ala Lys Tyr Ala Asn
     135                 140                 145
Phe Val Thr Glu Ser Gln Lys Val Ala Val Thr Asn Glu Phe Thr Glu
150                 155                 160                 165
Gln Asp Tyr Ile Asp Leu Ala Val Leu Phe Asn Leu Ala Trp Ile Asp
                 170                 175                 180
Tyr Asn Tyr Ile Thr Ser Thr Pro Glu Phe Lys Ala Leu Tyr Asp Lys
             185                 190                 195
Val Asp Glu Gly Gly Tyr Thr Arg Ala Asp Val Lys Thr Val Leu Asp
         200                 205                 210
Ala Gln Ile Trp Leu Leu Asn His Thr Phe Glu Glu His Glu Lys Ile
     215                 220                 225
Asn Leu Leu Leu Gly Asn Gly Asn Val Glu Val Thr Val Val Pro Tyr
230                 235                 240                 245
Ala His Pro Ile Gly Pro Ile Leu Asn Asp Phe Gly Trp Asp Ser Asp
                 250                 255                 260
Phe Asn Asp Gln Val Lys Lys Ala Asp Glu Leu Tyr Lys Pro Tyr Leu
             265                 270                 275
Gly Gly Gly Thr Ala Val Pro Lys Gly Gly Trp Ala Ala Glu Ser Ala
         280                 285                 290
Leu Asn Asp Lys Thr Leu Glu Ile Leu Ala Glu Asn Gly Trp Glu Trp
     295                 300                 305
Val Met Thr Asp Gln Met Val Leu Gly Lys Leu Gly Ile Glu Gly Thr
310                 315                 320                 325
Val Glu Asn Tyr His Lys Pro Trp Val Ala Glu Phe Asn Gly Lys Lys
                 330                 335                 340
Ile Tyr Leu Phe Pro Arg Asn His Asp Leu Ser Asp Arg Val Gly Phe
```

-continued

```
            345                 350                 355
Thr Tyr Ser Gly Met Asn Gln Gln Gln Ala Val Glu Asp Phe Val Asn
            360                 365                 370

Glu Leu Leu Lys Leu Gln Lys Gln Asn Tyr Asp Gly Ser Leu Val Tyr
    375                 380                 385

Val Val Thr Leu Asp Gly Glu Asn Pro Val Glu Asn Tyr Pro Tyr Asp
390                 395                 400                 405

Gly Glu Leu Phe Leu Thr Glu Leu Tyr Lys Lys Leu Thr Glu Leu Gln
                410                 415                 420

Glu Gln Gly Leu Ile Arg Thr Leu Thr Pro Ser Glu Tyr Ile Gln Leu
            425                 430                 435

Tyr Gly Asp Lys Ala Asn Lys Leu Thr Pro Arg Met Met Glu Arg Leu
            440                 445                 450

Asp Leu Thr Gly Asp Asn Val Asn Ala Leu Leu Lys Ala Gln Ser Leu
            455                 460                 465

Gly Glu Leu Tyr Asp Met Thr Gly Val Lys Glu Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
            520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580

Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
            600                 605                 610

Ser Pro Leu Ala Lys Gly Val Ser Val Tyr Phe Asp Gly Glu Gly Ile
    615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
            680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
            760                 765                 770
```

Asp Asp His Gly Pro Gly Asn Tyr Thr Tyr Pro Thr Asp Lys Val Phe
775                 780                 785

Lys Pro Gly Val Phe Asp Leu Leu Arg Phe Arg Met Leu Glu Gln Thr
790                 795                 800                 805

Glu Ser Tyr Val Met Glu Phe Tyr Phe Lys Asp Leu Gly Gly Asn Pro
            810                 815                 820

Trp Asn Gly Pro Asn Gly Phe Ser Leu Gln Ile Ile Glu Val Tyr Leu
            825                 830                 835

Asp Phe Lys Asp Gly Gly Asn Ser Ser Ala Ile Lys Met Phe Pro Asp
            840                 845                 850

Gly Pro Gly Ala Asn Val Asn Leu Asp Pro Glu His Pro Trp Asp Val
855                 860                 865

Ala Phe Arg Ile Ala Gly Trp Asp Tyr Gly Asn Leu Ile Ile Leu Pro
870                 875                 880                 885

Asn Gly Thr Ala Ile Gln Gly Glu Met Gln Ile Ser Ala Asp Pro Val
            890                 895                 900

Lys Asn Ala Ile Ile Val Lys Val Pro Lys Lys Tyr Ile Ala Ile Asn
            905                 910                 915

Glu Asp Tyr Gly Leu Trp Gly Asp Val Leu Val Gly Ser Gln Asp Gly
            920                 925                 930

Tyr Gly Pro Asp Lys Trp Arg Thr Ala Ala Val Asp Ala Glu Gln Trp
            935                 940                 945

Lys Leu Gly Gly Ala Asp Pro Gln Ala Val Ile Asn Gly Val Ala Pro
950                 955                 960                 965

Arg Val Ile Asp Glu Leu Val Pro Gln Gly Phe Glu Pro Thr Gln Glu
            970                 975                 980

Glu Gln Leu Ser Ser Tyr Asp Ala Asn Asp Met Lys Leu Ala Thr Val
            985                 990                 995

Lys Ala Leu Leu Leu Leu Lys Gln Gly Ile Val Val Thr Asp Pro
            1000                1005                1010

Glu Gly Asp Asp His Gly Pro Gly Thr Tyr Thr Tyr Pro Thr Asp
            1015                1020                1025

Lys Val Phe Lys Pro Gly Val Phe Asp Leu Leu Lys Phe Lys Val
            1030                1035                1040

Thr Glu Gly Ser Asp Asp Trp Thr Leu Glu Phe His Phe Lys Asp
            1045                1050                1055

Leu Gly Gly Asn Pro Trp Asn Gly Pro Asn Gly Phe Ser Leu Gln
            1060                1065                1070

Ile Ile Glu Val Tyr Phe Asp Phe Lys Glu Gly Gly Asn Val Ser
            1075                1080                1085

Ala Ile Lys Met Phe Pro Asp Gly Pro Gly Ser Asn Val Arg Leu
            1090                1095                1100

Asp Pro Asn His Pro Trp Asp Leu Ala Leu Arg Ile Ala Gly Trp
            1105                1110                1115

Asp Tyr Gly Asn Leu Ile Ile Leu Pro Asp Gly Thr Ala Tyr Gln
            1120                1125                1130

Gly Glu Met Gln Ile Ser Ala Asp Pro Val Lys Asn Ala Ile Ile
            1135                1140                1145

Val Lys Val Pro Lys Lys Tyr Leu Asn Ile Ser Asp Tyr Gly Leu
            1150                1155                1160

Tyr Thr Ala Val Ile Val Gly Ser Gln Asp Gly Tyr Gly Pro Asp
            1165                1170                1175

```
Lys Trp Arg Pro Val Ala Ala Glu Ala Glu Gln Trp Lys Leu Gly
        1180                1185                1190

Gly Ala Asp Pro Gln Ala Val Ile Asp Asn Leu Val Pro Arg Val
        1195                1200                1205

Val Asp Glu Leu Val Pro Glu Gly Phe Lys Pro Thr Gln Glu Glu
        1210                1215                1220

Gln Leu Ser Ser Tyr Asp Leu Glu Lys Lys Thr Leu Ala Thr Val
        1225                1230                1235

Leu Met Val Pro Leu Val Asn Gly Thr Gly Gly Glu Pro Thr
        1240                1245                1250

Pro Thr Glu Ser Pro Thr Glu Thr Thr Thr Thr Thr Pro Ser Glu
        1255                1260                1265

Thr Thr Thr Thr Thr Ser Thr Thr Thr Gly Pro Ser Ser Thr Thr
        1270                1275                1280

Thr Ser Thr Pro Gly Gly Gly Ile Cys Gly Pro Gly Ile Ile Ala
        1285                1290                1295

Gly Leu Ala Leu Ile Pro Leu Leu Leu Lys Arg Arg Asn
        1300                1305                1310

<210> SEQ ID NO 12
<211> LENGTH: 809
<212> TYPE: PRT
<213> ORGANISM: Artificial Sequence
<220> FEATURE:
<223> OTHER INFORMATION: Hybrid pullulanase of Thermoccus hydrothermalis
      and Thermococcus litoralis
<220> FEATURE:
<221> NAME/KEY: SIGNAL
<222> LOCATION: (1)..(27)
<220> FEATURE:
<221> NAME/KEY: mat_peptide
<222> LOCATION: (28)..(809)

<400> SEQUENCE: 12

Met Lys Lys Pro Leu Gly Lys Ile Val Ala Ser Thr Ala Leu Leu Ile
        -25              -20                  -15

Ser Val Ala Phe Ser Ser Ser Ile Ala Ser Glu Glu Pro Lys Pro
        -10              -5                   -1   1              5

Leu Asn Val Ile Ile Val Trp His Gln His Gln Pro Tyr Tyr Tyr Asp
                    10              15                  20

Pro Ile Gln Asp Ile Tyr Thr Arg Pro Trp Val Arg Leu His Ala Ala
                25                  30                  35

Asn Asn Tyr Trp Lys Met Ala Asn Tyr Leu Ser Lys Tyr Pro Asp Val
            40                  45                  50

His Val Ala Ile Asp Leu Ser Gly Ser Leu Ile Ala Gln Leu Ala Asp
55                  60                  65

Tyr Met Asn Gly Lys Lys Asp Thr Tyr Gln Ile Val Thr Glu Lys Ile
70                  75                  80                  85

Ala Asn Gly Glu Pro Leu Thr Leu Glu Asp Lys Trp Phe Met Leu Gln
                90                  95                  100

Ala Pro Gly Gly Phe Phe Asp His Thr Ile Pro Trp Asn Gly Glu Pro
            105                 110                 115

Val Ala Asp Glu Asn Gly Asn Pro Tyr Arg Glu Gln Trp Asp Arg Tyr
            120                 125                 130

Ala Glu Leu Lys Asp Lys Arg Asn Asn Ala Phe Lys Lys Tyr Ala Asn
        135                 140                 145

Leu Pro Leu Asn Glu Gln Lys Val Lys Ile Thr Ala Glu Phe Thr Glu
150                 155                 160                 165
```

-continued

```
Gln Asp Tyr Ile Asp Leu Ala Val Leu Phe Asn Leu Ala Trp Ile Asp
                170                 175                 180

Tyr Asn Tyr Ile Ile Asn Thr Pro Glu Leu Lys Ala Leu Tyr Asp Lys
            185                 190                 195

Val Asp Val Gly Gly Tyr Thr Lys Glu Asp Val Ala Thr Val Leu Lys
        200                 205                 210

His Gln Met Trp Leu Leu Asn His Thr Phe Glu Glu His Glu Lys Ile
    215                 220                 225

Asn Tyr Leu Leu Gly Asn Gly Asn Val Glu Val Thr Val Val Pro Tyr
230                 235                 240                 245

Ala His Pro Ile Gly Pro Leu Leu Asn Asp Phe Gly Trp Tyr Glu Asp
                250                 255                 260

Phe Asp Ala His Val Lys Lys Ala His Glu Leu Tyr Lys Lys Tyr Leu
            265                 270                 275

Gly Asp Asn Arg Val Glu Pro Gln Gly Gly Trp Ala Ala Glu Ser Ala
        280                 285                 290

Leu Asn Asp Lys Thr Leu Glu Ile Leu Thr Asn Asn Gly Trp Lys Trp
    295                 300                 305

Val Met Thr Asp Gln Met Val Leu Asp Ile Leu Gly Ile Pro Asn Thr
310                 315                 320                 325

Val Glu Asn Tyr Tyr Lys Pro Trp Val Ala Glu Phe Asn Gly Lys Lys
                330                 335                 340

Ile Tyr Leu Phe Pro Arg Asn His Asp Leu Ser Asp Arg Val Gly Phe
            345                 350                 355

Arg Tyr Ser Gly Met Asn Gln Tyr Gln Ala Val Glu Asp Phe Val Asn
        360                 365                 370

Glu Leu Leu Lys Val Gln Lys Glu Asn Tyr Asp Gly Ser Leu Val Tyr
    375                 380                 385

Val Val Thr Leu Asp Gly Glu Asn Pro Trp Glu His Tyr Pro Phe Asp
390                 395                 400                 405

Gly Lys Ile Phe Leu Glu Glu Leu Tyr Lys Lys Leu Thr Glu Leu Gln
                410                 415                 420

Lys Gln Gly Leu Ile Arg Thr Val Thr Pro Ser Glu Tyr Ile Gln Met
            425                 430                 435

Tyr Gly Asp Lys Ala Asn Lys Leu Thr Pro Arg Met Met Glu Arg Leu
        440                 445                 450

Asp Leu Thr Gly Asp Asn Val Asn Ala Leu Leu Lys Ala Gln Ser Leu
    455                 460                 465

Gly Glu Leu Tyr Asp Met Thr Gly Val Lys Glu Met Gln Trp Pro
470                 475                 480                 485

Glu Ser Ser Trp Ile Asp Gly Thr Leu Ser Thr Trp Ile Gly Glu Pro
                490                 495                 500

Gln Glu Asn Tyr Gly Trp Tyr Trp Leu Tyr Met Ala Arg Lys Ala Leu
            505                 510                 515

Met Glu Asn Lys Asp Lys Met Ser Gln Ala Asp Trp Glu Lys Ala Tyr
        520                 525                 530

Glu Tyr Leu Leu Arg Ala Glu Ala Ser Asp Trp Phe Trp Trp Tyr Gly
    535                 540                 545

Ser Asp Gln Asp Ser Gly Gln Asp Tyr Thr Phe Asp Arg Tyr Leu Lys
550                 555                 560                 565

Thr Tyr Leu Tyr Glu Met Tyr Lys Leu Ala Gly Val Glu Pro Pro Ser
                570                 575                 580
```

-continued

```
Tyr Leu Phe Gly Asn Tyr Phe Pro Asp Gly Glu Pro Tyr Thr Thr Arg
            585                 590                 595

Gly Leu Val Gly Leu Lys Asp Gly Glu Met Lys Asn Phe Ser Ser Met
        600                 605                 610

Ser Pro Leu Ala Lys Gly Val Ser Val Tyr Phe Asp Gly Glu Gly Ile
        615                 620                 625

His Phe Ile Val Lys Gly Asn Leu Asp Arg Phe Glu Val Ser Ile Trp
630                 635                 640                 645

Glu Lys Asp Glu Arg Val Gly Asn Thr Phe Thr Arg Leu Gln Glu Lys
                650                 655                 660

Pro Asp Glu Leu Ser Tyr Phe Met Phe Pro Phe Ser Arg Asp Ser Val
            665                 670                 675

Gly Leu Leu Ile Thr Lys His Val Val Tyr Glu Asn Gly Lys Ala Glu
        680                 685                 690

Ile Tyr Gly Ala Thr Asp Tyr Glu Lys Ser Glu Lys Leu Gly Glu Ala
    695                 700                 705

Thr Val Lys Asn Thr Ser Glu Gly Ile Glu Val Val Leu Pro Phe Asp
710                 715                 720                 725

Tyr Ile Glu Asn Pro Ser Asp Phe Tyr Phe Ala Val Ser Thr Val Lys
                730                 735                 740

Asp Gly Asp Leu Glu Val Ile Ser Thr Pro Val Glu Leu Lys Leu Pro
            745                 750                 755

Thr Glu Val Lys Gly Val Val Ile Ala Asp Ile Thr Asp Pro Glu Gly
        760                 765                 770

Asp Asp His Gly Pro Gly Asn Tyr Thr
775                 780
```

<210> SEQ ID NO 13
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 13

```
Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
```

```
            145                 150                 155                 160
        Val Val Val Ala Ala Gly Asn Ser Gly Pro Asn Lys Tyr Thr Ile Gly
                        165                 170                 175

Ser Pro Ala Ala Ala Ser Lys Val Ile Thr Val Gly Ala Val Asp Lys
                        180                 185                 190

Tyr Asp Val Ile Thr Ser Phe Ser Arg Gly Pro Thr Ala Asp Gly
                        195                 200                 205

Arg Leu Lys Pro Glu Val Val Ala Pro Gly Asn Trp Ile Ile Ala Ala
                        210                 215                 220

Arg Ala Ser Gly Thr Ser Met Gly Gln Pro Ile Asn Asp Tyr Tyr Thr
        225                 230                 235                 240

Ala Ala Pro Gly Thr Ser Met Ala Thr Pro His Val Ala Gly Ile Ala
                        245                 250                 255

Ala Leu Leu Leu Gln Ala His Pro Ser Trp Thr Pro Asp Lys Val Lys
                        260                 265                 270

Thr Ala Leu Ile Glu Thr Ala Asp Ile Val Lys Pro Asp Glu Ile Ala
                        275                 280                 285

Asp Ile Ala Tyr Gly Ala Gly Arg Val Asn Ala Tyr Lys Ala Ile Asn
                        290                 295                 300

Tyr Asp Asn Tyr Ala Lys Leu Val Phe Thr Gly Tyr Val Ala Asn Lys
        305                 310                 315                 320

Gly Ser Gln Thr His Gln Phe Val Ile Ser Ala Ser Phe Val Thr
                        325                 330                 335

Ala Thr Leu Tyr Trp Asp Asn Ala Asn Ser Asp Leu Asp Leu Tyr Leu
                        340                 345                 350

Tyr Asp Pro Asn Gly Asn Gln Val Asp Tyr Ser Tyr Thr Ala Tyr Tyr
                        355                 360                 365

Gly Phe Glu Lys Val Gly Tyr Tyr Asn Pro Thr Asp Gly Thr Trp Thr
                        370                 375                 380

Ile Lys Val Val Ser Tyr Ser Gly Ser Ala Asn Tyr Gln Val Asp Val
        385                 390                 395                 400

Val Ser Asp Gly Ser Leu Ser Gln Pro Gly Ser Ser
                        405                 410

<210> SEQ ID NO 14
<211> LENGTH: 595
<212> TYPE: PRT
<213> ORGANISM: Penicillium oxalicum
<220> FEATURE:
<221> NAME/KEY: mat_peptide
<222> LOCATION: (1)..(595)
<223> OTHER INFORMATION: mature Penicillium oxalicum glucoamylase
      sequence

<400> SEQUENCE: 14

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
                20                  25                  30

Lys Lys Thr Pro Gly Thr Ala Ala Gly Leu Phe Ile Ala Ser Pro Asn
            35                  40                  45

Thr Glu Asn Pro Asn Tyr Tyr Tyr Thr Trp Thr Arg Asp Ser Ala Leu
        50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
```

```
                    85                  90                  95
Ser Gln Ala Ile Leu Gln Ser Val Ser Asn Pro Ser Gly Thr Leu Lys
                100                 105                 110

Asp Gly Ser Gly Leu Gly Glu Pro Lys Phe Glu Ile Asp Leu Asn Pro
            115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ala Asn Asp Leu
                165                 170                 175

Ala Tyr Val Gly Gln Tyr Trp Asn Asn Thr Gly Phe Asp Leu Trp Glu
            180                 185                 190

Glu Val Asp Gly Ser Ser Phe Phe Thr Ile Ala Val Gln His Arg Ala
                195                 200                 205

Leu Val Glu Gly Ser Gln Leu Ala Lys Lys Leu Gly Lys Ser Cys Asp
            210                 215                 220

Ala Cys Asp Ser Gln Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
                275                 280                 285

Ala Leu Ala Asn His Lys Val Tyr Val Asp Ser Phe Arg Ser Ile Tyr
            290                 295                 300

Lys Ile Asn Ala Gly Leu Ala Glu Gly Ser Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
            340                 345                 350

Leu Gly Lys Leu Glu Val Ser Glu Thr Ser Leu Ser Phe Lys Asp
                355                 360                 365

Phe Asp Ala Thr Val Lys Ile Gly Ser Tyr Ser Arg Asn Ser Lys Thr
            370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
                435                 440                 445

Pro Pro Ser Trp Gly Ala Lys Ser Ala Asn Lys Val Pro Thr Thr Cys
            450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510
```

-continued

```
Gly Asn Ile Thr Ala Leu Gly Asn Trp Asp Ala Lys Lys Gly Phe Pro
            515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 15
<211> LENGTH: 573
<212> TYPE: PRT
<213> ORGANISM: Gloeophyllum sepiarium

<400> SEQUENCE: 15

Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
```

```
                275                 280                 285
Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 16
<211> LENGTH: 583
<212> TYPE: PRT
<213> ORGANISM: Rhizomucor pusillus

<400> SEQUENCE: 16

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80
```

```
Gln Leu Asn Ser Asn Phe Gly Asp Glu Ser Gln Leu Lys Ala Leu Ile
             85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
            165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
            210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
            245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
            355                 360                 365

Ala Tyr Ala Phe Lys His Gly Asp Ala Leu Val Val Leu Asn Asn Tyr
            370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Thr Ala Thr Pro
            435                 440                 445

Thr Gly Ser Gly Ser Val Thr Ser Thr Ser Lys Thr Thr Ala Thr Ala
            450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
            485                 490                 495

Asn Ile Tyr Leu Val Gly Ser Ile Ser Gln Leu Gly Asp Trp Glu Thr
```

```
            500                 505                 510
Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 17
<211> LENGTH: 559
<212> TYPE: PRT
<213> ORGANISM: Gloephyllum trabeum

<400> SEQUENCE: 17

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285
```

```
Asp Ser Phe Arg Ser Val Tyr Ser Ile Asn Ser Gly Ile Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Val Thr Ala Gly Thr
                355                 360                 365

Tyr Ala Ser Ser Ser Thr Thr Tyr Thr Thr Leu Thr Ser Ala Ile Lys
370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
                435                 440                 445

Thr Val Pro Thr Ser Cys Ser Ser Asn Ser Gly Gly Gly Gly Ser
450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
                515                 520                 525

Lys Asn Asn Gly Ala Val Thr Trp Glu Ser Asp Pro Asn Asn Ser Ile
            530                 535                 540

Thr Thr Pro Ala Ser Gly Ser Val Thr Glu Asn Asp Thr Trp Arg
545                 550                 555

<210> SEQ ID NO 18
<211> LENGTH: 573
<212> TYPE: PRT
<213> ORGANISM: Pycnoporus sanguineus

<400> SEQUENCE: 18

Met Arg Phe Thr Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
                20                  25                  30

Ile Ala Lys Gln Gly Val Leu Asn Asn Ile Gly Pro Asn Gly Ser Lys
            35                  40                  45

Ala His Gly Ala Lys Ala Gly Ile Val Val Ala Ser Pro Ser Thr Glu
50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
                100                 105                 110
```

```
Ser Asn Pro Ser Gly Thr Val Ser Thr Gly Gly Leu Gly Glu Pro Lys
        115                 120                 125

Phe Asn Ile Asp Glu Thr Ala Phe Thr Gly Ala Trp Gly Arg Pro Gln
130                 135                 140

Arg Asp Gly Pro Ala Leu Arg Ala Thr Ser Ile Ile Arg Tyr Ala Asn
145                 150                 155                 160

Trp Leu Asp Asn Gly Asn Thr Thr Tyr Val Ser Asn Thr Leu Trp
            165                 170                 175

Pro Val Ile Gln Leu Asp Leu Asp Tyr Val Ala Asp Asn Trp Asn Gln
                180                 185                 190

Ser Thr Phe Asp Leu Trp Glu Val Asp Ser Ser Phe Phe Thr
            195                 200                 205

Thr Ala Val Gln His Arg Ala Leu Arg Glu Gly Ala Thr Phe Ala Ser
        210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Arg Ser Gly Lys Asp Ser Asn Thr
            260                 265                 270

Val Leu Thr Ser Ile His Thr Phe Asp Pro Ala Ala Gly Cys Asp Ala
        275                 280                 285

Ala Thr Phe Gln Pro Cys Ser Asp Lys Ala Leu Ser Asn Leu Lys Val
        290                 295                 300

Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Tyr Val Trp Asp Gln Leu Gly Gly Leu Asn Val Thr
        355                 360                 365

Ser Thr Ser Leu Ala Phe Phe Gln Gln Phe Ala Ser Gly Leu Ser Thr
        370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
                420                 425                 430

Pro Leu Ser Ala Val Asp Leu Thr Trp Ser Tyr Ala Ala Ala Leu Thr
            435                 440                 445

Ala Phe Ala Ala Arg Glu Gly Lys Thr Tyr Gly Ser Trp Gly Ala Ala
450                 455                 460

Gly Leu Thr Val Pro Ala Ser Cys Ser Gly Gly Gly Ala Thr Val
465                 470                 475                 480

Ala Val Thr Phe Asn Val Gln Ala Thr Thr Val Phe Gly Glu Asn Ile
            485                 490                 495

Tyr Ile Thr Gly Ser Val Ala Ala Leu Gln Asn Trp Ser Pro Asp Asn
                500                 505                 510

Ala Leu Ile Leu Ser Ala Ala Asn Tyr Pro Thr Trp Ser Ile Thr Val
            515                 520                 525
```

-continued

```
Asn Leu Pro Ala Asn Thr Val Val Gln Tyr Lys Tyr Ile Arg Lys Phe
        530                 535                 540
Asn Gly Gln Val Thr Trp Glu Ser Asp Pro Asn Asn Gln Ile Thr Thr
545                 550                 555                 560
Pro Ser Gly Gly Ser Phe Thr Gln Asn Asp Val Trp Arg
                565                 570

<210> SEQ ID NO 19
<211> LENGTH: 618
<212> TYPE: PRT
<213> ORGANISM: Talaromyces emersonii

<400> SEQUENCE: 19

Met Ala Ser Leu Val Ala Gly Ala Leu Cys Ile Leu Gly Leu Thr Pro
1               5                   10                  15
Ala Ala Phe Ala Arg Ala Pro Val Ala Ala Arg Ala Thr Gly Ser Leu
            20                  25                  30
Asp Ser Phe Leu Ala Thr Glu Thr Pro Ile Ala Leu Gln Gly Val Leu
        35                  40                  45
Asn Asn Ile Gly Pro Asn Gly Ala Asp Val Ala Gly Ala Ser Ala Gly
    50                  55                  60
Ile Val Val Ala Ser Pro Ser Arg Ser Asp Pro Asn Tyr Phe Tyr Ser
65                  70                  75                  80
Trp Thr Arg Asp Ala Ala Leu Thr Ala Lys Tyr Leu Val Asp Ala Phe
                85                  90                  95
Ile Ala Gly Asn Lys Asp Leu Glu Gln Thr Ile Gln Gln Tyr Ile Ser
            100                 105                 110
Ala Gln Ala Lys Val Gln Thr Ile Ser Asn Pro Ser Gly Asp Leu Ser
        115                 120                 125
Thr Gly Gly Leu Gly Glu Pro Lys Phe Asn Val Asn Glu Thr Ala Phe
    130                 135                 140
Thr Gly Pro Trp Gly Arg Pro Gln Arg Asp Gly Pro Ala Leu Arg Ala
145                 150                 155                 160
Thr Ala Leu Ile Ala Tyr Ala Asn Tyr Leu Ile Asp Asn Gly Glu Ala
                165                 170                 175
Ser Thr Ala Asp Glu Ile Ile Trp Pro Ile Val Gln Asn Asp Leu Ser
            180                 185                 190
Tyr Ile Thr Gln Tyr Trp Asn Ser Ser Thr Phe Asp Leu Trp Glu Glu
        195                 200                 205
Val Glu Gly Ser Ser Phe Phe Thr Thr Ala Val Gln His Arg Ala Leu
    210                 215                 220
Val Glu Gly Asn Ala Leu Ala Thr Arg Leu Asn His Thr Cys Ser Asn
225                 230                 235                 240
Cys Val Ser Gln Ala Pro Gln Val Leu Cys Phe Leu Gln Ser Tyr Trp
                245                 250                 255
Thr Gly Ser Tyr Val Leu Ala Asn Phe Gly Gly Ser Gly Arg Ser Gly
            260                 265                 270
Lys Asp Val Asn Ser Ile Leu Gly Ser Ile His Thr Phe Asp Pro Ala
        275                 280                 285
Gly Gly Cys Asp Asp Ser Thr Phe Gln Pro Cys Ser Ala Arg Ala Leu
    290                 295                 300
Ala Asn His Lys Val Val Thr Asp Ser Phe Arg Ser Ile Tyr Ala Ile
305                 310                 315                 320
Asn Ser Gly Ile Ala Glu Gly Ser Ala Val Ala Val Gly Arg Tyr Pro
                325                 330                 335
```

```
Glu Asp Val Tyr Gln Gly Gly Asn Pro Trp Tyr Leu Ala Thr Ala Ala
                340                 345                 350

Ala Ala Glu Gln Leu Tyr Asp Ala Ile Tyr Gln Trp Lys Lys Ile Gly
            355                 360                 365

Ser Ile Ser Ile Thr Asp Val Ser Leu Pro Phe Phe Gln Asp Ile Tyr
        370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
        435                 440                 445

Ala Ser Leu Leu Thr Ala Ser Ala Arg Arg Gln Ser Val Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 20
<211> LENGTH: 574
<212> TYPE: PRT
<213> ORGANISM: Trametes cingulata

<400> SEQUENCE: 20

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45

Ser Asn Gly Ala Lys Ala Gly Ile Val Ile Ala Ser Pro Ser Thr Ser
    50                  55                  60

Asn Pro Asn Tyr Leu Tyr Thr Trp Thr Arg Asp Ser Ser Leu Val Phe
65                  70                  75                  80

Lys Ala Leu Ile Asp Gln Phe Thr Thr Gly Glu Asp Thr Ser Leu Arg
```

```
                    85                  90                  95
Thr Leu Ile Asp Glu Phe Thr Ser Ala Glu Ala Ile Leu Gln Gln Val
                100                 105                 110

Pro Asn Pro Ser Gly Thr Val Ser Thr Gly Gly Leu Gly Glu Pro Lys
            115                 120                 125

Phe Asn Ile Asp Glu Thr Ala Phe Thr Asp Ala Trp Gly Arg Pro Gln
        130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
                180                 185                 190

Ser Thr Phe Asp Leu Trp Glu Glu Ile Asn Ser Ser Phe Phe Thr
                195                 200                 205

Thr Ala Val Gln His Arg Ala Leu Arg Glu Gly Ala Thr Phe Ala Asn
        210                 215                 220

Arg Ile Gly Gln Thr Ser Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
                260                 265                 270

Val Leu Thr Ser Ile His Thr Phe Asp Pro Ala Ala Gly Cys Asp Ala
                275                 280                 285

Val Thr Phe Gln Pro Cys Ser Asp Lys Ala Leu Ser Asn Leu Lys Val
        290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
                340                 345                 350

Tyr Asp Ala Leu Ile Val Trp Asn Lys Leu Gly Ala Leu Asn Val Thr
            355                 360                 365

Ser Thr Ser Leu Pro Phe Phe Gln Gln Phe Ser Ser Gly Val Thr Val
        370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
        435                 440                 445

Ser Phe Ala Ala Arg Ser Gly Lys Thr Tyr Ala Ser Trp Gly Ala Ala
    450                 455                 460

Gly Leu Thr Val Pro Thr Thr Cys Ser Gly Ser Gly Gly Ala Gly Thr
465                 470                 475                 480

Val Ala Val Thr Phe Asn Val Gln Ala Thr Thr Val Phe Gly Glu Asn
                485                 490                 495

Ile Tyr Ile Thr Gly Ser Val Pro Ala Leu Gln Asn Trp Ser Pro Asp
                500                 505                 510
```

-continued

Asn Ala Leu Ile Leu Ser Ala Ala Asn Tyr Pro Thr Trp Ser Ile Thr
            515                 520                 525

Val Asn Leu Pro Ala Ser Thr Thr Ile Glu Tyr Lys Tyr Ile Arg Lys
    530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
            565                 570

<210> SEQ ID NO 21
<211> LENGTH: 483
<212> TYPE: PRT
<213> ORGANISM: Bacillus licheniformis

<400> SEQUENCE: 21

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser

-continued

```
                    305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 22
<211> LENGTH: 25
<212> TYPE: DNA
<213> ORGANISM: Artificial Sequence
<220> FEATURE:
<223> OTHER INFORMATION: Sense Primer

<400> SEQUENCE: 22
atgcgtctca ctctattatc aggtg                                          25

<210> SEQ ID NO 23
<211> LENGTH: 39
<212> TYPE: DNA
<213> ORGANISM: Artificial Sequence
<220> FEATURE:
<223> OTHER INFORMATION: Primer F

<400> SEQUENCE: 23
acacaactgg ggatccacca tgcgtctcac tctattatc                           39

<210> SEQ ID NO 24
<211> LENGTH: 37
<212> TYPE: DNA
<213> ORGANISM: Artificial Sequence
<220> FEATURE:
<223> OTHER INFORMATION: Primer R

<400> SEQUENCE: 24
agatctcgag aagcttaaaa ctgccacacg tcgttgg                             37

<210> SEQ ID NO 25
<211> LENGTH: 18
<212> TYPE: DNA
<213> ORGANISM: Artificial Sequence
<220> FEATURE:
<223> OTHER INFORMATION: Primer K79V F

<400> SEQUENCE: 25
```

```
gcagtctttc caattgac                                                    18

<210> SEQ ID NO 26
<211> LENGTH: 18
<212> TYPE: DNA
<213> ORGANISM: Artificial Sequence
<220> FEATURE:
<223> OTHER INFORMATION: Primer K79V R

<400> SEQUENCE: 26
aattggaaag actgcccg                                                    18

<210> SEQ ID NO 27
<211> LENGTH: 39
<212> TYPE: DNA
<213> ORGANISM: Artificial Sequence
<220> FEATURE:
<223> OTHER INFORMATION: Primer F-NP003940

<400> SEQUENCE: 27
acacaactgg ggatccacca tgcgtctcac tctattatc                              39

<210> SEQ ID NO 28
<211> LENGTH: 37
<212> TYPE: DNA
<213> ORGANISM: Artificial Sequence
<220> FEATURE:
<223> OTHER INFORMATION: Primer R-NP003940

<400> SEQUENCE: 28
agatctcgag aagcttaaaa ctgccacacg tcgttgg                                37

<210> SEQ ID NO 29
<211> LENGTH: 863
<212> TYPE: PRT
<213> ORGANISM: Aspergillus fumigatus

<400> SEQUENCE: 29
```

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

```
Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
            275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
            355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
            515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590
```

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
    610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 30
<211> LENGTH: 250
<212> TYPE: PRT
<213> ORGANISM: Thermoascus aurantiacus
<220> FEATURE:
<221> NAME/KEY: SIGNAL
<222> LOCATION: (1)..(22)

<400> SEQUENCE: 30

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

```
Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
            115                 120                 125

Thr Gln Leu Glu Phe Phe Lys Ile Ala Glu Ser Gly Leu Ile Asn Asp
        130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 31
<211> LENGTH: 253
<212> TYPE: PRT
<213> ORGANISM: Penicillium emersonii
<220> FEATURE:
<221> NAME/KEY: SIGNAL
<222> LOCATION: (1)..(25)

<400> SEQUENCE: 31

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
```

```
                195                 200                 205
Thr Gly Gly Ser Asp Ala Pro Glu Gly Thr Leu Gly Glu Asp Leu
    210                 215                 220
Tyr His Asp Thr Asp Pro Gly Ile Leu Val Asp Ile Tyr Glu Pro Ile
225                 230                 235                 240
Ala Thr Tyr Thr Ile Pro Gly Pro Pro Glu Pro Thr Phe
                245                 250
```

<210> SEQ ID NO 32
<211> LENGTH: 532
<212> TYPE: PRT
<213> ORGANISM: Aspergillus fumigatus

<400> SEQUENCE: 32

```
Met Leu Ala Ser Thr Phe Ser Tyr Arg Met Tyr Lys Thr Ala Leu Ile
1               5                   10                  15
Leu Ala Ala Leu Leu Gly Ser Gly Gln Ala Gln Gln Val Gly Thr Ser
                20                  25                  30
Gln Ala Glu Val His Pro Ser Met Thr Trp Gln Ser Cys Thr Ala Gly
            35                  40                  45
Gly Ser Cys Thr Thr Asn Asn Gly Lys Val Val Ile Asp Ala Asn Trp
        50                  55                  60
Arg Trp Val His Lys Val Gly Asp Tyr Thr Asn Cys Tyr Thr Gly Asn
65                  70                  75                  80
Thr Trp Asp Thr Thr Ile Cys Pro Asp Asp Ala Thr Cys Ala Ser Asn
                85                  90                  95
Cys Ala Leu Glu Gly Ala Asn Tyr Glu Ser Thr Tyr Gly Val Thr Ala
                100                 105                 110
Ser Gly Asn Ser Leu Arg Leu Asn Phe Val Thr Thr Ser Gln Gln Lys
            115                 120                 125
Asn Ile Gly Ser Arg Leu Tyr Met Met Lys Asp Asp Ser Thr Tyr Glu
        130                 135                 140
Met Phe Lys Leu Leu Asn Gln Glu Phe Thr Phe Asp Val Asp Val Ser
145                 150                 155                 160
Asn Leu Pro Cys Gly Leu Asn Gly Ala Leu Tyr Phe Val Ala Met Asp
                165                 170                 175
Ala Asp Gly Gly Met Ser Lys Tyr Pro Thr Asn Lys Ala Gly Ala Lys
            180                 185                 190
Tyr Gly Thr Gly Tyr Cys Asp Ser Gln Cys Pro Arg Asp Leu Lys Phe
        195                 200                 205
Ile Asn Gly Gln Ala Asn Val Glu Gly Trp Gln Pro Ser Ser Asn Asp
        210                 215                 220
Ala Asn Ala Gly Thr Gly Asn His Gly Ser Cys Cys Ala Glu Met Asp
225                 230                 235                 240
Ile Trp Glu Ala Asn Ser Ile Ser Thr Ala Phe Thr Pro His Pro Cys
                245                 250                 255
Asp Thr Pro Gly Gln Val Met Cys Thr Gly Asp Ala Cys Gly Gly Thr
            260                 265                 270
Tyr Ser Ser Asp Arg Tyr Gly Gly Thr Cys Asp Pro Asp Gly Cys Asp
        275                 280                 285
Phe Asn Ser Phe Arg Gln Gly Asn Lys Thr Phe Tyr Gly Pro Gly Met
        290                 295                 300
Thr Val Asp Thr Lys Ser Lys Phe Thr Val Val Thr Gln Phe Ile Thr
305                 310                 315                 320
```

```
Asp Asp Gly Thr Ser Ser Gly Thr Leu Lys Glu Ile Lys Arg Phe Tyr
            325                 330                 335

Val Gln Asn Gly Lys Val Ile Pro Asn Ser Glu Ser Thr Trp Thr Gly
        340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
                420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
    450                 455                 460

Ser Gly Gly Ser Asn Pro Gly Gly Thr Thr Thr Thr Thr Thr Thr Thr
465                 470                 475                 480

Gln Pro Thr Thr Thr Thr Thr Ala Gly Asn Pro Gly Gly Thr Gly
                485                 490                 495

Val Ala Gln His Tyr Gly Gln Cys Gly Ile Gly Trp Thr Gly Pro
                500                 505                 510

Thr Thr Cys Ala Ser Pro Tyr Thr Cys Gln Lys Leu Asn Asp Tyr Tyr
                515                 520                 525

Ser Gln Cys Leu
    530

<210> SEQ ID NO 33
<211> LENGTH: 454
<212> TYPE: PRT
<213> ORGANISM: Aspergillus fumigatus

<400> SEQUENCE: 33

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160
```

```
Ala Lys Asn Lys Ala Gly Ala Asn Pro Pro Ile Ala Gly Ile Phe Val
            165                 170                 175
Val Tyr Asp Leu Pro Asp Arg Asp Cys Ala Ala Leu Ala Ser Asn Gly
            180                 185                 190
Glu Tyr Ser Ile Ala Asn Asn Gly Val Ala Asn Tyr Lys Ala Tyr Ile
            195                 200                 205
Asp Ala Ile Arg Ala Gln Leu Val Lys Tyr Ser Asp Val His Thr Ile
            210                 215                 220
Leu Val Ile Glu Pro Asp Ser Leu Ala Asn Leu Val Thr Asn Leu Asn
225                 230                 235                 240
Val Ala Lys Cys Ala Asn Ala Gln Ser Ala Tyr Leu Glu Cys Val Asp
            245                 250                 255
Tyr Ala Leu Lys Gln Leu Asn Leu Pro Asn Val Ala Met Tyr Leu Asp
            260                 265                 270
Ala Gly His Ala Gly Trp Leu Gly Trp Pro Ala Asn Leu Gly Pro Ala
            275                 280                 285
Ala Thr Leu Phe Ala Lys Val Tyr Thr Asp Ala Gly Ser Pro Ala Ala
            290                 295                 300
Val Arg Gly Leu Ala Thr Asn Val Ala Asn Tyr Asn Ala Trp Ser Leu
305                 310                 315                 320
Ser Thr Cys Pro Ser Tyr Thr Gln Gly Asp Pro Asn Cys Asp Glu Lys
            325                 330                 335
Lys Tyr Ile Asn Ala Met Ala Pro Leu Leu Lys Glu Ala Gly Phe Asp
            340                 345                 350
Ala His Phe Ile Met Asp Thr Ser Arg Asn Gly Val Gln Pro Thr Lys
            355                 360                 365
Gln Asn Ala Trp Gly Asp Trp Cys Asn Val Ile Gly Thr Gly Phe Gly
            370                 375                 380
Val Arg Pro Ser Thr Asn Thr Gly Asp Pro Leu Gln Asp Ala Phe Val
385                 390                 395                 400
Trp Ile Lys Pro Gly Gly Glu Ser Asp Gly Thr Ser Asn Ser Thr Ser
            405                 410                 415
Pro Arg Tyr Asp Ala His Cys Gly Tyr Ser Asp Ala Leu Gln Pro Ala
            420                 425                 430
Pro Glu Ala Gly Thr Trp Phe Gln Ala Tyr Phe Glu Gln Leu Leu Thr
            435                 440                 445
Asn Ala Asn Pro Ser Phe
            450
```